(12) United States Patent
Flasinski et al.

(10) Patent No.: US 11,414,669 B2
(45) Date of Patent: Aug. 16, 2022

(54) COMPOSITIONS AND METHODS FOR GENOME EDITING IN PLANTA

(71) Applicant: MONSANTO TECHNOLOGY LLC, St. Louis, MO (US)

(72) Inventors: Stanislaw Flasinski, Ballwin, MO (US); Elysia Krieger, Kirkwood, MO (US); Ervin Nagy, Lake Saint Louis, MO (US); Krishnakumar Sridharan, Cary, NC (US); Xudong Ye, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 2 days.

(21) Appl. No.: 16/563,581

(22) Filed: Sep. 6, 2019

(65) Prior Publication Data
US 2020/0080096 A1    Mar. 12, 2020

Related U.S. Application Data

(60) Provisional application No. 62/727,784, filed on Sep. 6, 2018.

(51) Int. Cl.
C12N 15/82    (2006.01)

(52) U.S. Cl.
CPC ..... *C12N 15/8213* (2013.01); *C12N 15/8205* (2013.01); *C12N 2310/20* (2017.05); *C12N 2800/80* (2013.01)

(58) Field of Classification Search
CPC ............ C12N 15/8205; C12N 15/8213; C12N 2310/20; C12N 2800/80
See application file for complete search history.

(56) References Cited

U.S. PATENT DOCUMENTS

| | | |
|---|---|---|
| 7,022,896 B1 | 4/2006 | Weeks et al. |
| 9,938,535 B2 | 4/2018 | Chittoor et al. |
| 2009/0029861 A1 | 1/2009 | Feng et al. |
| 2014/0283200 A1 | 9/2014 | Chittoor et al. |
| 2017/0166912 A1 | 6/2017 | Brower-Toland et al. |
| 2018/0105823 A1 | 4/2018 | Flasinski |

FOREIGN PATENT DOCUMENTS

| | | | |
|---|---|---|---|
| WO | WO 97/41228 | 11/1997 | |
| WO | WO 2015/131101 A1 | 9/2015 | |
| WO | WO-2018138385 A1 * | 8/2018 | ............... C12N 9/22 |
| WO | WO 2019/084148 A1 | 5/2019 | |

OTHER PUBLICATIONS

Dipak Kumar Sahoo & Shayan Sarkar & Sumita Raha & Narayan Chandra Das & Joydeep Banerjee & Nrisingha Dey & Indu B. Maiti, Analysis of Dahlia Mosaic Virus Full-length Transcript Promoter-Driven Gene Expression in Transgenic Plants, May 28, 2014, Plant Molecular Biology Reports, (2015) 33:178-199 (Year: 2014).*

Goon-Bo Kim & Young-Woo Nam, Isolation and Characterization of Medicago truncatula U6 Promoters for the Construction of Small Hairpin RNA-Mediated Gene Silencing Vectors, Nov. 27, 2012, Plant Molecular Biology Reports, (2013) 31:581-593 (Year: 2012).*

Chandrashekhar P. Joshi, Hao Zhou. Xiaoqiu Huang, and Vincent L. Chiang, Context sequences of translation initiation codon in plants, 1997, Plant Molecular Biology, 35: 993-1001 (Year: 1997).*

Christensen, Ubiquitin promoter-based vectors for high-level expression of selectable and/or screenable marker genes in monocotyledonous plants, Transgenic Research, 1995 (Year: 1995).*

Yang, The 3'-untranslated region of rice glutelin GluB-1 affects accumulation of heterologous protein in transgenic rice, Biotechnology Letters, 2009 (Year: 2009).*

Sharf, The Tomato Hsf System: HsfA2 Needs Interaction with HsfA1 for Efficient Nuclear Import and May Be Localized in Cytoplasmic Heat Stress Granules, Molecular and Cellular Biology, Apr. 2018 and in further view of Joshi, Context Sequences of Translation Initiation Codon in Plants (Year: 2018).*

Begemann et al. "Precise insertion and guided editing of higher plant genomes using Cpf1 CRISPR nucleases." *Scientific reports* 7.1 (2017): 1-6.

Endo et al. "Efficient targeted mutagenesis of rice and tobacco genomes using Cpf1 from Francisella novicida." *Scientific reports* 6 (2016): 38169.

Gao et al. "Engineered Cpf1 variants with altered PAM specificities." *Nature biotechnology* 35.8 (2017): 789.

Misawa et al. "Functional expression of the Erwinia uredovora carotenoid biosynthesis gene crtI in transgenic plants showing an increase of β-carotene biosynthesis activity and resistance to the bleaching herbicide norflurazon." *The Plant Journal* 4.5 (1993): 833-840.

Takebe et al. "SR alpha promoter: an efficient and versatile mammalian cDNA expression system composed of the simian virus 40 early promoter and the R-U5 segment of human T-cell leukemia virus type 1 long terminal repeat." *Molecular and cellular biology* 8.1 (1988): 466-472.

Tang et al. "A CRISPR-Cpf1 system for efficient genome editing and transcriptional repression in plants." *Nature plants* 3.3 (2017): 1-5.

(Continued)

*Primary Examiner* — Matthew R Keogh
*Assistant Examiner* — Brian James Sullivan
(74) *Attorney, Agent, or Firm* — Morrison & Foerster LLP

(57) ABSTRACT

This disclosure is related to plant-optimized recombinant nucleic acids encoding Cpf1 and their use in planta. Also disclosed are compositions, expression cassettes, and plant cells comprising the recombinant nucleic acids as well as methods and kits for modifying a target sequence in a plant genome using the recombinant nucleic acids.

20 Claims, 2 Drawing Sheets
Specification includes a Sequence Listing.

(56) References Cited

OTHER PUBLICATIONS

Thompson et al., "CLUSTAL W: improving the sensitivity of progressive multiple sequence alignment through sequence weighting, position-specific gap penalties and weight matrix choice." *Nucleic acids research* 22.22 (1994): 4673-4680.
Xu et al. "Generation of targeted mutant rice using a CRISPR-Cpf1 system." *Plant, biotechnology journal* 15.6 (2017): 713-717.
Zetsche et al. "Cpf1 is a single RNA-guided endonuclease of a class 2 CRISPR-Cas system." *Cell* 163.3 (2015): 759-771.

* cited by examiner

COMPOSITIONS AND METHODS FOR GENOME EDITING IN PLANTA

CROSS-REFERENCE TO RELATED APPLICATION

This application claims the benefit of U.S. Provisional Application No. 62/727,784, filed Sep. 6, 2018, which is incorporated by reference in its entirety herein.

INCORPORATION OF SEQUENCE LISTING

A sequence listing contained in the file named P34668US01_SL.txt, which is 373,411 bytes (measured in MS-Windows®) and created on Sep. 5, 2019, and comprises 76 sequences, is filed electronically herewith and incorporated by reference in its entirety.

FIELD

This disclosure relates to plant-optimized recombinant nucleic acids encoding Cpf1 and their use in planta.

BACKGROUND

Clustered Regularly Interspaced Short Palindromic Repeats from Prevotella and *Francisella* 1 or CRISPR/Cpf1 (also known as Cas12a) was first demonstrated for genome editing in mammalian cells in 2015 (Zetsche et al., 2015, Cell 163, 759-771). Cpf1 (CRISPR from Prevotella and *Francisella* 1) is a large, 1,300 amino acid protein, belonging to class 2 CRISPR system. Different from Cas9 nuclease, the PAM motif of Cpf1 is located at 5' of the target site and the mature gRNA is a single strand of approximately 44 bp.

Cpf1 genome editing in plants was first observed in rice (Xu et al., 2017, Plant Biotechnology Journal 15, 713-717), where up to 41% mutation rate was achieved at OsBel locus using pre-crRNA gRNA structure and LbCpf1. Subsequently, Cpf1 genome editing of rice and tobacco were observed in different laboratories using both LbCpf1 and FnCpf1 (Endo et al., Scientific Reports volume 6, Article number: 38169 (2016); Hu et al., 2017, Journal of Genetics and Genomics 44, 71-73; Tang et al., Nature Plants volume 3, Article number: 17018 (2017); Begemann et al., 2017, Sci Rep. 7, 11606). However, there remains a need for more effective Cpf1-based genome editing technologies in plants.

SUMMARY

Several embodiments relate to a recombinant nucleic acid comprising a sequence selected from the group consisting of: SEQ ID NOs 1, 10, 38, 45-51 and 75. In some embodiments, the recombinant nucleic acid further comprises a nucleic acid sequence encoding one or more nuclear localization signals operably linked to the recombinant nucleic acid comprising a sequence selected from the group consisting of: SEQ ID NOs 1, 10, 38, 45-51 and 75. In some embodiments, the nuclear localization signal is provided on the 5' end of Cpf1. In some embodiments, the nuclear localization signal is provided on the 3' end of Cpf1. In some embodiments, the nuclear localization signal is provided on the 5' and 3' end of Cpf1. In some embodiments, the recombinant nucleic acid further comprises a promoter operably linked to the recombinant nucleic acid comprising a sequence selected from the group consisting of: SEQ ID NOs 1, 10, 38, 45-51 and 75. In some embodiments, the promoter comprises a sequence selected from the group consisting of SEQ ID NOs 7, 22, 27, and 32. In some embodiments, the recombinant nucleic acid further comprising one or more of an intron, a kozak sequence, a leader sequence and a terminator sequence. Several embodiments relate to a recombinant nucleic acid comprising a sequence selected from the group consisting of SEQ ID NOs 4, 6, 12, 14, 41, 63, 66, 68, 70, and 72.

Several embodiments relate to a plant cell comprising a recombinant nucleic acid comprising a sequence selected from the group consisting of: SEQ ID NOs 1, 10, 38, 45-51 and 75. Several embodiments relate to a plant cell comprising a recombinant nucleic acid comprising a nucleic acid sequence encoding one or more nuclear localization signals operably linked to the recombinant nucleic acid comprising a sequence selected from the group consisting of: SEQ ID NOs 1, 10, 38, 45-51 and 75. In some embodiments, the nuclear localization signal is provided on the 5' end of Cpf1. In some embodiments, the nuclear localization signal is provided on the 3' end of Cpf1. In some embodiments, the nuclear localization signal is provided on the 5' and 3' end of Cpf1. Several embodiments relate to a plant cell comprising a promoter operably linked to a recombinant nucleic acid comprising a sequence selected from the group consisting of: SEQ ID NOs 1, 10, 38, 45-51 and 75, and optionally one or more nuclear localization signals, an intron, a kozak sequence, a leader sequence and a terminator sequence. In some embodiments, the promoter comprises a sequence selected from the group consisting of SEQ ID NOs 7, 22, 27, and 32. Several embodiments relate to a plant cell comprising recombinant nucleic acid comprising a sequence selected from the group consisting of SEQ ID NOs 4, 6, 12, 14, 41, 63, 66, 68, 70, and 72. In some embodiments, the plant cell is a monocot or a dicot. In some embodiments, the plant cell is a maize, cotton, soybean, canola, wheat, tomato, rice, brassica, melon, cucurbit, or lettuce cell.

Several embodiments relate to an expression cassette comprising a recombinant nucleic acid sequence selected from the group consisting of SEQ ID NOs 15, 20, 26, 31, 36, 40, 56, 59, 65, 67, 69, 71, and 73. Several embodiments relate to a plant cell comprising an expression cassette comprising a recombinant nucleic acid sequence selected from the group consisting of SEQ ID NOs 15, 20, 26, 31, 36, 40, 56, 59, 65, 67, 69, 71, and 73. Several embodiments relate to an *Agrobacterium* T-DNA vector comprising an expression SEQ ID NOs 15, 20, 26, 31, 36, 40, 56, 59, 65, 67, 69, 71, and 73. Several embodiments relate to an *Agrobacterium* cell comprising an *Agrobacterium* T-DNA vector comprising an expression SEQ ID NOs 15, 20, 26, 31, 36, 40, 56, 59, 65, 67, 69, 71, and 73. In some embodiments, the *Agrobacterium* T-DNA vector further comprises an expression cassette for a selectable marker gene. In some embodiments, the *Agrobacterium* T-DNA vector further comprising a promoter operably linked to a one or more crRNA sequences and one or more spacer sequences, where in the spacer sequence is complementary to at least 23 base pairs of a target site. In some embodiments, the crRNA sequence is a pre-crRNA or a mature crRNA.

Several embodiments relate to a composition comprising: (a) recombinant nucleic acid comprising a sequence selected from the group consisting of: SEQ ID NOs 1, 10, 38, 45-51 and 75, and (b) a recombinant nucleic acid encoding a guide RNA comprised of at least one crRNA and at least one spacer RNA sequence. Several embodiments relate to a composition comprising: (a) recombinant nucleic acid comprising a sequence selected from the group consisting of: SEQ ID NOs 6, 12, 14, 41, 63, 66, 68, 70, and 72, and (b)

a recombinant nucleic acid encoding a guide RNA comprised of at least one crRNA and at least one spacer RNA sequence. In some embodiments, the composition is provided on a particle suitable for biolistic delivery to a plant cell.

Several embodiments relate to a method for modifying a target sequence in the genome of a plant cell, comprising: introducing into the plant cell a recombinant nucleic acid comprising a sequence selected from the group consisting of: SEQ ID NOs 1, 10, 38, 45-51 and 75 operably linked to a promoter, and introducing into the plant cell a guide polynucleotide comprising a nucleic acid sequence that is complementary to a target sequence or a recombinant nucleic acid encoding the guide polynucleotide, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence. Several embodiments relate to a method for modifying a target sequence in the genome of a plant cell, comprising: introducing into the plant cell a recombinant nucleic acid comprising a sequence selected from the group consisting of: SEQ ID NOs 1, 10, 38, 45-51 and 75 operably linked to a promoter, and introducing into the plant cell a guide polynucleotide comprising a nucleic acid sequence that is complementary to a target sequence or a recombinant nucleic acid encoding the guide polynucleotide, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence, wherein the recombinant nucleic acid comprising a sequence selected from the group consisting of: SEQ ID NOs 1, 10, 38, 45-51 and 75 is operably linked to a promoter comprising a sequence selected from the group consisting of SEQ ID NOs 7, 22, 27, and 32. In some embodiments, the method further comprises incubating the plant cell at temperatures between 24° C. and 35° C. for a period of at least about 1-8 hours. In some embodiments, the method further comprises incubating the plant cell at temperatures between 28° C. and 35° C. for a period of at least about 4 hours. In some embodiments, the plant cell is a monocot or a dicot. In some embodiments, the plant cell is a maize, cotton, soybean, canola, wheat, tomato, rice, brassica, melon, cucurbit, or lettuce cell. In some embodiments, the method further comprises introducing a donor DNA to the plant cell. In some embodiments, the method further comprises identifying at least one plant cell comprising in its genome the donor DNA, or a portion thereof, integrated into or near said target sequence.

Several embodiments relate to a method for modifying a target sequence in the genome of a plant cell, the method comprising: introducing a guide polynucleotide comprising a nucleic acid sequence that is substantially complementary to the target sequence, or a recombinant nucleic acid encoding the guide polynucleotide, into a plant cell comprising in its genome a recombinant nucleic acid comprising a sequence selected from the group consisting of: SEQ ID NOs 1, 10, 38, 45-51 and 75 operably linked to a promoter, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence. Several embodiments relate to a method for modifying a target sequence in the genome of a plant cell, the method comprising: introducing a guide polynucleotide comprising a nucleic acid sequence that is substantially complementary to the target sequence, or a recombinant nucleic acid encoding the guide polynucleotide, into a plant cell comprising in its genome a recombinant nucleic acid comprising a sequence selected from the group consisting of: SEQ ID NOs 1, 10, 38, 45-51 and 75 operably linked to a promoter comprising a sequence selected from the group consisting of SEQ ID NOs 7, 22, 27, and 32, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence. In some embodiments, the method further comprises incubating the plant cell at temperatures between 24° C. and 35° C. for a period of at least about 1-8 hours. In some embodiments, the method further comprises incubating the plant cell at temperatures between 28° C. and 35° C. for a period of at least about 4 hours. In some embodiments, the plant cell is a monocot or a dicot. In some embodiments, the plant cell is a maize, cotton, soybean, canola, wheat, tomato, rice, brassica, melon, cucurbit, or lettuce cell. In some embodiments, the method further comprises introducing a donor DNA to the plant cell. In some embodiments, the method further comprises identifying at least one plant cell comprising in its genome the donor DNA, or a portion thereof, integrated into or near said target sequence.

Several embodiments relate to a kit for modifying a target sequence in the genome of a plant cell, the kit comprising a guide polynucleotide comprising a nucleic acid sequence that is complementary to a target sequence or a recombinant nucleic acid encoding the guide polynucleotide, and recombinant nucleic acid comprising a sequence selected from the group consisting of: SEQ ID NOs 1, 10, 38, 45-51 and 75. Several embodiments relate to a kit for modifying a target sequence in the genome of a plant cell, the kit comprising a guide polynucleotide comprising a nucleic acid sequence that is complementary to a target sequence or a recombinant nucleic acid encoding the guide polynucleotide, and recombinant nucleic acid comprising a sequence selected from the group consisting of: SEQ ID NOs 4, 6, 7, 12, 14, 15, 20, 22, 26, 27, 31, 32, 36, 40, 41, 56, 59, 63, 65, 66, 67, 68, 69, 70, 71, 72 and 73. Several embodiments relate to a kit for modifying a target sequence in the genome of a plant cell, the kit comprising a guide polynucleotide comprising a nucleic acid sequence that is complementary to a target sequence or a recombinant nucleic acid encoding the guide polynucleotide, a recombinant nucleic acid comprising a sequence selected from the group consisting of: SEQ ID NOs 1, 4, 6, 7, 10, 12, 14, 15, 20, 22, 26, 27, 31, 32, 36, 40, 41, 56, 59, 63, 65, 66, 67, 68, 69, 70, 71, 72, 73 and 75, and a recombinant nucleic acid encoding a selectable marker.

BRIEF DESCRIPTION OF THE DRAWINGS

The accompanying drawings, which are incorporated in and form a part of the specification, illustrate the aspects of this disclosure and together with the description, serve to explain the principles of the disclosure. In the drawings.

DETAILED DESCRIPTION

Figure 1:
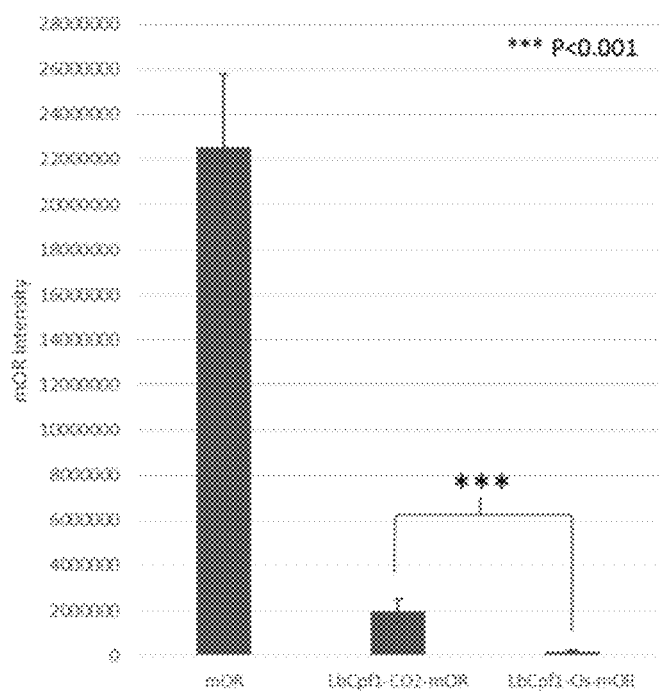
FIG. 1 illustrates the expression of LbCpf1-mOrange fluorescent proteins in corn protoplasts denoted by average mOrange intensities.

Unless defined otherwise, all technical and scientific terms used herein have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used.

The practice of the present disclosure employs, unless otherwise indicated, conventional techniques of biochemistry, chemistry, molecular biology, microbiology, cell biology, genomics, plant breeding, and biotechnology, which are within the skill of the art. See, e.g., Green and Sambrook, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)); Harlow and Lane, eds. (1988) ANTIBODIES, A LABORATORY MANUAL; ANIMAL CELL CULTURE (R. I. Freshney, ed. (1987)); RECOMBINANT PROTEIN PURIFICATION: PRINCIPLES AND METHODS, 18-1142-75, GE Healthcare Life Sciences; C. N. Stewart, A. Touraev, V. Citovsky, T. Tzfira eds. (2011) PLANT TRANSFORMATION TECHNOLOGIES (Wiley-Blackwell); and R. H. Smith (2013) PLANT TISSUE CULTURE. TECHNIQUES AND EXPERIMENTS (Academic Press, Inc.). The inventors do not intend to be limited to a mechanism or mode of action. Reference thereto is provided for illustrative purposes only.

Any references cited herein are incorporated by reference in their entireties.

As used herein, the singular form "a," "an," and "the" include plural references unless the context clearly dictates otherwise. For example, the term "a compound" or "at least one compound" may include a plurality of compounds, including mixtures thereof. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule.

As used herein, the term "about" indicates that a value includes the inherent variation of error for the method being employed to determine a value, or the variation that exists among experiments.

As used herein, "encoding" refers either to a polynucleotide (DNA or RNA) encoding for the amino acids of a polypeptide or a DNA encoding for the nucleotides of an RNA. As used herein, "coding sequence" and "coding region" are used interchangeably and refer to a polynucleotide that encodes a polypeptide. The boundaries of a coding region are generally determined by a translation start codon at its 5' end and a translation stop codon at its 3' end.

As used herein, the term "identity" when used in relation to nucleic acids, describes the degree of similarity between two or more nucleotide sequences. The percentage of "sequence identity" between two sequences can be determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. (1994) Nucl. Acids Res., 22: 4673-4680).

As used herein, the terms "nucleic acid," "polynucleotide," and "oligonucleotide" are used interchangeably and refer to deoxyribonuclotides (DNA), ribonucleotides (RNA), and functional analogues thereof, such as complementary DNA (cDNA) in linear or circular conformation. Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. Analogues of the natural nucleotide bases, as well as nucleotide bases that are modified in the base, sugar, and/or phosphate moieties are also provided herein. The symbol "N" can be used to represent any nucleotide base (e.g., A, G, C, T, or U). The symbol "Y" can be used to represent thymine or cytosine bases. The symbol "V" can be used to represent the nucleotide bases A, C or G. As used herein, "complementary" in reference to a nucleic acid molecule or nucleotide bases refers to A being complementary to T (or U), and G being complementary to C. Two complementary nucleic acid molecules are capable of hybridizing with each other under appropriate conditions. In an aspect of the present disclosure, two nucleic acid sequences are homologous if they have at least 70%, at least 75%, at least 80%, at least 85%, at least 90%, at least 95%, at least 96%, at least 97%, at least 98%, at least 99% or 100% sequence identity with each other.

As used herein, the term "plant" refers to any photosynthetic, eukaryotic, unicellular or multicellular organism of the kingdom Plantae and includes a whole plant or a cell or tissue culture derived from a plant, comprising any of: whole plants, plant components or organs (e.g., leaves, stems, roots, etc.), plant tissues, seeds, plant cells, protoplasts and/or progeny of the same. A progeny plant can be from any filial generation, e.g., F1, F2, F3, F4, F5, F6, F7, etc. A "plant cell" is a biological cell of a plant, taken from a plant or derived through culture from a cell taken from a plant. The term plant encompasses monocotyledonous and dicotyledonous plants. The methods, systems, and compositions described herein are useful across a broad range of plants. Suitable plants in which the methods, systems, and compositions disclosed herein can be used include, but are not limited to, cereals and forage grasses (e.g., alfalfa, rice, maize, wheat, barley, oat, sorghum, pearl millet, finger millet, cool-season forage grasses, and bahiagrass), oilseed crops (e.g., soybean, oilseed brassicas including canola and oilseed rape, sunflower, peanut, flax, sesame, and safflower), legume grains and forages (e.g., common bean, cowpea, pea, faba bean, lentil, tepary bean, Asiatic beans, pigeonpea, vetch, chickpea, lupine, alfalfa, and clovers), temperate fruits and nuts (e.g., apple, pear, peach, plums, berry crops, cherries, grapes, olive, almond, and Persian walnut), tropical and subtropical fruits and nuts (e.g., citrus including limes, oranges, and grapefruit; banana and plantain, pineapple, papaya, mango, avocado, kiwifruit, passionfruit, and persimmon), vegetable crops (e.g., solanaceous plants including tomato, eggplant, and peppers; vegetable brassicas; radish, carrot, cucurbits, alliums, asparagus, and leafy vegetables), sugar cane, tubers (e.g., beets, parsnips, potatoes, turnips, sweet potatoes), and fiber crops (sugarcane, sugar beet, stevia, potato, sweet potato, cassava, and cotton), plantation crops, ornamentals, and turf grasses (tobacco, coffee, cocoa, tea, rubber tree, medicinal plants, ornamentals, and turf grasses), and forest tree species.

As used herein, "plant genome" refers to a nuclear genome, a mitochondrial genome, or a plastid (e.g., chloroplast) genome of a plant cell. In some embodiments, a plant genome may comprise a parental genome contributed by the male and a parental genome contributed by the female. In some embodiments, a plant genome may comprise only one parental genome.

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Aspects of this disclosure include compositions including oligonucleotides having a length of 18-25 nucleotides (e.g., 18-mers, 19-mers, 20-mers, 21-mers, 22-mers, 23-mers, 24-mers, or 25-mers), or medium-length polynucleotides having a length of 26 or more nucleotides (e.g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e.g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

As used herein, terms "polypeptide", "peptide" and "protein" are used interchangeably to refer to a polymer of amino acid residues. The term also applies to amino acid polymers in which one or more amino acids are chemical analogues or modified derivatives of a corresponding naturally-occurring amino acids.

As used herein, "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

As used herein, a "recombinant nucleic acid" refers to a nucleic acid molecule (DNA or RNA) having a coding and/or non-coding sequence distinguishable from endogenous nucleic acids found in natural systems. In some aspects, a recombinant nucleic acid provided herein is used in any composition, system or method provided herein. In some aspects, a recombinant nucleic acid may encode any CRISPR enzyme provided herein can be used in any composition, system or method provided herein. In some aspects, a recombinant nucleic acid may comprise or encode any guide RNA provided herein can be used in any composition, system or method provided herein. In an aspect, a vector provided herein comprises any recombinant nucleic acid provided herein. In another aspect, a cell provided herein comprises a recombinant nucleic acid provided herein. In another aspect, a cell provided herein comprises a vector provided herein.

As used herein, the term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as meristem, or particular cell types (e.g., pollen). Regulatory elements may also direct expression in a temporal-dependent manner, such as in a cell-cycle dependent or developmental stage-dependent manner, which may or may not also be tissue or cell-type specific. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); and SV40 enhancer.

As used herein, the terms "target sequence" or "target site" refer to a nucleotide sequence against which a guide RNA is capable of hybridizing. A target sequence may be genic or non-genic. In some aspects, a target sequence provided herein comprises a genic region. In other aspects, a target sequence provided herein comprises an intergenic region. In yet another aspect, a target sequence provided herein comprises both a genic region and an intergenic region. In an aspect, a target sequence provided herein comprises a coding nucleic acid sequence. In another aspect, a target sequence provided herein comprises a non-coding nucleic acid sequence. In an aspect, a target sequence provided herein is located in a promoter. In another aspect, a target sequence provided herein comprises an enhancer sequence. In yet another aspect, a target sequence provided herein comprises both a coding nucleic acid sequence and a non-coding nucleic acid sequence. In one aspect, a target sequence provided herein is recognized and cleaved by a double-strand break inducing agent, such as a system comprising a Cpf1 enzyme and a guide RNA.

As used herein, the term "donor" or "donor DNA" means a single stranded or double stranded DNA that comprises a polynucleotide sequence to be inserted at or near the target site of a Cpf1 enzyme and guide system. In some embodiments, the donor DNA comprises a transgene for insertion into the plant cell genome. In some embodiments, the donor DNA comprises a first and a second region of homology that flank the transgene, where the first and second regions of homology share homology to a first and a second genomic region present in or flanking the target site. A region of homology can be of any length that is sufficient to promote homologous recombination at the target site. For example, a region of homology can comprise at least 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1,000, 1,000-1,150, 1,150-1,200, 1,200-1,250, 1,250-1,300, 1,300-1,350, 1,350-1,400, 1,400-1,450, 1,450-1,500, 1,500-1,550, 1,550-1,600, 1,600-1,650, 1,650-1,700, 1,700-1,750, 1,750-1,800, 1,800-1,850, 1,850-1,900, 1,900-1,950, 1,950-2,000, or more bases in length. In some embodiments, the donor DNA comprises a polynucleotide sequence that comprises at least 1, 2, 3, 4, 5, 6, 7, 8, 9, 10 or more nucleotide modifications compared to the target site. In some embodiments, the donor DNA comprises a polynucleotide sequence that is at least 80%, 81%, 82%, 83%, 84%, 85%, 86%, 87%, 88%, 89%, 90%, 91%, 92%, 93%, 94%, 95%, 96%, 97%, 98%, 99% identical to a polynucleotide sequence at or adjacent to the target site. In some embodiments, the donor DNA is 20, 25, 26, 27, 28, 29, 30, 31, 30-35, 35-40, 40-45, 45-50, 50-55, 55-60, 60-65, 65-70, 70-75, 75-80, 80-85, 85-90, 90-95, 95-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1,000, 1,000-1,150, 1,150-1,200, 1,200-1,250, 1,250-1,300, 1,300-1,350, 1,350-1,400, 1,400-1,450, 1,450-1,500, 1,500-1,550, 1,550-1,600, 1,600-1,650, 1,650-1,700, 1,700-1,750, 1,750-1,800, 1,800-1,850, 1,850-1,900, 1,900-1,950, 1,950-2,000, 2,000-2,100, 2,000-2,200, 2,000-2,300, 2,000-2,400, 2,000-2,500, 2,000-2,600, 2,000-2,700, 2,000-2,800, 2,000-2,900, 2,000-3,000, 3,000-3,100, 3,000-3,200, 3,000-3,300, 3,000-3,400, 3,000-3,500, 3,000-3,600, 3,000-3,700, 3,000-3,800, 3,000-3,900, 3,000-4,000, 4,000-4,100, 4,000-4,200, 4,000-4,300, 4,000-4,400, 4,000-4,500, 4,000-4,600, 4,000-4,700, 4,000-4,800, 4,000-4,900, 4,000-5,000, or more nucleotides in length.

In an aspect, a Cpf1 nuclease provided herein is a *Lachnospiraceae bacterium* Cpf1 (LbCpf1) nuclease. In another aspect, a Cpf1 nuclease provided herein is a *Francisella novicida* Cpf1 (FnCpf1) nuclease.

A prerequisite for cleavage of the target site by a CRISPR ribonucleoprotein is the presence of a conserved Protospacer Adjacent Motif (PAM) near the target site. Depending on the CRISPR nuclease, cleavage can occur within a certain number of nucleotides (e.g., between 18-23 nucleotides for Cpf1) from the PAM site. PAM sites are only required for type I and type II CRISPR associated proteins, and different CRISPR endonucleases recognize different PAM sites. Without being limiting, the Cpf1 from *Lachnospiraceae bacterium* can recognize at least the following PAM sites: TTTN, and YTN; (where T is thymine; Y is thymine or cytosine; and N is thymine, cytosine, guanine, or adenine). Without being limiting, the Cpf1 from *Francisella novicida* can recognize at least the following PAM sites: TTN (where T is thymine; and N is thymine, cytosine, guanine, or adenine). In certain embodiments, the LbCpf1 protein disclosed here has been modified to recognize a non-natural PAM. LbCpf1 variants comprising one or more amino acid substitutions resulting in altered PAM sequence specificities have been disclosed in the art (for example see Gao et. al., Nature Biotech., 2017 August; 35(8):789-792). Gao et. al. have disclosed two LbCpf1 variants: SEQ ID NO: 39 comprising the amino acid substitutions G532R/K595R that can recognize TYCV PAM (where T is thymine; Y is thymine or cytosine; C is cytosine and V is cytosine, guanine, or adenine) and SEQ ID NO: 76 comprising the amino acid substitutions G532R/K538V/Y542R that can recognize the TATV PAM (where T is thymine; A is adenine; and V is cytosine, guanine, or adenine). As used herein, LbCpf1(TYC) variant refers to an LbCpf1 nuclease comprising the amino acid substitutions G532R/K595R. As used herein, LbCpf1(TAT) variant (SEQ ID NO: 76) refers to an LbCpf1 nuclease comprising the mutations G532R/K538V/Y542R.

The instant disclosure provides a recombinant nucleic acid encoding the Cpf1 nuclease of SEQ ID NO 2, 39, 43, 76 or a fragment thereof, wherein the recombinant nucleic acid is optimized for expression in a plant cell. A sequence can be optimized for expression in a plant cell by modifying a nucleotide sequence encoding a protein such as, for example, the nucleic acid sequence encoding the Cpf1 nuclease of SEQ ID NO 2, 39, 43 or a fragment thereof, using one or more plant-preferred codons for improved expression. In some embodiments, the plant-optimized recombinant nucleic acid encoding the Cpf1 nuclease of SEQ ID NO 2, or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 1 and 10, or a fragment thereof. In some embodiments, the plant-optimized recombinant nucleic acid encoding the LbCpf1(TYC) nuclease (SEQ ID NO: 39), or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 38, or a fragment thereof. In some embodiments, the plant-optimized recombinant nucleic acid encoding the LbCpf1 (TAT) nuclease (SEQ ID NO: 76) or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 75, or a fragment thereof.

In some embodiments, the plant-optimized recombinant nucleic acid encoding the FnCpf1 nuclease (SEQ ID NO 43), or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 45-48, 50, 51 or a fragment thereof.

In some embodiments, the plant-optimized recombinant nucleic acid is operably linked to a heterologous promoter. In one aspect, a recombinant nucleic acid provided herein comprises one or more, two or more, three or more, four or more, five or more, six or more, seven or more, eight or more, nine or more, or ten or more heterologous promoters operably linked to one or more, two or more, three or more, four or more, five or more, six or more, seven or more, eight or more, nine or more, or ten or more plant-optimized recombinant nucleic acids encoding a Cpf1 nuclease. In some embodiments, a plant-optimized recombinant nucleic acids encoding a Cpf1 nuclease provided herein is provided to a plant cell in combination with one or more, two or more, three or more, four or more, five or more, six or more, seven or more, eight or more, nine or more, or ten or more guide polynucleotides. As used herein, the term "guide polynucleotide" refers to a polynucleotide sequence that can form a complex with a Cpf1 endonuclease and enables the Cpf1 endonuclease to bind to, and optionally cleave, a target site. The guide polynucleotide sequence can be a RNA sequence, a DNA sequence, or any combination thereof (e.g., a RNA-DNA hybrid sequence). In one aspect, a guide polynucleotide provided herein comprises a CRISPR repeat sequence and a spacer sequence that is complementary to a target site. In one aspect, a guide polynucleotide provided herein comprises one or more repeats of a CRISPR repeat sequence, a spacer sequence, and a CRISPR repeat sequence. In some embodiments, the guide polynucleotide comprises two or more spacer sequences that are complementary to different target sites. In some embodiments, the guide polynucleotide comprises one or more CRISPR repeat sequences selected from a pre-crRNA and a mature cr-RNA. In some embodiments, the guide polynucleotide is operably linked to a promoter. In certain embodiments, recombinant nucleic acids encoding guide polynucleotides may be designed in an array format such that multiple guide polynucleotides can be simultaneously released. In some embodiments, expression of one or more guide polynucleotides is U6-driven. In some embodiments, Cpf1 enzymes complex with multiple guide polynucleotides to mediate genome editing and at multiple target sequences. Some embodiments relate to expression of singly or in tandem array format from 1 up to 4 or more different guide sequences; e.g. up to about 20 or about 30 guides sequences. Each individual guide sequence may target a different target sequence. Such may be processed from, e.g. one chimeric pol3 transcript. Pol3 promoters such as U6 or H1 promoters may be used.

In some embodiments, a plant-optimized recombinant nucleic acid as disclosed herein is expressed or delivered in a vector. As used herein, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is an *Agrobacterium* T-DNA. Another type of vector is a viral vector, wherein virally-derived DNA or RNA sequences are present in the vector for packaging into a virus (e.g., retroviruses, replication defective retroviruses, Tobacco mosaic virus (TMV), Potato virus X (PVX) and Cowpea mosaic virus (CPMV), tobamovirus, Gemini viruses, adenoviruses, replication defective adenoviruses, and adeno-associated viruses). Viral vectors also include polynucleotides carried by a virus for transfection into a host cell. In some embodiments, a viral vector may be delivered to a plant using *Agrobacterium*. Certain vectors are capable of autonomous replication in a host cell into which they are introduced. Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). In some embodiments, an expression vector can comprise a plant-optimized recombinant nucleic acid in a form suitable for expression of the plant-optimized recombinant nucleic acid in a plant cell, which means that the expression vector comprises one or more regulatory elements that are operatively-linked to the plant-optimized recombinant nucleic acid to be expressed. Regulatory elements may include enhancers, termination sequences, introns, etc.

In certain embodiments, the plant-optimized recombinant nucleic acid may be operably linked to a nucleic acid sequence encoding one or more nuclear localization signal (NLS), nuclear export signal (NES), functional domains, and flexible linkers. The one or more of the NLS, the NES or the functional domain may be conditionally activated or inactivated. In particular embodiments it can be of interest to target the Cpf1 encoded by the plant-optimized recombinant nucleic acid to the chloroplast. In many cases, this targeting may be achieved by the operably linking the plant-optimized recombinant nucleic acid encoding Cpf1 to a nucleic acid encoding a chloroplast transit peptide (CTP) or plastid transit peptide. Other options for targeting to the chloroplast which have been described are the maize cab-m7 signal sequence (U.S. Pat. No. 7,022,896, WO 97/41228, incorporated by reference herein) a pea glutathione reductase signal sequence (WO 97/41228, incorporated by reference herein) and the CTP described in US2009029861, incorporated by reference herein.

Several embodiments relate to a method for modifying a target sequence in the genome of a plant cell, the method comprising: introducing a recombinant nucleic acid optimized for expression in a plant cell comprising one or more of SEQ ID NOs: 1, 4, 6, 10, 12, 14, 15, 26, 31, 36, 38, 40, 41, 45, 46, 47, 48, 49, 50, 51, 63, 65, 66, 67, 68, 68, 70, 71, 72, 73, and 75 and a guide polynucleotide comprising a targeting domain that is complementary to a target sequence into the plant cell, where the recombinant nucleic acid expresses Cpf1 endonuclease in the plant cell and the Cpf1 endonuclease and the guide polynucleotide are capable of forming a complex that can recognize, bind to, and optionally nick or cleave the target sequence. In some embodiments, the guide polynucleotide and/or the recombinant nucleic acid are introduced into the plant cell by biolistic delivery. Several embodiments relate to a method for modifying a target sequence in the genome of a plant cell, the method comprising: introducing a guide polynucleotide comprising a targeting domain that is complementary to a target sequence in the plant genome into a plant cell comprising a recombinant nucleic acid optimized for expression in a plant cell, wherein the recombinant nucleic acid comprises one or more of SEQ ID NOs: 11, 4, 6, 10, 12, 14, 15, 26, 31, 36, 38, 40, 41, 45, 46, 47, 48, 49, 50, 51, 63, 65, 66, 67, 68, 68, 70, 71, 72, 73, and 75 where the recombinant nucleic acid expresses Cpf1 endonuclease in the plant cell and the Cpf1 endonuclease and the guide polynucleotide are capable of forming a complex that can recognize, bind to, and optionally nick or cleave the target sequence. In some embodiments, the guide polynucleotide is introduced into the plant cell by biolistic delivery. In some embodiments, the method further comprises incubating the plant cell at temperatures between 24° C. and 25° C., 25° C. and 26° C., 26° C. and 27° C., 27° C. and 28° C., 28° C. and 29° C., 29° C. and 30° C., 30° C. and 31° C., 31° C. and 32° C., 32° C. and 33° C., 33° C. and 34° C., 34° C. and 35° C., 35° C. and 36° C., 36° C. and 37° C., 37° C. and 38° C., 38° C. and 39° C., 39° C. and 40° C., for a period of at least about 10 min., 15 min., 20 min., 25 min., 30 min., 35 min., 40 min., 45 min., 50 min., 55 min., 1 hr., 2 hrs., 3 hr., 4 hrs., 5 hrs., 6 hrs., 7 hrs., 8 hrs., 9 hrs., 10 hrs., 11 hrs., 12 hrs., 13 hrs., 14 hrs., 15 hrs., 16 hrs., 17 hrs., 18 hrs, 19 hrs., 20 hrs. 21 hrs., 22 hrs., 23 hrs., 24 hrs., 25 hrs., 26 hrs., 27 hrs., 28 hrs., 29 hrs., 30 hrs., 31 hrs., 32 hrs., 33 hrs., 34 hrs., 35 hrs., 36 hrs., 37 hrs., 38 hrs., 39 hrs., 40 hrs., 41 hrs., 42 hrs., 43 hrs. 44 hrs., 45 hrs., 46 hrs., 47 hrs., 48 hrs., 3 days, 4 days, 5 days, 6 days, or 7 days. In some embodiments, the methods described herein can further comprise identifying at least one plant cell, plant or progeny plant that has a modification at the target sequence, where the modification at the target sequence is selected from the group consisting of (i) a replacement of at least one nucleotide, (ii) a deletion of at least one nucleotide, (iii) an insertion of at least one nucleotide, and (iv) any combination of (i)-(iii). The method can further provide a donor DNA to the plant cell, where the donor DNA comprises a polynucleotide sequence of interest. This can produce a plant cell or plant having a detectable targeted genome modification.

Several embodiments relate to a method for modifying a target sequence in the genome of a plant cell, method comprising: obtaining a plant cell comprising in its genome a recombinant nucleic acid comprising a sequence selected from the group consisting of: SEQ ID NOs 1, 4, 6, 10, 12, 14, 15, 26, 31, 36, 38, 40, 41, 45, 46, 47, 48, 49, 50, 51, 63, 65, 66, 67, 68, 68, 70, 71, 72, 73, and 75 and introducing into the plant cell a guide polynucleotide comprising a targeting domain that is complementary to a target sequence in the plant genome or a recombinant nucleic acid encoding the guide polynucleotide, where the guide polynucleotide and Cpf1 endonuclease encoded by the recombinant nucleic acid are capable of forming a complex that can bind to, and modify the target sequence. In some embodiments, the guide polynucleotide is introduced into the plant cell by biolistic delivery. In some embodiments, the method further comprises incubating the plant cell at temperatures between 24° C. and 25° C., 25° C. and 26° C., 26° C. and 27° C., 27° C. and 28° C., 28° C. and 29° C., 29° C. and 30° C., 30° C. and 31° C., 31° C. and 32° C., 32° C. and 33° C., 33° C. and 34° C., 34° C. and 35° C., 35° C. and 36° C., 36° C. and 37° C., 37° C. and 38° C., 38° C. and 39° C., 39° C. and 40° C., for a period of at least about 10 min., 15 min., 20 min., 25 min., 30 min., 35 min., 40 min., 45 min., 50 min., 55 min., 1 hr., 2 hrs., 3 hr., 4 hrs., 5 hrs., 6 hrs., 7 hrs., 8 hrs., 9 hrs., 10 hrs., 11 hrs., 12 hrs., 13 hrs., 14 hrs., 15 hrs., 16 hrs., 17 hrs., 18 hrs, 19 hrs., 20 hrs. 21 hrs., 22 hrs., 23 hrs., 24 hrs., 25 hrs., 26 hrs., 27 hrs., 28 hrs., 29 hrs., 30 hrs., 31 hrs., 32 hrs., 33 hrs., 34 hrs., 35 hrs., 36 hrs., 37 hrs., 38 hrs., 39 hrs., 40 hrs., 41 hrs., 42 hrs., 43 hrs. 44 hrs., 45 hrs., 46 hrs., 47 hrs., 48 hrs., 3 days, 4 days, 5 days, 6 days, or 7 days. In some embodiments, the methods described herein can further comprise identifying at least one plant cell, plant or progeny plant that has a modification at the target sequence, where the modification at the target sequence is selected from the group consisting of (i) a replacement of at least one nucleotide, (ii) a deletion of at least one nucleotide, (iii) an insertion of at least one nucleotide, and (iv) any combination of (i)-(iii). The method can further provide a donor DNA to the plant cell, where the donor DNA comprises a polynucleotide sequence of interest. This can produce a plant cell or plant having a detectable targeted genome modification.

The plant cell may be of a monocot or dicot. In some embodiments, the plant cell may be from or of a crop or grain plant such as cassava, corn, sorghum, alfalfa, cotton, soybean, canola, wheat, oat or rice. The plant cell may also be of an algae, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinacia*; plants of the genus *Capsicum*; cotton, tobacco, asparagus, avocado, papaya, cassava, carrot, cabbage, broccoli, cauliflower, tomato, eggplant, pepper, lettuce, spinach, strawberry, potato, squash, melon, blueberry, raspberry, blackberry, grape, coffee, cocoa, etc).

The methods for genome editing using the recombinant nucleic acid molecules as described herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above.

EXAMPLES

The following examples are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); ss, single stranded; ds, double stranded and the like.

Example 1

Design and Analysis of LbCpf1-CO1, an Engineered Polynucleotide Optimized for Expression in Plant Cells.

This example describes the creation and testing of a synthetic polynucleotide encoding *Lachnospiraceae bacterium* ND2006 (LbCpf1) nuclease that is optimized for expression in plant cells.

A nucleotide sequence of Cpf1 from *Lachnospiraceae bacterium* ND2006 (LbCpf1) that was codon optimized for expression in human cells has been described by Zetsche et. al, (Cell 2015, 163, 759-771). The human codon optimized sequence disclosed by Zetsche et. al., was modified through algorithmic methods, partly based on corn codon preference, to design LbCpf1-CO1 (Coding sequence Optimized version 1) (SEQ ID NO: 1) to optimize the sequence for expression of the LbCpf1 protein (SEQ ID NO: 2) in plant cells.

The plant-optimized LbCpf1-CO1 sequence was then incorporated into six different expression vectors to test its activity in corn cells. Three of the expression vectors were designed with an expression cassette (SEQ ID NO: 3) comprising the LbCpf1-CO1 nuclease and a nucleotide sequence encoding the Nuclear Localization Sequence (NLS) from the heat stress transcription factor 1 (HSFA1) gene from *Solanum lycopersicum* (SEQ ID NO:4) on the 5' and 3' ends. Three of the expression vectors were designed with an expression cassette (SEQ ID NO:5) comprising a processable potato LS1 intron sequence (SEQ ID NO: 6) introduced into the NLS-LbCpf1-CO1-NLS sequence to eliminate expression of the LbCpf1 protein in *Agrobacterium*. The NLS-LbCpf1-CO1-NLS expression cassettes also comprised a *Zea mays* Ubiquitin M1 promoter leader and intron sequence (SEQ ID NOs:7) operably linked to the NLS-LbCpf1-CO1-NLS nuclease and a transcription terminator sequence from a rice Lipid transfer protein (LTP) gene (SEQ ID NO:8). Each plant vector also comprised a gRNA expression array comprising either 2 or 4 guide RNA sequences (mature crRNA+spacer) positioned in tandem and targeting 2 or 4 sites in a corn chromosome. The first crRNA sequence was 35 nt while the remaining ones were 20 nt and the spacer sequence was 30 nt. The gRNA arrays were operably linked to the maize U6 Pol III promoter (SEQ ID NO:9) and a poly T terminator sequence. All the expression vectors also included a third expression cassette containing the selectable marker gene CP4 that provides resistance to the herbicide glyphosate. See Table 1.

quently analyzed for fragment length variation to identify plants with mutations at the target sites. As shown in Table 1, 258 plants returned high quality FLA data, out of which only 1 plant was identified as having mutations at one of the target sites.

Example 2

Design and Analysis of LbCpf1-CO2, an Engineered Polynucleotide Optimized for Expression in Plant Cells This example describes the design and expression analysis of *Lachnospiraceae bacterium* ND2006 (LbCpf1) nuclease that is optimized for expression in plant cells.

The LbCpf1-CO1 nucleotide sequence described in Example 1 was manually analyzed for the presence of deleterious motifs that could potentially reduce gene expression. These deleterious motifs were given a higher priority for removal/replacement by nucleotide sequences coding for synonymous codons. Additionally, a monocot-specific codon frequency table was used for optimization of the nucleotide sequence for expression in monocots. Based on these criteria, a second optimized LbCpf1 (referred to as LbCpf1-CO2) nucleotide sequence was generated (SEQ ID NO: 10) for expression of the LbCpf1 protein (SEQ ID NO: 2) in planta. When compared to LbCpf1-CO1, the LbCpf1-CO2 sequence was determined to have a threefold reduction

TABLE 1

SUMMARY OF RESULTS OF FRAGMENT LENGTH ANALYSIS (FLA) GENERATED FROM CORN PLANTS STABLY TRANSFORMED WITH LBCPF1-CO1 AND GRNAS TARGETING 8 UNIQUE GENOMIC TARGET SITES.

| Vector | Intron in Cpf1-CO1 cassette | Genomic sites targeted (TS) | Plants tested | Plants returning data | # Edited samples by FLA | Mutation efficiency (%) |
|---|---|---|---|---|---|---|
| 1 | No | ZmTS1, ZmTS2 | 47 | 34 | 0 | 0 |
| 2 | No | ZmTS3, ZmTS4, ZmTS5, ZmTS6 | 55 | 50 | 0 | 0 |
| 3 | No | ZmTS7, ZmTS8 | 45 | 44 | 0 | 0 |
| 4 | Yes | ZmTS7, ZmTS8 | 38 | 37 | 1 | 2.63 |
| 5 | Yes | ZmTS1, Zm TS2 | 65 | 64 | 0 | 0 |
| 6 | Yes | ZmTS3, ZmTS4, ZmTS5, ZmTS6 | 35 | 29 | 0 | 0 |
| Total | | | 285 | 258 | 1 | |

Corn 01DKD2 cultivar embryos were transformed with *Agrobacterium* containing the plant expression vectors described in Table 1. Transformed plants were selected on glyphosate, leaf samples from regenerated plantlets were harvested after 2 weeks and genomic DNA was extracted for Fragment Length Analysis (FLA). FLA is a PCR-based molecular assay that can be used to identify indel (insertion or deletion) mutations introduced at the target site by NHEJ-mediated (Non Homologous End Joining) DNA repair following dsDNA cleavage by the Cpf1-guide complex. Genomic DNA was subjected to a PCR reaction with primers flanking the target site to generate amplicons. The amplicons fragment length was then compared to a wild type amplicon to identify mutants. PCR reactions were carried out using 5' FAM-labeled primer, a standard primer and Phusion™ polymerase (New England Biolabs, MA) according to manufactures instructions to generate 200 to 500 bp PCR fragments. 1 ul PCR product was combined with 0.5 ul GeneScan 1200 LIZ Size Standard (Thermo Fisher, MA), 8.5 ul formamide and run on ABI sequencer (Thermo Fisher, MA). Two FLA reactions were multiplexed and subsein the presence of deleterious motifs within its coding sequence. The full length LbCpf1-CO2 nucleotide sequence shows only 85.6% sequence identity with the human codon optimized LbCpf1 nucleotide sequence disclosed by Zetsche et. al., (Cell 2015, 163, 759-771), only 77.5% sequence identity with LbCpf1-CO1 and only 69.4% sequence identity with the native bacterial LbCpf1 sequence.

Three expression cassettes (Prom35S::HIStag:NLS:LbCpf1-CO2:mOrange:NLS::TermNOS; Prom35S::HIStag:NLS:LbCpf1-Os:mOrange:NLS::TermNOS; and Prom$_{35S}$::HIStag:NLS:mOrange:NLS::Term$_{NOS}$) were generated by standard cloning techniques and as described below:

(1) Prom35S::HIS tag:NLS:LbCpf1-CO2:mOrange:NLS::TermNOS

The LbCpf1-CO2 coding sequence was fused 5' to the coding sequence of mOrange (mOr) from *Entacmaea quadricolor* (SEQ ID NO: 52). The LbCpf1-CO2:mOrange fusion gene was then flanked at the 5' and 3' ends with the NLS sequence from tomato HSFA1 gene (SEQ ID NO:3) and a nucleotide sequence encoding a HIS tag (MGSS7H)

(SEQ ID NO: 54) was introduced to the 5' end. The nucleotide sequence was operably linked to the Cauliflower mosaic virus 35S promoter and an *Agrobacterium* NOS terminator.

(2) Prom$_{35S}$::HIS tag:NLS:LbCpf1-Os:mOrange:NLS::Term$_{NOS}$

The rice codon-optimized Cpf1 (LbCpf1-Os) nucleotide sequence described by Xu et. al. (Plant Biotechnology Journal, 2017, 15, 713-717) (SEQ ID NO:11) was used as a control to compare in planta expression. The LbCpf1-Os coding sequence was fused 5' to the coding sequence of mOrange (mOr) from *Entacmaea quadricolor* (SEQ ID NO: 52). The LbCpf1-Os:mOrange fusion gene was then flanked at the 5' and 3' ends with the NLS sequence from tomato HSFA1 gene (SEQ ID NO:3) and a nucleotide sequence encoding a HIS tag (MGSS7H) (SEQ ID NO:54) was introduced to the 5' end. The nucleotide sequence was operably linked to the Cauliflower mosaic virus 35S promoter and an *Agrobacterium* NOS terminator.

(3) Prom$_{35S}$::HIS tag:NLS:mOrange:NLS::Term$_{NOS}$

The coding sequence of mOrange (mOr) gene (SEQ ID NO:52) from *Entacmaea quadricolor* was flanked at the 5' and 3' ends with the NLS sequence from tomato HSFA1 gene (SEQ ID NO:3) and a nucleotide sequence encoding a HIS tag (MGSS7H) (SEQ ID NO:54) was introduced to the 5' end. The nucleotide sequence was operably linked to the Cauliflower mosaic virus 35S promoter and an *Agrobacterium* NOS terminator.

The expression cassettes described above were cloned into plant expression constructs. Corn leaf protoplasts were transfected with either the LbCpf1-CO2-mOr construct, the LbCpf1-Os-mOr construct, or the control mOr construct to evaluate expression levels (Table 2). Since mOrange was fused to LbCpf1-CO2 and LbCpf1-Os, the relative mOrange fluorescence levels reflects LbCpf-CO2 and LbCpf1-Os expression levels. Transformations were carried out using standard polyethylene glycol (PEG) based transfection methods. To quantify transformation frequency, an expression vector comprising the luciferase gene was co-transfected. Following transformation, the protoplasts were incubated in the dark in incubation buffer and harvested after 48 hours. Transformation efficiency was calculated by quantifying luciferase expression. The average mOrange expression from 3 technical replicates was determined using Operetta™ (Perkin Elmer) analysis software. As shown in FIG. 1 and Table 2, mOrange intensity was significantly higher in protoplasts expressing LbCpf1-CO2-mOrange than in cells expressing LbCpf1-Os-mOrange.

TABLE 2

EXPRESSION ANALYSIS OF LBCPF1-CO2-MOR AND LBCPF1-OS-MOR FLUORESCENT PROTEINS IN CORN PROTOPLASTS

| Expression Construct | Fluorescence detected | Fold increase in expression compared to Cpf1-Os-mOr |
|---|---|---|
| Prom35S::HIStag:NLS:LbCpf1-CO2:mOrange:NLS::TermNOS | Yes | 14 |
| Prom35S::HIStag:NLS:LbCpf1-Os:mOrange:NLS::TermNOS | Yes | 1 |
| Prom$_{35S}$:: HIS tag:NLS:mOrange:NLS::Term$_{NOS}$ | Yes | 135 |

Example 3

Analysis of LbCpf1-CO2 Activity in Corn Plants.

This example describes testing the LbCpf1-CO2 nucleotide sequence for activity at multiple genomic sites in corn plants using multiplexed guide RNAs.

An *Agrobacterium* LbCpf1-CO2 T-DNA vector comprising: an expression cassette for a selectable marker conferring resistance to the herbicide glyphosate; an expression cassette (SEQ ID NO:15) comprising NLS-LbCpf1-CO2-NLS (SEQ ID NO: 12) linked to a 5' Kozak sequence (SEQ ID NO:13) resulting in Koz-NLS-LbCpf1-CO2-NLS (SEQ ID NO: 14), which was operably linked to a *Zea mays* Ubiquitin M1 promoter cassette (SEQ ID NOs:7) and the transcription terminator sequence from rice LTP (SEQ ID NO:8); and an expression cassette comprising the *Zea mays* U6 promoter (SEQ ID NO:9) and a polyT terminator operably linked to gRNA expression array comprising three gRNAs positioned in tandem and targeting the three genomic sites, was created. Each gRNA comprised a 21 bp crRNA sequence linked to a 23 bp spacer sequence that was complementary to target site ZmTS9, ZmTS10 or ZmTS11 in the corn genome.

As a control, an *Agrobacterium* LbCpf1-Os T-DNA vector comprising: an expression cassette for a selectable marker conferring resistance to the herbicide glyphosate; an expression cassette (SEQ ID NO:18) comprising a Kozak sequence immediately upstream of the coding sequence of LbCpf1-Os (SEQ ID NO: 11) fused to the tomato HSFA NLS (SEQ ID NO:3) at the 5' end and the 3' end which was operably linked to the *Zea mays* Ubiquitin M1 promoter cassette (SEQ ID NO: 7) and to the rice LTP terminator (SEQ ID NO: 8); and an expression cassette comprising the *Zea mays* U6 promoter (SEQ ID NO:9) operably linked to gRNA expression array comprising three gRNAs positioned in tandem and targeting the three genomic sites, was created. Each gRNA comprised a 21 bp crRNA sequence linked to a 23 bp spacer sequence that was complementary to target site ZmTS9, ZmTS10 or ZmTS11 in the corn genome.

Corn 01DKD2 cultivar embryos were transformed with either the LbCpf1-CO2 or LbCpf1-Os T-DNA vectors described above by *Agrobacterium*-mediated transformation. Transformed plants were selected on glyphosate, leaf samples from regenerated plantlets were harvested after 2 weeks and genomic DNA was extracted for Fragment Length Analysis (FLA) to determine genome mutation rates, as described in Example 1. Table 3 summarizes the results and shows the mutation rate detected at each site in stably transformed corn plants.

TABLE 3

SUMMARY OF RESULTS OF FLA GENERATED FROM CORN PLANTS STABLY TRANSFORMED WITH EITHER LBCPF1-CO2 OR LBCPF1-OS AND GRNA ARRAY TARGETING 3 UNIQUE GENOMIC TARGET SITES

| T-DNA Vector | Target site | Plants assayed | # Edited plants by FLA analysis | Mutation frequency |
|---|---|---|---|---|
| LbCpf1-CO2 | ZmTS9 | 48 | 20 | 41.6% |
|  | ZmTS10 | 47 | 6 | 12.7% |
|  | ZmTS11 | 46 | 2 | 4.3% |
| LbCpf1-Os | ZmTS9 | 49 | 4 | 8% |
|  | ZmTS10 | 49 | 1 | 2% |
|  | ZmTS11 | 47 | 2 | 4.3% |

As shown in Table 3, all three sites targeted for cleavage with the guide/LbCpf1-CO2 system described above exhibited the presence of mutations which is indicative of DNA cleavage and repair. The frequency of mutations at the three sites ranged from 4.3% at ZmTS11, 12.7% for ZmTS10 to almost 42% at ZmTS9. 20 plants identified as having mutations in ZmTS9 were further analyzed to confirm the presence of mutations at the target site. PCR primers flanking the target site were used to generate amplicons which were cloned via Zero blunt-end Topo™ cloning (LifeTechnologies), sequenced and compared to the reference sequence. The presence of mutations was confirmed in all 20 events. For the guide/LbCpf1-Os system, mutations were identified at all three sites and the frequency of mutations at the three sites ranged from 2% at TS10, 4.3% for TS11 to almost 9% at TS1. Taken together, the data shows that the plant coding sequence optimized LbCpf1-CO2 is properly transcribed and translated in the corn host cell, is functional and can successfully promote gRNA directed chromosomal cleavage at target sites.

Example 4

Analysis of LbCpf1-CO2 Activity in Combination with a Single gRNA Expression System in Corn Plants.

This example describes the testing the LbCpf1-CO2 nucleotide sequence for the ability to induce cleavage and subsequent edits at a genomic target site in corn plants utilizing a single gRNA expression cassette.

An *Agrobacterium* T-DNA vector comprising: an expression cassette for a selectable marker gene that conferred resistance to the herbicide glyphosate; an expression cassette (SEQ ID NO:15) comprising a Kozak sequence introduced 5' to the NLS-LbCpf1-CO2-NLS nucleotide sequence and operably linked to a *Zea mays* Ubiquitin M1 promoter cassette and the transcription terminator sequence from rice LTP; and an expression cassette comprising the *Zea mays* U6 Pol III promoter (SEQ ID NO: 9) and a poly T terminator operably linked to a single guide RNA (gRNA) comprising a crRNA sequence linked to a 23 bp spacer sequence complementary to a unique target site (ZmTS12) in the corn chromosome.

Corn 01DKD2 cultivar embryos were transformed with *Agrobacterium* containing the T-DNA vector and stably transformed plants were selected on glyphosate. Leaf samples from regenerated plantlets were harvested after 2 weeks and genomic DNA was extracted for Fragment Length Analysis (FLA) to determine genome mutation rates, as described in Example 1.

TABLE 4

FLA RESULTS GENERATED FROM CORN PLANTS STABLY TRANSFORMED WITH LBCPF1-CO2 AND GRNA TARGETING ZMTS12 GENOMIC TARGET SITE.

| Nuclease sequence | Target site | Plants assayed | # Edited plants by FLA analysis | Mutation frequency |
|---|---|---|---|---|
| LbCpf1-CO2 | ZmTS12 | 247 | 158 | 64% |

As shown in Table 4, mutations were identified at the target site in 64% of corn plants stably transformed with a vector comprising the LbCp1-CO2 nucleotide sequence and a single guide RNA.

Example 5

Analysis of the Effect of the Addition of a Kozak Fragment Upstream of the LbCpf1-Os Nucleotide Sequence on Nuclease Activity in Plant Cells.

This example describes testing the addition of the Kozak sequence (SEQ ID NO:15) upstream of the LbCpf1-Os nucleotide sequence for the ability to enhance nuclease activity in corn plants.

An *Agrobacterium* LbCpf1-Os (Kozak minus) T-DNA vector comprising: an expression cassette for a selectable marker conferring resistance to the herbicide glyphosate; an expression cassette (SEQ ID NO:19) comprising NLS-LbCpf1-Os-NLS (SEQ ID NO:16), with an ATG sequence incorporated immediately 5' to SEQ ID NO:16 and operably linked to a *Zea mays* Ubiquitin M1 promoter cassette (SEQ ID NOs:7) and the transcription terminator sequence from rice LTP (SEQ ID NO:8); and an expression cassette comprising the *Zea mays* U6 promoter (SEQ ID NO:9) operably linked to gRNA expression array comprising three gRNAs positioned in tandem and targeting the three genomic sites, was created. Each gRNA comprised a 21 bp crRNA sequence linked to a 23 bp spacer sequence that was complementary to target site ZmTS9, ZmTS10 or ZmTS11 in the corn genome.

Corn plants were transformed with *Agrobacterium* containing either the T-DNA vector described above comprising the LbCpf1-Os (Kozak minus) expression cassette (SEQ ID NO:19) or the T-DNA vector described in Example 3 comprising a Kozak sequence immediately upstream of the coding sequence of LbCpf1-Os (SEQ ID NO:18). Transformed plants were selected on glyphosate, leaf samples from regenerated plantlets were harvested after 2 weeks and genomic DNA was extracted for Fragment Length Analysis (FLA) to determine genome mutation rates, as described in Example 1. Table 5 summarizes the results and shows the mutation rate for each site in stably transformed corn plants.

TABLE 5

SUMMARY OF FLA RESULTS GENERATED FROM CORN PLANTS STABLY TRANSFORMED WITH LBCPF1-OS AND GRNA ARRAY TARGETING 3 UNIQUE GENOMIC TARGET SITES

| Kozak sequence | Nuclease sequence | Target site | Plants assayed | # Edited plants by FLA analysis | Mutation frequency |
|---|---|---|---|---|---|
| + | LbCpf1-Os | ZmTS9 | 49 | 4 | 8% |
|   |           | ZmTS10 | 49 | 1 | 2% |
|   |           | ZmTS11 | 47 | 2 | 4.3% |
| − | LbCpf1-Os | ZmTS9 | 33 | 0 | 0% |
|   |           | ZmTS10 | 35 | 0 | 0% |
|   |           | ZmTS11 | 35 | 0 | 0% |

Plants transformed with the LbCpf1-Os comprising a Kozak sequence upstream of the nuclease coding sequence exhibited mutations at all three target sites at frequency ranging from 2% at ZmTS10, 4.3% for ZmTS11 to almost 8% at ZmTS9. No mutants were identified at any of the three target sites in plants transformed with the LbCpf1-Os expression cassette lacking the Kozak sequence.

Example 6

Analysis of LbCpf1-CO2 Activity in Soybean Plants.

This example describes testing the LbCpf1-CO2 nucleotide sequence for activity in soybean plants by assaying the ability of the nuclease to target cleavage at multiple unique genomic sites using multiplexed guides.

An *Agrobacterium* LbCpf1-CO2 T-DNA vector was created comprising: an expression cassette for a selectable marker conferring resistance to the antibiotic spectinomycin; an expression cassette (SEQ ID NO: 20) comprising NLS-LbCpf1-CO2-NLS (SEQ ID NO:12) with ATGGCG fused in frame 5' to SEQ ID NO 12 as the translational start site, which was operably linked to a promoter sequence (SEQ ID NO:37) and a transcriptional terminator sequence from *Medicago truncatula* (disclosed in US20140283200); and an expression cassette comprising the *Glycine max* U6 Pol III promoter (disclosed in US20170166912) and a polyT terminator operably linked to a gRNA array comprising three gRNAs arranged in tandem and a transcriptional terminator sequence. Each gRNA comprised a 21 bp mature crRNA sequence linked to a 23 bp spacer sequence that was complementary to either the GmFAD2-1A-TS, GmPDS-TS1 or GmPDS-TS2 target site.

An *Agrobacterium* LbCpf1-Os T-DNA control vector was created comprising: an expression cassette for a selectable marker conferring resistance to the antibiotic spectinomycin; an expression cassette (SEQ ID NO: 21) comprising NLS-LbCpf1-Os-NLS with ATGGCG fused in frame 5' as the translational start site, which was operably linked to a promoter sequence (SEQ ID NO:37) and a transcriptional terminator sequence from *Medicago truncatula* (disclosed in US20140283200); and an expression cassette comprising the *Glycine max* U6 Pol III promoter (disclosed in US20170166912) and polyT terminator operably linked to a gRNA array comprising three gRNAs arranged in tandem and a transcriptional terminator sequence. Each gRNA comprised a 21 bp mature crRNA sequence linked to a 23 bp spacer sequence that was complementary to either the GmFAD2-1A-TS, GmPDS-TS1 or GmPDS-TS2 target site.

Excised embryos from A3555 soybean plants were co-cultured with the *Agrobacterium* containing either the LbCpf1-CO2 T-DNA vector or the LbCpf1-Os T-DNA control vector described above. Transformed plants were selected on spectinomycin, leaf samples from regenerated plantlets were harvested after 4 weeks, and genomic DNA was extracted for Fragment Length Analysis (FLA) to determine genome mutation rates, as described in Example 1. A summary of FLA results generated from soy plants stably transformed with either LbCpf1-CO2 or LbCpf1-Os and gRNA array targeting 3 unique genomic target sites is provided in Table 6.

The plants were also scored for the albino phenotype typically associated with reduction/loss of PDS gene function (Table 7). PDS catalyzes a rate-limiting step in the biosynthesis of carotenoids in plants (Misawa, et. al., *The Plant Journal*, 1993, 4; 833-840). Reducing the endogenous PDS gene expression will therefore result in plants with a bleached phenotype and lowered chlorophyll content. Presence of an albino phenotype is therefore indicative of mutations at the PDS locus.

TABLE 6

SUMMARY OF FLA RESULTS GENERATED FROM SOY PLANTS STABLY TRANSFORMED WITH EITHER LBCPF1-CO2 OR LBCPF1-OS AND GRNA ARRAY TARGETING 3 UNIQUE GENOMIC TARGET SITES

| Nuclease seq variant | Target sites | Plants assayed | # Edited plants by FLA | Mutation rate |
|---|---|---|---|---|
| LbCpf1-CO2 | GmFAD2-1A | 62 | 22 | 36% |
| | GmPDS-TS1 | 62 | 0 | 0% |
| | GmPDS-TS2 | 62 | 28 | 45% |
| LbCpf1-Os | GmFAD2-1A | 88 | 20 | 22% |
| | GmPDS-TS1 | 88 | 0 | 0% |
| | GmPDS-TS2 | 88 | 37 | 42% |

TABLE 7

SUMMARY OF PLANTS SCORED FOR PDS GENE MUTATIONS INDICATED BY AN ALBINO PHENOTYPE.

| Nuclease | Plants assayed | Albino plants | Albino frequency rate |
|---|---|---|---|
| LbCpf1-CO2 | 62 | 52 | 84% |
| LbCpf1-Os | 88 | 60 | 68% |

As summarized in Table 6, of the 3 sites targeted by LbCpf1-Os and LbCpf1-CO2, soybean plants were recovered where mutations were identified at FAD2 and PDS1-TS2 sites. The mutations at the PDS locus was further confirmed by scoring for the albino phenotype (see Table 7).

Example 7

Plant Expression Vectors with Unique Cpf1-CO2 Expression Cassettes

Prom$_{Mt.Ubiq}$::NLS:LbCpf1-CO2:NLS::Term$_{Mt}$: An expression cassette (SEQ ID NO: 26) for the expression of a Cpf1-CO2 endonuclease was created comprising: a promoter (SEQ ID NO:22), leader (SEQ ID NO:23) and intron (SEQ ID NO:24) derived from *Medicago truncatula* Ubiquitin operably linked 5' to the NLS-LbCpf1-CO2-NLS coding sequence (SEQ ID NO: 12) wherein ATGGCG sequence was fused in frame 5' to SEQ ID NO 12 and served as the translational start site. The resulting sequence was in turn operably linked 5' to a UTR sequence from a gene from *Medicago truncatula* (SEQ ID NO:25).

The expression cassette was introduced into an *Agrobacterium* vector that also comprised a gRNA cassette designed to guide LbCpf1 to a unique GmTS1 target site on the soy chromosome. The gRNA comprised a 21 bp crRNA sequence linked to a 23 bp spacer sequence that was complementary to GmTS1 within the soy genome. The gRNA was operably linked to *Glycine max* U6 Pol III promoter (disclosed in US20170166912, incorporated by reference herein) and a poly T terminator. The vector also comprised an expression cassette for a selectable marker conferring resistance to the antibiotic spectinomycin.

Prom$_{EFIα}$::NLS:LbCpf1-CO2:NLS::Term$_{Mt}$: An expression cassette (SEQ ID NO: 31) for the expression of a Cpf1-CO2 endonuclease was created comprising: a promoter (SEQ ID NO:27), leader 5' (SEQ ID NO:28), intron (SEQ ID NO:29), leader 3' (SEQ ID NO:30) derived from *Cucumis melo* EIF1alpha gene operably linked 5' to the NLS-LbCpf1-CO2-NLS coding sequence (SEQ ID NO: 12) wherein ATGGCG sequence was fused in frame 5' to SEQ ID NO 12 and served as the translational start site. The resulting sequence was operably linked to a UTR sequence from a gene from *Medicago truncatula* (SEQ ID NO:25). The expression cassette was introduced into an *Agrobacterium* vector that also comprised a gRNA cassette designed to guide LbCpf1 to a unique GmTS2 target site on the soy chromosome. The gRNA comprised a 21 bp crRNA sequence linked to a 23 bp spacer sequence that was complementary to GmTS2 within the soy genome. The gRNA was operably linked to *Glycine max* U6 Pol III promoter (disclosed in US20170166912) and a poly T terminator. The vector also comprised an expression cassette for a selectable marker conferring resistance to the antibiotic spectinomycin.

Prom$_{At.Ubiq}$::NLS:LbCpf1-CO2:NLS::Term$_{Gb}$: An expression cassette (SEQ ID NO: 36) for the expression of a Cpf1-CO2 endonuclease was created comprising a promoter (SEQ ID NO:32), leader (SEQ ID NO:33) and intron (SEQ ID NO:34) derived from *Arabidopsis* Ubiquitin 10 gene operably linked 5' to the NLS-LbCpf1-CO2-NLS coding sequence (SEQ ID NO: 12) where ATGGCG sequence was fused in frame 5' to SEQ ID NO 12 and served as the translational start site. The resulting sequence was operably linked to a UTR sequence from a gene from *Gossypium barbadense* (SEQ ID NO: 35).

The expression cassette was introduced into an *Agrobacterium* vector that also comprised a gRNA cassette designed to guide LbCpf1 to a unique GmTS3 target site on the soy chromosome. The gRNA comprised a 21 bp crRNA sequence linked to a 23 bp spacer sequence that was complementary to GmTS3 within the soy genome. The gRNA was operably linked to *Glycine max* U6 Pol III promoter (disclosed in US20170166912) and a poly T terminator. The vector also comprised an expression cassette for a selectable marker conferring resistance to the antibiotic spectinomycin.

Example 8

Testing the Activity of LbCpf1-CO2 Expression Cassettes

The *Agrobacterium* T-DNA vectors described in Example 7, were introduced into *A. tumefaciens*. Excised embryos from A3555 Soybean plants were co-cultured with the *Agrobacterium* containing the vectors by standard methods known in the art and grown on spectinomycin to select for transformed plants. Leaf samples from regenerated plantlets were harvested after 2 weeks and genomic DNA was extracted for Fragment Length Analysis (FLA) to determine genome mutation rates at the target sites GmTS1, GmTS2 and GmTS3 as described in Example 1. A summary of FLA results generated from soy plants stably transformed with the three LbCpf1-CO2 expression cassettes and gRNAs targeting the unique soy genomic target sites is provided in Table 8.

TABLE 8

SUMMARY OF FLA RESULTS GENERATED FROM SOY PLANTS STABLY TRANSFORMED WITH LBCPF1-CO2 EXPRESSION CASSETTES AND GRNA TARGETING 3 UNIQUE GENOMIC TARGET SITES

| Expression vector with LbCpf1 cassette | Genomic target site | Plants assayed | # of edited plants by FLA | Target site mutation |
|---|---|---|---|---|
| Prom$_{Mt.Ubiq}$::NLS:LbCpf1-CO2:NLS::Term$_{Mt}$ | GmTS1 | 84 | 68 | 81% |
| Prom$_{EFIa}$::NLS:LbCpf1-CO2:NLS::Term$_{Mt}$ | GmTS2 | 84 | 58 | 69% |
| Prom$_{At.Ubiq}$::NLS:LbCpf1-CO2:NLS::Term$_{Gb}$ | GmTS3 | 84 | 72 | 86% |

As shown in Table 8, all three sites targeted for cleavage with the guide/LbCpf1-CO2 expression systems described above exhibited the presence of mutations which is indicative of DNA cleavage and repair.

Example 9

Analysis of LbCpf1(TYC)-CO2 Variant Activity in Corn Plants.

This example describes the testing of a recombinant polynucleotide encoding *Lachnospiraceae* LbCpf1(TYC) PAM variant nuclease that is optimized for expression in plant cells.

LbCpf1 variants comprising amino acid mutations resulting in altered PAM sequence specificities have been described by Gao et. al. (see Nature Biotech., 2017 August; 35(8):789-792). For example, Gao et. al. have described an LbCpf1(TYC) variant comprising the mutations G532R/K595R that can be engineered to recognize TYCV PAM. Two nucleotide substitutions were introduced into the LbCpf1-CO2 sequence (SEQ ID NO:10) resulting in LbCpf1(TYC)-CO2 (SEQ ID NO:38) encoding the LbCpf1 (TYC) protein (SEQ ID NO:39) comprising the mutations G532R/K595R.

To test the activity of LbCpf1(TYC), an *Agrobacterium* T-DNA vector was generated. The vector comprised a Cpf1 expression cassette (SEQ ID NO:40) comprising the maize ubiquitin promoter (SEQ ID NO: 7) operably linked to a sequence (SEQ ID NO: 41) encoding LbCpf1(TYC)-CO2 comprising two nuclear localization signals (SEQ ID NOs: 42 and 3). The NLS-LbCpf1(TYC)-CO2-NLS was operably linked to a transcription terminator sequence from a rice Lipid transfer protein (LTP) gene (disclosed in US201801058230-0175, incorporated herein by reference). The vector also comprised a gRNA expression cassette encoding gRNAs designed to target two unique target sites in the corn genome, ZmTS13 and ZMTS14. The ZmTS13 and ZMTS14 sites were chosen since the TYCV PAM was present immediately upstream to each site. The 5'PAM for ZmTS13 was the sequence TTCA. The 5'PAM for ZmTS14 was the sequence TCCA. The gRNA expression cassette comprised the *Zea mays* U6 Pol III promoter (SEQ ID NO: 9) operably linked to two guide RNAs positioned in tandem and targeting the ZmTS13 and ZmTS14 sites. The expression vector also included a third expression cassette containing the selectable marker gene that provides resistance to the herbicide glyphosate.

Corn 01DKD2 cultivar embryos were transformed with the LbCpf1(TYC)-CO2 vector described above by *Agrobacterium*-mediated transformation. Transformed plants were selected on glyphosate, leaf samples from regenerated plantlets were harvested and genomic DNA was extracted for Fragment Length Analysis (FLA) to determine genome mutation rates specifically at ZmTS13 and ZmTS14 sites, as described in Example 1. ZmTS13 and ZmTS14 are arrayed in antisense orientation relative to each other in the genome and overlap by 8 nts, thus individual editing rates at each gRNA target site were not able to be ascertained. Table 9 summarizes the results and shows the cumulative mutation rate detected at or near the two sites in stably transformed corn plants. As shown in Table 9, 48% (40 of the 83) plants tested exhibited the presence of mutations at the expected region which is indicative of DNA cleavage by LbCpf1 (TYC) and subsequent repair.

TABLE 9

FLA RESULTS GENERATED FROM CORN PLANTS STABLY TRANSFORMED WITH LBCPF1(TYC)-CO2 EXPRESSION CASSETTE AND GRNA TARGETING 2 UNIQUE GENOMIC TARGET SITES.

| T-DNA Vector | Target sites tested | Plants assayed | # Edited plants by FLA analysis | Cumulative Mutation frequency |
|---|---|---|---|---|
| LbCpf1(TYC)-CO2 | ZmTS13 ZmTS14 | 83 | 40 | 48% |

Example 10

Analysis of FnCpf1 Engineered Polynucleotides Optimized for Expression in Plant Cells.

This example describes the design and expression analysis of polynucleotide sequences encoding *Francisella novicida* (FnCpf1) nuclease that are optimized for expression in plant cells.

A nucleotide sequence of Cpf1 from *Francisella novicida* (FnCpf1) that was codon optimized for expression in human cells has been described by Zetsche et. al, (Cell 2015, 163, 759-771). To optimize the expression of the FnCpf1 protein (SEQ ID NO:43) in plant cells, the human codon optimized sequence disclosed by Zetsche et. al., (SEQ ID NO:44), described here as FnCpf1-Hs was modified through algorithmic methods, partly based on plant codon frequency tables, to design seven FnCpf1 CO (Codon optimized) sequences (see Table 10).

TABLE 10

CODON OPTIMIZED FNCPF1 AND THE CODON FREQUENCY TABLES USED TO DESIGN EACH SEQUENCE.

| Codon optimized FnCpf1 | Codon frequency table | SEQ ID NO: |
|---|---|---|
| FnCpf1-CO1 | *Glycine max* | 45 |
| FnCpf1-CO2 | Monocot | 46 |
| FnCpf1-CO3 | *Glycine max* | 47 |
| FnCpf1-CO4 | Monocot | 48 |
| FnCpf1-CO5 | *Oryza sativa* | 49 |
| FnCpf1-CO6 | *Oryza sativa* | 50 |
| FnCpf1-CO7 | *Zea mays* | 51 |

Expression Analysis of FnCpf1-CO Variants Via Quantification of FnCpf1-mOr Intensity:

Three expression cassettes (Prom35S::HIStag:NLS: FnCpf1-CO1:mOrange:NLS::TermNOS; Prom35S::HIStag: NLS:FnCpf1-CO2:mOrange:NLS::TermNOS; and Prom$_{35S}$::HIStag:NLS:FnCpf1-Hs:mOrange:NLS:: Term$_{NOS}$) were generated by standard cloning techniques and are described below:

(1) Prom$_{35S}$::HIS tag:NLS:FnCpf1-CO1:mOrange:NLS:: Term$_{NOS}$

The FnCpf1-CO1 coding sequence (SEQ ID NO: 45) was fused 5' to the coding sequence of mOrange (mOr) from *Entacmaea quadricolor*(SEQ ID NO:52) The FnCpf1-CO1: mOrange fusion gene was flanked at the 5' end with an NLS sequence from potato (SEQ ID NO: 42) and at the 3' end with an NLS sequence from tomato HSFA1 gene (SEQ ID NO:3) resulting in NLS:FnCpf1-CO1:mOrange:NLS (SEQ ID NO: 53). A nucleotide sequence encoding a HIS tag (MGSS7H) (SEQ ID NO: 54) was introduced at the 5' end of SEQ ID NO:53. A 'TAG' termination codon was introduced to the 3' end of the resulting nucleotide sequence (SEQ ID NO: 55) which was then operably linked to the Cauliflower mosaic virus 35S promoter (disclosed in U.S. Pat. No. 9,938,535-0047, incorporated herein by reference) and an *Agrobacterium* NOS terminator (MK078637). The expression cassette (SEQ ID NO: 56) was cloned into a plant expression vector.

(2) Prom$_{35S}$::HIS tag:NLS:FnCpf1-CO2:mOrange:NLS:: Term$_{NOS}$

The FnCpf1-CO2 coding sequence (SEQ ID NO: 46) was fused 5' to the coding sequence of mOrange (mOr) from *Entacmaea quadricolor*. (SEQ ID NO:52). The FnCpf1-CO2:mOrange fusion gene was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO2-NLS(SEQ ID NO:57). A nucleotide sequence encoding a HIS tag (MGSS7H) (SEQ ID NO: 54) was introduced at the 5' end of SEQ ID NO:57. A 'TAG' termination codon was introduced to the 3' end of the resulting nucleotide sequence (SEQ ID NO:58) which was then operably linked to the Cauliflower mosaic virus 35S promoter and an *Agrobacterium* NOS terminator (MK078637). The expression cassette (SEQ ID NO:59) was cloned into a plant expression vector.

(3) Prom$_{35S}$::HIS tag:NLS:FnCpf1-Hs:mOrange:NLS::Term$_{NOS}$

The human codon-optimized Cpf1 (FnCpf1-Hs) nucleotide sequence described by Zetsche et. al, (Cell 2015, 163, 759-771) (SEQ ID NO:44) was fused 5' to the coding sequence of mOrange (mOr) from *Entacmaea quadricolor*. (SEQ ID NO:52). The FnCpf1-Hs:mOrange fusion gene was then flanked at the 5' end with an NLS sequence from potato (SEQ ID NO: 42) and at the 3' end with an NLS sequence from tomato HSFA1 gene (SEQ ID NO:3) resulting in NLS-FnCpf1-Hs:mOrange-NLS(SEQ ID NO: 60). A nucleotide sequence encoding a HIS tag (MGSS7H) (SEQ ID NO: 54) was introduced at the 5' end of SEQ ID NO:60. A 'TAG' termination codon was introduced to the 3' end of the resulting nucleotide sequence (SEQ ID NO:61) which was then operably linked to the Cauliflower mosaic virus 35S promoter and an *Agrobacterium* NOS terminator (MK078637). The expression cassette (SEQ ID NO:62) was cloned into a plant expression vector.

Figure 2:
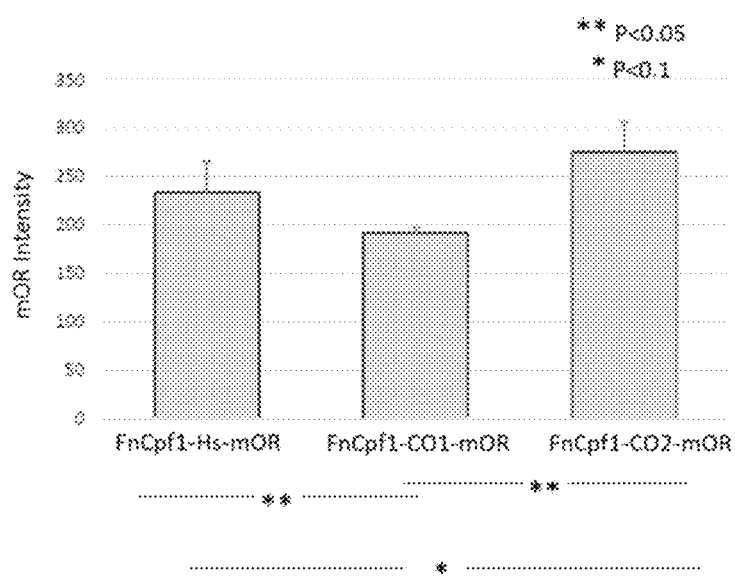
FIG. 2 illustrates the expression of FnCpf1-mOrange fluorescent proteins in corn protoplasts denoted by average mOrange intensities.

To evaluate and quantify the expression of the fusion proteins, corn leaf protoplasts were transfected with expression vectors comprising either of the three expression cassettes described above. Since mOrange was fused to FnCpf1-CO1, FnCpf1-CO2 and FnCpf1-Hs, the relative mOrange fluorescence levels reflects FnCpf1 expression levels. Transformations were carried out using standard polyethylene glycol (PEG) based transfection methods. To quantify transformation frequency, an expression vector comprising the luciferase gene was co-transfected. Following transformation, the protoplasts were incubated in the dark in incubation buffer and harvested after 48 hours. Transformation efficiency was calculated by quantifying luciferase expression. The average mOrange expression from 5 technical replicates was determined using Operetta™ (Perkin Elmer) analysis software. As shown in FIG. 2, mOrange fluorescence was detected from all three samples. The observed intensity was the highest in protoplasts expressing the FnCpf1-CO2-mOrange expression construct. Expression Analysis FnCpf1-CO Variants Via Qualitative Western Blots:

In addition to the three expression constructs described above, five expression constructs were generated and are described below:

(4) $Prom_{Ubiq}$::NLS:FnCpf1-CO3:NLS::$Term_{Os}$:

The FnCpf1-CO3 sequence (SEQ ID NO:47) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO3-NLS (SEQ ID NO:63). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO:64). The FnCpf1-CO3 expression cassette sequence is set forth as SEQ ID NO:65. The expression cassette was cloned into a plant expression vector.

(5) $Prom_{Ubiq}$::NLS:FnCpf1-CO4:NLS::$Term_{Os}$:

The FnCpf1-CO4 sequence (SEQ ID NO:48) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO4-NLS(SEQ ID NO:66). An ATG sequence encoding the translation initiation codon was added 5' to the potato NLS sequence and a TAG termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO4 expression cassette sequence is set forth as SEQ ID NO:67. The expression cassette was cloned into a plant expression vector.

(6) $Prom_{Ubiq}$::NLS:FnCpf1-CO5:NLS::$Term_{Os}$:

The FnCpf1-CO5 sequence (SEQ ID NO:49) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO5-NLS (SEQ ID NO:68). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO5 expression cassette sequence is set forth as SEQ ID NO:69. The expression cassette was cloned into a plant expression vector.

(7) $Prom_{Ubiq}$::NLS:FnCpf1-CO6:NLS::$Term_{Os}$:

The FnCpf1-CO6 sequence (SEQ ID NO:50) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO6-NLS (SEQ ID NO:70). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO6 expression cassette sequence is set forth as SEQ ID NO:71. The expression cassette was cloned into a plant expression vector.

(8) $Prom_{Ubiq}$::NLS:FnCpf1-CO7:NLS::$Term_{Os}$:

The FnCpf1-CO7 sequence (SEQ ID NO:51) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO7-NLS (SEQ ID NO:72). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO7 expression cassette sequence is set forth as SEQ ID NO:73. The expression cassette was cloned into a plant expression vector.

Corn protoplast cells were transformed with the eight plant expression vectors described above and in Table 11. As a negative control, cells were transformed with an expression vector for GFP. Transformations were carried out using standard polyethylene glycol (PEG) based transfection methods. Following transformation, the protoplasts were incubated in the dark in incubation buffer and harvested after 48 hours. $32*10^4$ cells from each transformation were lysed using 50 uL of lysis buffer. Total protein was extracted from each of the lysed samples and 30 ug protein per sample was resolved on an SDS-PAGE gel and electro-blotted onto nitrocellulose membranes by standard methods. 5 ng, 1 ng and 500 pg of purified FnCpf1 protein were loaded as positive controls. Western blots using anti-FnCpf1 antibody (Cell Signaling Technology, Danvers, Mass.) were performed to detect the presence of FnCpf1 proteins using standard methods. As noted in Table 11, a band corresponding to the FnCpf1-mOr was visually observed in the lanes containing protein extract from protoplasts expressing FnCpf1-CO2-mOr (Sample 3). Similarly, bands corresponding to FnCpf1 were visually observed in the lanes containing protein extract from protoplasts expressing FnCpf1-CO3 and FnCpf1-CO4 (Samples 4 and 5).

TABLE 11

EXPRESSION ANALYSIS FNCPF1-CODON OPTIMIZED VARIANTS VIA QUALITATIVE WESTERN BLOTS

| Sample | Expression cassette | Protein band observed |
|---|---|---|
| 1 | $Prom_{35S}$::HIStag:NLS:FnCpf1 Hs:mOrange:NLS::$Term_{NOS}$ | No |
| 2 | $Prom_{35S}$:: HIS tag:NLS:FnCpf1-CO1:mOrange:NLS::$Term_{NOS}$ | No |
| 3 | $Prom_{35S}$:: HIS tag:NLS:FnCpf1-CO2:mOrange:NLS::$Term_{NOS}$ | Yes |
| 4 | $Prom_{Ubiq}$::NLS:FnCpf1-CO3:NLS::$Term_{Os}$ | Yes |

TABLE 11-continued

EXPRESSION ANALYSIS FNCPF1-CODON OPTIMIZED VARIANTS VIA QUALITATIVE WESTERN BLOTS

| Sample | Expression cassette | Protein band observed |
|---|---|---|
| 5 | Prom$_{Ubiq}$::NLS:FnCpf1-CO4:NLS::Term$_{Os}$ | Yes |
| 6 | Prom$_{Ubiq}$::NLS:FnCpf1-CO5:NLS::Term$_{Os}$ | No |
| 7 | Prom$_{Ubiq}$::NLS:FnCpf1-CO6:NLS::Term$_{Os}$ | No |
| 8 | Prom$_{Ubiq}$::NLS:FnCpf1-CO7:NLS::Term$_{Os}$ | No |
| 9 | 5 ng purified FnCpf1 protein (Positive control) | Yes |
| 10 | 1 ng purified FnCpf1 protein (Positive control) | Yes |
| 11 | 500 pg purified FnCpf1 protein (Positive control) | Yes |
| 12 | Prom$_{35S}$::GFP::Term$_{NOS}$ (Negative control) | No |

Example 11

Analysis of FnCpf1 Activity in Corn Protoplasts.

The assay used to evaluate FnCpf1 activity in corn protoplasts was integration of a blunt-end, double-stranded DNA (dsDNA) fragment into the DSB (Double stranded break) created by FnCpf1 protein at a specific target site.

The blunt-end dsDNA fragment (disclosed in WO2019084148-021, incorporated herein by reference) was prepared by pre-annealing complementary ssDNA oligonucleotides. The ZmTS9 target site was chosen as the insertion site and a gRNA expression cassette targeting TS9 was designed. The expression cassette comprised a synthetic U6 promoter operably linked to a 21 bp crRNA sequence linked to a 23 bp spacer sequence that was complementary to ZmTS9 in the corn genome. The gRNA expression cassette was introduced into a plant expression vector. The gRNA vector and the eight plant vectors described in Example 11, each containing an expression cassette for a codon optimized FnCpf1 variant were co-transformed into isolated corn leaf protoplasts along with the double-stranded DNA (dsDNA) fragment essentially as described in patent application publication WO2015131101 (incorporated herein by reference), with minor modifications. Approximately 3.2×10$^5$ protoplasts were transformed using PEG with a total of 12 µg of plasmid DNA and 50 pmoles of the dsDNA fragment (assays 2-9 in Table 12). Protoplast samples lacking the nuclease expressing plasmids served as a negative control (see assay 10 in Table 12). Additionally, protoplast samples transformed with nuclease vectors and gRNA cassettes lacking the spacer sequence were used as negative controls (see assays 11-19 in Table 12). As a positive control (assay 1 in Table 12), protoplasts were transformed with the gRNA cassette and a vector comprising an expression cassette (SEQ ID NO:74) for LbCpf1-CO2 that has been shown to be active in corn (see Examples 3-4). The expression cassette (SEQ ID NO: 20) comprised NLS-LbCpf1-CO2-NLS (SEQ ID NO:12) with ATGGCG fused in frame 5' to SEQ ID NO 12 as the translational start site, and TGA termination codon fused 3' to SEQ ID NO:12. The resulting sequence was operably linked to the maize ubiquitin promoter (SEQ ID NO: 7) and a transcription terminator sequence from a rice (SEQ ID NO:64). To determine transformation efficiency, 3 ug of GFP internal control plasmid was transformed along with test constructs. Following transformation, the corn protoplasts were incubated in the dark and harvested after 48 hours. Genomic DNA was extracted and assayed for integration of the dsDNA fragment. Integration of the dsDNA fragment into the genomic DNA was detected by standard PCR and agarose gel electrophoresis to assess PCR amplicons. The dsDNA fragment may have integrated in either a 5' or 3' orientation with respect to the 5'- and 3'-ends of the DSB. Therefore, two PCR primer sets were run for the target site where the primer sets contained a primer specific to the dsDNA fragment and a primer specific to either the 5' side or the 3' side of the DSB at TS11. The PCR amplicons were separated using standard agarose gel electrophoresis and the size of the amplicon was confirmed by comparison to a molecular weight marker. The presence of a band of expected size was indicative of site-directed integration of the donor oligo at the ZmTS9 site following FnCpf1 mediated dsDNA cleavage. As shown in Table 12, expected bands were amplified from protoplasts expressing LbCpf1-CO2, FnCpf1-CO1, FnCpf1-CO2, FnCpf1-CO3, FnCpf1-CO4, FnCpf1-CO6, FnCpf1-CO7 along with the cognate gRNA cassette and ds DNA. Expected bands were not amplified from protoplasts expressing FnCpf1-CO5 or any of the negative controls.

TABLE 12

FNCPF1 MEDIATED SITE DIRECTED INTEGRATION OF DSDNA OLIGO AT ZMTS9 TARGET SITE.

| Assay | Nuclease Expression cassette | gRNA targeting ZmTS9 | Expected band amplified |
|---|---|---|---|
| 1 | Prom$_{Ubiq}$::NLS:LbCpf1-CO2:NLS::Term$_{Os}$ (Positive control) | + | Yes |
| 2 | Prom$_{35S}$::HIStag:NLS:FnCpf1Hs:mOrange:NLS::Term$_{NOS}$ | + | No |
| 3 | Prom$_{35S}$:: HIS tag:NLS:FnCpf1-CO1:mOrange:NLS::Term$_{NOS}$ | + | Yes |
| 4 | Prom$_{35S}$:: HIS tag:NLS:FnCpf1-CO2:mOrange:NLS::Term$_{NOS}$ | + | Yes |
| 5 | Prom$_{Ubiq}$::NLS:FnCpf1-CO3:NLS::Term$_{Os}$ | + | Yes |
| 6 | Prom$_{Ubiq}$::NLS:FnCpf1-CO4:NLS::Term$_{Os}$ | + | Yes |
| 7 | Prom$_{Ubiq}$::NLS:FnCpf1-CO5:NLS::Term$_{Os}$ | + | No |
| 8 | Prom$_{Ubiq}$::NLS:FnCpf1-CO6:NLS::Term$_{Os}$ | + | Yes |
| 9 | Prom$_{Ubiq}$::NLS:FnCpf1-CO7:NLS::Term$_{Os}$ | + | Yes |
| 10 | None | + | No |

TABLE 12-continued

FNCPF1 MEDIATED SITE DIRECTED INTEGRATION OF DSDNA OLIGO AT ZMTS9 TARGET SITE.

| Assay | Nuclease Expression cassette | gRNA targeting ZmTS9 | Expected band amplified |
|---|---|---|---|
| 11 | Prom$_{Ubiq}$::NLS:LbCpf1-CO2:NLS::Term$_{Os}$ | − | No |
| 12 | Prom$_{35S}$::HIStag:NLS:FnCpf1Hs:mOrange:NLS::Term$_{NOS}$ | − | No |
| 13 | Prom$_{35S}$:: HIS tag:NLS:FnCpf1-CO1:mOrange:NLS::Term$_{NOS}$ | − | No |
| 14 | Prom$_{35S}$:: HIS tag:NLS:FnCpf1-CO2:mOrange:NLS::Term$_{NOS}$ | − | No |
| 15 | Prom$_{Ubiq}$::NLS:FnCpf1-CO3:NLS::Term$_{Os}$ | − | No |
| 16 | Prom$_{Ubiq}$::NLS:FnCpf1-CO4:NLS::Term$_{Os}$ | − | No |
| 17 | Prom$_{Ubiq}$::NLS:FnCpf1-CO5:NLS::Term$_{Os}$ | − | No |
| 18 | Prom$_{Ubiq}$::NLS:FnCpf1-CO6:NLS::Term$_{Os}$ | − | No |
| 19 | Prom$_{Ubiq}$::NLS:FnCpf1-CO7:NLS::Term$_{Os}$ | − | No |

The invention claimed is:

1. A recombinant nucleic acid comprising the sequence of: SEQ ID No 10.

2. The recombinant nucleic acid of claim 1, further comprising one or more components selected from the group consisting of: a nucleic acid sequence encoding one or more nuclear localization signals, an operably linked promoter, one or more of an intron, one or more of a kozak sequence, one or more of a leader sequence, and one or more of a terminator sequence.

3. The recombinant nucleic acid of claim 1, wherein the recombinant nucleic acid comprises a sequence selected from the group consisting of SEQ ID Nos: 12, and 14.

4. A plant cell comprising the recombinant nucleic acid of claim 1.

5. An expression cassette comprising a recombinant nucleic acid sequence selected from the group consisting of SEQ ID Nos: 15, 20, 26, 31, 36, 40, and 59.

6. An *Agrobacterium* T-DNA vector comprising an expression cassette of claim 5.

7. The *Agrobacterium* T-DNA vector of claim 6 further comprising a promoter operably linked to one or more crRNA sequences and one or more spacer sequences, wherein the spacer sequence is complementary to at least 23 base pairs of a target site.

8. An *Agrobacterium* comprising the T-DNA vector of claim 6.

9. A plant cell comprising the expression cassette of claim 5.

10. A composition comprising: (a) the recombinant nucleic acid of claim 1, and (b) a recombinant nucleic acid encoding a guide RNA comprised of at least one crRNA and at least one spacer RNA sequence.

11. A method for modifying a target sequence in the genome of a plant cell, comprising:
    a) introducing into the plant cell the recombinant nucleic acid of claim 1, operably linked to a promoter, and
    b) introducing into the plant cell a guide polynucleotide comprising a nucleic acid sequence that is complementary to a target sequence or a recombinant nucleic acid encoding the guide polynucleotide, wherein the guide polynucleotide and a Cpf1 nuclease expressed from the recombinant nucleic acid form a complex that can bind to and modify the target sequence.

12. The method of claim 11, wherein the plant cell is a maize, cotton, soybean, canola, wheat, tomato, rice, brassica, melon, cucurbit, or lettuce cell.

13. The method of claim 11, further comprising introducing a donor DNA to the plant cell.

14. The method of claim 13, further comprising identifying at least one plant cell comprising in its genome the donor DNA, or a portion thereof, integrated into or near said target sequence.

15. A method for modifying a target sequence in the genome of a plant cell, the method comprising: introducing a guide polynucleotide comprising a nucleic acid sequence that is substantially complementary to the target sequence, or a recombinant nucleic acid encoding the guide polynucleotide, into a plant cell comprising in its genome the recombinant nucleic acid of claim 1 operably linked to a promoter, wherein the guide polynucleotide and a Cpf1 nuclease expressed from the recombinant nucleic acid form a complex that can bind to and modify the target sequence.

16. The method of claim 15, wherein the plant cell is a maize, cotton, soybean, canola, wheat, tomato, rice, brassica, melon, cucurbit, or lettuce cell.

17. The method of claim 15, further comprising introducing a donor DNA to the plant cell.

18. The method of claim 17, further comprising identifying at least one plant cell comprising in its genome the donor DNA, or a portion thereof, integrated into or near said target sequence.

19. A kit for modifying a target sequence in the genome of a plant cell, the kit comprising a guide polynucleotide comprising a nucleic acid sequence that is complementary to a target sequence or a recombinant nucleic acid encoding the guide polynucleotide, and the recombinant nucleic acid of claim 1.

20. The kit of claim 19, wherein the recombinant nucleic acid comprises one or more sequences selected from the group consisting of: SEQ ID Nos: 12, 14, 15, 20, 26, 31, and 36.

* * * * *

SEQUENCE LISTING

<160> NUMBER OF SEQ ID NOS: 76

<210> SEQ ID NO 1
<211> LENGTH: 3684
<212> TYPE: DNA
<213> ORGANISM: Artificial Sequence
<220> FEATURE:
<223> OTHER INFORMATION: Synthetic polynucleotide. Codon optimized LbCpf1-CO1

<400> SEQUENCE: 1

```
atgtccaagc ttgagaagtt tactaattgc tatagcctgt ctaagaccct tcgctttaag      60
gcgattcctg tgggcaagac gcaggaaaac atcgacaaca agcgactgct ggtggaagac     120
gagaagcgcg ctgaggacta aagggcgta agaagctgc tcgatcggta ctacctgagt      180
tttatcaacg atgtgttgca ttccataaag ttgaagaatc ttaataacta catctccttg     240
tttcggaaaa agaccaggac cgagaaggag aataaagagt tggaaaatct ggagatcaac     300
ttgcgtaagg agatcgcgaa ggcgttcaag ggtaatgagg ttataagag tctctttaaa     360 aaagatataa ttgaaacgat tctacccgaa tttctggatg ataaggatga gattgccctc     420
gtcaattcgt tcaatggctt tacaacagcg tttacaggtt tcttcgataa cagggaaaat     480
atgtttagcg aggaggcaaa gtcgacctct atcgcttttc gctgtataaa cgaaaattta     540
actcgatata tctccaatat ggatattttc gagaaagtcg atgcgatctt tgataagcat     600
gaagtccagg agattaagga aaagattctt aattcagatt atgatgtgga agattttttc     660
gaaggtgagt tctttaactt cgtgcttacg caagaaggaa tcgacgttta caatgcaata     720
attggtgggt tgttactga atctggtgaa aagatcaaag ccctcaatga gtacattaac     780
ttgtacaatc agaagacgaa gcagaagtta ccaaaattca agccgctgta caagcaagtg     840
ttatctgaca gggaatcttt gtcctttac ggtgaaggat acacttctga tgaagaggtg     900
cttgaggtct tcaggaatac actgaacaag aattctgaga tcttctcctc aattaagaaa     960
ctcgaaaaac tttcaagaa ctttgatgaa tacagctctg ctggaatttt cgtaaagaat    1020
ggtcccgcca taagcactat ctcaaaggac attttcggtg agtggaatgt tataagagat    1080
aaatggaatg cagagtacga cgatatccat ttgaagaaaa aggcggtagt taccgaaaag    1140
tacgaggatg acagaaggaa atcgttcaag aagattggct cattctccct ggagcagctt    1200
caggagtacg cggacgcgga ccttctgtt gttgaaaagc tcaaggagat catcatacaa    1260
aaggtagacg agatttataa ggtctatggg agctcagaga aattgttcga cgccgatttc    1320
```

-continued

| | |
|---|---|
| gttttggaga agtcactgaa aaagaacgac gctgtcgtcg ctattatgaa agaccttttg | 1380 |
| gattctgtca agtctttga gaactatatt aaggcttttt tcggtgaggg taaggagacg | 1440 |
| aaccgcgacg agtcattcta cggagacttt gtactcgcat atgacatact gctcaaagtt | 1500 |
| gatcatattt atgacgcgat ccgcaattac gttacacaaa aaccatactc taaagataaa | 1560 |
| ttcaagctgt atttccaaaa cccgcaattc atgggggggct gggataagga taaggaaacc | 1620 |
| gattataggg cgaccatatt gcgctacggg agcaagtatt acttagcgat catggataaa | 1680 |
| aaatacgcaa agtgtttgca aaagatagac aaggacgatg tcaatggcaa ttatgagaag | 1740 |
| attaactata agttgctgcc aggacccaat aagatgttgc ccaaagtttt tttctccaaa | 1800 |
| aaatggatgg cttattataa ccctagcgag gacatccaga aaatatacaa aaacggcaca | 1860 |
| tttaagaagg gggatatgtt caatcttaat gattgtcaca agctgataga cttttttcaag | 1920 |
| gactcaatct ctcggtatcc caagtggtcg aatgcgtacg atttttaattt ttctgagacc | 1980 |
| gaaaagtaca aggatattgc aggcttttat cgcgaagtgg aggaacaagg atacaaggtt | 2040 |
| tcattcgaat ccgcctcaaa aaaggaggtc gacaaactcg tcgaagaggg taaactgtac | 2100 |
| atgttccaaa tttacaataa agactttttca gacaaatcac acggaactcc taaccttcac | 2160 |
| acaatgtact ttaaattgct gttcgatgaa ataatcacg gtcaaattag gctgtcaggc | 2220 |
| ggagctgagc ttttcatgag gagggctagt ctgaagaaag aggagctggt ggtccatcct | 2280 |
| gcaaatagtc ccatagctaa taagaatcct gataacccta agaaaccac cactctctcc | 2340 |
| tacgacgttt ataaggataa acggttcagt gaagatcagt atgagttgca tattcccatt | 2400 |
| gccataaata agtgccctaa gaacatcttc aaaattaaca cagaagtgag agttctcttg | 2460 |
| aaacacgatg ataatccata tgtgattggg atagataggg gagagcgtaa cctcctttat | 2520 |
| attgtcgtgg ttgacggaaa gggtaacata gtggagcaat acagcctcaa tgaaattatt | 2580 |
| aacaacttta atggtattag aataaagact gactatcata gtctcttgga taaaaaagag | 2640 |
| aaggagaggt tcgaagctag gcagaattgg acgtctattg aaaatattaa agaactcaaa | 2700 |
| gcagggtaca ttagccaagt cgttcacaag atatgcgagt tggttgagaa atatgatgct | 2760 |
| gtcattgcac tggaggatct caatagcggt tcaaaaaaca gtcgtgttaa ggtggagaag | 2820 |
| caggtttacc agaaattcga gaagatgctg attgataagc ttaactatat ggtggacaaa | 2880 |
| aagtctaatc catgcgcgac cggtggcgca cttaagggct atcagatcac aaacaagttc | 2940 |
| gagtcgttta agtccatgtc aacacagaac ggtttcatct tctatatccc ggcatggctg | 3000 |
| acctcaaaaa ttgatcctag cacggggttc gtaaacttac ttaaaactaa atacacctca | 3060 |
| attgctgatt caaaaaagtt tatatcctca tttgaccgaa ttatgtatgt gcccgaggag | 3120 |
| gacctgttcg aattcgctct ggactataag aacttttcaa gaacagatgc ggattatatc | 3180 |
| aagaagtgga aactttacag ttatggtaac cgcattagga tattccggaa ccccaaaaaa | 3240 |
| aataatgtct ttgattggga ggaggtatgt ctgacgtctg cttataagga gctatttaat | 3300 |
| aagtacggca tcaattatca gcaggggac atccgcgcgc ttctctgcga gcaatccgat | 3360 |
| aaggctttct acagctcctt catggcattg atgagcctca tgctgcagat gagaaacagt | 3420 |
| atcacaggta aacgacgt agacttccta atttctccag tgaagaattc agatggcatc | 3480 |
| ttctatgata gccgcaacta tgaggcacag gagaacgcca tcctgcccaa aaatgctgat | 3540 |
| gccaacggtg cgtataacat tgctaggaag gtcctctggg ccataggtca attcaagaaa | 3600 |
| gctgaagacg agaagctcga caaggtaaaa attgccatat ccaacaagga gtggctcgaa | 3660 |
| tatgcacaga cctctgtgaa gcat | 3684 |

<210> SEQ ID NO 2
<211> LENGTH: 1228
<212> TYPE: PRT
<213> ORGANISM: Lachnospiraceae bacterium ND2006

<400> SEQUENCE: 2

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
```

-continued

```
                370                 375                 380
Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
                435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
                515                 520                 525

Gln Phe Met Gly Gly Trp Asp Lys Asp Lys Glu Thr Asp Tyr Arg Ala
530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
                595                 600                 605

Ser Glu Asp Ile Gln Lys Ile Tyr Lys Asn Gly Thr Phe Lys Lys Gly
                610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Glu Gly Lys Leu Tyr Met Phe Gln Ile
                690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
                755                 760                 765

Asn Pro Asp Asn Pro Lys Lys Thr Thr Thr Leu Ser Tyr Asp Val Tyr
                770                 775                 780

Lys Asp Lys Arg Phe Ser Glu Asp Gln Tyr Glu Leu His Ile Pro Ile
785                 790                 795                 800
```

-continued

```
Ala Ile Asn Lys Cys Pro Lys Asn Ile Phe Lys Ile Asn Thr Glu Val
                805                 810                 815
Arg Val Leu Leu Lys His Asp Asp Asn Pro Tyr Val Ile Gly Ile Asp
                820                 825                 830
Arg Gly Glu Arg Asn Leu Leu Tyr Ile Val Val Asp Gly Lys Gly
            835                 840                 845
Asn Ile Val Glu Gln Tyr Ser Leu Asn Glu Ile Ile Asn Asn Phe Asn
        850                 855                 860
Gly Ile Arg Ile Lys Thr Asp Tyr His Ser Leu Leu Asp Lys Lys Glu
865                 870                 875                 880
Lys Glu Arg Phe Glu Ala Arg Gln Asn Trp Thr Ser Ile Glu Asn Ile
                885                 890                 895
Lys Glu Leu Lys Ala Gly Tyr Ile Ser Gln Val Val His Lys Ile Cys
            900                 905                 910
Glu Leu Val Glu Lys Tyr Asp Ala Val Ile Ala Leu Glu Asp Leu Asn
        915                 920                 925
Ser Gly Phe Lys Asn Ser Arg Val Lys Val Glu Lys Gln Val Tyr Gln
    930                 935                 940
Lys Phe Glu Lys Met Leu Ile Asp Lys Leu Asn Tyr Met Val Asp Lys
945                 950                 955                 960
Lys Ser Asn Pro Cys Ala Thr Gly Gly Ala Leu Lys Gly Tyr Gln Ile
                965                 970                 975
Thr Asn Lys Phe Glu Ser Phe Lys Ser Met Ser Thr Gln Asn Gly Phe
            980                 985                 990
Ile Phe Tyr Ile Pro Ala Trp Leu Thr Ser Lys Ile Asp Pro Ser Thr
        995                 1000                1005
Gly Phe Val Asn Leu Leu Lys Thr Lys Tyr Thr Ser Ile Ala Asp
    1010                1015                1020
Ser Lys Lys Phe Ile Ser Ser Phe Asp Arg Ile Met Tyr Val Pro
    1025                1030                1035
Glu Glu Asp Leu Phe Glu Phe Ala Leu Asp Tyr Lys Asn Phe Ser
    1040                1045                1050
Arg Thr Asp Ala Asp Tyr Ile Lys Lys Trp Lys Leu Tyr Ser Tyr
    1055                1060                1065
Gly Asn Arg Ile Arg Ile Phe Arg Asn Pro Lys Lys Asn Asn Val
    1070                1075                1080
Phe Asp Trp Glu Glu Val Cys Leu Thr Ser Ala Tyr Lys Glu Leu
    1085                1090                1095
Phe Asn Lys Tyr Gly Ile Asn Tyr Gln Gln Gly Asp Ile Arg Ala
    1100                1105                1110
Leu Leu Cys Glu Gln Ser Asp Lys Ala Phe Tyr Ser Ser Phe Met
    1115                1120                1125
Ala Leu Met Ser Leu Met Leu Gln Met Arg Asn Ser Ile Thr Gly
    1130                1135                1140
Arg Thr Asp Val Asp Phe Leu Ile Ser Pro Val Lys Asn Ser Asp
    1145                1150                1155
Gly Ile Phe Tyr Asp Ser Arg Asn Tyr Glu Ala Gln Glu Asn Ala
    1160                1165                1170
Ile Leu Pro Lys Asn Ala Asp Ala Asn Gly Ala Tyr Asn Ile Ala
    1175                1180                1185
Arg Lys Val Leu Trp Ala Ile Gly Gln Phe Lys Lys Ala Glu Asp
    1190                1195                1200
```

```
Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 3
<211> LENGTH: 30
<212> TYPE: DNA
<213> ORGANISM: Lycopersicon esculentum

<400> SEQUENCE: 3
ggatctaaga agagaagaat taaacaagat                                    30

<210> SEQ ID NO 4
<211> LENGTH: 3750
<212> TYPE: DNA
<213> ORGANISM: Artificial Sequence
<220> FEATURE:
<223> OTHER INFORMATION: Synthetic polynucleotide.NLS-LbCpf1-CO1-NLS

<400> SEQUENCE: 4
atgggatcta agaagagaag aattaaacaa gatatgtcca agcttgagaa gtttactaat       60
tgctatagcc tgtctaagac ccttcgcttt aaggcgattc tgtgggcaa dacgcaggaa      120 aacatcgaca caagcgact gctggtggaa gacgagaagc gcgctgagga ctataagggc      180
gtaaagaagc tgctcgatcg gtactacctg agttttatca cgatgtgtt gcattccata     240 aagttgaaga atcttaataa ctacatctcc ttgtttcgga aaaagaccag gaccgagaag     300
gagaataaag agttggaaaa tctggagatc aacttgcgta aggagatcgc gaaggcgttc     360
aagggtaatg agggttataa gagtctcttt aaaaaagata taattgaaac gattctaccc     420
gaatttctgg atgataagga tgagattgcc ctcgtcaatt cgttcaatgg ctttacaaca     480
gcgtttacag gtttcttcga taacagggaa atatgtttta gcgaggaggc aaagtcgacc     540
tctatcgctt tcgctgtat aaacgaaaat ttaactcgat atatctccaa tatggatatt     600
ttcgagaaag tcgatgcgat ctttgataag catgaagtcc aggagattaa ggaaaagatt     660
cttaattcag attatgatgt ggaagatttt tcgaaggtg agttcttaa cttcgtgctt     720 acgcaagaag gaatcgacgt ttacaatgca ataattggtg ggtttgttac tgaatctggt     780
gaaaagatca aaggcctcaa tgagtacatt aacttgtaca atcagaagac gaagcagaag     840
ttaccaaaat tcaagccgct gtacaagcaa gtgttatctg acagggaatc tttgtccttt     900
tacggtgaag atacacttc tgatgaagag gtgcttgagg tcttcaggaa tacactgaac     960
aagaattctg agatcttctc ctcaattaag aaactcgaaa actttttcaa gaactttgat    1020
gaatacagct ctgctggaat tttcgtaaag aatggtcccg ccataagcac tatctcaaag    1080
gacattttcg gtgagtggaa tgttataaga gataaatgga atgcagagta cgacgatatc    1140
catttgaaga aaaggcggt agttaccgaa aagtacgagg atgacagaag gaaatcgttc    1200
aagaagattg gctcattctc cctggagcag cttcaggagt acgcggacgc ggaccttct    1260 gttgttgaaa agctcaagga gatcatcata caaaaggtag acgagattta aggtctat     1320 gggagctcag agaaattgtt cgacgccgat tcgttttgg agaagtcact gaaaagaac    1380 gacgctgtcg tcgctattat gaaagacctt ttggattctg tcaagtcttt tgagaactat    1440
attaaggctt ttttcggtga gggtaaggag acgaaccgcg acgagtcatt ctacggagac    1500
tttgtactcg catatgacat actgctcaaa gttgatcata tttatgacgc gatccgcaat    1560
tacgttacac aaaaaccata ctctaaagat aaattcaagc tgtatttcca aaacccgcaa    1620
```

```
ttcatggggg gctgggataa ggataaggaa accgattata gggcgaccat attgcgctac    1680
gggagcaagt attacttagc gatcatggat aaaaaatacg caaagtgttt gcaaaagata    1740
gacaaggacg atgtcaatgg caattatgag aagattaact ataagttgct gccaggaccc    1800
aataagatgt tgcccaaagt ttttttctcc aaaaaatgga tggcttatta taaccctagc    1860
gaggacatcc agaaaatata caaaaacggc acatttaaga aggggatat gttcaatctt    1920 aatgattgtc acaagctgat agactttttc aaggactcaa tctctcggta tcccaagtgg    1980
tcgaatgcgt acgattttaa tttttctgag accgaaaagt acaaggatat tgcaggcttt    2040
tatcgcgaag tggaggaaca aggatacaag gtttcattcg aatccgcctc aaaaaaggag    2100
gtcgacaaac tcgtcgaaga gggtaaactg tacatgttcc aaatttacaa taaagacttt    2160
tcagacaaat cacacggaac tcctaacctt cacacaatgt actttaaatt gctgttcgat    2220
gaaaataatc acggtcaaat taggctgtca ggcggagctg agcttttcat gaggagggct    2280
agtctgaaga agaggagct ggtggtccat cctgcaaata gtcccatagc taataagaat    2340
cctgataacc ctaagaaaac caccactctc tcctacgacg tttataagga taaacggttc    2400
agtgaagatc agtatgagtt gcatattccc attgccataa ataagtgccc taagaacatc    2460
ttcaaaatta acacagaagt gagagttctc ttgaaacacg atgataatcc atatgtgatt    2520
gggatagata ggggagagcg taacctcctt tatattgtcg tggttgacgg aaagggtaac    2580
atagtggagc aatacagcct caatgaaatt attaacaact ttaatggtat tagaataaag    2640
actgactatc atagtctctt ggataaaaaa gagaaggaga ggttcgaagc taggcagaat    2700
tggacgtcta ttgaaaatat taaagaactc aaagcagggt acattagcca agtcgttcac    2760
aagatatgcg agttggttga gaaatatgat gctgtcattg cactggagga tctcaataagc    2820 ggtttcaaaa acagtcgtgt taaggtggag aagcaggttt accagaaatt cgagaagatg    2880
ctgattgata agcttaacta tatggtggac aaaaagtcta atccatgcgc gaccggtggc    2940
gcacttaagg gctatcagat cacaaacaag ttcgagtcgt ttaagtccat gtcaacacag    3000
aacggtttca tcttctatat cccggcatgg ctgacctcaa aaattgatcc tagcacgggg    3060
ttcgtaaact tacttaaaac taaatacacc tcaattgctg attcaaaaaa gtttatatcc    3120 tcattgacc gaattatgta tgtgcccgag gaggacctgt tcgaattcgc tctggactat    3180 aagaacttt caagaacaga tgcggattat atcaagaagt ggaaacttta cagttatggt    3240
aaccgcatta ggatattccg gaaccccaaa aaaaataatg tctttgattg ggaggaggta    3300
tgtctgacgt ctgcttataa ggagctattt aataagtacg gcatcaatta tcagcagggg    3360
gacatccgcg cgcttctctg cgagcaatcc gataaggctt tctacagctc cttcatggca    3420
ttgatgagcc tcatgctgca gatgagaaac agtatcacag gtagaacgga cgtagacttc    3480
ctaatttctc cagtgaagaa ttcagatggc atcttctatg atagccgcaa ctatgaggca    3540
caggagaacg ccatcctgcc caaaaatgct gatgccaacg gtgcgtataa cattgctagg    3600
aaggtcctct gggccatagg tcaattcaag aaagctgaag acgagaagct cgacaaggta    3660
aaaattgcca tatccaacaa ggagtggctc gaatatgcac agacctctgt gaagcatgga    3720
tctaagaaga gaagaattaa acaagattga                                     3750
```

<210> SEQ ID NO 5
<211> LENGTH: 189
<212> TYPE: DNA
<213> ORGANISM: Solanum tuberosum -continued

<400> SEQUENCE: 5

```
gtaagtttct gcttctacct ttgatatata tataataatt atcattaatt agtagtaata      60
taatatttca aatattttt tcaaaataaa agaatgtagt atatagcaat tgcttttctg     120
tagtttataa gtgtgtatat tttaatttat aacttttcta atatatgacc aaaatttgtt     180
gatgtgcag                                                            189
```

<210> SEQ ID NO 6
<211> LENGTH: 3939
<212> TYPE: DNA
<213> ORGANISM: Artificial Sequence
<220> FEATURE:
<223> OTHER INFORMATION: Synthetic polynucleotide.NLS- LbCpf15'-Intron-
      LbCpf13'-NLS

<400> SEQUENCE: 6

```
atgggatcta agaagagaag aattaaacaa gatatgtcca agcttgagaa gtttactaat      60
tgctatagcc tgtctaagac ccttcgcttt aaggcgattc ctgtgggcaa gacgcaggaa     120
aacatcgaca acaagcgact gctggtggaa gacgagaagc gcgctgagga ctataagggc     180
gtaaagaagc tgctcgatcg gtactacctg agttttatca acgatgtgtt gcattccata     240
aagttgaaga atcttaataa ctacatctcc ttgtttcgga aaaagaccag gaccgagaag     300
gagaataaag agttggaaaa tctggagatc aacttgcgta aggagatcgc gaaggcgttc     360
aagggtaatg agggttataa gagtctcttt aaaaagata taattgaaac gattctaccc     420
gaatttctgg atgataagga tgagattgcc ctcgtcaatt cgttcaatgg ctttacaaca     480
gcgtttacag gtaagtttct gcttctacct ttgatatata tataataatt atcattaatt     540
agtagtaata taatatttca aatattttt tcaaaataaa agaatgtagt atatagcaat     600
tgcttttctg tagtttataa gtgtgtatat tttaatttat aacttttcta atatatgacc     660
aaaatttgtt gatgtgcagg tttcttcgat aacagggaaa atatgtttag cgaggaggca     720
aagtcgacct ctatcgcttt tcgctgtata acgaaaatt taactcgata tatctccaat     780
atggatattt tcgagaaagt cgatgcgatc tttgataagc atgaagtcca ggagattaag     840
gaaaagattc ttaattcaga ttatgatgtg aagattttt tcgaaggtga gttcttaac     900
ttcgtgctta cgcaagaagg aatcgacgtt acaatgcaa taattggtgg gtttgttact     960
gaatctggtg aaaagatcaa aggcctcaat gagtacatta acttgtacaa tcagaagacg    1020
aagcagaagt taccaaaatt caagccgctg tacaagcaag tgttatctga cagggaatct    1080
ttgtcctttt acggtgaagg atacacttct gatgaagagg tgcttgaggt cttcaggaat    1140
acactgaaca agaattctga gatcttctcc tcaattaaga aactcgaaaa acttttcaag    1200
aactttgatg aatacagctc tgctggaatt ttcgtaaaga atggtcccgc cataagcact    1260
atctcaaagg acattttcgg tgagtggaat gttataagag ataaatggaa tgcagagtac    1320
gacgatatcc atttgaagaa aaaggcggta gttaccgaaa agtacgagga tgacagaagg    1380
aaatcgttca agaagattgg ctcattctcc ctggagcagc ttcaggagta cgcggacgcg    1440
gaccttctg ttgttgaaaa gctcaaggag atcatcatac aaaaggtaga cgagatttat    1500
aaggtctatg ggagctcaga gaattgttc gacgccgatt tcgttttgga agtcactg      1560
aaaaagaacg acgctgtcgt cgctattatg aaagaccttt tggattctgt caagtctttt    1620
gagaactata ttaaggcttt tttcggtgag ggtaaggaga cgaaccgcga cgagtcattc    1680
tacggagact ttgtactcgc atatgacata ctgctcaaag ttgatcatat ttatgacgcg    1740
```

```
atccgcaatt acgttacaca aaaaccatac tctaaagata aattcaagct gtatttccaa    1800
aacccgcaat tcatgggggg ctgggataag gataaggaaa ccgattatag ggcgaccata    1860
ttgcgctacg ggagcaagta ttacttagcg atcatggata aaaaatacgc aaagtgtttg    1920
caaaagatag acaaggacga tgtcaatggc aattatgaga agattaacta taagttgctg    1980
ccaggaccca ataagatgtt gcccaaagtt ttttttctcca aaaaatggat ggcttattat    2040
aaccctagcg aggacatcca gaaaatatac aaaaacggca catttaagaa gggggatatg    2100
ttcaatctta atgattgtca caagctgata gacttttttca aggactcaat ctctcggtat    2160
cccaagtggt cgaatgcgta cgattttaat ttttctgaga ccgaaaagta caaggatatt    2220
gcaggctttt atcgcgaagt ggaggaacaa ggatacaagg tttcattcga atccgcctca    2280
aaaaaggagg tcgacaaact cgtcgaagag ggtaaactgt acatgttcca aatttacaat    2340
aaagactttt cagacaaatc acacggaact cctaaccttc acacaatgta ctttaaattg    2400
ctgttcgatg aaaataatca cggtcaaatt aggctgtcag gcggagctga gcttttcatg    2460
aggagggcta gtctgaagaa agaggagctg gtggtccatc ctgcaaatag tcccatagct    2520
aataagaatc ctgataaccc taagaaaacc accactctct cctacgacgt ttataaggat    2580
aaacggttca gtgaagatca gtatgagttg catattccca ttgccataaa taagtgccct    2640
aagaacatct tcaaaattaa cacagaagtg agagttctct tgaaacacga tgataatcca    2700
tatgtgattg ggatagatag gggagagcgt aacctccttt atattgtcgt ggttgacgga    2760
aagggtaaca tagtggagca atacagcctc aatgaaatta ttaacaactt taatggtatt    2820
agaataaaga ctgactatca tagtctcttg gataaaaaag agaaggagag gttcgaagct    2880
aggcagaatt ggacgtctat tgaaaatatt aaagaactca agcagggta cattagccaa    2940 gtcgttcaca agatatgcga gttggttgag aaatatgatg ctgtcattgc actggaggat    3000
ctcaatagcg gtttcaaaaa cagtcgtgtt aaggtggaga agcaggttta ccagaaattc    3060
gagaagatgc tgattgataa gcttaactat atggtgaca aaaagtctaa tccatgcgcg    3120
accggtggcg cacttaaggg ctatcagatc acaaacaagt tcgagtcgtt aagtccatg    3180 tcaacacaga acggtttcat cttctatatc ccggcatggc tgacctcaaa aattgatcct    3240
agcacggggt tcgtaaactt acttaaaact aaatacacct caattgctga ttcaaaaag    3300 tttatatcct catttgaccg aattatgtat gtgcccgagg aggacctgtt cgaattcgct    3360
ctggactata agaacttttc aagaacagat gcggattata tcaagaagtg gaaactttac    3420
agttatggta accgcattag gatattccgg aaccccaaaa aaataatgt ctttgattgg    3480 gaggagggtat gtctgacgtc tgcttataag gagctattta ataagtacgg catcaattat    3540
cagcaggggg acatccgcgc gcttctctgc gagcaatccg ataaggcttt ctacagctcc    3600
ttcatggcat tgatgagcct catgctgcag atgagaaaca gtatcacagg tagaacggac    3660
gtagacttcc taatttctcc agtgaagaat tcagatggca tcttctatga tagccgcaac    3720
tatgaggcac aggagaacgc catcctgccc aaaaatgctg atgccaacgg tgcgtataac    3780
attgctagga aggtcctctg ggccataggt caattcaaga agctgaaga cgagaagctc    3840 gacaaggtaa aaattgccat atccaacaag gagtggctcg aatatgcaca gacctctgtg    3900
aagcatggat ctaagaagag aagaattaaa caagattga                            3939
```

<210> SEQ ID NO 7
<211> LENGTH: 2008
<212> TYPE: DNA
<213> ORGANISM: Zea mays

<400> SEQUENCE: 7

```
gtcgtgcccc tctctagaga taaagagcat tgcatgtcta aagtataaaa aattaccaca      60
tattttttg  tcacacttat  ttgaagtgta  gtttatctat  ctctatacat  atatttaaac  120
ttcactctac aaataatata gtctataata ctaaaataat attagtgttt tagaggatca     180
tataaataaa ctgctagaca tggtctaaag gataattgaa tattttgaca atctacagtt     240
ttatcttttt agtgtgcatg tgatctctct gttttttttg caaatagctt gacctatata     300
atacttcatc cattttatta gtacatccat ttaggattta gggttgatgg tttctataga     360
ctaattttta gtacatccat tttattcttt ttagtctcta aattttttaa aactaaaact     420
ctatttagt  tttttattta ataatttaga tataaaatga aataaaataa attgactaca     480
aataaaacaa ataccctta  agaaataaaa aaactaagca aacattttc  ttgtttcgag     540
tagataatga caggctgttc aacgccgtcg acgagtctaa cggacaccaa ccagcgaacc     600
agcagcgtcg cgtcgggcca agcgaagcag acggcacggc atctgtag   ctgcctctgg     660
accctctcg  agagttccgc tccaccgttg gacttgctcc gctgtcggca tccagaaatt     720
gcgtggcgga gcggcagacg tgaggcggca cggcaggcgg cctcttcctc ctctcacggc     780
accggcagct acgggggatt cctttcccac cgctccttcg cttcccttc  ctcgcccgcc     840
gtaataaata gacacccct  ccacaccctc tttcccccaac ctcgtgttcg ttcggagcgc    900
acacacacgc aaccagatct cccccaaatc cagccgtcgg cacctccgct tcaaggtacg     960
ccgctcatcc tccccccccc cctctctcta ccttctctag atcggcgatc cggtccatgg    1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt    1140
caagctacct ggtggattta ttaattttgt atctgtatgt gtgtgccata catcttcata    1200
gttacgagtt taagatgatg gatggaaata tcgatctagg ataggtatac atgttgatgc    1260
gggttttact gatgcatata cagagatgct tttttctcg  cttggttgtg atgatatggt    1320
ctggttgggc ggtcgttcta gatcggagta gaatactgtt tcaaactacc tggtggattt    1380
attaaaggat aaagggtcgt tctagatcgg agtagaaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc ttttttcgc  ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttatttgat  cttgatatac ttggatgatg gcatatgcag cagctatatg tggattttt     1920
agccctgcct tcatacgcta tttatttgct tggtactgtt tcttttgtcc gatgctcacc    1980
ctgttgtttg gtgatacttc tgcaggtc                                       2008
```

<210> SEQ ID NO 8
<211> LENGTH: 298
<212> TYPE: DNA
<213> ORGANISM: Oryza sativa

<400> SEQUENCE: 8

```
taatcgatcc tccgatcccc taattaccat accattacac catgcatcaa tatccatata    60
tatataaacc ctttcgcacg tactatact atgttttgtc atacatatat atgtgtcgaa    120
cgatcgatct atcactgata tgatatgatt gatccatcag cctgatctct gtatcttgtt   180
atttgtatac cgtcaaataa aagtttcttc cacttgtgtt aataattagc tactctcatc   240
tcatgaaccc tatatataac tagtttaatt tgctgtcaat tgaacatgat gatcgatg    298
```

<210> SEQ ID NO 9
<211> LENGTH: 200
<212> TYPE: DNA
<213> ORGANISM: Zea mays

<400> SEQUENCE: 9

```
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt                                              200
```

<210> SEQ ID NO 10
<211> LENGTH: 3681
<212> TYPE: DNA
<213> ORGANISM: Artificial Sequence
<220> FEATURE:
<223> OTHER INFORMATION: Synthetic polynucleotide.Codon optimized
      LbCpf1-CO2

<400> SEQUENCE: 10

```
tcgaagctcg agaagttcac caactgctac tcgctgagca agacgctgcg gttcaaggcg    60
atccccgtcg ggaagaccca ggagaacatc gacaacaagc ggctcctggt cgaggacgag   120
aagcgcgccg aggactacaa gggcgtcaag aagctgctgg accggtacta cctctccttc   180
atcaacgacg tcctgcactc gatcaagctc aagaacctga caactacat ctcgctgttc   240 cgcaagaaga cacggaccga aaggagaac aaggagctcg agaacctcga gatcaacctg   300
cgcaaggaga tcgcgaaggc gttcaagggc aacgagggt acaagagcct gttcaagaaa   360
gacatcatcg agaccatcct gccggagttc ctggacgaca ggacgagat cgcgctggtg   420 aactcgttca cgggttcac cacgccttc accgggtttt tcgacaaccg ggagaacatg   480
ttcagcgagg aggccaagtc gaccagcatc gccttccggt gcatcaacga aaccctcacc   540
cgctacatca gcaacatgga catcttcgag aaggtggacg ccatcttcga caagcacgag   600
gtccaggaga tcaaggaaaa gatcctgaac tcggactacg acgtggaaga cttcttgag   660 ggcgagttct tcaacttcgt cctcacccag gagggcatcg acgtctacaa cgccatcatc   720
ggcggcttcg tgacggagag cggcgagaag atcaagggcc tcaacgagta catcaacctc   780
tacaaccaga gactaagca gaagctcccg aagttcaagc cgctgtacaa gcaagtcctg   840
agcgaccggg agtccctctc gttctacggc gagggctaca cgagcgacga ggaggtgctg   900
gaggtgttcc gcaacacgct gaacaagaac agcgagatct tcagctcgat caagaaactc   960
gagaagctgt tcaagaactt cgacgagtac agcagcgccg gcatcttcgt caagaacggg  1020
cccgcgatca gcaccatcag caaggacatc ttcggggagt ggaacgtgat ccgcgacaag  1080
tggaacgccg agtacgacga catccacctc aagaaaaagg cggtggtcac ggagaagtac  1140
gaggacgacc gccggaagtc cttcaagaaa atcgggagct cagcctcga gcagctccag  1200 gagtacgcgg acgccgacct gagcgtggtg gagaagctca aggagatcat catccagaag  1260
```

```
gtcgacgaga tctacaaggt ctacggctcg agcgagaagc tgttcgacgc ggacttcgtg    1320
ctggagaagt ccctcaagaa gaacgacgcc gtggtggcca tcatgaagga tctgctcgac    1380
agcgtgaagt cgttcgagaa ctacatcaag gcattctttg gggagggcaa ggagacgaac    1440
cgggacgagt ccttctacgg ggacttcgtg ctcgcgtacg acatcctcct gaaggtcgac    1500
cacatctacg acgcgatccg gaactacgtc acgcagaagc cctacagcaa ggacaagttc    1560
aagctctact ccagaacccc gcagttcatg ggcgggtggg acaaggacaa ggagaccgac    1620
taccgggcca cgatcctgcg gtacgggtcc aagtactacc tcgccatcat ggacaagaag    1680
tacgccaagt gcctccagaa gattgacaag gacgacgtga acgggaacta cgagaagatc    1740
aactacaagc tcctcccggg gcccaacaag atgctgccga aggtgttctt cagcaagaag    1800
tggatggcct actacaaccc ctcggaggac atccagaaga tatacaagaa cggcacgttc    1860 aaaaagggg acatgttcaa cctgaacgac tgccacaagc tgatcgactt tttcaaggac    1920
agcatcagcc gctaccccgaa gtggtcgaac gcctacgact tcaacttctc ggagacggag    1980
aagtacaagg acattgcggg cttctaccgg gaggtggagg agcagggcta caaggtctcc    2040
ttcgagagcg cctccaagaa agaggtggac aagctcgtgg aggagggcaa gctgtacatg    2100
ttccagatct acaacaagga cttctcggac aagtcgcacg gcaccccgaa cctccacacg    2160
atgtacttca agctgctgtt cgacgagaac aaccacgggc agatccgcct cagcggcggg    2220
gcggagctgt tcatgcgccg cgcgtccctc aagaaggagg agctggtcgt gcaccccgcc    2280
aactccccga tcgcgaacaa gaaccccgac aaccccaaga gacaaccac cctctcgtac    2340 gacgtctaca aggacaagcg gttctcggag gaccagtacg agctgcacat cccgatcgcc    2400
atcaacaagt gccccaagaa catcttcaag atcaacaccg aggtgcgggt gctgctcaag    2460
cacgacgaca cccctacgt catcgggatc gaccgcggcg agcggaacct gctctacatc    2520
gtggtcgtgg acgggaaggg gaacatcgtg gagcagtaca gcctgaacga gatcatcaac    2580
aacttcaacg gcatccgcat caagacggac taccacagcc tcctggacaa gaaggagaag    2640
gagcggttcg aggcgcggca gaactggacc tccatcgaga acatcaagga gctgaaggcc    2700
ggctacatca gccaggtcgt gcacaagatc tgcgagctcg tggagaagta cgacgcggtg    2760
atcgcgctgg aggacttgaa cagcgggttc aagaactccc gggtcaaggt cgagaagcag    2820
gtctaccaga agttcgagaa gatgctgatc gacaagctca actacatggt ggacaagaag    2880
tccaacccct gcgccaccgg cggcgccctc aagggctacc agatcaccaa caagttcgag    2940
tccttcaagt cgatgtctac gcagaacggg ttcattttct acatcccggc gtggctcacc    3000
agcaagatcg acccgagcac gggcttcgtc aacctcctga gaccaagta caccagcatc    3060 gcggacagca agaagttcat ctcctcgttc gaccgcatca tgtacgtccc cgaggaagac    3120
ctgttcgagt tcgccctcga ctacaagaac ttctcccgga cggacgccga ctacatcaaa    3180
aagtggaagc tctacagcta cggcaaccgg atccgcatct ccgcaaccc caagaagaac    3240 aatgtgttcg actgggagga ggtgtgcctg acgagcgcct acaaggagct cttcaacaag    3300
tacggcatca actaccagca aggggacatc cgcgcgctgc tctgcgagca gtccgacaag    3360
gcgttctact cgtcgttcat ggccctgatg agcctcatgc tccagatgcg caacagcatc    3420
accggccgga cggacgtgga cttcctgatc agcccggtca gaacagcga cggcattttc    3480 tacgacagcc ggaactacga ggcccaggag aacgccatcc tccccaagaa cgccgacgcg    3540 aacgcgcct acaacatcgc gcggaaggtg ctgtgggcca tcggccagtt taaaaaggcg    3600
gaggacgaga agctggacaa ggtcaagatc gccatcagca acaaggagtg gctcgagtac    3660
```
gcgcagacga gcgtgaagca c                                              3681

<210> SEQ ID NO 11
<211> LENGTH: 3681
<212> TYPE: DNA
<213> ORGANISM: Artificial Sequence
<220> FEATURE:
<223> OTHER INFORMATION: Synthetic polynucleotide.Codon optimized
      LbCpf1-Os

<400> SEQUENCE: 11

| | |
|---|---:|
| tccaagctgg agaagtttac aaactgttac agcctctcca aaaccctcag gtttaaagcg | 60 |
| atcccggtgg gcaagaccca ggagaacatc gacaacaaga ggctcctggt ggaagacgag | 120 |
| aagcgcgccg aagactacaa gggcgtgaag aagctgctcg ataggtacta cctcagcttt | 180 |
| attaacgacg tgctgcacag catcaaactc aagaatctca caactacat ctccctcttc | 240 |
| cgcaaaaaga cccgcaccga aggagaaac aaggagctgg agaacctgga gatcaacctc | 300 |
| cgcaaggaaa tcgccaaagc gttcaagggc aatgaagggt acaagagcct cttcaagaaa | 360 |
| gacatcatcg aaactatcct cccagagttt ctcgatgaca aggacgagat cgcgctggtg | 420 |
| aactcccttta cgggttcac aaccgcgttt accggcttct tgataacag gaaaatatg | 480 |
| ttctccgagg aggccaagtc caccagcatc gccttcaggt gtatcaacga gaacctcacc | 540 |
| cgctacattt ccaatatgga cattttcgag aaggtggatg cgatcttcga taagcacgag | 600 |
| gtgcaggaga tcaaagagaa gattctcaat ccgattatg acgtcgagga tttcttcgaa | 660 |
| ggggagttct ttaattttgt gctcacacaa gagggcattg acgtgtacaa cgcgattatc | 720 |
| gggggcttcg tcacagagtc cggggagaag attaaggggc tgaatgagta catcaatctg | 780 |
| tacaatcaga gaccaagca gaaactgccg aaattcaagc cgctctacaa gcaagtcctg | 840 |
| tccgataggg aaagcctctc cttctacggc gagggctata ccagcgacga ggaggtgctg | 900 |
| gaagtcttcc gcaacacact gaataagaat agcgagattt ctcctccat caagaagctc | 960 |
| gagaagctct ttaagaactt tgacgagtac agctccgccg gattttcgt gaagaacggg | 1020 |
| ccggcgatca gcaccatctc caaggacatc tttggcgagt ggaacgtcat cagggacaag | 1080 |
| tggaacgccg agtacgacga catccaccctg aagaagaagg cggtggtgac cgagaagtat | 1140 |
| gaggacgatc gcaggaagtc cttcaaaaaa atcggctcct tcagcctcga acagctccag | 1200 |
| gagtatgccg atgcggatct gtccgtcgtc gagaagctga aggaaatcat cattcagaag | 1260 |
| gtcgacgaga tctataaagt gtacgggtcc agcgagaagc tgttcgacgc cgactttgtg | 1320 |
| ctcgagaagt ccctcaaaaa gaatgacgcc gtggtggcca ttatgaaaga cctgctcgac | 1380 |
| tccgtgaagt ccttcgaaaa ttacattaaa gcgttctttg ggagggggaa ggaaactaac | 1440 |
| agggatgagt ccttctatgg cgactttgtc ctcgcgtacg acatcctgct gaaggtcgac | 1500 |
| cacatttacg acgcgatccg caactacgtg acacagaagc cgtactccaa agacaagttc | 1560 |
| aagctgtact ccagaacccc gcaatttatg ggggctggg acaaggataa agagacagac | 1620 |
| taccgcgcga caattctccg ctatggctcc aaatactatc tggccatcat ggacaagaag | 1680 |
| tacgcgaagt gcctgcagaa gatcgacaaa gacgacgtca tggcaacta tgaaaagatc | 1740 |
| aactacaagc tgctgccggg cccgaacaag atgctcccga aggtgttctt cagcaagaag | 1800 |
| tggatggcct actacaatcc aagcgaggat attcagaaaa tctataaaaa cgggaccttc | 1860 |
| aagaagggg acatgtttaa cctcaacgac tgccacaagc tcattgattt cttcaaggat | 1920 |
| agcatttccc gctacccgaa atggtccaat gcgtacgatt ttaacttctc cgagacagaa | 1980 |

```
aagtacaaag acatcgcggg cttttacagg gaggtggagg agcaagggta taaagtttct    2040
tttgaatccg cgagcaagaa ggaagtcgac aagctcgtcg aggagggcaa gctctacatg    2100
ttccaaattt ataacaagga cttttccgac aagagccatg ggaccccaaa cctccacacc    2160
atgtacttca aactgctctt tgacgagaac aaccacgggc aaatcaggct gagcggcggc    2220
gccgaattat tcatgcgcag ggcctccctc aagaaggaag agctggtcgt ccatccagcc    2280
aattccccga tcgcgaacaa gaacccggac aatccgaaaa agaccaccac cctgtcctac    2340
gacgtctaca aggacaaacg cttcagcgaa gaccagtacg aattacacat cccaattgcg    2400
attaataagt gcccaaagaa tatcttcaaa attaatacag aggtcagggt gctgctcaaa    2460
cacgacgaca atccgtatgt catcggcatt gacaggggcg agcgcaatct gctctatatc    2520
gtggtcgtgg atgggaaggg caatattgtg gagcagtact ccctgaacga gattatcaac    2580
aacttcaatg ggattaggat taagaccgac tatcacagcc tgctcgacaa gaaagaaaaa    2640
gagaggtttg aggcccgcca aaactggacc tccattgaga atatcaaaga attaaaggcc    2700
ggctatattt cccaagtcgt ccacaagatc tgcgagctgg tggagaaata tgacgccgtg    2760
attgcgctcg aagacttaaa ttctgggttc aagaactccc gcgtgaaggt ggaaaaacag    2820
gtgtatcaga aattcgagaa aatgctgatc gacaaactca attatatggt ggataagaag    2880
tccaacccgt gtgccacagg gggcgcgctg aagggctatc agatcaccaa caagttcgag    2940
agcttcaaga gcatgagcac ccagaacggg tttatttct acatcccggc gtggctcacc    3000
tccaagattg acccgagcac cggcttcgtg aacctcctga agacaaagta tacctccatt    3060
gccgacagca agaagtttat ctcctccttc gaccgcatta tgtatgtgcc ggaggaggac    3120
ctcttcgagt cgcccctcga ctacaaaaac ttcagccgca cagatgcgga ttacatcaag    3180
aagtggaagc tgtactccta cgggaacagg atccgcatct tcaggaatcc aaaaaaaaat    3240
aacgtctttg actgggagga agtgtgcctc acatccgcct acaaggaact gttcaataaa    3300
tacggcatca attaccagca gggcgacatt cgcgccctcc tctgtgagca gtccgacaaa    3360
gcgttttact ccagcttcat ggccctcatg tccctgatgc tccaaatgag gaatagcatc    3420
acagggcgca ccgacgtcga cttcctcatc agcccggtga agaactccga cgggatcttt    3480
tacgactccc gcaactatga ggcgcaagag aatgcgatcc tcccgaagaa cgccgatgcg    3540
aacgggccct ataatatcgc caggaaagtg ctctgggcca tcgggcagtt caaaaaggcg    3600
gaggatgaga agctcgacaa ggtgaaaatt gccatttcca acaaggagtg gctggagtac    3660
gcgcagacct ccgtgaagca c                                              3681
```

<210> SEQ ID NO 12
<211> LENGTH: 3744
<212> TYPE: DNA
<213> ORGANISM: Artificial Sequence
<220> FEATURE:
<223> OTHER INFORMATION: Synthetic polynucleotide.NLS-LbCpf1-CO2-NLS

<400> SEQUENCE: 12

```
ggatctaaga agagaagaat taaacaagat tcgaagctcg agaagttcac caactgctac     60
tcgctgagca gacgctgcg gttcaaggcg atccccgtcg ggaagaccca ggagaacatc     120
gacaacaagc ggctcctggt cgaggacgag aagcgcgccg aggactacaa gggcgtcaag     180
aagctgctgg accggtacta cctctccctt atcaacgacg tcctgcactc gatcaagctc     240
aagaacctga caactacat ctcgctgttc cgcaagaaga cacggaccga gaaggagaac     300
```

```
aaggagctcg agaacctcga gatcaacctg cgcaaggaga tcgcgaaggc gttcaagggc      360
aacgaggggt acaagagcct gttcaagaaa gacatcatcg agaccatcct gccggagttc      420
ctggacgaca aggacgagat cgcgctggtg aactcgttca cgggttcac cacggccttc       480 accgggtttt tcgacaaccg ggagaacatg ttcagcgagg aggccaagtc gaccagcatc      540
gccttccggt gcatcaacga gaacctcacc cgctacatca gcaacatgga catcttcgag      600
aaggtggacg ccatcttcga caagcacgag gtccaggaga tcaaggaaaa gatcctgaac      660
tcggactacg acgtggaaga cttctttgag ggcgagttct tcaacttcgt cctcacccag      720
gagggcatcg acgtctacaa cgccatcatc ggcggcttcg tgacgagag cggcgagaag       780 atcaagggcc tcaacgagta catcaacctc tacaaccaga agactaagca gaagctcccg      840
aagttcaagc cgctgtacaa gcaagtcctg agcgaccggg agtccctctc gttctacggc      900
gagggctaca cgagcgacga ggaggtgctg gaggtgttcc gcaacacgct gaacaagaac      960
agcgagatct tcagctcgat caagaaactc gagaagctgt tcaagaactt cgacgagtac     1020
agcagcgccg gcatcttcgt caagaacggg cccgcgatca gcaccatcag caaggacatc     1080
ttcggggagt ggaacgtgat ccgcgacaag tggaacgccg agtacgacga catccacctc     1140
aagaaaaagg cggtggtcac ggagaagtac gaggacgacc gccggaagtc cttcaagaaa     1200
atcgggagct tcagcctcga gcagctccag gagtacgcgg acgccgacct gagcgtggtg     1260
gagaagctca aggagatcat catccagaag gtcgacgaga tctacaaggt ctacggctcg     1320
agcgagaagc tgttcgacgc ggacttcgtg ctggagaagt ccctcaagaa gaacgacgcc     1380
gtggtggcca tcatgaagga tctgctcgac agcgtgaagt cgttcgagaa ctacatcaag     1440
gcattctttg gggagggcaa ggagacgaac cgggacgagt ccttctacgg ggacttcgtg     1500
ctcgcgtacg acatcctcct gaaggtcgac cacatctacg acgcgatccg gaactacgtc     1560
acgcagaagc cctacagcaa ggacaagttc aagctctact tccagaaccc gcagttcatg     1620
ggcgggtggg acaaggacaa ggagaccgac taccgggcca cgatcctgcg gtacgggtcc     1680
aagtactacc tcgccatcat ggacaagaag tacgccaagt gcctccagaa gattgacaag     1740
gacgacgtga cgggaactac cgagaagatc aactacaagc cctcccggg gcccaacaag     1800 atgctgccga aggtgttctt cagcaagaag tggatggcct actacaaccc ctcggaggac      1860
atccagaaga tatacaagaa cggcacgttc aaaaagggg acatgttcaa cctgaacgac      1920
tgccacaagc tgatcgactt tttcaaggac agcatcagcc gctacccgaa gtggtcgaac     1980
gcctacgact tcaacttctc ggagacggag aagtacaagg acattgcggg cttctaccgg     2040
gaggtggagg agcagggcta caaggtctcc ttcgagagcg cctccaagaa agaggtggac     2100
aagctcgtgg aggagggcaa gctgtacatg ttccagatct acaacaagga cttctcggac     2160
aagtcgcacg gcaccccgaa cctccacacg atgtacttca gctgctgtt cgacgagaac     2220 aaccacgggc agatccgcct cagcggcggg gcggagctgt tcatgcgccg cgcgtccctc     2280
aagaaggagg agctggtcgt gcaccccgcc aactccccga tcgcgaacaa gaaccccgac     2340
aaccccaaga agacaaccac cctctcgtac gacgtctaca aggacaagcg gttctcggag     2400
gaccagtacg agctgcacat cccgatcgcc atcaacaagt gccccaagaa catcttcaag     2460
atcaacaccg aggtgcgggt gctgctcaag cacgacgaca accccatacgt catcgggatc     2520 gaccgcggcg agcggaacct gctctacatc gtggtcgtgg acgggaaggg gaacatcgtg     2580
gagcagtaca gcctgaacga gatcatcaac aacttcaacg gcatccgcat caagacggac     2640
taccacagcc tcctggacaa gaaggagaag gagcggttcg aggcgcggca gaactggacc     2700
```

```
tccatcgaga acatcaagga gctgaaggcc ggctacatca gccaggtcgt gcacaagatc    2760
tgcgagctcg tggagaagta cgacgcggtg atcgcgctgg aggacttgaa cagcggttc     2820 aagaactccc gggtcaaggt cgagaagcag gtctaccaga agttcgagaa gatgctgatc    2880
gacaagctca actacatggt ggacaagaag tccaacccct gcgccaccgg cggcgccctc    2940
aagggctacc agatcaccaa caagttcgag tccttcaagt cgatgtctac gcagaacggg    3000
ttcattttct acatcccggc gtggctcacc agcaagatcg acccgagcac gggcttcgtc    3060
aacctcctga gaccaagta  caccagcatc gcggacagca agaagttcat ctcctcgttc    3120
gaccgcatca tgtacgtccc cgaggaagac ctgttcgagt cgccctcga  ctacaagaac    3180 ttctcccgga cggacgccga ctacatcaaa agtggaagc  tctacagcta cggcaaccgg    3240
atccgcatct tccgcaaccc caagaagaac aatgtgttcg actgggagga ggtgtgcctg    3300
acgagcgcct acaaggagct cttcaacaag tacggcatca actaccagca agggacatc     3360 cgcgcgctgc tctgcgagca gtccgacaag gcgttctact cgtcgttcat ggccctgatg    3420
agcctcatgc tccagatgcg caacagcatc accggccgga cggacgtgga cttcctgatc    3480
agcccggtca gaacagcga  cggcatttc  tacgacagcc ggaactacga ggcccaggag    3540
aacgccatcc tccccaagaa cgccgacgcg aacggcgcct acaacatcgc gcggaaggtg    3600
ctgtgggcca tcggccagtt taaaaaggcg gaggacgaga gctggacaa  ggtcaagatc    3660 gccatcagca acaaggagtg gctcgagtac gcgcagacga gcgtgaagca cggatctaag    3720
aagagaagaa ttaaacaaga ttga                                            3744

<210> SEQ ID NO 13
<211> LENGTH: 12
<212> TYPE: DNA
<213> ORGANISM: Artificial Sequence
<220> FEATURE:
<223> OTHER INFORMATION: Synthetic polynucleotide.kozak sequence

<400> SEQUENCE: 13
gccgccatgg cg                                                         12

<210> SEQ ID NO 14
<211> LENGTH: 3756
<212> TYPE: DNA
<213> ORGANISM: Artificial Sequence
<220> FEATURE:
<223> OTHER INFORMATION: Synthetic polynucleotide.kozak-NLS-LbCpf1-CO2-
      NLS

<400> SEQUENCE: 14
gccgccatgg cgggatctaa gaagagaaga attaaacaag attcgaagct cgagaagttc     60
accaactgct actcgctgag caagacgctg cggttcaagg cgatccccgt cgggaagacc    120
caggagaaca tcgacaacaa gcggctcctg gtcgaggacg agaagcgcgc cgaggactac    180
aagggcgtca gaagctgct  ggaccggtac tacctctcct tcatcaacga cgtcctgcac    240
tcgatcaagc tcaagaacct gaacaactac atctcgctgt tccgcaagaa gacacggacc    300
gagaaggaga caaggagct  cgagaacctc gagatcaacc tgcgcaagga gatcgcgaag    360
gcgttcaagg gcaacgaggg gtacaagagc ctgttcaaga aagacatcat cgagaccatc    420
ctgccggagt cctggacga  caaggacgag atcgcgctgg tgaactcgtt caacgggttc    480
accacggcct tcaccgggtt tttcgacaac cgggagaaca tgttcagcga ggaggccaag    540
tcgaccagca tcgccttccg gtgcatcaac gagaacctca cccgctacat cagcaacatg    600
```

```
gacatcttcg agaaggtgga cgccatcttc gacaagcacg aggtccagga gatcaaggaa      660
aagatcctga actcggacta cgacgtggaa gacttctttg agggcgagtt cttcaacttc      720
gtcctcaccc aggagggcat cgacgtctac aacgccatca tcggcggctt cgtgacggag      780
agcggcgaga agatcaaggg cctcaacgag tacatcaacc tctacaacca gaagactaag      840
cagaagctcc cgaagttcaa gccgctgtac aagcaagtcc tgagcgaccg ggagtccctc      900
tcgttctacg gcgagggcta cacgagcgac gaggaggtgc tggaggtgtt ccgcaacacg      960
ctgaacaaga acagcgagat cttcagctcg atcaagaaac tcgagaagct gttcaagaac     1020
ttcgacgagt acagcagcgc cggcatcttc gtcaagaacg gcccgcgat cagcaccatc      1080 agcaaggaca tcttcgggga gtggaacgtg atccgcgaca gtggaacgc cgagtacgac      1140 gacatccacc tcaagaaaaa ggcggtggtc acggagaagt acgaggacga ccgccggaag     1200
tccttcaaga aaatcgggag cttcagcctc gagcagctcc aggagtacgc ggacgccgac     1260
ctgagcgtgg tggagaagct caaggagatc atcatccaga aggtcgacga gatctacaag     1320
gtctacggct cgagcgagaa gctgttcgac gcggacttcg tgctggagaa gtccctcaag     1380
aagaacgacg ccgtggtggc catcatgaag gatctgctcg acagcgtgaa gtcgttcgag     1440
aactacatca aggcattctt tggggagggc aaggagacga accgggacga gtccttctac     1500
ggggacttcg tgctcgcgta cgacatcctc ctgaaggtcg accacatcta cgacgcgatc     1560
cggaactacg tcacgcagaa gccctacagc aaggacaagt tcaagctcta cttccagaac     1620
ccgcagttca tgggcgggtg ggacaaggac aaggagaccg actaccgggc cacgatcctg     1680
cggtacgggt ccaagtacta cctcgccatc atggacaaga agtacgccaa gtgcctccag     1740
aagattgaca aggacgacgt gaacgggaac tacgagaaga tcaactacaa gctcctcccg     1800
gggcccaaca agatgctgcc gaaggtgttc ttcagcaaga agtggatggc ctactacaac     1860
ccctcggagg acatccagaa gatatacaag aacggcacgt tcaaaaaggg ggacatgttc     1920
aacctgaacg actgccacaa gctgatcgac ttttcaagg acagcatcag ccgctacccg     1980
aagtggtcga cgcctacga cttcaacttc tcggagacgg agaagtacaa ggacattgcg     2040
ggcttctacc gggaggtgga ggagcagggc tacaaggtct ccttcgagag cgcctccaag     2100
aaagaggtgg acaagctcgt ggaggagggc aagctgtaca tgttccagat ctacaacaag     2160
gacttctcgg acaagtcgca cggcaccccg aacctccaca cgatgtactt caagctgctg     2220
ttcgacgaga caaccacgg gcagatccgc ctcagcggcg gggcggagct gttcatgcgc     2280
cgcgcgtccc tcaagaagga ggagctggtc gtgcaccccg ccaactcccc gatcgcgaac     2340
aagaaccccg acaaccccaa gaagacaacc accctctcgt acgacgtcta caaggacaag     2400
cggttctcgg aggaccagta cgagctgcac atcccgatcg ccatcaacaa gtgccccaag     2460
aacatcttca gatcaacac cgaggtgcgg gtgctgctca gcacgacga caacccctac     2520 gtcatcggga tcgaccgcgg cgagcggaac ctgctctaca tcgtggtcgt ggacgggaag     2580
gggaacatcg tggagcagta cagcctgaac gagatcatca acaacttcaa cggcatccgc     2640
atcaagacgg actaccacag cctcctggac aagaaggaga aggagcggtt cgaggcgcgg     2700
cagaactgga ccctccatcga aacatcaag gagctgaagg ccggctacat cagccaggtc     2760
gtgcacaaga tctgcgagct cgtggagaag tacgacgcgg tgatcgcgct ggaggacttg     2820
aacagcgggt tcaagaactc ccgggtcaag gtcgagaagc aggtctacca gaagttcgag     2880
aagatgctga tcgacaagct caactacatg gtggacaaga agtccaaccc ctgcgccacc     2940
```

| | | | |
|---|---|---|---|
| ggcggcgccc | tcaagggcta | ccagatcacc | aacaagttcg | agtccttcaa | gtcgatgtct | 3000 |
| acgcagaacg | ggttcatttt | ctacatcccg | gcgtggctca | ccagcaagat | cgacccgagc | 3060 |
| acgggcttcg | tcaacctcct | gaagaccaag | tacaccagca | tcgcggacag | caagaagttc | 3120 |
| atctcctcgt | tcgaccgcat | catgtacgtc | cccgaggaag | acctgttcga | gttcgccctc | 3180 |
| gactacaaga | acttctcccg | gacggacgcc | gactacatca | aaagtggaa | gctctacagc | 3240 |
| tacggcaacc | ggatccgcat | cttccgcaac | cccaagaaga | caatgtgtt | cgactgggag | 3300 |
| gaggtgtgcc | tgacgagcgc | ctacaaggag | ctcttcaaca | agtacggcat | caactaccag | 3360 |
| caaggggaca | tccgcgcgct | gctctgcgag | cagtccgaca | aggcgttcta | ctcgtcgttc | 3420 |
| atggccctga | tgagcctcat | gctccagatg | cgcaacagca | tcaccggccg | gacggacgtg | 3480 |
| gacttcctga | tcagcccggt | caagaacagc | gacggcattt | tctacgcag | ccggaactac | 3540 |
| gaggcccagg | agaacgccat | cctccccaag | aacgccgacg | cgaacggcgc | ctacaacatc | 3600 |
| gcgcggaagg | tgctgtgggc | catcggccag | tttaaaaagg | cggaggacga | gaagctggac | 3660 |
| aaggtcaaga | tcgccatcag | caacaaggag | tggctcgagt | acgcgcagac | gagcgtgaag | 3720 |
| cacggatcta | agaagagaag | aattaaacaa | gattga | | | 3756 |

<210> SEQ ID NO 15
<211> LENGTH: 6062
<212> TYPE: DNA
<213> ORGANISM: Artificial Sequence
<220> FEATURE:
<223> OTHER INFORMATION: Synthetic polynucleotide.Expression Cassette
 comprising the Zm Ubiqitin promoter cassette, koz-NLS-LbCpf1-CO2-
 NLS cassette and the Oryza sativa LTP termination sequence

<400> SEQUENCE: 15

| | | | |
|---|---|---|---|
| gtcgtgcccc | tctctagaga | taaagagcat | tgcatgtcta | aagtataaaa | aattaccaca | 60 |
| tattttttg | tcacacttat | ttgaagtgta | gtttatctat | ctctatacat | atatttaaac | 120 |
| ttcactctac | aaataatata | gtctataata | ctaaaataat | attagtgttt | tagaggatca | 180 |
| tataaataaa | ctgctagaca | tggtctaaag | gataattgaa | tattttgaca | atctacagtt | 240 |
| ttatcttttt | agtgtgcatg | tgatctctct | gttttttttg | caaatagctt | gacctatata | 300 |
| atacttcatc | cattttatta | gtacatccat | ttaggattta | gggttgatgg | tttctataga | 360 |
| ctaatttta | gtacatccat | tttattcttt | ttagtctcta | aattttttaa | aactaaaact | 420 |
| ctattttagt | ttttatttta | ataatttaga | tataaaatga | aataaaataa | attgactaca | 480 |
| aataaaacaa | ataccctta | agaaataaaa | aaactaagca | aacatttttc | ttgtttcgag | 540 |
| tagataatga | caggctgttc | aacgccgtcg | acgagtctaa | cggacaccaa | ccagcgaacc | 600 |
| agcagcgtcg | cgtcgggcca | agcgaagcag | acggcacggc | atctctgtag | ctgcctctgg | 660 |
| accctctcg | agagttccgc | tccaccgttg | gacttgctcc | gctgtcggca | tccagaaatt | 720 |
| gcgtggcgga | gcggcagacg | tgaggcggca | cggcaggcgg | cctcttcctc | ctctcacggc | 780 |
| accggcagct | acggggatt | cctttcccac | cgctccttcg | ctttcccttc | ctcgcccgcc | 840 |
| gtaataaata | gacacccct | ccacaccctc | tttcccaac | ctcgtgttcg | ttcggagcgc | 900 |
| acacacacgc | aaccagatct | cccccaaatc | cagccgtcgg | cacctccgct | tcaaggtacg | 960 |
| ccgctcatcc | tccccccccc | cctctctcta | ccttctctag | atcggcgatc | cggtccatgg | 1020 |
| ttagggcccg | gtagttctac | ttctgttcat | gtttgtgtta | gagcaaacat | gttcatgttc | 1080 |
| atgtttgtga | tgatgtggtc | tggttgggcg | gtcgttctag | atcggagtag | gatactgttt | 1140 |
| caagctacct | ggtggattta | ttaattttgt | atctgtatgt | gtgtgccata | catcttcata | 1200 |

-continued

```
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt taagatgat   1500
ggatggaaat atcgatctag gataggtata catgttgatg cgggttttac tgatgcatat  1560
acagagatgc ttttttcgc ttggttgtga tgatgtggtc tggttgggcg gtcgttctag   1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtcgc cgccatggcg ggatctaaga agagaagaat  2040
taaacaagat tcgaagctcg agaagttcac caactgctac tcgctgagca agacgctgcg  2100
gttcaaggcg atccccgtcg ggaagaccca ggagaacatc gacaacaagc ggctcctggt  2160
cgaggacgag aagcgcgccg aggactacaa gggcgtcaag aagctgctgg accggtacta  2220
cctctccttc atcaacgacg tcctgcactc gatcaagctc aagaacctga caaactacat  2280
ctcgctgttc cgcaagaaga cacggaccga gaaggagaac aaggagctcg agaacctcga  2340
gatcaacctg cgcaaggaga tcgcgaaggc gttcaagggc aacgaggggt acaagagcct  2400
gttcaagaaa gacatcatcg agaccatcct gccggagttc ctggacgaca aggacgagat  2460
cgcgctggtg aactcgttca acgggttcac cacggccttc accgggtttt tcgacaaccg  2520
ggagaacatg ttcagcgagg aggccaagtc gaccagcatc gccttccggt gcatcaacga  2580
gaacctcacc cgctacatca gcaacatgga catcttcgag aaggtggacg ccatcttcga  2640
caagcacgag gtccaggaga tcaaggaaaa gatcctgaac tcggactacg acgtggaaga  2700
cttctttgag ggcgagttct tcaacttcgt cctcacccag gagggcatcg acgtctacaa  2760
cgccatcatc ggcggcttcg tgacggagag cggcgagaag atcaagggcc tcaacgagta  2820
catcaacctc tacaaccaga agactaagca gaagctcccg aagttcaagc cgctgtacaa  2880
gcaagtcctg agcgaccggg agtccctctc gttctacggc gagggctaca cgagcgacga  2940
ggaggtgctg gaggtgttcc gcaacacgct gaacaagaac agcgagatct cagctcgat   3000
caagaaactc gagaagctgt tcaagaactt cgacgagtac agcagcgccg gcatcttcgt  3060
caagaacggg cccgcgatca gcaccatcag caaggacatc ttcggggagt ggaacgtgat  3120
ccgcgacaag tggaacgccg agtacgacga catccacctc aagaaaaagg cggtggtcac  3180
ggagaagtac gaggacgacc gccggaagtc cttcaagaaa atcgggagct tcagcctcga  3240
gcagctccag gagtacgcgg acgccgacct gagcgtggtg agaagctca aggagatcat   3300
catccagaag gtcgacgaga tctacaaggt ctacggctcg agcgagaagc tgttcgacgc  3360
ggacttcgtg ctggagaagt ccctcaagaa gaacgacgcc gtggtggcca tcatgaagga  3420
tctgctcgac agcgtgaagt cgttcgagaa ctacatcaag gcattctttg gggagggcaa  3480
ggagacgaac cgggacgagt ccttctacgg ggacttcgtg ctcgcgtacg acatcctcct  3540
```

-continued

```
gaaggtcgac cacatctacg acgcgatccg gaactacgtc acgcagaagc cctacagcaa    3600
ggacaagttc aagctctact tccagaaccc gcagttcatg ggcgggtggg acaaggacaa    3660
ggagaccgac taccgggcca cgatcctgcg gtacgggtcc aagtactacc tcgccatcat    3720
ggacaagaag tacgccaagt gcctccagaa gattgacaag gacgacgtga acgggaacta    3780
cgagaagatc aactacaagc tcctcccggg gcccaacaag atgctgccga aggtgttctt    3840
cagcaagaag tggatggcct actacaaccc ctcggaggac atccagaaga tatacaagaa    3900
cggcacgttc aaaaaggggg acatgttcaa cctgaacgac tgccacaagc tgatcgactt    3960
tttcaaggac agcatcagcc gctacccgaa gtggtcgaac gcctacgact tcaacttctc    4020
ggagacggag aagtacaagg acattgcggg cttctaccgg gaggtggagg agcagggcta    4080
caaggtctcc ttcgagacgc cctccaagaa agaggtggac aagctcgtgg aggagggcaa    4140
gctgtacatg ttccagatct acaacaagga cttctcggac aagtcgcacg gcaccccgaa    4200
cctccacacg atgtacttca agctgctgtt cgacgagaac aacccacggg c agatccgcct    4260
cagcggcggg gcggagctgt tcatgcgccg cgcgtccctc aagaaggagg agctggtcgt    4320
gcaccccgcc aactccccga tcgcgaacaa gaaccccgac aaccccaaga agacaaccac    4380
cctctcgtac gacgtctaca aggacaagcg gttctcggag gaccagtacg agctgcacat    4440
cccgatcgcc atcaacaagt gccccaagaa catcttcaag atcaacaccg aggtgcgggt    4500
gctgctcaag cacgacgaca cccctacgt catcgggatc gaccgcggcg agcggaacct    4560
gctctacatc gtggtcgtgg acgggaaggg gaacatcgtg gagcagtaca gcctgaacga    4620
gatcatcaac aacttcaacg gcatccgcat caagacggac taccacagcc tcctggacaa    4680
gaaggagaag gagcggttcg aggcgcggca gaactggacc tccatcgaga acatcaagga    4740
gctgaaggcc ggctacatca gccaggtcgt gcacaagatc tgcgagctcg tggagaagta    4800
cgacgcggtg atcgcgctgg aggacttgaa cagcgggttc aagaactccc gggtcaaggt    4860
cgagaagcag gtctaccaga agttcgagaa gatgctgatc gacaagctca actacatggt    4920
ggacaagaag tccaacccct gcgccaccgg cggcgccctc aagggctacc agatcaccaa    4980
caagttcgag tccttcaagt cgatgtctac gcagaacggg ttcattttct acatcccggc    5040
gtggctcacc agcaagatcg acccgagcac gggcttcgtc aacctcctga agaccaagta    5100
caccagcatc gcggacagca agaagttcat ctcctcgttc gaccgcatca tgtacgtccc    5160
cgaggaagac ctgttcgagt cgccctcga ctacaagaac ttctcccgga cggacgccga    5220
ctacatcaaa aagtggaagc tctacagcta cggcaaccgg atccgcatct tccgcaaccc    5280
caagaagaac aatgtgttcg actgggagga ggtgtgcctg acgagcgcct acaaggagct    5340
cttcaacaag tacggcatca actaccagca agggacatc cgcgcgctgc tctgcgagca    5400
gtccgacaag gcgttctact cgtcgttcat ggccctgatg agcctcatgc tccagatgcg    5460
caacagcatc accggccgga cggacgtgga cttcctgatc agcccggtca agaacagcga    5520
cggcattttc tacgacagcc ggaactacga ggcccaggag aacgcatcc tccccaagaa    5580
cgccgacgcg aacggcgcct acaacatcgc gcggaaggtg ctgtgggcca tcggccagtt    5640
taaaaaggcg gaggacgaga agctggacaa ggtcaagatc gccatcagca acaaggagtg    5700
gctcgagtac gcgcagacga gcgtgaagca cggatctaag aagagaagaa ttaaacaaga    5760
ttgataatcg atcctccgat cccttaatta ccataccatt acaccatgca tcaatatcca    5820
tatatatata aaccctttcg cacgtactta tactatgttt tgtcatacat atatatgtgt    5880
cgaacgatcg atctatcact gatatgatat gattgatcca tcagcctgat ctctgtatct    5940
```

```
tgttatttgt ataccgtcaa ataaaagttt cttccacttg tgttaataat tagctactct    6000
catctcatga accctatata taactagttt aatttgctgt caattgaaca tgatgatcga    6060
tg                                                                  6062
```

<210> SEQ ID NO 16
<211> LENGTH: 3744
<212> TYPE: DNA
<213> ORGANISM: Artificial Sequence
<220> FEATURE:
<223> OTHER INFORMATION: Synthetic polynucleotide.NLS-LbCpf1-Os-NLS

<400> SEQUENCE: 16

```
ggatctaaga agagaagaat taaacaagat tccaagctgg agaagtttac aaactgttac      60
agcctctcca aaaccctcag gtttaaagcg atcccggtgg gcaagaccca ggagaacatc     120
gacaacaaga ggctcctggt ggaagacgag aagcgcgccg aagactacaa gggcgtgaag     180
aagctgctcg ataggtacta cctcagcttt attaacgacg tgctgcacag catcaaactc     240
aagaatctca caactacat ctccctcttc cgcaaaaaga cccgcaccga aaggagaac      300 aaggagctgg agaacctgga gatcaacctc cgcaaggaaa tcgccaaagc gttcaagggc     360
aatgaagggt acaagagcct cttcaagaaa gacatcatcg aaactatcct cccagagttt     420
ctcgatgaca aggacgagat cgcgctggtg aactcctta acgggttcac aaccgcgttt     480
accggcttct ttgataacag gaaaatatg ttctccgagg aggccaagtc caccagcatc     540
gccttcaggt gtatcaacga aacctcacc cgctacattt ccaatatgga cattttcgag     600
aaggtggatg cgatcttcga taagcacgag gtgcaggaga tcaaagagaa gattctcaat     660
tccgattatg acgtcgagga tttcttcgaa ggggagttct ttaattttgt gctcacacaa     720
gagggcattg acgtgtacaa cgcgattatc ggggcttcg tcacagagtc cggggagaag     780
attaaggggc tgaatgagta catcaatctg tacaatcaga agaccaagca gaaactgccg     840
aaattcaagc cgctctacaa gcaagtcctg tccgataggg aaagcctctc cttctacggc     900
gagggctata ccagcgacga ggaggtgctg aagtcttcc gcaacacact gaataagaat     960
agcgagattt tctcctccat caagaagctc gagaagctct ttaagaactt tgacgagtac    1020
agctccgccg ggatttcgt gaagaacggg ccggcgatca gcaccatctc caaggacatc    1080
tttggcgagt ggaacgtcat cagggacaag tggaacgccg agtacgacga catccacctg    1140
aagaagaagg cggtggtgac cgagaagtat gaggacgatc gcaggaagtc cttcaaaaaa    1200
atcggctcct tcagcctcga acagctccag gagtatgccg atgcggatct gtccgtcgtc    1260
gagaagctga aggaaatcat cattcagaag gtcgacgaga tctataaagt gtacgggtcc    1320
agcgagaagc tgttcgacgc cgactttgtg ctcgagaagt ccctcaaaaa gaatgacgcc    1380
gtggtggcca ttatgaaaga cctgctcgac tccgtgaagt ccttcgaaaa ttacattaaa    1440
gcgttctttg ggagggaa ggaaactaac agggatgagt ccttctatgg cgactttgtc    1500
ctcgcgtacg acatcctgct gaaggtcgac acatttacg acgcgatccg caactacgtg    1560
acacagaagc cgtactccaa agacaagttc aagctgtact tccagaaccc gcaatttatg    1620
gggggctggg acaaggataa agagacagac taccgcgcga caattctccg ctatggctcc    1680
aaatactatc tggccatcat ggacaagaag tacgcgaagt gcctgcagaa gatcgacaaa    1740
gacgacgtca atgcaactat tgaaagatc aactacaagc tgctgccggg cccgaacaag    1800
atgctcccga aggtgttctt cagcaagaag tggatggcct actacaatcc aagcgaggat    1860
```

| | |
|---|---|
| attcagaaaa tctataaaaa cgggaccttc aagaagggg acatgtttaa cctcaacgac | 1920 |
| tgccacaagc tcattgattt cttcaaggat agcatttccc gctacccgaa atggtccaat | 1980 |
| gcgtacgatt ttaacttctc cgagacagaa aagtacaaag acatcgcggg cttttacagg | 2040 |
| gaggtggagg agcaagggta taaagtttct tttgaatccg cgagcaagaa ggaagtcgac | 2100 |
| aagctcgtcg aggagggcaa gctctacatg ttccaaattt ataacaagga cttttccgac | 2160 |
| aagagccatg ggaccccaaa cctccacacc atgtacttca aactgctctt tgacgagaac | 2220 |
| aaccacgggc aaatcaggct gagcggcggc gccgaattat tcatgcgcag ggcctccctc | 2280 |
| aagaaggaag agctggtcgt ccatccagcc aattccccga tcgcgaacaa gaacccggac | 2340 |
| aatccgaaaa agaccaccac cctgtcctac gacgtctaca aggacaaacg cttcagcgaa | 2400 |
| gaccagtacg aattacacat cccaattgcg attaataagt gcccaaagaa tatcttcaaa | 2460 |
| attaatacag aggtcagggt gctgctcaaa cacgacgaca atccgtatgt catcggcatt | 2520 |
| gacaggggcg agcgcaatct gctctatatc gtggtcgtgg atgggaaggg caatattgtg | 2580 |
| gagcagtact ccctgaacga gattatcaac aacttcaatg ggattaggat taagaccgac | 2640 |
| tatcacagcc tgctcgacaa gaaagaaaaa gagaggtttg aggcccgcca aaactggacc | 2700 |
| tccattgaga atatcaaaga attaaaggcc ggctatattt cccaagtcgt ccacaagatc | 2760 |
| tgcgagctgg tggagaaata tgacgccgtg attgcgctcg aagacttaaa ttctgggttc | 2820 |
| aagaactccc gcgtgaaggt ggaaaaacag gtgtatcaga aattcgagaa aatgctgatc | 2880 |
| gacaaactca attatatggt ggataagaag tccaacccgt gtgccacagg gggcgcgctg | 2940 |
| aagggctatc agatcaccaa caagttcgag agcttcaaga gcatgagcac ccagaacggg | 3000 |
| tttattttct acatcccggc gtggctcacc tccaagattg acccgagcac cggcttcgtg | 3060 |
| aacctcctga agacaaagta tacctccatt gccgacagca agaagtttat ctcctccttc | 3120 |
| gaccgcatta tgtatgtgcc ggaggaggac ctcttcgagt tcgccctcga ctacaaaaac | 3180 |
| ttcagccgca cagatgcgga ttacatcaag aagtggaagc tgtactccta cgggaacagg | 3240 |
| atccgcatct tcaggaatcc aaaaaaaaat aacgtctttg actgggagga agtgtgcctg | 3300 |
| acatccgcct acaaggaact gttcaataaa tacggcatca attaccagca gggcgacatt | 3360 |
| cgcgccctcc tctgtgagca gtccgacaaa gcgttttact ccagcttcat ggccctcatg | 3420 |
| tccctgatgc tccaaatgag gaatagcatc acagggcgca ccgacgtcga cttcctcatc | 3480 |
| agcccggtga agaactccga cgggatcttt tacgactccc gcaactatga ggcgcaagag | 3540 |
| aatgcgatcc tcccgaagaa cgccgatgcg aacgggccta taatatcgc caggaaagtg | 3600 |
| ctctgggcca tcgggcagtt caaaaaggcg gaggatgaga agctcgacaa ggtgaaaatt | 3660 |
| gccatttcca acaaggagtg gctggagtac gcgcagacct ccgtgaagca cggatctaag | 3720 |
| aagagaagaa ttaaacaaga ttga | 3744 |

<210> SEQ ID NO 17
<211> LENGTH: 3756
<212> TYPE: DNA
<213> ORGANISM: Artificial Sequence
<220> FEATURE:
<223> OTHER INFORMATION: Synthetic polynucleotide.kozak-NLS-LbCpf1-Os-NLS

<400> SEQUENCE: 17

| | |
|---|---|
| gccgccatgg cgggatctaa gaagagaaga attaaacaag attccaagct ggagaagttt | 60 |
| acaaactgtt acagcctctc caaaaccctc aggtttaaag cgatcccggt gggcaagacc | 120 |

```
caggagaaca tcgacaacaa gaggctcctg gtggaagacg agaagcgcgc cgaagactac      180
aagggcgtga agaagctgct cgataggtac tacctcagct ttattaacga cgtgctgcac      240
agcatcaaac tcaagaatct caacaactac atctccctct ccgcaaaaaa gacccgcacc      300
gagaaggaga acaaggagct ggagaacctg gagatcaacc tccgcaagga aatcgccaaa      360
gcgttcaagg gcaatgaagg gtacaagagc ctcttcaaga aagacatcat cgaaactatc      420
ctcccagagt ttctcgatga caaggacgag atcgcgctgg tgaactcctt taacgggttc      480
acaaccgcgt ttaccggctt cttttgataac agggaaaata tgttctccga ggaggccaag      540
tccaccagca tcgccttcag gtgtatcaac gagaacctca cccgctacat ttccaatatg      600
gacattttcg agaaggtgga tgcgatcttc gataagcacg aggtgcagga gatcaaagag      660
aagattctca attccgatta tgacgtcgag gatttcttcg aagggagtt ctttaatttt      720 gtgctcacac aagagggcat tgacgtgtac aacgcgatta tcggggcgctt cgtcacagag      780 tccggggaga agattaaggg gctgaatgag tacatcaatc tgtacaatca gaagaccaag      840
cagaaactgc cgaaattcaa gccgctctac aagcaagtcc tgtccgatag ggaaagcctc      900
tccttctacg gcgagggcta taccagcgac gaggaggtgc tggaagtctt ccgcaacaca      960
ctgaataaga atagcgagat tttctcctcc atcaagaagc tcgagaagct ctttaagaac     1020
tttgacgagt acagctccgc cgggatttc gtgaagaacg ggccggcgat cagcaccatc     1080
tccaaggaca tctttggcga gtggaacgtc atcagggaca gtggaacgc cgagtacgac     1140 gacatccacc tgaagaagaa ggcggtggtg accgagaagt atgaggacga tcgcaggaag     1200
tccttcaaaa aaatcggctc cttcagcctc gaacagctcc aggagtatgc cgatgcggat     1260
ctgtccgtcg tcgagaagct gaaggaaatc atcattcaga aggtcgacga gatctataaa     1320
gtgtacgggt ccagcgagaa gctgttcgac gccgactttg tgctcgagaa gtccctcaaa     1380
aagaatgacg ccgtggtggc cattatgaaa gacctgctcg actccgtgaa gtccttcgaa     1440
aattacatta aagcgttctt tggggagggg aaggaaacta acaggatga gtccttctat     1500 ggcgactttg tcctcgcgta cgacatcctg ctgaaggtcg accacattta cgacgcgatc     1560
cgcaactacg tgacacagaa gccgtactcc aaagacaagt tcaagctgta cttccagaac     1620
ccgcaattta tgggggctg ggacaaggat aaagagacag actaccgcgc gacaattctc     1680
cgctatggct ccaaatacta tctggccatc atggacaaga gtacgcgaa gtgcctgcag     1740 aagatcgaca aagacgacgt caatggcaac tatgaaaaga tcaactacaa gctgctgccg     1800
ggcccgaaca agatgctccc gaaggtgttc ttcagcaaga gtggatggc ctactacaat     1860 ccaagcgagg atattcagaa aatctataaa aacgggacct tcaagaaggg ggacatgttt     1920
aacctcaacg actgccacaa gctcattgat ttcttcaagg atagcatttc ccgctacccg     1980
aaatggtcca atgcgtacga ttttaacttc tccgagacag aaaagtacaa agacatcgcg     2040
ggcttttaca gggaggtgga ggagcaaggg tataaagttt cttttgaatc cgcgagcaag     2100
aaggaagtcg acaagctcgt cgaggagggc aagctctaca tgttccaaat ttataacaag     2160
gacttttccg acaagagcca tgggaccccca aacctccaca ccatgtactt caaactgctc     2220
tttgacgaga caaccacgg gcaaatcagg ctgagcggcg cgccgaatt attcatgcgc     2280 agggcctccc tcaagaagga agagctggtc gtccatccag ccaattcccc gatcgcgaac     2340
aagaacccgg acaatccgaa aaagaccacc accctgtcct acgacgtcta caaggacaaa     2400
cgcttcagcg aagaccagta cgaattacac atcccaattg cgattaataa gtgcccaaag     2460
aatatcttca aaattaatac agaggtcagg gtgctgctca acacgacga caatccgtat     2520
```

| | |
|---|---|
| gtcatcggca ttgacagggg cgagcgcaat ctgctctata tcgtggtcgt ggatgggaag | 2580 |
| ggcaatattg tggagcagta ctccctgaac gagattatca acaacttcaa tgggattagg | 2640 |
| attaagaccg actatcacag cctgctcgac aagaaagaaa agagaggtt tgaggcccgc | 2700 |
| caaaactgga cctccattga gaatatcaaa gaattaaagg ccggctatat ttcccaagtc | 2760 |
| gtccacaaga tctgcgagct ggtggagaaa tatgacgccg tgattgcgct cgaagactta | 2820 |
| aattctgggt tcaagaactc ccgcgtgaag gtggaaaaac aggtgtatca gaaattcgag | 2880 |
| aaaatgctga tcgacaaact caattatatg gtggataaga agtccaaccc gtgtgccaca | 2940 |
| gggggcgcgc tgaagggcta tcagatcacc aacaagttcg agagcttcaa gagcatgagc | 3000 |
| acccagaacg ggtttatttt ctacatcccg gcgtggctca cctccaagat tgacccgagc | 3060 |
| accggcttcg tgaacctcct gaagacaaag tatacctcca ttgccgacag caagaagttt | 3120 |
| atctcctcct tcgaccgcat tatgtatgtg ccggaggagg acctcttcga gttcgccctc | 3180 |
| gactacaaaa acttcagccg cacagatgcg gattacatca gaagtggaa gctgtactcc | 3240 |
| tacgggaaca ggatccgcat cttcaggaat ccaaaaaaaa ataacgtctt tgactgggag | 3300 |
| gaagtgtgcc tgcatccgc ctacaaggaa ctgttcaata atacggcat caattaccag | 3360 |
| cagggcgaca ttcgcgccct cctctgtgag cagtccgaca aagcgtttta ctccagcttc | 3420 |
| atggccctca tgtccctgat gctccaaatg aggaatagca tcacagggcg caccgacgtc | 3480 |
| gacttcctca tcagcccggt gaagaactcc gacgggatct tttacgactc ccgcaactat | 3540 |
| gaggcgcaag agaatgcgat cctcccgaag aacgccgatg cgaacggggc ctataatatc | 3600 |
| gccaggaaag tgctctgggc catcgggcag ttcaaaaagg cggaggatga aagctcgac | 3660 |
| aaggtgaaaa ttgccatttc caacaaggag tggctggagt acgcgcagac ctccgtgaag | 3720 |
| cacggatcta agaagagaag aattaaacaa gattga | 3756 |

<210> SEQ ID NO 18
<211> LENGTH: 6062
<212> TYPE: DNA
<213> ORGANISM: Artificial Sequence
<220> FEATURE:
<223> OTHER INFORMATION: Synthetic polynucleotide.Expression Cassette
    comprising the Zm Ubiqitin promoter cassette, koz-NLS-LbCpf1-Os-
    NLS cassette and the Oryza sativa LTP termination sequence

<400> SEQUENCE: 18

| | |
|---|---|
| gtcgtgcccc tctctagaga taaagagcat tgcatgtcta agtataaaa aattaccaca | 60 |
| tatttttttg tcacacttat ttgaagtgta gtttatctat ctctatacat atatttaaac | 120 |
| ttcactctac aaataatata gtctataata ctaaaataat attagtgttt tagaggatca | 180 |
| tataaataaa ctgctagaca tggtctaaag gataattgaa tattttgaca atctacagtt | 240 |
| ttatcttttt agtgtgcatg tgatctctct gttttttttg caaatagctt gacctatata | 300 |
| atacttcatc catttattta gtacatccat ttaggattta gggttgatgg tttctataga | 360 |
| ctaattttta gtacatccat tttattcttt ttagtctcta aattttttaa aactaaaact | 420 |
| ctatttagt ttttttattta ataatttaga tataaaatga aataaaataa attgactaca | 480 |
| aataaaacaa ataccccttta agaaaataaaa aaactaagca acatttttc ttgtttcgag | 540 |
| tagataatga caggctgttc aacgccgtcg acgagtctaa cggacaccaa ccagcgaacc | 600 |
| agcagcgtcg cgtcgggcca agcgaagcag acggcacggc atctctgtag ctgcctctgg | 660 |
| accccctctcg agagttccgc tccaccgttg gacttgctcc gctgtcggca tccagaaatt | 720 |

```
gcgtggcgga gcggcagacg tgaggcggca cggcaggcgg cctcttcctc ctctcacggc    780
accggcagct acgggggatt cctttcccac cgctccttcg cttttcccttc ctcgcccgcc    840
gtaataaata gacaccccct ccacaccctc tttccccaac ctcgtgttcg ttcggagcgc    900
acacacacgc aaccagatct cccccaaatc cagccgtcgg cacctccgct tcaaggtacg    960
ccgctcatcc tcccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt aagatgatg gatggaaata tcgatctagg ataggtatac atgttgatgc   1260
gggtttact gatgcatata cagagatgct ttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc ttttttctcgc ttggttgtga tgatgtggtc tggttgggcg gtcgttctag   1620
atcggagtag aatactgttt caaactacct ggtggattta ttaattttgt atctttatgt   1680
gtgtgccata catcttcata gttacgagtt aagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggattttt   1920
agccctgcct tcatacgcta tttatttgct tggtactgtt tcttttgtcc gatgctcacc   1980
ctgttgtttg gtgatacttc tgcaggtcgc cgccatggcg ggatctaaga agagaagaat   2040
taaacaagat tccaagctgg agaagtttac aaactgttac agcctctcca aaaccctcag   2100
gtttaaagcg atcccggtgg gcaagaccca ggagaacatc gacaacaaga ggctcctggt   2160
ggaagacgag aagcgcgccg aagactacaa gggcgtgaag aagctgctcg ataggtacta   2220
cctcagcttt attaacgacg tgctgcacag catcaaactc aagaatctca acaactacat   2280
ctccctcttc cgcaaaaaga cccgcaccga aaggagaaac aaggagctgg agaacctgga   2340
gatcaacctc cgcaaggaaa tcgccaaagc gttcaagggc aatgaagggt acaagagcct   2400
cttcaagaaa gacatcatcg aaactatcct cccagagttt ctcgatgaca aggacgagat   2460
cgcgctggtg aactcctttta cggggttcac aaccgcgttt accggcttct ttgataacag   2520
ggaaaatatg ttctccgagg aggccaagtc caccagcatc gccttcaggt gtatcaacga   2580
gaacctcacc cgctacattt ccaatatgga cattttcgag aaggtggatg cgatcttcga   2640
taagcacgag gtgcaggaga tcaaagagaa gattctcaat tccgattatg acgtcgagga   2700
tttcttcgaa ggggagttct ttaattttgt gctcacacaa gagggcattg acgtgtacaa   2760
cgcgattatc gggggcttcg tcacagagtc cggggagaag attaaggggc tgaatgagta   2820
catcaatctg tacaatcaga agaccaagca gaaactgccg aaattcaagc cgctctacaa   2880
gcaagtcctg tccgataggg aaagcctctc cttctacggc gagggctata ccagcgacga   2940
ggaggtgctg gaagtcttcc gcaacacact gaataagaat agcgagattt ctcctccat   3000
caagaagctc gagaagctct ttaagaactt tgacgagtac agctccgccg ggattttcgt   3060
gaagaacggg ccggcgatca gcaccatctc caaggacatc tttggcgagt ggaacgtcat   3120
```

```
cagggacaag tggaacgccg agtacgacga catccacctg aagaagaagg cggtggtgac    3180
cgagaagtat gaggacgatc gcaggaagtc cttcaaaaaa atcggctcct tcagcctcga    3240
acagctccag gagtatgccg atgcggatct gtccgtcgtc gagaagctga aggaaatcat    3300
cattcagaag gtcgacgaga tctataaagt gtacgggtcc agcgagaagc tgttcgacgc    3360
cgactttgtg ctcgagaagt ccctcaaaaa gaatgacgcc gtggtggcca ttatgaaaga    3420
cctgctcgac tccgtgaagt ccttcgaaaa ttacattaaa gcgttctttg ggaggggaa     3480
ggaaactaac agggatgagt ccttctatgg cgactttgtc ctcgcgtacg acatcctgct    3540
gaaggtcgac cacatttacg acgcgatccg caactacgtg acacagaagc cgtactccaa    3600
agacaagttc aagctgtact tccagaaccc gcaatttatg ggggctggg acaaggataa     3660
agagacagac taccgcgcga caattctccg ctatggctcc aaatactatc tggccatcat    3720
ggacaagaag tacgcgaagt gcctgcagaa gatcgacaaa gacgacgtca atggcaacta    3780
tgaaaagatc aactcaaagc tgctgccggg cccgaacaag atgctcccga aggtgttctt    3840
cagcaagaag tggatggcct actacaatcc aagcgaggat attcagaaaa tctataaaaa    3900
cgggaccttc aagaaggggg acatgtttaa cctcaacgac tgccacaagc tcattgattt    3960
cttcaaggat agcatttccc gctacccgaa atggtccaat gcgtacgatt ttaacttctc    4020
cgagacagaa aagtacaaag acatcgcggg cttttacagg gaggtggagg agcaagggta    4080
taaagtttct tttgaatccg cgagcaagaa ggaagtcgac aagctcgtcg aggagggcaa    4140
gctctacatg ttccaaattt ataacaagga cttttccgac aagagccatg gaccccaaa     4200
cctccacacc atgtacttca aactgctctt tgacgagaac aaccacgggc aaatcaggct    4260
gagcggcggc gccgaattat tcatgcgcag ggcctccctc aagaaggaag agctggtcgt    4320
ccatccagcc aattccccga tcgcgaacaa gaacccggac aatccgaaaa agaccaccac    4380
cctgtcctac gacgtctaca aggacaaacg cttcagcgaa gaccagtacg aattacacat    4440
cccaattgcg attaataagt gcccaaagaa tatcttcaaa attaatacag aggtcagggt    4500
gctgctcaaa cacgacgaca atccgtatgt catcggcatt gacaggggcg agcgcaatct    4560
gctctatatc gtggtcgtgg atgggaaggg caatattgtg gagcagtact ccctgaacga    4620
gattatcaac aacttcaatg ggattaggat taagaccgac tatcacagcc tgctcgacaa    4680
gaaagaaaaa gagaggtttg aggcccgcca aaactggacc tccattgaga atatcaaaga    4740
attaaaggcc ggctatattt cccaagtcgt ccacaagatc tgcgagctgg tggagaaata    4800
tgacgccgtg attgcgctcg aagacttaaa ttctgggttc aagaactccc gcgtgaaggt    4860
ggaaaaacag gtgtatcaga aattcgagaa aatgctgatc gacaaactca attatatggt    4920
ggataagaag tccaacccgt gtgccacagg gggcgcgctg aagggctatc agatcaccaa    4980
caagttcgag agcttcaaga gcatgagcac ccagaacggg tttatttttct acatcccggc    5040
gtggctcacc tccaagattg acccgagcac cggcttcgtg aacctcctga agacaaagta    5100
tacctccatt gccgacagca agaagtttat ctcctccttc gaccgcatta tgtatgtgcc    5160
ggaggaggac ctcttcgagt tcgccctcga ctacaaaaac ttcagccgca cagatgcgga    5220
ttacatcaag aagtggaagc tgtactccta cgggaacagg atccgcatct tcaggaatcc    5280
aaaaaaaaat aacgtctttg actgggagga agtgtgcctg acatccgcct acaaggaact    5340
gttcaataaa tacggcatca attaccagca gggcgacatt cgcgcccccc tctgtgagca    5400
gtccgacaaa gcgttttact ccagcttcat ggccctcatg tccctgatgc tccaaatgag    5460
```

-continued

| | | |
|---|---|---|
| gaatagcatc acagggcgca ccgacgtcga cttcctcatc agcccggtga agaactccga | 5520 |
| cgggatcttt tacgactccc gcaactatga ggcgcaagag aatgcgatcc tcccgaagaa | 5580 |
| cgccgatgcg aacggggcct ataatatcgc caggaaagtg ctctgggcca tcggcagtt | 5640 |
| caaaaaggcg gaggatgaga agctcgacaa ggtgaaaatt gccatttcca acaaggagtg | 5700 |
| gctggagtac gcgcagacct ccgtgaagca cggatctaag aagagaagaa ttaaacaaga | 5760 |
| ttgataatcg atcctccgat cccttaatta ccataccatt acaccatgca tcaatatcca | 5820 |
| tatatatata aacccttcg cacgtactta tactatgttt tgtcatacat atatatgtgt | 5880 |
| cgaacgatcg atctatcact gatatgatat gattgatcca tcagcctgat ctctgtatct | 5940 |
| tgttatttgt ataccgtcaa ataaaagttt cttccacttg tgttaataat tagctactct | 6000 |
| catctcatga accctatata aactagttt aatttgctgt caattgaaca tgatgatcga | 6060 |
| tg | 6062 |

<210> SEQ ID NO 19
<211> LENGTH: 6072
<212> TYPE: DNA
<213> ORGANISM: Artificial Sequence
<220> FEATURE:
<223> OTHER INFORMATION: Synthetic polynucleotide.Expression Cassette
  comprising the Zm Ubiqitin promoter cassette, NLS-LbCpf1-Os-NLS
  cassette and the Oryza sativa LTP termination sequence

<400> SEQUENCE: 19

| | | |
|---|---|---|
| gtcgtgcccc tctctagaga taaagagcat tgcatgtcta aagtataaaa aattaccaca | 60 |
| tattttttg tcacacttat ttgaagtgta gtttatctat ctctatacat atatttaaac | 120 |
| ttcactctac aaataatata gtctataata ctaaaataat attagtgttt tagaggatca | 180 |
| tataaataaa ctgctagaca tggtctaaag gataattgaa tattttgaca atctacagtt | 240 |
| ttatcttttt agtgtgcatg tgatctctct gttttttttg caaatagctt gacctatata | 300 |
| atacttcatc cattttatta gtacatccat ttaggattta gggttgatgg tttctataga | 360 |
| ctaattttta gtacatccat tttattcttt ttagtctcta aattttttaa aactaaaact | 420 |
| ctattttagt tttttattta ataatttaga tataaaatga aataaaataa attgactaca | 480 |
| aataaaacaa ataccctta agaaataaaa aaactaagca acattttttc ttgtttcgag | 540 |
| tagataatga caggctgttc aacgccgtcg acgagtctaa cggacaccaa ccagcgaacc | 600 |
| agcagcgtcg cgtcgggcca agcgaagcag acggcacggc atctctgtag ctgcctctgg | 660 |
| accctctcg agagttccgc tccaccgttg gacttgctcc gctgtcggca tccagaaatt | 720 |
| gcgtggcgga gcggcagacg tgaggcggca cggcaggcgg cctcttcctc ctctcacggc | 780 |
| accggcagct acgggggatt cctttcccac cgctccttcg cttcccttc ctcgcccgcc | 840 |
| gtaataaata gacacccct ccacaccctc tttcccaac ctcgtgttcg ttcggagcgc | 900 |
| acacacacgc aaccagatct cccccaaatc cagccgtcgg cacctccgct tcaaggtacg | 960 |
| ccgctcatcc tcccccccc cctctctcta ccttctctag atcggcgatc cggtccatgg | 1020 |
| ttagggcccg gtagttctac ttctgttcat gtttgtgtta gagcaaacat gttcatgttc | 1080 |
| atgtttgtga tgatgtggtc tggttgggcg gtcgttctag atcggagtag gatactgttt | 1140 |
| caagctacct ggtggattta ttaattttgt atctgtatgt gtgtgccata catcttcata | 1200 |
| gttacgagtt taagatgatg gatggaaata tcgatctagg ataggtatac atgttgatgc | 1260 |
| gggttttact gatgcatata cagagatgct ttttttctcg cttggttgtg atgatatggt | 1320 |
| ctggttgggc ggtcgttcta gatcggagta gaatactgtt tcaaactacc tggtggattt | 1380 |

```
attaaaggat aaagggtcgt tctagatcgg agtagaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc ttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttt    1920 agccctgcct tcatacgcta tttatttgct tggtactgtt tcttttgtcc gatgctcacc    1980
ctgttgtttg gtgatacttc tgcaggtccg gtaccatggg atcaagaag agaagaatta    2040 aacaagatat gtccaagctg gagaagttta caaactgtta cagcctctcc aaaaccctca    2100
ggtttaaagc gatcccggtg ggcaagaccc aggagaacat cgacaacaag aggctcctgg    2160
tggaagacga gaagcgcgcc gaagactaca agggcgtgaa gaagctgctc gataggtact    2220
acctcagctt tattaacgac gtgctgcaca gcatcaaact caagaatctc aacaactaca    2280
tctccctctt ccgcaaaaag acccgcaccg agaaggagaa caaggagctg agaacctgg    2340 agatcaacct ccgcaaggaa atcgccaaag cgttcaaggg caatgaaggg tacaagagcc    2400
tcttcaagaa agacatcatc gaaactatcc tcccagagtt tctcgatgac aaggacgaga    2460
tcgcgctggt gaactccttt aacgggttca caaccgcgtt taccggcttc tttgataaca    2520
gggaaaatat gttctccgag gaggccaagt ccaccagcat cgccttcagg tgtatcaacg    2580
agaacctcac ccgctacatt tccaatatgg acattttcga aaggtggat gcgatcttcg    2640 ataagcacga ggtgcaggag atcaaagaga agattctcaa ttccgattat gacgtcgagg    2700
atttcttcga aggggagttc tttaattttg tgctcacaca agagggcatt gacgtgtaca    2760
acgcgattat cggggcttc gtcacagagt ccggggagaa gattaagggg ctgaatgagt    2820
acatcaatct gtacaatcag aagaccaagc agaaactgcc gaaattcaag ccgctctaca    2880
agcaagtcct gtccgatagg gaaagcctct ccttctacgg cgagggctat accagcgacg    2940
aggaggtgct ggaagtcttc cgcaacacac tgaataagaa tagcgagatt ttctcctcca    3000
tcaagaagct cgagaagctc tttaagaact tgacgagta cagctccgcc gggattttcg    3060
tgaagaacgg gccggcgatc agcaccatct ccaaggacat ctttggcgag tggaacgtca    3120
tcagggacaa gtggaacgcc gagtacgacg acatccacct gaagaagaag gcggtggtga    3180
ccgagaagta tgaggacgat cgcaggaagt ccttcaaaaa atcggctcc ttcagcctcg    3240 aacagctcca ggagtatgcc gatgcggatc tgtccgtcgt cgagaagctg aaggaaatca    3300
tcattcagaa ggtcgacgag atctataaag tgtacgggtc cagcgagaag ctgttcgacg    3360
ccgactttgt gctcgagaag tccctcaaaa agaatgacgc cgtggtggcc attatgaaag    3420
acctgctcga ctccgtgaag tccttcgaaa attacattaa agcgttcttt ggggagggga    3480
aggaaactaa cagggatgag tccttctatg gcgactttgt cctcgcgtac gacatcctgc    3540
tgaaggtcga ccacatttac gacgcgatcc gcaactacgt gacacagaag ccgtactcca    3600
aagacaagtt caagctgtac ttccagaacc cgcaatttat gggggctgg acaaggata    3660 aagagacaga ctaccgcgcg acaattctcc gctatggctc caaatactat ctggccatca    3720
```

```
tggacaagaa gtacgcgaag tgcctgcaga agatcgacaa agacgacgtc aatggcaact    3780
atgaaaagat caactacaag ctgctgccgg gcccgaacaa gatgctcccg aaggtgttct    3840
tcagcaagaa gtggatggcc tactacaatc caagcgagga tattcagaaa atctataaaa    3900
acgggacctt caagaagggg gacatgttta acctcaacga ctgccacaag ctcattgatt    3960
tcttcaagga tagcatttcc cgctacccga aatggtccaa tgcgtacgat tttaacttct    4020
ccgagacaga aaagtacaaa gacatcgcgg gcttttacag ggaggtggag gagcaagggt    4080
ataaagtttc ttttgaatcc gcgagcaaga aggaagtcga caagctcgtc gaggagggca    4140
agctctacat gttccaaatt tataacaagg acttttccga caagagccat gggaccccaa    4200
acctccacac catgtacttc aaactgctct ttgacgagaa caaccacggg caaatcaggc    4260
tgagcggcgg cgccgaatta ttcatgcgca gggcctccct caagaaggaa gagctggtcg    4320
tccatccagc caattccccg atcgcgaaca agaacccgga caatccgaaa aagaccacca    4380
ccctgtccta cgacgtctac aaggacaaac gcttcagcga agaccagtac gaattacaca    4440
tcccaattgc gattaataag tgcccaaaga atatcttcaa aattaataca gaggtcaggg    4500
tgctgctcaa acacgacgac aatccgtatg tcatcggcat tgacaggggc gagcgcaatc    4560
tgctctatat cgtggtcgtg gatgggaagg gcaatattgt ggagcagtac tccctgaacg    4620
agattatcaa caacttcaat gggattagga ttaagaccga ctatcacagc ctgctcgaca    4680
agaaagaaaa agagaggttt gaggcccgcc aaaactggac ctccattgag aatatcaaag    4740
aattaaaggc cggctatatt tcccaagtcg tccacaagat ctgcgagctg gtggagaaat    4800
atgacgccgt gattgcgctc gaagacttaa attctgggtt caagaactcc cgcgtgaagg    4860
tggaaaaaca ggtgtatcag aaattcgaga aaatgctgat cgacaaactc aattatatgg    4920
tggataagaa gtccaacccg tgtgccacag ggggcgcgct gaagggctat cagatcacca    4980
acaagttcga gagcttcaag agcatgagca cccagaacgg gtttatttc tacatcccgg    5040 cgtggctcac ctccaagatt gacccgagca ccggcttcgt gaacctcctg aagacaaagt    5100
atacctccat tgccgacagc aagaagttta tctcctcctt cgaccgcatt atgtatgtgc    5160
cggaggagga cctcttcgag ttcgccctcg actacaaaaa cttcagccgc acagatgcgg    5220
attacatcaa gaagtggaag ctgtactcct acggaacag atccgcatc ttcaggaatc    5280 caaaaaaaaa taacgtcttt gactgggagg aagtgtgcct gacatccgcc tacaaggaac    5340
tgttcaataa atacggcatc aattaccagc agggcgacat tcgcgccctc ctctgtgagc    5400
agtccgacaa agcgttttac tccagcttca tggcctcat gtccctgatg ctccaaatga    5460
ggaatagcat cacagggcgc accgacgtcg acttcctcat cagcccggtg aagaactccg    5520
acgggatctt ttacgactcc cgcaactatg aggcgcaaga gaatgcgatc ctcccgaaga    5580
acgccgatgc gaacggggcc tataatatcg ccaggaaagt gctctgggcc atcgggcagt    5640
tcaaaaaggc ggaggatgag aagctcgaca aggtgaaaat tgccatttcc aacaaggagt    5700
ggctggagta cgcgcagacc tccgtgaagc acggatctaa gaagagaaga attaaacaag    5760
attgattaat taatcgatcc tccgatccct aattaccat gccattacac catgcatcaa    5820
tatccatata tatataaacc ctttcgcacg tacttatact atgttttgtc atacatatat    5880
atgtgtcgaa cgatcgatct atcactgata tgatatgatt gatccatcag cctgatctct    5940
gtatcttgtt atttgtatac cgtcaaataa aagtttcttc cacttgtgtt aataattagc    6000
tactctcatc tcatgaaccc tatatataac tagtttaatt tgctgtcaat tgaacatgat    6060
gatcgatgcc tg                                                        6072
```

<210> SEQ ID NO 20
<211> LENGTH: 5091
<212> TYPE: DNA
<213> ORGANISM: Artificial Sequence
<220> FEATURE:
<223> OTHER INFORMATION: Synthetic polynucleotide.Expression Cassette
      comprising the DaMV promoter cassette, NLS-LbCpf1-CO2-NLS cassette
      and a Medicago truncatula termination sequence

<400> SEQUENCE: 20

```
agacatcctg gaccaatatg ctgaagatta tgctacctac accaggatag gacttgaagc      60
acttaacctt gaagattggt tcgaagaacc agaacccgat ccacctaacc ctgtggaccg     120
ccagaggata gaggacatcc tggacctact gaacgtcagc aatgacgact gaaagattcc     180
caggacaccg gcggaagtgg tggacccagt ctaggtgcga tgcttagtcg cgcacgatga     240
ctatgtcgga aggcatcttt gctttcggca aactttagta atactttaag gaaagtattg     300
tacaagttag gtgcagagac aataatgcac ccagctttag ctttgtttat ggaattattg     360
tgtcggttgc attattggat gcctgcgtgc accctaagca atcaacggag aaacaaagat     420
aaaaatcaat tactcacatg aaagagtatt gatcacgagt cactatggag cgacaatctc     480
cagacaggat gtcagcatct tatcttcctt tgaagaaagc atcatcaata acgatgtaat     540
ggtgggggaca tccactaagt tattgctctg caaacagctc aaaaagctac tggccgacaa     600
tcataattgc tcggcatgtg caggtggggc ctccactagc aataatacaa gctttacagc     660
ttgcagtgac tcatcctcca ataatggaga aaaagacgtc agcagtgacg aacaagggtc     720
gaaagacttg cctatataag ggcattctcc cctcagttga agatcatcga agttggagc     780
aataaactct ctcttcaaca aatctatctt ttatctttta tcggtaccaa aaaatggcgg     840
gatctaagaa gagaagaatt aaacaagatt cgaagctcga gaagttcacc aactgctact     900
cgctgagcaa gacgctgcgg ttcaaggcga tccccgtcgg gaagacccag gagaacatcg     960
acaacaagcg gctcctggtc gaggacgaga agcgcgccga ggactacaag ggcgtcaaga    1020
agctgctgga ccggtactac ctctccttca tcaacgacgt cctgcactcg atcaagctca    1080
agaacctgaa caactacatc tcgctgttcc gcaagaagac acggaccgag aaggagaaca    1140
aggagctcga gaacctcgag atcaacctgc gcaaggagat cgcgaaggcg ttcaagggca    1200
acgagggta caagagcctg ttcaagaaag acatcatcga gaccatcctg ccggagttcc    1260
tggacgacaa ggacgagatc gcgctggtga actcgttcaa cgggttcacc acggccttca    1320
ccgggttttt cgacaaccgg gagaacatgt tcagcgagga ggccaagtcg accagcatcg    1380
ccttccggtg catcaacgag aacctcaccc gctacatcag caacatggac atcttcgaga    1440
aggtggacgc catcttcgac aagcacgagg tccaggagat caaggaaaag atcctgaact    1500
cggactacga cgtggaagac ttctttgagg gcgagttctt caacttcgtc ctcacccagg    1560
agggcatcga cgtctacaac gccatcatcg gcggcttcgt gacggagagc ggcgagaaga    1620
tcaagggcct caacgagtac atcaacctct acaaccagaa gactaagcag aagctcccga    1680
agttcaagcc gctgtacaag caagtcctga gcgaccggga gtccctctcg ttctacggcg    1740
agggctacac gagcgacgag gaggtgctgg aggtgttccg caacacgctg aacaagaaca    1800
gcgagatctt cagctcgatc aagaaactcg agaagctgtt caagaacttc gacgagtaca    1860
gcagcgccgg catcttcgtc aagaacgggc ccgcgatcag caccatcagc aaggacatct    1920
tcggggagtg gaacgtgatc cgcgacaagt ggaacgccga gtacgacgac atccaccta   1980
```

```
agaaaaaggc ggtggtcacg gagaagtacg aggacgaccg ccggaagtcc ttcaagaaaa    2040
tcgggagctt cagcctcgag cagctccagg agtacgcgga cgccgacctg agcgtggtgg    2100
agaagctcaa ggagatcatc atccagaagg tcgacgagat ctacaaggtc tacggctcga    2160
gcgagaagct gttcgacgcg gacttcgtgc tggagaagtc cctcaagaag aacgacgccg    2220
tggtggccat catgaaggat ctgctcgaca gcgtgaagtc gttcgagaac tacatcaagg    2280
cattctttgg ggagggcaag gagacgaacc gggacgagtc cttctacggg gacttcgtgc    2340
tcgcgtacga catcctcctg aaggtcgacc acatctacga cgcgatccgg aactacgtca    2400
cgcagaagcc ctacagcaag gacaagttca agctctactt ccagaacccg cagttcatgg    2460
gcgggtggga caaggacaag gagaccgact accgggccac gatcctgcgg tacgggtcca    2520
agtactacct cgccatcatg gacaagaagt acgccaagtg cctccagaag attgacaagg    2580
acgacgtgaa cgggaactac gagaagatca actacaagct cctcccgggg cccaacaaga    2640
tgctgccgaa ggtgttcttc agcaagaagt ggatggccta ctacaacccc tcggaggaca    2700
tccagaagat atacaagaac ggcacgttca aaaaggggga catgttcaac ctgaacgact    2760
gccacaagct gatcgacttt ttcaaggaca gcatcagccg ctacccgaag tggtcgaacg    2820
cctacgactt caacttctcg gagacggaga agtacaagga cattgcgggc ttctaccggg    2880
aggtggagga gcagggctac aaggtctcct tcgagagcgc ctccaagaaa gaggtggaca    2940
agctcgtgga ggagggcaag ctgtacatgt tccagatcta caacaaggac ttctcggaca    3000
agtcgcacgg caccccgaac ctccacacga tgtacttcaa gctgctgttc gacgagaaca    3060
accacgggca gatccgcctc agcggcgggg cggagctgtt catgcgccgc gcgtccctca    3120
agaaggagga gctggtcgtg caccccgcca actcccgat cgcgaacaag aaccccgaca    3180
accccaagaa gacaaccacc ctctcgtacg acgtctacaa ggacaagcgg ttctcggagg    3240
accagtacga gctgcacatc ccgatcgcca tcaacaagtg ccccaagaac atcttcaaga    3300
tcaacaccga ggtgcgggtg ctgctcaagc acgacgacaa cccctacgtc atcgggatcg    3360
accgcggcga gcggaacctg ctctacatcg tggtcgtgga cgggaagggg aacatcgtgg    3420
agcagtacag cctgaacgag atcatcaaca acttcaacgg catccgcatc aagacggact    3480
accacagcct cctggacaag aaggagaagg agcggttcga ggcgcggcag aactggacct    3540
ccatcgagaa catcaaggag ctgaaggccg gctacatcag ccaggtcgtg cacaagatct    3600
gcgagctcgt ggagaagtac gacgcggtga tcgcgctgga ggacttgaac agcgggttca    3660
agaactcccg ggtcaaggtc gagaagcagg tctaccagaa gttcgagaag atgctgatcg    3720
acaagctcaa ctacatggtg gacaagaagt ccaacccctg cgccaccggc ggcgccctca    3780
agggctacca gatcaccaac aagttcgagt ccttcaagtc gatgtctacg cagaacgggt    3840 tcatttcta catcccggcg tggctcacca gcaagatcga cccgagcacg ggcttcgtca    3900
acctcctgaa gaccaagtac accagcatcg cggacagcaa gaagttcatc tcctcgttcg    3960
accgcatcat gtacgtcccc gaggaagacc tgttcgagtt cgccctcgac tacaagaact    4020
tctcccggac ggacgccgac tacatcaaaa agtggaagct ctacagctac ggcaaccgga    4080
tccgcatctt ccgcaacccc aagaagaaca atgtgttcga ctgggaggag gtgtgcctga    4140
cgagcgccta caaggagctc ttcaacaagt acggcatcaa ctaccagcaa ggggacatcc    4200
gcgcgctgct ctgcgagcag tccgacaagg cgttctacta gtcgttcatg gccctgatga    4260
gcctcatgct ccagatgcgc aacagcatca ccggccggac ggacgtggac ttcctgatca    4320
gcccggtcaa gaacagcgac ggcattttct acgacagccg gaactacgag gcccaggaga    4380
```

```
acgccatcct ccccaagaac gccgacgcga acggcgccta caacatcgcg cggaaggtgc    4440
tgtgggccat cggccagttt aaaaaggcgg aggacgagaa gctggacaag gtcaagatcg    4500
ccatcagcaa caaggagtgg ctcgagtacg cgcagacgag cgtgaagcac ggatctaaga    4560
agagaagaat taaacaagat tgacttaatt aaagggctct ctgtcatgat ttcatacttt    4620
cattattgag ctctgtaatt acaattatga ccatgagaac atctcttatt gtgtggcctt    4680
ttaattgctg atgttagtac tgaaccaaag cttatcgtga tgatgtaaaa gcaataagta    4740
cttgtttgta gcttctttgt gtctcccttt gggcttaata catctgttta gtgttgtggc    4800
tttggcatag acttctcttg gtaataatgc cttgcaatgc aaaatttcaa ttatcaaatt    4860
ctattatgtt ctcaccttat ggtaacagct taccctgtgg aagatgagat tcttgagttg    4920
agtcattgcc aattttggc attagctttt gaattagtga atttgacaa aaattaccgt    4980 gacactgatt tgttgaagc tcttaagtgt agtttttaca aatttcagt ggctcgttgt    5040 gattatgtca aactcacggc gaatgtagtt cttacagaat ttcagtggct c            5091
```

<210> SEQ ID NO 21
<211> LENGTH: 5091
<212> TYPE: DNA
<213> ORGANISM: Artificial Sequence
<220> FEATURE:
<223> OTHER INFORMATION: Synthetic polynucleotide.Expression Cassette
      comprising the DaMV promoter cassette, NLS-LbCpf1-Os-NLS cassette
      and a Medicago truncatula termination sequence

<400> SEQUENCE: 21

```
agacatcctg gaccaatatg ctgaagatta tgctacctac accaggatag gacttgaagc      60
acttaacctt gaagattggt tcgaagaacc agaacccgat ccacctaacc ctgtggaccg     120
ccagaggata gaggacatcc tggacctact gaacgtcagc aatgacgact gaaagattcc     180
caggacaccg gcggaagtgg tggacccagt ctaggtgcga tgcttagtcg cgcacgatga     240
ctatgtcgga aggcatcttt gctttcggca aactttagta atactttaag gaaagtattg     300
tacaagttag gtgcagagac aataatgcac ccagctttag cttgttttat ggaattattg     360
tgtcggttgc attattggat gcctgcgtgc accctaagca atcaacggag aaacaaagat     420
aaaaatcaat tactcacatg aaagagtatt gatcacgagt cactatggag cgacaatctc     480
cagacaggat gtcagcatct tatcttcctt tgaagaaagc atcatcaata acgatgtaat     540
ggtggggaca tccactaagt tattgctctg caaacagctc aaaaagctac tggccgacaa     600
tcataattgc tcggcatgtg caggtggggc tccactagc aataatacaa gctttacagc      660
ttgcagtgac tcatcctcca ataatggaga aaaagacgtc agcagtgacg aacaagggtc     720
gaaagacttg cctatataag ggcattctcc cctcagttga agatcatcga agttggagc      780 aataaactct ctcttcaaca aatctatctt ttatctttta tcggtaccaa aaaatggcgg     840
gatctaagaa gagaagaatt aaacaagatt ccaagctgga gaagtttaca aactgttaca     900
gcctctccaa aaccctcagg tttaaagcga tcccggtggg caagacccag agaacatcg      960 acaacaagag gctcctggtg gaagacgaga agcgcgccga agactacaag ggcgtgaaga    1020
agctgctcga taggtactac ctcagcttta ttaacgacgt gctgcacagc atcaaactca    1080
agaatctcaa caactacatc tccctcttcc gcaaaaagac ccgcaccgag aaggagaaca    1140
aggagctgga gaacctggag atcaacctcc gcaaggaaat cgccaaagcg ttcaaggca     1200 atgaagggta caagagcctc ttcaagaaag acatcatcga aactatcctc ccagagtttc    1260
```

```
tcgatgacaa ggacgagatc gcgctggtga actcctttaa cgggttcaca accgcgttta   1320
ccggcttctt tgataacagg gaaaatatgt tctccgagga ggccaagtcc accagcatcg   1380
ccttcaggtg tatcaacgag aacctcaccc gctacatttc caatatggac attttcgaga   1440
aggtggatgc gatcttcgat aagcacgagg tgcaggagat caaagagaag attctcaatt   1500
ccgattatga cgtcgaggat ttcttcgaag gggagttctt taattttgtg ctcacacaag   1560
agggcattga cgtgtacaac gcgattatcg ggggcttcgt cacagagtcc ggggagaaga   1620
ttaaggggct gaatgagtac atcaatctgt acaatcagaa gaccaagcag aaactgccga   1680
aattcaagcc gctctacaag caagtcctgt ccgataggga aagcctctcc ttctacggcg   1740
agggctatac cagcgacgag gaggtgctgg aagtcttccg caacacactg aataagaata   1800
gcgagatttt ctcctccatc aagaagctcg agaagctctt taagaacttt gacgagtaca   1860
gctccgccgg gattttcgtg aagaacgggc cggcgatcag caccatctcc aaggacatct   1920
ttggcgagtg gaacgtcatc agggacaagt ggaacgccga gtacgacgac atccacctga   1980
agaagaaggc ggtggtgacc gagaagtatg aggacgatcg caggaagtcc ttcaaaaaaa   2040
tcggctcctt cagcctcgaa cagctccagg agtatgccga tgcggatctg tccgtcgtcg   2100
agaagctgaa ggaaatcatc attcagaagg tcgacgagat ctataaagtg tacgggtcca   2160
gcgagaagct gttcgacgcc gactttgtgc tcgagaagtc cctcaaaaag aatgacgccg   2220
tggtggccat tatgaaagac ctgctcgact ccgtgaagtc cttcgaaaat tacattaaag   2280
cgttctttgg ggaggggaag gaaactaaca gggatgagtc cttctatggc gactttgtcc   2340
tcgcgtacga catcctgctg aaggtcgacc acatttacga cgcgatccgc aactacgtga   2400
cacagaagcc gtactccaaa gacaagttca gctgtactt ccagaacccg caatttatgg   2460
ggggctggga caaggataaa gagacagact accgcgcgac aattctccgc tatggctcca   2520
aatactatct ggccatcatg gacaagaagt acgcgaagtg cctgcagaag atcgacaaag   2580
acgacgtcaa tggcaactat gaaaagatca actacaagct gctgccgggc cgaacaaga   2640
tgctcccgaa ggtgttcttc agcaagaagt ggatggccta ctacaatcca gcgaggata   2700
ttcagaaaat ctataaaaac gggaccttca agaaggggga catgtttaac ctcaacgact   2760
gccacaagct cattgatttc ttcaaggata gcatttcccg ctacccgaaa tggtccaatg   2820
cgtacgattt taacttctcc gagacagaaa agtacaaaga catcgcgggc ttttacaggg   2880
aggtggagga gcaagggtat aaagtttctt ttgaatccgc gagcaagaag gaagtcgaca   2940
agctcgtcga ggagggcaag ctctacatgt tccaaattta taacaaggac ttttccgaca   3000
agagccatgg gaccccaaac ctccacacca tgtacttcaa actgctcttt gacgagaaca   3060
accacgggca aatcaggctg agcggcggcg ccgaattatt catgcgcagg gcctccctca   3120
agaaggaaga gctggtcgtc catccagcca attccccgat cgcgaacaag aacccggaca   3180
atccgaaaaa gaccaccacc ctgtcctacg acgtctacaa ggacaaacgc ttcagcgaag   3240
accagtacga attacacatc ccaattgcga ttaataagtg cccaaagaat atcttcaaaa   3300
ttaatacaga ggtcagggtg ctgctcaaac gacgacaa tccgtatgtc atcggcattg   3360
acaggggcga gcgcaatctg ctctatatcg tggtcgtgga tgggaagggc aatattgtgg   3420
agcagtactc cctgaacgag attatcaaca acttcaatgg gattaggatt aagaccgact   3480
atcacagccc tgctcgacaag aaagaaaaag agaggtttga ggcccgccaa aactggacct   3540
ccattgagaa tatcaaagaa ttaaaggccg gctatatttc ccaagtcgtc cacaagatct   3600
gcgagctggt ggagaaatat gacgccgtga ttgcgctcga agacttaaat tctgggttca   3660
```

```
agaactcccg cgtgaaggtg gaaaaacagg tgtatcagaa attcgagaaa atgctgatcg    3720
acaaactcaa ttatatggtg gataagaagt ccaacccgtg tgccacaggg ggcgcgctga    3780
agggctatca gatcaccaac aagttcgaga gcttcaagag catgagcacc cagaacgggt    3840
ttattttcta catcccggcg tggctcacct ccaagattga cccgagcacc ggcttcgtga    3900
acctcctgaa gacaaagtat acctccattg ccgacagcaa gaagtttatc tcctccttcg    3960
accgcattat gtatgtgccg gaggaggacc tcttcgagtt cgccctcgac tacaaaaact    4020
tcagccgcac agatgcggat tacatcaaga agtggaagct gtactcctac gggaacagga    4080
tccgcatctt caggaatcca aaaaaaaata acgtctttga ctgggaggaa gtgtgcctga    4140
catccgccta caaggaactg ttcaataaat acggcatcaa ttaccagcag ggcgacattc    4200
gcgccctcct ctgtgagcag tccgacaaag cgttttactc cagcttcatg gccctcatgt    4260
ccctgatgct ccaaatgagg aatagcatca cagggcgcac cgacgtcgac ttcctcatca    4320
gcccggtgaa gaactccgac gggatctttt acgactcccg caactatgag gcgcaagaga    4380
atgcgatcct cccgaagaac gccgatgcga acggggccta atatcgcc aggaaagtgc      4440 tctgggccat cgggcagttc aaaaaggcgg aggatgagaa gctcgacaag gtgaaaattg    4500
ccatttccaa caaggagtgg ctggagtacg cgcagacctc cgtgaagcac ggatctaaga    4560
agagaagaat taaacaagat tgacttaatt aaagggctct ctgtcatgat ttcatacttt    4620
cattattgag ctctgtaatt acaattatga ccatgagaac atctcttatt gtgtggcctt    4680
ttaattgctg atgttagtac tgaaccaaag cttatcgtga tgatgtaaaa gcaataagta    4740
cttgtttgta gcttctttgt gtctcccttt gggcttaata catctgttta gtgttgtggc    4800
tttggcatag acttctcttg gtaataatgc cttgcaatgc aaaatttcaa ttatcaaatt    4860
ctattatgtt ctcaccttat ggtaacagct taccctgtgg aagatgagat tcttgagttg    4920
agtcattgcc aattttggc attagctttt gaattagtga attttgacaa aaattaccgt     4980
gacactgatt tgttgaagc tcttaagtgt agtttttaca aaatttcagt ggctcgttgt      5040
gattatgtca aactcacggc gaatgtagtt cttacagaat ttcagtggct c              5091
```

<210> SEQ ID NO 22
<211> LENGTH: 1000
<212> TYPE: DNA
<213> ORGANISM: Medicago truncatula

<400> SEQUENCE: 22

```
actgttaata attttttaaac gtcagcgcac taaaaaaacg aaaagacgga cacgtgaaaa      60
taaaaaacac acactagttt atgacgcaat actattttac ttatgatttg ggtacattag     120
acaaaaccgt gaaagagatg tatcagctat gaaacctgta tacttcaata cagagacgta     180
ctcatatcgg atacgtacgc acgaagtatc atattaatta ttttaatttt taataaatat     240
tttatcggat acttatgtga tactctacat atacacaagg atatttctaa gatactttat     300
agatacgtat cctagaaaaa catgaagagt aaaaagtga gacaatgttg taaaaattca       360
ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttcttttaa tgatgtttct ctcaatatca catcatatga    540
aaatgtaata tgatttataa gaaaatttt aaaaaaattta ttttaataat cacatgtact    600
attttttaaa aattgtatct tttataataa tacaataata aagagtaatc agtgttaatt    660
```

```
tttcttcaaa tataagtttt attataaatc attgttaacg tatcataagt cattaccgta      720
tcgtatctta attttttttt aaaaaccgct aattcacgta cccgtattgt attgtacccg      780
cacctgtatc acaatcgatc ttagttagaa gaattgtctc gaggcggtgc aagacagcat      840
ataatagacg tggactctct tataccaaac gttgtcgtat cacaaagggt taggtaacaa      900
gtcacagttt gtccacgtgt cacgttttaa ttggaagagc tgccgttggc gtaatataac      960
agccaatcga tttttgctat aaaagcaaat caggtaaact                           1000

<210> SEQ ID NO 23
<211> LENGTH: 92
<212> TYPE: DNA
<213> ORGANISM: Medicago truncatula

<400> SEQUENCE: 23
aaacttcttc attcttttct tccccatcgc tacaaaaccg gttcctttgg aaaagagatt       60
cattcaaacc tagcacccaa ttccgtttca ag                                     92

<210> SEQ ID NO 24
<211> LENGTH: 499
<212> TYPE: DNA
<213> ORGANISM: Medicago truncatula

<400> SEQUENCE: 24
gtataatcta ctttctattc ttcgattatt ttattattat tagctactat cgtttaatcg       60
atcttttctt ttgatccgtc aaatttaaat tcaattaggg ttttgttctt ttctttcatc      120
tgattgaaat ccttctgaat tgaaccgttt acttgatttt actgtttatt gtatgattta      180
atcctttgtt tttcaaagac agtctttaga ttgtgattag gggttcatat aaatttttag      240
atttggattt ttgtattgta tgattcaaaa aatacgtcct ttaattagat tagtacatgg      300
atatttttta cccgatttat tgattgtcag ggagaatttg atgagcaagt ttttttgatg      360
tctgttgtaa attgaattga ttataattgc tgatctgctg cttccagttt tcataaccca      420
tattctttta accttgttgt acacacaatg aaaaattggt gattgattca tttgttttc       480 tttgttttgg attatacag                                                   499

<210> SEQ ID NO 25
<211> LENGTH: 500
<212> TYPE: DNA
<213> ORGANISM: Medicago truncatula

<400> SEQUENCE: 25
ttaatcatct gaaactgttc accatgcatg caatcttgtg aaatatatgg ttttaattag       60
acttcaatct tatgttggct attgtactaa taaaagcatg tcatgttatt ttcatttgat      120
tttatctgta ctttggtttg tttgaagaat aaagatgagc ttgctatgca tgcatgcatg      180
ccatcgatta tcagggtttc cttttttctt ttctggcttc ccatcaattt ggtgtgaatt      240
agtgtgtgtg atatattata ttatgctatt tatgaaataa attgttggtt atatttgatc      300
tacaatctac atacatgtga tttttatcaa caaaatatct cgggaaacaa tacctttttg      360
gtagcaaaat tcaaataata ctattttaaa taaatcaaag ttaaccaata ccttattcaa      420
gttggagggg tctcaaacaa gcaaagaat tcaagttgtt aatgaacttc ggttaatgat       480
aaaagaattc gcatttaaaa                                                  500

<210> SEQ ID NO 26
<211> LENGTH: 5856
```

<212> TYPE: DNA
<213> ORGANISM: Artificial Sequence
<220> FEATURE:
<223> OTHER INFORMATION: Synthetic polynucleotide.Expression cassette
      comprising Medicago truncatula promoter cassette, NLS-LbCpf1-CO2-
      NLS and Medicago truncatula termination sequence

<400> SEQUENCE: 26

```
actgttaata attttaaac gtcagcgcac taaaaaacg aaaagacgga cacgtgaaaa       60
taaaaaacac acactagttt atgacgcaat actatttac ttatgatttg ggtacattag     120
acaaaaccgt gaaagagatg tatcagctat gaaacctgta tacttcaata cagagacgta   180
ctcatatcgg atacgtacgc acgaagtatc atattaatta ttttaatttt taataaatat   240
tttatcggat acttatgtga tactctacat atacacaagg atatttctaa gatactttat   300
agatacgtat cctagaaaaa catgaagagt aaaaagtga acaatgttg taaaaattca      360
ttataaatgt atatgattca attttagata tgcatcagta taattgattc tcgatgaaac   420
acttaaaatt atatttcttg tggaagaacg tagcgagaga ggtgattcag ttagacaaca   480
ttaaataaaa ttaatgttaa gttctttaa tgatgtttct ctcaatatca catcatatga     540
aaatgtaata tgatttataa gaaattttt aaaaaattta ttttaataat cacatgtact     600
atttttaaa aattgtatct tttataataa tacaataata aagagtaatc agtgttaatt     660
tttcttcaaa tataagtttt attataaatc attgttaacg tatcataagt cattaccgta   720
tcgtatctta attttttttt aaaaaccgct aattcacgta cccgtattgt attgtacccg   780
cacctgtatc acaatcgatc ttagttagaa gaattgtctc gaggcggtgc aagacagcat   840
ataatagacg tggactctct tataccaaac gttgtcgtat cacaagggt taggtaacaa    900
gtcacagttt gtccacgtgt cacgtttaa ttggaagagc tgccgttggc gtaatataac    960
agccaatcga tttttgctat aaaagcaaat caggtaaact aaacttcttc attcttttct   1020
tccccatcgc tacaaaaccg gttcctttgg aaaagagatt cattcaaacc tagcacccaa  1080
ttccgtttca aggtataatc tactttctat tcttcgatta ttttattatt attagctact   1140
atcgttaat cgatcttttc ttttgatccg tcaaatttaa attcaattag ggttttgttc    1200
ttttctttca tctgattgaa atccttctga attgaaccgt ttacttgatt ttactgttta   1260
ttgtatgatt taatccttg tttttcaaag acagtcttta gattgtgatt aggggttcat    1320
ataattttt agatttggat ttttgtattg tatgattcaa aaaatacgtc ctttaattag    1380
attagtacat ggatatttt tacccgattt attgattgtc agggagaatt tgatgagcaa    1440
gttttttga tgtctgttgt aaattgaatt gattataatt gctgatctgc tgcttccagt    1500
tttcataacc catattcttt taaccttgtt gtacacacaa tgaaaaattg gtgattgatt  1560
catttgtttt tctttgtttt ggattataca gggtaccaaa aatggcgggg atctaagaag  1620
agaagaatta acaagattc gaagctcgag aagttcacca actgctactc gctgagcaag   1680
acgctgcggt tcaaggcgat ccccgtcggg aagacccagg agaacatcga caacaagcgg   1740
ctcctggtcg aggacgagaa gcgcgccgag gactacaagg gcgtcaagaa gctgctggac   1800
cggtactacc tctccttcat caacgacgtc ctgcactcga tcaagctcaa gaacctgaac   1860
aactacatct cgctgttccg caagaagaca cggaccgaga aggagaacaa ggagctcgag   1920
aacctcgaga tcaacctgcg caaggagatc gcgaaggcgt tcaagggcaa cgagggtac    1980
aagagcctgt tcaagaaaga catcatcgag accatcctgc cggagttcct ggacgacaag   2040
gacgagatcg cgctggtgaa ctcgttcaac gggttccacca cggccttcac cgggttttc   2100
```

```
gacaaccggg agaacatgtt cagcgaggag gccaagtcga ccagcatcgc cttccggtgc    2160
atcaacgaga acctcacccg ctacatcagc aacatggaca tcttcgagaa ggtggacgcc    2220
atcttcgaca agcacgaggt ccaggagatc aaggaaaaga tcctgaactc ggactacgac    2280
gtggaagact tctttgaggg cgagttcttc aacttcgtcc tcacccagga gggcatcgac    2340
gtctacaacg ccatcatcgg cggcttcgtg acggagagcg gcgagaagat caagggcctc    2400
aacgagtaca tcaacctcta caaccagaag actaagcaga agctcccgaa gttcaagccg    2460
ctgtacaagc aagtcctgag cgaccgggag tccctctcgt tctacggcga gggctacacg    2520
agcgacgagg aggtgctgga ggtgttccgc aacacgctga caagaacag cgagatcttc    2580 agctcgatca agaaactcga gaagctgttc aagaacttcg acgagtacag cagcgccggc    2640
atcttcgtca agaacgggcc cgcgatcagc accatcagca aggacatctt cggggagtgg    2700
aacgtgatcc gcgacaagtg gaacgccgag tacgacgaca tccacctcaa gaaaaaggcg    2760
gtggtcacgg agaagtacga ggacgaccgc cggaagtcct tcaagaaaat cgggagcttc    2820
agcctcgagc agctccagga gtacgcggac gccgacctga gcgtggtgga gaagctcaag    2880
gagatcatca tccagaaggt cgacgagatc tacaaggtct acggctcgag cgagaagctg    2940
ttcgacgcgg acttcgtgct ggagaagtcc ctcaagaaga cgacgccgt ggtggccatc    3000 atgaaggatc tgctcgacag cgtgaagtcg ttcgagaact acatcaaggc attctttggg    3060
gagggcaagg agacgaaccg ggacgagtcc ttctacgggg acttcgtgct cgcgtacgac    3120
atcctcctga aggtcgacca catctacgac gcgatccgga actacgtcac gcagaagccc    3180
tacagcaagg acaagttcaa gctctacttc cagaacccgc agttcatggg cgggtgggac    3240
aaggacaagg agaccgacta ccgggccacg atcctgcggt acgggtccaa gtactacctc    3300
gccatcatgg acaagaagta cgccaagtgc ctccagaaga ttgacaagga cgacgtgaac    3360
gggaactacg agaagatcaa ctacaagctc ctcccggggc ccaacaagat gctgccgaag    3420
gtgttcttca gcaagaagtg gatggcctac tacaacccct cggaggacat ccagaagata    3480
tacaagaacg gcacgttcaa aaagggggac atgttcaacc tgaacgactg ccacaagctg    3540
atcgactttt tcaaggacag catcagccgc tacccgaagt ggtcgaacgc ctacgacttc    3600
aacttctcgg agacggagaa gtacaaggac attgcgggct ctaccggga ggtggaggag    3660 cagggctaca aggtctcctt cgagagcgcc tccaagaaag aggtggacaa gctcgtggag    3720
gagggcaagc tgtacatgtt ccagatctac aacaaggact tctcggacaa gtcgcacggc    3780
accccgaacc tccacacgat gtacttcaag ctgctgttcg acgagaacaa ccacgggcag    3840
atccgcctca gcggcggggc ggagctgttc atgcgccgcg cgtccctcaa gaaggaggag    3900
ctggtcgtgc accccgccaa ctccccgatc gcgaacaaga accccgacaa ccccaagaag    3960
acaaccaccc tctcgtacga cgtctacaag gacaagcggt tctcggagga ccagtacgag    4020
ctgcacatcc cgatcgccat caacaagtgc cccaagaaca tcttcaagat caacaccgag    4080
gtgcgggtgc tgctcaagca cgacgacaac ccctacgtca tcgggatcga ccgcggcgag    4140
cggaacctgc tctacatcgt ggtcgtggac gggaagggga acatcgtgga gcagtacagc    4200
ctgaacgaga tcatcaacaa cttcaacggc atccgcatca agacggacta ccacagcctc    4260
ctggacaaga aggagaagga gcggttcgag gcgcggcaga actggaccc catcgagaac    4320 atcaaggagc tgaaggccgg ctacatcagc aggtcgtgc acaagatctg cgagctcgtg    4380
gagaagtacg acgcggtgat cgcgctggag gacttgaaca gcgggttcaa gaactcccgg    4440
gtcaaggtcg agaagcaggt ctaccagaag ttcgagaaga tgctgatcga caagctcaac    4500
```

```
tacatggtgg acaagaagtc caaccectge gccaccggcg gcgccctcaa gggctaccag    4560
atcaccaaca agttcgagtc cttcaagtcg atgtctacgc agaacgggtt cattttctac    4620
atcccggcgt ggctcaccag caagatcgac ccgagcacgg gcttcgtcaa cctcctgaag    4680
accaagtaca ccagcatcgc ggacagcaag aagttcatct cctcgttcga ccgcatcatg    4740
tacgtccccg aggaagacct gttcgagttc gccctcgact acaagaactt ctcccggacg    4800
gacgccgact acatcaaaaa gtggaagctc tacagctacg caaccggat ccgcatcttc     4860 cgcaaccca agaagaacaa tgtgttcgac tgggaggagg tgtgcctgac gagcgcctac     4920
aaggagctct tcaacaagta cggcatcaac taccagcaag gggacatccg ccgcgctgctc    4980 tgcgagcagt ccgacaaggc gttctactcg tcgttcatgg ccctgatgag cctcatgctc    5040
cagatgcgca acagcatcac cggccggacg gacgtggact tcctgatcag cccggtcaag    5100
aacagcgacg gcattttcta cgacagccgg aactacgagg cccaggagaa cgccatcctc    5160
cccaagaacg ccgacgcgaa cggcgcctac aacatcgcgc ggaaggtgct gtgggccatc    5220
ggccagttta aaaaggcgga ggacgagaag ctggacaagg tcaagatcgc catcagcaac    5280
aaggagtggc tcgagtacgc gcagacgagc gtgaagcacg gatctaagaa gagaagaatt    5340
aaacaagatt gattaattaa tcatctgaaa ctgttcacca tgcatgcaat cttgtgaaat    5400
atatggtttt aattagactt caatcttatg ttggctattg tactaataaa agcatgtcat    5460 gttatttca tttgattta tctgtacttt ggtttgtttg aagaataaag atgagcttgc       5520
tatgcatgca tgcatgccat cgattatcag ggtttccttt tttctttttct ggcttcccat    5580 caatttggtg tgaattagtg tgtgtgatat attatattat gctatttatg aaataaattg    5640
ttggttatat ttgatctaca atctacatac atgtgatttt tatcaacaaa atatctcggg    5700
aaacaatacc ttttggtag caaaattcaa ataatactat tttaaataaa tcaaagttaa     5760
ccaatacctt attcaagttg gagggtctc aaacaagcaa agaattcaa gttgttaatg      5820 aacttcggtt aatgataaaa gaattcgcat ttaaaaa                             5856

<210> SEQ ID NO 27
<211> LENGTH: 617
<212> TYPE: DNA
<213> ORGANISM: Cucumis melo

<400> SEQUENCE: 27
aaattttaat aattaaaatg aacaattttt caagagtaat agagtttgag agatgtcaga      60
gaagtttgag gaagaagata acaagtggga gaagagaata agtttgttgt gtgaaagaga    120 agggaaatt tcattcaagg gtatattgaa cttttactc aaattttgta agtctatttt      180
ttccgatcaa tcctaaaatc acacacaccc ttaaaaatg gattatattt ggcaattttc      240
catgataaac tcatttttaa tttagagtta ttttttcaac gagatattaa cagttttagt      300
tcatatacta attgtaagaa tagtttcttt taagttgaat agaattttttg aaacttttaa     360 tagttcaaaa ggtattttg aaacaaaata agaatgtttt tgaactttttt ataaaaagaa      420 ttgagatttt tttgaaattt ttgataaaga gaaagaaaa gaagaaagaa aaagaaaaa       480 caagtttgta gaactccgtg ggaaaatcgt cgagggccct gtgaaggaat ttgaaatta     540 taatgagggt atttcgtca acaagggaat ttagacatcg tatataagca tcctcaaacc    600
ctataattaa gccctc                                                    617

<210> SEQ ID NO 28
```

```
<211> LENGTH: 54
<212> TYPE: DNA
<213> ORGANISM: Cucumis melo

<400> SEQUENCE: 28
aatccaattg ccattctcca tctctcgccg caagggttta agagcagctt ctct      54

<210> SEQ ID NO 29
<211> LENGTH: 545
<212> TYPE: DNA
<213> ORGANISM: Cucumis melo

<400> SEQUENCE: 29
cctcaggttg gggtttcccc ctatcttctt cattcttcct cttctcgatt tctttcttct      60
atttgctcga tagtctctta tttcttgagc ttttgctgtt tttctcctgt acatcctaac     120
atgaattata acttggtttt gattttgtct tttacttctg tattaaacaa cttttcttac     180 cctttattc ttctcttctt cttcgtgtcc ctgccctttt gttttatgc taattttatg       240 tttctgttta tcaatctatc gaggcgtgac ctgtcgttct tccaatagcg tagatctgca     300
cttaatctat tctagctgat tggattggtc gttttttcgtt tttttaatttt attttctctg   360 ttctagttcc gataaatttt tttatatata attaacaagt tctccagcca aaagggttaa     420
tattgcgttg atatttttaa ttttttacgtt atttagatgt gtgaatctaa taaaattagg    480
gttattcata aatttcagta atgatatttt ggttatctgt tcttgctgtt cctgtttcgc     540
agttc                                                                 545

<210> SEQ ID NO 30
<211> LENGTH: 19
<212> TYPE: DNA
<213> ORGANISM: Cucumis melo

<400> SEQUENCE: 30
ttttacctaa tattcaagc                                                   19

<210> SEQ ID NO 31
<211> LENGTH: 5500
<212> TYPE: DNA
<213> ORGANISM: Artificial Sequence
<220> FEATURE:
<223> OTHER INFORMATION: Synthetic polynucleotide.Expression cassette
      comprising Cucumis melo EF1a promoter cassette, NLS-LbCpf1-CO2-NLS
      and Medicago truncatula termination sequence

<400> SEQUENCE: 31
aaattttaat aattaaaatg aacaattttt caagagtaat agagtttgag agatgtcaga      60
gaagtttgag gaagaagata acaagtggga gaagagaata agtttgttgt gtgaaagaga    120
aggggaaatt tcattcaagg gtatattgaa cttttttactc aaattttgta agtctatttt    180
ttccgatcaa tcctaaaatc acacacaccc ttaaaaaatg gattatattt ggcaattttc    240
catgataaac tcatttttaa tttagagtta tttttttcaac gagatattaa cagttttagt    300
tcatatacta attgtaagaa tagtttctttt taagttgaat agaattttttg aaacttttaa    360 tagttcaaaa ggtattttttg aaacaaaata agaatgtttt tgaactttttt ataaaaagaa    420 ttgagatttt tttgaaattt ttgataaaga gaaagaaaa gaagaaagaa aaagaaaaa       480 caagtttgta gaactccgtg ggaaaatcgt cgagggccct gtgaaggaat ttgaaatta      540 taatgagggt attttcgtca acaagggaat ttagacatcg tatataagca tcctcaaacc    600
ctataattaa gcccttcaat ccaattgcca ttctccatct ctcgccgcaa gggtttaaga   660
```

```
gcagcttctc tcctcaggtt ggggtttccc cctatcttct tcattcttcc tcttctcgat      720
ttctttcttc tatttgctcg atagtctctt atttcttgag cttttgctgt ttttctcctg      780
tacatcctaa catgaattat aacttggttt tgattttgtc ttttacttct gtattaaaca      840
acttttctta ccctttatt cttctcttct tcttcgtgtc cctgcccttt tgttttatg      900 ctaattttat gtttctgttt atcaatctat cgaggcgtga cctgtcgttc ttccaatagc      960
gtagatctgc acttaatcta ttctagctga ttggattggt cgttttcgt ttttttaatt     1020 tattttctct gttctagttc cgataaattt ttttatatat aattaacaag ttctccagcc     1080 aaagggtta atattgcgtt ggatatttta attttacgt tatttagatg tgtgaatcta     1140 ataaattag ggttattcat aaatttcagt aatgatattt tggttatctg ttcttgctgt     1200
tcctgtttcg cagttctttt acctaatatt caagcggtac caaaaaatgg cgggatctaa     1260
gaagagaaga attaaacaag attcgaagct cgagaagttc accaactgct actcgctgag     1320
caagacgctg cggttcaagg cgatccccgt cgggaagacc caggagaaca tcgacaacaa     1380
gcggctcctg gtcgaggacg agaagcgcgc cgaggactac aagggcgtca gaagctgct     1440 ggaccggtac tacctctcct tcatcaacga cgtcctgcac tcgatcaagc tcaagaacct     1500
gaacaactac atctcgctgt ccgcaagaa gacacggacc gagaaggaga caaggagct     1560 cgagaacctc gagatcaacc tgcgcaagga gatcgcgaag gcgttcaagg gcaacgaggg     1620
gtacaagagc ctgttcaaga aagacatcat cgagaccatc ctgccggagt cctggacga     1680 caaggacgag atcgcgctgg tgaactcgtt caacggcttc accacggcct tcaccgggtt     1740
tttcgacaac cgggagaaca tgttcagcga ggaggccaag tcgaccagca tcgccttccg     1800
gtgcatcaac gagaacctca cccgctacat cagcaacatg gacatcttcg agaaggtgga     1860
cgccatcttc gacaagcacg aggtccagga gatcaaggaa aagatcctga actcggacta     1920
cgacgtggaa gacttctttg agggcgagtt cttcaacttc gtcctcaccc aggagggcat     1980
cgacgtctac aacgccatca tcggcggctt cgtgacggga agcggcgaga agatcaaggg     2040
cctcaacgag tacatcaacc tctacaacca gaagactaag cagaagctcc cgaagttcaa     2100
gccgctgtac aagcaagtcc tgagcgaccg ggagtccctc tcgttctacg gcgagggcta     2160
cacgagcgac gaggaggtgc tggaggtgtt ccgcaacacg ctgaacaaga acagcgagat     2220
cttcagctcg atcaagaaac tcgagaagct gttcaagaac ttcgacgagt acagcagcgc     2280
cggcatcttc gtcaagaacg ggcccgcgat cagcaccatc agcaaggaca tcttcgggga     2340
gtggaacgtg atccgcgaca gtggaacgc cgagtacgac gacatccacc tcaagaaaaa     2400
ggcggtggtc acggagaagt acgaggacga ccgccggaag tccttcaaga aaatcgggag     2460
cttcagcctc gagcagctcc aggagtacgc ggacgccgac ctgagcgtgg tggagaagct     2520
caaggagatc atcatccaga aggtcgacga gatctacaag gtctacggct cgagcgagaa     2580
gctgttcgac gcggacttcg tgctggagaa gtccctcaag aagaacgacg ccgtggtggc     2640
catcatgaag gatctgctcg acagcgtgaa gtcgttcgag aactacatca aggcattctt     2700 tgggagggc aaggagacga accgggacga gtccttctac ggggacttcg tgctcgcgta     2760
cgacatcctc ctgaaggtcg accacatcta cgacgcgatc cggaactacg tcacgcagaa     2820 gcccctacagc aaggacaagt tcaagctcta cttccagaac ccgcagttca tgggcgggtg     2880
ggacaaggac aaggagaccg actaccgggc cacgatcctg cggtacgggt ccaagtacta     2940
cctcgccatc atggacaaga gtacgccaa gtgcctccag aagattgaca aggacgacgt     3000
```

```
gaacgggaac tacgagaaga tcaactacaa gctcctcccg gggcccaaca agatgctgcc    3060
gaaggtgttc ttcagcaaga agtggatggc ctactacaac ccctcggagg acatccagaa    3120
gatatacaag aacggcacgt tcaaaaaggg ggacatgttc aacctgaacg actgccacaa    3180
gctgatcgac tttttcaagg acagcatcag ccgctacccg aagtggtcga acgcctacga    3240
cttcaacttc tcggagacgg agaagtacaa ggacattgcg ggcttctacc gggaggtgga    3300
ggagcagggc tacaaggtct ccttcgagag cgcctccaag aaagaggtgg acaagctcgt    3360
ggaggagggc aagctgtaca tgttccagat ctacaacaag gacttctcgg acaagtcgca    3420
cggcaccccg aacctccaca cgatgtactt caagctgctg ttcgacgaga caaccacgg    3480 gcagatccgc ctcagcggcg gggcggagct gttcatgcgc cgcgcgtccc tcaagaagga    3540
ggagctggtc gtgcaccccg ccaactcccc gatcgcgaac aagaaccccg caaccccaa    3600 gaagacaacc accctctcgt acgacgtcta caaggacaag cggttctcgg aggaccagta    3660
cgagctgcac atcccgatcg ccatcaacaa gtgcccaag aacatcttca agatcaacac    3720
cgaggtgcgg gtgctgctca gcacgacga caaccctac gtcatcggga tcgaccgcgg    3780
cgagcggaac ctgctctaca tcgtggtcgt ggacgggaag gggaacatcg tggagcagta    3840
cagcctgaac gagatcatca acaacttcaa cggcatccgc atcaagacgg actaccacag    3900
cctcctggac aagaaggaga aggagcggtt cgaggcgcgg cagaactgga cctccatcga    3960
gaacatcaag gagctgaagg ccggctacat cagccaggtc gtgcacaaga tctgcgagct    4020
cgtggagaag tacgacgcgg tgatcgcgct ggaggacttg aacagcgggt tcaagaactc    4080
ccgggtcaag gtcgagaagc aggtctacca gaagttcgag aagatgctga tcgacaagct    4140
caactacatg gtggacaaga agtccaaccc ctgcgccacc ggcggcgccc tcaagggcta    4200
ccagatcacc aacaagttcg agtccttcaa gtcgatgtct acgcagaacg ggttcatttt    4260
ctacatcccg gcgtggctca ccagcaagat cgacccgagc acgggcttcg tcaacctcct    4320
gaagaccaag tacaccagca tcgcggacag caagaagttc atctcctcgt tcgaccgcat    4380
catgtacgtc cccgaggaag acctgttcga gttcgccctc gactacaaga acttctcccg    4440
gacggacgcc gactacatca aaaagtggaa gctctacagc tacggcaacc ggatccgcat    4500
cttccgcaac cccaagaaga acaatgtgtt cgactgggag gaggtgtgcc tgacgagcgc    4560
ctacaaggag ctcttcaaca agtacggcat caactaccag caaggggaca tccgcgcgct    4620
gctctgcgag cagtccgaca aggcgttcta ctcgtcgttc atggccctga tgagcctcat    4680
gctccagatg cgcaacagca tcaccggccg gacggacgtg gacttcctga tcagcccggt    4740
caagaacagc gacggcattt tctacgacag ccggaactac gaggcccagg agaacgccat    4800
cctccccaag aacgccgacg cgaacggcgc ctacaacatc gcgcggaagg tgctgtgggc    4860
catcggccag tttaaaaagg cggaggacga gaagctggac aaggtcaaga tcgccatcag    4920
caacaaggag tggctcgagt acgcgcgac gagcgtgaag cacggatcta agaagagaag    4980
aattaaacaa gattgattaa ttaatcatct gaaactgttc accatgcatg caatcttgtg    5040
aaatatatgg tttaattag acttcaatct tatgttggct attgtactaa taaaagcatg    5100
tcatgttatt ttcatttgat tttatctgta ctttggtttg tttgaagaat aaagatgagc    5160
ttgctatgca tgcatgcatg ccatcgatta tcagggtttc cttttttctt ttctggcttc    5220
ccatcaattt ggtgtgaatt agtgtgtgtg atatattata ttatgctatt tatgaaataa    5280
attgttggtt atatttgatc tacaatctac atacatgtga tttttatcaa caaaatatct    5340
cgggaaacaa tacctttttg gtagcaaaat tcaaataata ctattttaaa taaatcaaag    5400
```

```
ttaaccaata ccttattcaa gttggagggg tctcaaacaa gcaaaagaat tcaagttgtt      5460
aatgaacttc ggttaatgat aaaagaattc gcatttaaaa                           5500

<210> SEQ ID NO 32
<211> LENGTH: 829
<212> TYPE: DNA
<213> ORGANISM: Arabidopsis thaliana

<400> SEQUENCE: 32
gttttgtgta tcattcttgt tacattgtta ttaatgaaaa aatattattg gtcattggac       60
tgaacacgag tgttaaatat ggaccaggcc ccaaataaga tccattgata tatgaattaa      120
ataacaagaa taaatcgagt caccaaacca cttgcctttt ttaacgagac ttgttcacca      180
acttgataca aaagtcatta tcctatgcaa atcaataatc atacaaaaat atccaataac      240
actaaaaaat taaagaaat ggataatttc acaatatgtt atacgataaa gaagttactt       300
ttccaagaaa ttcactgatt ttataagccc acttgcatta gataaatggc aaaaaaaaac      360
aaaaaggaaa agaaataaag cacgaagaat tctagaaaat acgaaatacg cttcaatgca      420
gtgggaccca cggttcaatt attgccaatt ttcagctcca ccgtatattt aaaaaataaa      480
acgataatgc taaaaaaata taaatcgtaa cgatcgttaa atctcaacgg ctggatctta      540
tgacgaccgt tagaaattgt ggttgtcgac gagtcagtaa taaacggcgt caaagtggtt      600
gcagccggca cacgagtc gtgtttatca actcaaagca caaatacttt tcctcaacct       660
aaaaataagg caattagcca aaacaactt tgcgtgtaaa caacgctcaa tacacgtgtc      720
attttattat tagctattgc ttcaccgcct tagctttctc gtgacctagt cgtcctcgtc      780
ttttcttctt cttcttctat aaaacaatac ccaaagagct cttcttctt                 829

<210> SEQ ID NO 33
<211> LENGTH: 67
<212> TYPE: DNA
<213> ORGANISM: Arabidopsis thaliana

<400> SEQUENCE: 33
cacaattcag atttcaattt ctcaaaatct taaaactttt ctctcaattc tctctaccgt       60
gatcaag                                                                67

<210> SEQ ID NO 34
<211> LENGTH: 306
<212> TYPE: DNA
<213> ORGANISM: Arabidopsis thaliana

<400> SEQUENCE: 34
gtaaatttct gtgttcctta ttctctcaaa atcttcgatt ttgttttcgt tcgatcccaa       60
tttcgtatat gttctttggt ttagattctg ttaatcttag atcgaagacg atttttctggg    120 tttgatcgtt agatatcatc ttaattctcg attagggttt catagatatc atccgatttg     180
ttcaaataat ttgagttttg tcgaataatt actcttcgat ttgtgatttc tatctagatc     240
tggtgttagt ttctagtttg tgcgatcgaa tttgtcgatt aatctgagtt tttctgatta     300
acaggt                                                                306

<210> SEQ ID NO 35
<211> LENGTH: 315
<212> TYPE: DNA
<213> ORGANISM: Gossypium barbadense
```

```
<400> SEQUENCE: 35
accatatgac actggtgcat gtgccatcat catgcagtaa tttcatggta tatcttaatt    60
atatggttaa taaaaaaaag atggtgagtg aataatgtgc gtgcattcct ccatgcacca   120
atggtgaatc tctttgcata catagagatt ctgaatgatt atagtttatg ttgtagtgaa   180
attaattttg aatgttgttt ttaaatttta atgtcacttg gcttgattta tgttttaacg   240
aagcttatgt tatgtatttt actttaatga tattgcatgt attgttaatt taacattgct   300
tgatcagtat actct                                                    315

<210> SEQ ID NO 36
<211> LENGTH: 5292
<212> TYPE: DNA
<213> ORGANISM: Artificial Sequence
<220> FEATURE:
<223> OTHER INFORMATION: Synthetic polynucleotide.Expression cassette
      comprising Arabidopsis thaliana Ubiquitin promoter cassette,
      NLS-LbCpf1-CO2-NLS and Gossypium barbadense termination sequence.

<400> SEQUENCE: 36
gttttgtgta tcattcttgt tacattgtta ttaatgaaaa atattattg gtcattggac     60 tgaacacgag tgttaaatat ggaccaggcc ccaaataaga tccattgata tatgaattaa   120
ataacaagaa taaatcgagt caccaaacca cttgcctttt ttaacgagac ttgttcacca   180
acttgataca aaagtcatta tcctatgcaa atcaataatc atacaaaaat atccaataac   240
actaaaaaat taaagaaat ggataatttc acaatatgtt atacgataaa gaagttactt    300
ttccaagaaa ttcactgatt ttataagccc acttgcatta gataaatggc aaaaaaaaac   360
aaaaaggaaa agaaataaag cacgaagaat tctagaaaat acgaaatacg cttcaatgca   420
gtgggaccca cggttcaatt attgccaatt ttcagctcca ccgtatattt aaaaaataaa   480
acgataatgc taaaaaaata taaatcgtaa cgatcgttaa atctcaacgg ctggatctta   540
tgacgaccgt tagaaattgt ggttgtcgac gagtcagtaa taaacggcgt caaagtggtt   600
gcagccggca cacgagtc gtgtttatca actcaaagca caaatacttt tcctcaacct     660
aaaaataagg caattagcca aaaacaactt tgcgtgtaaa caacgctcaa tacacgtgtc   720
attttattat tagctattgc ttcaccgcct tagctttctc gtgacctagt cgtcctcgtc   780 tttttcttctt cttcttctat aaaacaatac ccaaagagct cttcttcttc acaattcaga   840
tttcaatttc tcaaaatctt aaaaacttttc tctcaattct ctctaccgtg atcaaggtaa   900
atttctgtgt tccttattct ctcaaaatct tcgattttgt tttcgttcga tcccaatttc    960
gtatatgttc tttggtttag attctgttaa tcttagatcg aagacgattt tctgggtttg  1020
atcgttagat atcatcttaa ttctcgatta gggtttcata gatatcatcc gatttgttca  1080
aataatttga gttttgtcga ataattactc ttcgatttgt gatttctatc tagatctggt  1140
gttagtttct agtttgtgcg atcgaatttg tcgattaatc tgagttttc tgattaacag   1200 gtggtaccaa aaaatggcgg gatctaagaa gagaagaatt aaacaagatt cgaagctcga  1260
gaagttcacc aactgctact cgctgagcaa gacgctgcgg ttcaaggcga tccccgtcgg  1320
gaagacccag gagaacatcg acaacaagcg gctcctggtc gaggacgaga gcgcgccga  1380 ggactacaag ggcgtcaaga agctgctgga ccggtactac ctctccttca tcaacgacgt  1440
cctgcactcg atcaagctca gaacctgaa caactacatc tcgctgttcc gcaagaagac  1500
acggaccgag aaggagaaca aggagctcga gaacctcgag atcaacctgc gcaaggagat  1560
cgcgaaggcg ttcaagggca cgagggggta caagagcctg ttcaagaaag acatcatcga  1620
```

-continued

```
gaccatcctg ccggagttcc tggacgacaa ggacgagatc gcgctggtga actcgttcaa    1680
cgggttcacc acggccttca ccgggttttt cgacaaccgg gagaacatgt tcagcgagga    1740
ggccaagtcg accagcatcg ccttccggtg catcaacgag aacctcaccc gctacatcag    1800
caacatggac atcttcgaga aggtggacgc catcttcgac aagcacgagg tccaggagat    1860
caaggaaaag atcctgaact cggactacga cgtggaagac ttctttgagg gcgagttctt    1920
caacttcgtc ctcacccagg agggcatcga cgtctacaac gccatcatcg gcggcttcgt    1980
gacggagagc ggcgagaaga tcaagggcct caacgagtac atcaacctct acaaccagaa    2040
gactaagcag aagctcccga gttcaagcc gctgtacaag caagtcctga gcgaccggga    2100
gtccctctcg ttctacggcg agggctacac gagcgacgag gaggtgctgg aggtgttccg    2160
caacacgctg aacaagaaca gcgagatctt cagctcgatc aagaaactcg agaagctgtt    2220
caagaacttc gacgagtaca gcagcgccgg catcttcgtc aagaacgggc cgcgatcag    2280 caccatcagc aaggacatct cggggagtg aacgtgatc cgcgacaagt ggaacgccga    2340
gtacgacgac atccacctca agaaaaggc ggtggtcacg gagaagtacg aggacgaccg    2400
ccggaagtcc ttcaagaaaa tcgggagctt cagcctcgag cagctccagg agtacgcgga    2460
cgccgacctg agcgtggtgg agaagctcaa ggagatcatc atccagaagg tcgacgagat    2520
ctacaaggtc tacggctcga gcgagaagct gttcgacgcg gacttcgtgc tggagaagtc    2580
cctcaagaag aacgacgccg tggtggccat catgaaggat ctgctcgaca gcgtgaagtc    2640
gttcgagaac tacatcaagg cattctttgg ggagggcaag gagacgaacc gggacgagtc    2700
cttctacggg gacttcgtgc tcgcgtacga catcctcctg aaggtcgacc acatctacga    2760
cgcgatccgg aactacgtca cgcagaagcc ctacagcaag gacaagttca gctctactt    2820 ccagaacccg cagttcatgg gcgggtggga caaggacaag gagaccgact accgggccac    2880
gatcctgcgg tacgggtcca agtactacct cgccatcatg gacaagaagt acgccaagtg    2940
cctccagaag attgacaagg acgacgtgaa cgggaactac gagaagatca actacaagct    3000
cctcccgggg cccaacaaga tgctgccgaa ggtgttcttc agcaagaagt ggatggccta    3060
ctacaacccc tcggaggaca tccagaagat atacaagaac ggcacgttca aaagggggga    3120
catgttcaac ctgaacgact gccacaagct gatcgacttt ttcaaggaca gcatcagccg    3180
ctacccgaag tggtcgaacg cctacgactt caacttctcg gagacggaga agtacaagga    3240
cattgcgggc ttctaccggg aggtggagga gcagggctac aaggtctcct cgagagcgc    3300 ctccaagaaa gaggtggaca agctcgtgga ggagggcaag ctgtacatgt tccagatcta    3360
caacaaggac ttctcggaca agtcgcacgg cacccgaac ctccacacga tgtacttcaa    3420
gctgctgttc gacgagaaca accacgggca gatccgcctc agcggcgggg cggagctgtt    3480
catgcgccgc gcgtccctca gaaggagga gctggtcgtg caccccgcca actccccgat    3540
cgcgaacaag aaccccgaca cccccaagaa gacaaccacc ctctcgtacg acgtctacaa    3600
ggacaagcgg ttctcggagg accagtacga gctgcacatc ccgatcgcca tcaacaagtg    3660
ccccaagaac atcttcaaga tcaacaccga ggtgcgggtg ctgctcaagc acgacgacaa    3720 ccctacgtc atcgggatcg accgcggcga gcggaacctg ctctacatcg tggtcgtgga    3780
cgggaagggg aacatcgtgg agcagtacag cctgaacgag atcatcaaca acttcaacgg    3840
catccgcatc aagacggact accacagcct cctggacaag aaggagaagg agcggttcga    3900
ggcgcggcag aactggacct ccatcgagaa catcaaggag ctgaaggccg gctacatcag    3960
```

```
ccaggtcgtg cacaagatct gcgagctcgt ggagaagtac gacgcggtga tcgcgctgga    4020
ggacttgaac agcgggttca agaactcccg ggtcaaggtc gagaagcagg tctaccagaa    4080
gttcgagaag atgctgatcg acaagctcaa ctacatggtg gacaagaagt ccaaccccctg   4140 cgccaccggc ggcgccctca agggctacca gatcaccaac aagttcgagt ccttcaagtc    4200
gatgtctacg cagaacgggt tcattttcta catcccggcg tggctcacca gcaagatcga    4260
cccgagcacg ggcttcgtca acctcctgaa gaccaagtac accagcatcg cggacagcaa    4320
gaagttcatc tcctcgttcg accgcatcat gtacgtcccc gaggaagacc tgttcgagtt    4380
cgccctcgac tacaagaact ctcccggac ggacgccgac tacatcaaaa agtggaagct    4440
ctacagctac ggcaaccgga tccgcatctt ccgcaacccc aagaagaaca atgtgttcga    4500
ctgggaggag gtgtgcctga cgagcgccta caaggagctc ttcaacaagt acggcatcaa    4560
ctaccagcaa ggggacatcc gcgcgctgct ctgcgagcag tccgacaagg cgttctactc    4620
gtcgttcatg gccctgatga gcctcatgct ccagatgcgc aacagcatca ccggccggac    4680
ggacgtggac ttcctgatca gcccggtcaa gaacagcgac ggcattttct acgacagccg    4740
gaactacgag gcccaggaga acgccatcct ccccaagaac gccgacgcga acggcgccta    4800
caacatcgcg cggaaggtgc tgtgggccat cggccagttt aaaaaggcgg aggacgagaa    4860
gctggacaag gtcaagatcg ccatcagcaa caaggagtgg ctcgagtacg cgcagacgag    4920
cgtgaagcac ggatctaaga agagaagaat taaacaagat tgattaatta agggcccacc    4980
atatgacact ggtgcatgtg ccatcatcat gcagtaattt catggtatat cttaattata    5040
tggttaataa aaaaaagatg gtgagtgaat aatgtgcgtg cattcctcca tgcaccaatg    5100
gtgaatctct ttgcatacat agagattctg aatgattata gtttatgttg tagtgaaatt    5160
aattttgaat gttgttttta aatttttaatg tcacttggct tgatttatgt tttaacgaag    5220
cttatgttat gtattttact ttaatgatat tgcatgtatt gttaatttaa cattgcttga    5280
tcagtatact ct                                                        5292
```

<210> SEQ ID NO 37
<211> LENGTH: 822
<212> TYPE: DNA
<213> ORGANISM: Artificial Sequence
<220> FEATURE:
<223> OTHER INFORMATION: Synthetic polynucleotide.Chimeric promoter
    cassette comprising the enhancer sequence from the Banana Streak
    Virus strain Acuminata Vietnam fused to a promoter sequence from
    Dahlia Mosaic Virus (DaMV).

<400> SEQUENCE: 37

```
agacatcctg gaccaatatg ctgaagatta tgctacctac accaggatag gacttgaagc      60
acttaacctt gaagattggt tcgaagaacc agaacccgat ccacctaacc ctgtggaccg     120
ccagaggata gaggacatcc tggacctact gaacgtcagc aatgacgact gaaagattcc     180
caggacaccg gcgaagtgg tggacccagt ctaggtgcga tgcttagtcg cgcacgatga     240
ctatgtcgga aggcatcttt gctttcggca aactttagta atactttaag gaaagtattg     300
tacaagttag gtgcagagac aataatgcac ccagctttag ctttgtttat ggaattattg     360
tgtcggttgc attattggat gcctgcgtgc accctaagca atcaacggag aaacaaagat     420
aaaaatcaat tactcacatg aaagagtatt gatcacgagt cactatggag cgacaatctc     480
cagacaggat gtcagcatct tatcttcctt tgaagaaagc atcatcaata acgatgtaat     540
ggtggggaca tccactaagt tattgctctg caaacagctc aaaaagctac tggccgacaa     600
```

```
tcataattgc tcggcatgtg caggtggggc ctccactagc aataatacaa gctttacagc    660
ttgcagtgac tcatcctcca ataatggaga aaaagacgtc agcagtgacg aacaagggtc    720
gaaagacttg cctatataag ggcattctcc cctcagttga agatcatcga aagttggagc    780
aataaactct ctcttcaaca aatctatctt ttatcttta tc                        822
```

<210> SEQ ID NO 38
<211> LENGTH: 3681
<212> TYPE: DNA
<213> ORGANISM: Artificial Sequence
<220> FEATURE:
<223> OTHER INFORMATION: Synthetic polynucleotide.Codon optimized
      LbCpf1(TYC)-CO2

<400> SEQUENCE: 38

```
tcgaagctcg agaagttcac caactgctac tcgctgagca agacgctgcg gttcaaggcg     60
atccccgtcg ggaagaccca ggagaacatc gacaacaagc ggctcctggt cgaggacgag    120
aagcgcgccg aggactacaa gggcgtcaag aagctgctgg accggtacta cctctccttc    180
atcaacgacg tcctgcactc gatcaagctc aagaacctga caactacat ctcgctgttc     240 cgcaagaaga cacggaccga aaggagaac aaggagctcg agaacctcga gatcaacctg     300
cgcaaggaga tcgcgaaggc gttcaagggc aacgaggggt acaagagcct gttcaagaaa    360
gacatcatcg agaccatcct gccggagttc ctggacgaca aggacgagat cgcgctggtg    420
aactcgttca acgggttcac cacggccttc accgggtttt tcgacaaccg ggagaacatg    480
ttcagcgagg aggccaagtc gaccagcatc gccttccgtg catcaacga aacctcacc    540 cgctacatca gcaacatgga catcttcgag aaggtggacg ccatcttcga caagcacgag    600
gtccaggaga tcaaggaaaa gatcctgaac tcggactacg acgtggaaga cttctttgag    660
ggcgagttct tcaacttcgt cctcacccag gagggcatcg acgtctacaa cgccatcatc    720
ggcggcttcg tgacggagag cggcgagaag atcaagggcc tcaacgagta catcaacctc    780
tacaaccaga gactaagca gaagctcccg aagttcaagc cgctgtacaa gcaagtcctg    840
agcgaccggg agtccctctc gttctacggc gagggctaca cgagcgacga ggaggtgctg    900
gaggtgttcc gcaacacgct gaacaagaac agcgagatct tcagctcgat caagaaactc    960
gagaagctgt tcaagaactt cgacgagtac agcagcgccg gcatcttcgt caagaacggg   1020
cccgcgatca gcaccatcag caaggacatc ttcggggagt ggaacgtgat cgccgacaag   1080
tggaacgccg agtacgacga catccacctc aagaaaaagg cggtggtcac ggagaagtac   1140
gaggacgacc gccggaagtc cttcaagaaa atcgggagct tcagcctcga gcagctccag   1200
gagtacgcgg acgccgacct gagcgtggtg gagaagctca aggagatcat catccagaag   1260
gtcgacgaga tctacaaggt ctacggctcg agcgagaagc tgttcgacgc ggacttcgtg   1320
ctggagaagt ccctcaagaa gaacgacgcc gtggtggcca tcatgaagga tctgctcgac   1380
agcgtgaagt cgttcgagaa ctacatcaag gcattctttg gggagggcaa ggagacgaac   1440
cgggacgagt ccttctacgg ggacttcgtg ctcgcgtacg acatcctcct gaaggtcgac   1500
cacatctacg acgcgatccg gaactacgtc acgcagaagc cctacagcaa ggacaagttc   1560
aagctctact ccagaacccc gcagttcatg cgcgggtggg acaaggacaa ggagaccgac   1620
taccggccca cgatcctgcg gtacgggtcc aagtactacc tcgccatcat ggacaagaag   1680
tacgccaagt gcctccagaa gattgacaag gacgacgtga acggaactac gagaagatc   1740 aactacaagc tcctcccggg gcccaacaag atgctgccga gggtgttctt cagcaagaag   1800
```

```
tggatggcct actacaaccc ctcggaggac atccagaaga tatacaagaa cggcacgttc    1860
aaaaaggggg acatgttcaa cctgaacgac tgccacaagc tgatcgactt tttcaaggac    1920
agcatcagcc gctacccgaa gtggtcgaac gcctacgact tcaacttctc ggagacggag    1980
aagtacaagg acattgcggg cttctaccgg gaggtggagg agcagggcta caaggtctcc    2040
ttcgagagcg cctccaagaa agaggtggac aagctcgtgg aggagggcaa gctgtacatg    2100
ttccagatct acaacaagga cttctcggac aagtcgcacg gcaccccgaa cctccacacg    2160
atgtacttca agctgctgtt cgacgagaac aaccacgggc agatccgcct cagcggcggg    2220
gcggagctgt tcatgcgccg cgcgtccctc aagaaggagg agctggtcgt gcaccccgcc    2280
aactccccga tcgcgaacaa gaaccccgac aaccccaaga agacaaccac cctctcgtac    2340
gacgtctaca aggacaagcg gttctcggag gaccagtacg agctgcacat cccgatcgcc    2400
atcaacaagt gccccaagaa catcttcaag atcaacaccg aggtgcgggt gctgctcaag    2460
cacgacgaca cccctacgt catcgggatc gaccgcggcg agcggaacct gctctacatc    2520
gtggtcgtgg acgggaaggg gaacatcgtg gagcagtaca gcctgaacga gatcatcaac    2580
aacttcaacg gcatccgcat caagacggac taccacagcc tcctggacaa gaaggagaag    2640
gagcggttcg aggcgcggca gaactggacc tccatcgaga acatcaagga gctgaaggcc    2700
ggctacatca gccaggtcgt gcacaagatc tgcgagctcg tggagaagta cgacgcggtg    2760
atcgcgctgg aggacttgaa cagcgggttc aagaactccc gggtcaaggt cgagaagcag    2820
gtctaccaga agttcgagaa gatgctgatc gacaagctca actacatggt ggacaagaag    2880 tccaaccccct gcgccaccgg cggcgccctc aagggctacc agatcaccaa caagttcgag    2940
tccttcaagt cgatgtctac gcagaacggg ttcatttttct acatcccggc gtggctcacc    3000
agcaagatcg acccgagcac gggcttcgtc aacctcctga agaccaagta caccagcatc    3060
gcggacagca agaagttcat ctcctcgttc gaccgcatca tgtacgtccc cgaggaagac    3120
ctgttcgagt cgcccctcga ctacaagaac ttctcccgga cggacgccga ctacatcaaa    3180
aagtggaagc tctacagcta cggcaaccgg atccgcatct ccgcaacccc caagaagaac    3240
aatgtgttcg actgggagga ggtgtgcctg acgagcgcct acaaggagct cttcaacaag    3300
tacggcatca actaccagca aggggacatc cgcgcgctgc tctgcgagca gtccgacaag    3360
gcgttctact cgtcgttcat ggccctgatg agcctcatgc tccagatgcg caacagcatc    3420
accggccgga cggacgtgga cttcctgatc agcccggtca gaacagcga cggcattttc    3480 tacgacagcc ggaactacga ggcccaggag aacgccatcc tccccaagaa cgccgacgcg    3540
aacggcgcct acaacatcgc gcggaaggtg ctgtgggcca tcggccagtt taaaaaggcg    3600
gaggacgaga gctggacaa ggtcaagatc gccatcagca caaggagtg gctcgagtac    3660 gcgcagacga gcgtgaagca t                                              3681
```

<210> SEQ ID NO 39
<211> LENGTH: 1227
<212> TYPE: PRT
<213> ORGANISM: Artificial Sequence
<220> FEATURE:
<223> OTHER INFORMATION: Synthetic polypeptide.LbCpf1(TYC) variant
    comprising G532R and K595R substitutions

<400> SEQUENCE: 39

```
Ser Lys Leu Glu Lys Phe Thr Asn Cys Tyr Ser Leu Ser Lys Thr Leu
1               5                   10                  15

Arg Phe Lys Ala Ile Pro Val Gly Lys Thr Gln Glu Asn Ile Asp Asn
```

```
                20                  25                  30
Lys Arg Leu Leu Val Glu Asp Glu Lys Arg Ala Glu Asp Tyr Lys Gly
                    35                  40                  45
Val Lys Lys Leu Leu Asp Arg Tyr Tyr Leu Ser Phe Ile Asn Asp Val
         50                  55                  60
Leu His Ser Ile Lys Leu Lys Asn Leu Asn Asn Tyr Ile Ser Leu Phe
 65                  70                  75                  80
Arg Lys Lys Thr Arg Thr Glu Lys Glu Asn Lys Glu Leu Glu Asn Leu
                     85                  90                  95
Glu Ile Asn Leu Arg Lys Glu Ile Ala Lys Ala Phe Lys Gly Asn Glu
                100                 105                 110
Gly Tyr Lys Ser Leu Phe Lys Lys Asp Ile Ile Glu Thr Ile Leu Pro
            115                 120                 125
Glu Phe Leu Asp Asp Lys Asp Glu Ile Ala Leu Val Asn Ser Phe Asn
            130                 135                 140
Gly Phe Thr Thr Ala Phe Thr Gly Phe Phe Asp Asn Arg Glu Asn Met
145                 150                 155                 160
Phe Ser Glu Glu Ala Lys Ser Thr Ser Ile Ala Phe Arg Cys Ile Asn
                165                 170                 175
Glu Asn Leu Thr Arg Tyr Ile Ser Asn Met Asp Ile Phe Glu Lys Val
                180                 185                 190
Asp Ala Ile Phe Asp Lys His Glu Val Gln Glu Ile Lys Glu Lys Ile
            195                 200                 205
Leu Asn Ser Asp Tyr Asp Val Glu Asp Phe Phe Glu Gly Glu Phe Phe
            210                 215                 220
Asn Phe Val Leu Thr Gln Glu Gly Ile Asp Val Tyr Asn Ala Ile Ile
225                 230                 235                 240
Gly Gly Phe Val Thr Glu Ser Gly Glu Lys Ile Lys Gly Leu Asn Glu
                245                 250                 255
Tyr Ile Asn Leu Tyr Asn Gln Lys Thr Lys Gln Lys Leu Pro Lys Phe
                260                 265                 270
Lys Pro Leu Tyr Lys Gln Val Leu Ser Asp Arg Glu Ser Leu Ser Phe
            275                 280                 285
Tyr Gly Glu Gly Tyr Thr Ser Asp Glu Glu Val Leu Glu Val Phe Arg
            290                 295                 300
Asn Thr Leu Asn Lys Asn Ser Glu Ile Phe Ser Ser Ile Lys Lys Leu
305                 310                 315                 320
Glu Lys Leu Phe Lys Asn Phe Asp Glu Tyr Ser Ser Ala Gly Ile Phe
                325                 330                 335
Val Lys Asn Gly Pro Ala Ile Ser Thr Ile Ser Lys Asp Ile Phe Gly
            340                 345                 350
Glu Trp Asn Val Ile Arg Asp Lys Trp Asn Ala Glu Tyr Asp Asp Ile
            355                 360                 365
His Leu Lys Lys Lys Ala Val Val Thr Glu Lys Tyr Glu Asp Asp Arg
            370                 375                 380
Arg Lys Ser Phe Lys Lys Ile Gly Ser Phe Ser Leu Glu Gln Leu Gln
385                 390                 395                 400
Glu Tyr Ala Asp Ala Asp Leu Ser Val Val Glu Lys Leu Lys Glu Ile
                405                 410                 415
Ile Ile Gln Lys Val Asp Glu Ile Tyr Lys Val Tyr Gly Ser Ser Glu
            420                 425                 430
Lys Leu Phe Asp Ala Asp Phe Val Leu Glu Lys Ser Leu Lys Lys Asn
            435                 440                 445
```

```
Asp Ala Val Ala Ile Met Lys Asp Leu Leu Asp Ser Val Lys Ser
    450                 455                 460

Phe Glu Asn Tyr Ile Lys Ala Phe Phe Gly Glu Gly Lys Glu Thr Asn
465                 470                 475                 480

Arg Asp Glu Ser Phe Tyr Gly Asp Phe Val Leu Ala Tyr Asp Ile Leu
                485                 490                 495

Leu Lys Val Asp His Ile Tyr Asp Ala Ile Arg Asn Tyr Val Thr Gln
                500                 505                 510

Lys Pro Tyr Ser Lys Asp Lys Phe Lys Leu Tyr Phe Gln Asn Pro Gln
            515                 520                 525

Phe Met Arg Gly Trp Asp Lys Glu Thr Asp Tyr Arg Ala Thr
530                 535                 540

Ile Leu Arg Tyr Gly Ser Lys Tyr Tyr Leu Ala Ile Met Asp Lys Lys
545                 550                 555                 560

Tyr Ala Lys Cys Leu Gln Lys Ile Asp Lys Asp Val Asn Gly Asn
                565                 570                 575

Tyr Glu Lys Ile Asn Tyr Lys Leu Leu Pro Gly Pro Asn Lys Met Leu
                580                 585                 590

Pro Arg Val Phe Phe Ser Lys Lys Trp Met Ala Tyr Tyr Asn Pro Ser
            595                 600                 605

Glu Asp Ile Gln Lys Ile Tyr Lys Asn Gly Thr Phe Lys Lys Gly Asp
    610                 615                 620

Met Phe Asn Leu Asn Asp Cys His Lys Leu Ile Asp Phe Phe Lys Asp
625                 630                 635                 640

Ser Ile Ser Arg Tyr Pro Lys Trp Ser Asn Ala Tyr Asp Phe Asn Phe
                645                 650                 655

Ser Glu Thr Glu Lys Tyr Lys Asp Ile Ala Gly Phe Tyr Arg Glu Val
                660                 665                 670

Glu Glu Gln Gly Tyr Lys Val Ser Phe Glu Ser Ala Ser Lys Lys Glu
            675                 680                 685

Val Asp Lys Leu Val Glu Glu Gly Lys Leu Tyr Met Phe Gln Ile Tyr
    690                 695                 700

Asn Lys Asp Phe Ser Asp Lys Ser His Gly Thr Pro Asn Leu His Thr
705                 710                 715                 720

Met Tyr Phe Lys Leu Leu Phe Asp Glu Asn Asn His Gly Gln Ile Arg
                725                 730                 735

Leu Ser Gly Gly Ala Glu Leu Phe Met Arg Arg Ala Ser Leu Lys Lys
                740                 745                 750

Glu Glu Leu Val Val His Pro Ala Asn Ser Pro Ile Ala Asn Lys Asn
            755                 760                 765

Pro Asp Asn Pro Lys Lys Thr Thr Thr Leu Ser Tyr Asp Val Tyr Lys
    770                 775                 780

Asp Lys Arg Phe Ser Glu Asp Gln Tyr Glu Leu His Ile Pro Ile Ala
785                 790                 795                 800

Ile Asn Lys Cys Pro Lys Asn Ile Phe Lys Ile Asn Thr Glu Val Arg
                805                 810                 815

Val Leu Leu Lys His Asp Asp Asn Pro Tyr Val Ile Gly Ile Asp Arg
                820                 825                 830

Gly Glu Arg Asn Leu Leu Tyr Ile Val Val Asp Gly Lys Gly Asn
            835                 840                 845

Ile Val Glu Gln Tyr Ser Leu Asn Glu Ile Ile Asn Asn Phe Asn Gly
    850                 855                 860
```

```
Ile Arg Ile Lys Thr Asp Tyr His Ser Leu Leu Asp Lys Lys Glu Lys
865                 870                 875                 880

Glu Arg Phe Glu Ala Arg Gln Asn Trp Thr Ser Ile Glu Asn Ile Lys
            885                 890                 895

Glu Leu Lys Ala Gly Tyr Ile Ser Gln Val Val His Lys Ile Cys Glu
        900                 905                 910

Leu Val Glu Lys Tyr Asp Ala Val Ile Ala Leu Glu Asp Leu Asn Ser
        915                 920                 925

Gly Phe Lys Asn Ser Arg Val Lys Val Glu Lys Gln Val Tyr Gln Lys
    930                 935                 940

Phe Glu Lys Met Leu Ile Asp Lys Leu Asn Tyr Met Val Asp Lys Lys
945                 950                 955                 960

Ser Asn Pro Cys Ala Thr Gly Gly Ala Leu Lys Gly Tyr Gln Ile Thr
                965                 970                 975

Asn Lys Phe Glu Ser Phe Lys Ser Met Ser Thr Gln Asn Gly Phe Ile
            980                 985                 990

Phe Tyr Ile Pro Ala Trp Leu Thr Ser Lys Ile Asp Pro Ser Thr Gly
        995                 1000                1005

Phe Val Asn Leu Leu Lys Thr Lys Tyr Thr Ser Ile Ala Asp Ser
    1010                1015                1020

Lys Lys Phe Ile Ser Ser Phe Asp Arg Ile Met Tyr Val Pro Glu
    1025                1030                1035

Glu Asp Leu Phe Glu Phe Ala Leu Asp Tyr Lys Asn Phe Ser Arg
    1040                1045                1050

Thr Asp Ala Asp Tyr Ile Lys Lys Trp Lys Leu Tyr Ser Tyr Gly
    1055                1060                1065

Asn Arg Ile Arg Ile Phe Arg Asn Pro Lys Lys Asn Asn Val Phe
    1070                1075                1080

Asp Trp Glu Glu Val Cys Leu Thr Ser Ala Tyr Lys Glu Leu Phe
    1085                1090                1095

Asn Lys Tyr Gly Ile Asn Tyr Gln Gln Gly Asp Ile Arg Ala Leu
    1100                1105                1110

Leu Cys Glu Gln Ser Asp Lys Ala Phe Tyr Ser Ser Phe Met Ala
    1115                1120                1125

Leu Met Ser Leu Met Leu Gln Met Arg Asn Ser Ile Thr Gly Arg
    1130                1135                1140

Thr Asp Val Asp Phe Leu Ile Ser Pro Val Lys Asn Ser Asp Gly
    1145                1150                1155

Ile Phe Tyr Asp Ser Arg Asn Tyr Glu Ala Gln Glu Asn Ala Ile
    1160                1165                1170

Leu Pro Lys Asn Ala Asp Ala Asn Gly Ala Tyr Asn Ile Ala Arg
    1175                1180                1185

Lys Val Leu Trp Ala Ile Gly Gln Phe Lys Lys Ala Glu Asp Glu
    1190                1195                1200

Lys Leu Asp Lys Val Lys Ile Ala Ile Ser Asn Lys Glu Trp Leu
    1205                1210                1215

Glu Tyr Ala Gln Thr Ser Val Lys His
    1220                1225
```

<210> SEQ ID NO 40
<211> LENGTH: 6080
<212> TYPE: DNA
<213> ORGANISM: Artificial Sequence
<220> FEATURE:
<223> OTHER INFORMATION: Synthetic polynucleotide.Expression cassette comprising Zea mays Ubiquitin promoter cassette, NLS-LbCpf1(TYC)-
CO2-NLS and an Oryza sativa transcription termination sequence

<400> SEQUENCE: 40

```
gtcgtgcccc tctctagaga taaagagcat tgcatgtcta aagtataaaa aattaccaca      60
tatttttttg tcacacttat ttgaagtgta gtttatctat ctctatacat atatttaaac     120
ttcactctac aaataatata gtctataata ctaaaataat attagtgttt tagaggatca     180
tataaataaa ctgctagaca tggtctaaag gataattgaa tattttgaca atctacagtt     240
ttatctttttt agtgtgcatg tgatctctct gttttttttg caaatagctt gacctatata     300
atacttcatc cattttatta gtacatccat ttaggattta gggttgatgg tttctataga     360
ctaattttta gtacatccat tttattcttt ttagtctcta aatttttttaa aactaaaact     420
ctattttagt ttttttattta ataatttaga tataaaatga aataaaataa attgactaca     480
aataaaacaa ataccctttta agaaataaaaa aaactaagca aacatttttc ttgtttcgag     540
tagataatga caggctgttc aacgccgtcg acgagtctaa cggacaccaa ccagcgaacc     600
agcagcgtcg cgtcgggcca agcgaagcag acggcacggc atctctgtag ctgcctctgg     660
acccctctcg agagttccgc tccaccgttg gacttgctcc gctgtcggca tccagaaatt     720
gcgtggcgga gcggcagacg tgaggcggca cggcaggcgg cctcttcctc ctctcacggc     780
accggcagct acgggggatt cctttcccac cgctccttcg ctttcccttc ctcgcccgcc     840
gtaataaata gacacccccct ccacaccctc tttccccaac ctcgtgttcg ttcggagcgc     900
acacacacgc aaccagatct cccccaaatc cagccgtcgg cacctccgct tcaaggtacg     960
ccgctcatcc tcccccccccc cctctctcta ccttctctag atcggcgatc cggtccatgg    1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt    1140
caagctacct ggtggattta ttaattttgt atctgtatgt gtgtgccata catcttcata    1200
gttacgagtt taagatgatg gatggaaata tcgatctagg ataggtatac atgttgatgc    1260
gggttttact gatgcatata cagagatgct ttttttctcg cttggttgtg atgatatggt    1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc ttttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggatttttt    1920
agccctgcct tcatacgcta tttatttgct tggtactgtt tcttttgtcc gatgctcacc    1980
ctgttgtttg gtgatacttc tgcaggtccg gtacctcagc atgggtagca aaagaggcg    2040
tatcaagcag gacgcgtcga agctcgagaa gttcaccaac tgctactcgc tgagcaagac    2100
gctgcggttc aaggcgatcc ccgtcgggaa gacccaggag aacatcgaca caagcggct    2160
cctggtcgag gacgagaagc gcgccgagga ctacaagggc gtcaagaagc tgctggaccg    2220
```

```
gtactacctc tccttcatca acgacgtcct gcactcgatc aagctcaaga acctgaacaa    2280
ctacatctcg ctgttccgca agaagacacg gaccgagaag gagaacaagg agctcgagaa    2340
cctcgagatc aacctgcgca aggagatcgc gaaggcgttc aagggcaacg aggggtacaa    2400
gagcctgttc aagaaagaca tcatcgagac catcctgccg gagttcctgg acgacaagga    2460
cgagatcgcg ctggtgaact cgttcaacgg gttcaccacg gccttcaccg gttttttcga    2520
caaccgggag aacatgttca gcaggaggc caagtcgacc agcatcgcct tccggtgcat    2580
caacgagaac ctcacccgct acatcagcaa catggacatc ttcgagaagg tggacgccat    2640
cttcgacaag cacgaggtcc aggagatcaa ggaaaagatc ctgaactcgg actacgacgt    2700
ggaagacttc tttgagggcg agttcttcaa cttcgtcctc acccaggagg gcatcgacgt    2760
ctacaacgcc atcatcggcg gcttcgtgac ggagagcggc gagaagatca agggcctcaa    2820
cgagtacatc aacctctaca accagaagac taagcagaag ctcccgaagt tcaagccgct    2880
gtacaagcaa gtcctgagcg accgggagtc cctctcgttc tacggcgagg gctacacgag    2940
cgacgaggag gtgctggagg tgttccgcaa cacgctgaac aagaacagcg agatcttcag    3000
ctcgatcaag aaactcgaga agctgttcaa gaacttcgac gagtacagca gcgccggcat    3060
cttcgtcaag aacgggcccg cgatcagcac catcagcaag gacatcttcg gggagtggaa    3120
cgtgatccgc gacaagtgga acgccgagta cgacgacatc caccctcaaga aaaaggcggt    3180 ggtcacggag aagtacgagg acgaccgccg gaagtccttc aagaaaatcg ggagcttcag    3240
cctcgagcag ctccaggagt acgcggacgc cgacctgagc gtggtggaga agctcaagga    3300
gatcatcatc cagaaggtcg acgagatcta caaggtctac ggctcgagcg agaagctgtt    3360
cgacgcggac ttcgtgctgg agaagtccct caagaagaac gacgccgtgg tggccatcat    3420
gaaggatctg ctcgacagcg tgaagtcgtt cgagaactac atcaaggcat tcttgggga    3480 gggcaaggag acgaaccggg acgagtcctt ctacggggac ttcgtgctcg cgtacgacat    3540
cctcctgaag gtcgaccaca tctacgacgc gatccggaac tacgtcacgc agaagcccta    3600
cagcaaggac aagttcaagc tctacttcca gaacccgcag ttcatgcgcg ggtgggacaa    3660
ggacaaggag accgactacc gggccacgat cctgcggtac gggtccaagt actacctcgc    3720
catcatggac aagaagtacg ccaagtgcct ccagaagatt gacaaggacg acgtgaacgg    3780
gaactacgag aagatcaact acaagctcct cccgggccc aacaagatgc tgccgagggt    3840
gttcttcagc aagaagtgga tggcctacta caacccctcg gaggacatcc agaagatata    3900
caagaacggc acgttcaaaa aggggacat gttcaacctg aacgactgcc acaagctgat    3960 cgacttttc aaggacagca tcagccgcta cccgaagtgg tcgaacgcct acgacttcaa    4020
cttctcggag acggagaagt acaaggacat tgcgggcttc taccgggagg tggaggagca    4080
gggctacaag gtctcccttcg agagcgcctc caagaaagag gtggacaagc tcgtggagga    4140
gggcaagctg tacatgttcc agatctacaa caaggacttc tcggacaagt cgcacggcac    4200
cccgaacctc cacacgatgt acttcaagct gctgttcgac gagaacaacc acgggcagat    4260
ccgcctcagc ggcggggcgg agctgttcat gcgccgcgcg tccctcaaga aggaggagct    4320
ggtcgtgcac cccgccaact ccccgatcgc gaacaagaac cccgacaacc ccaagaagac    4380
aaccaccctc tcgtacgacg tctacaagga caagcggttc tcggaggacc agtacgagct    4440
gcacatcccg atcgccatca acaagtgccc caagaacatc ttcaagatca acaccgaggt    4500
gcgggtgctc ctcaagcacg acgacaaccc ctacgtcatc gggatcgacc gcggcgagcg    4560
gaacctgctc tacatcgtgg tcgtggacgg gaaggggaac atcgtggagc agtacagcct    4620
```

```
gaacgagatc atcaacaact tcaacggcat ccgcatcaag acggactacc acagcctcct    4680
ggacaagaag gagaaggagc ggttcgaggc gcggcagaac tggacctcca tcgagaacat    4740
caaggagctg aaggccggct acatcagcca ggtcgtgcac aagatctgcg agctcgtgga    4800
gaagtacgac gcggtgatcg cgctggagga cttgaacagc gggttcaaga actcccgggt    4860
caaggtcgag aagcaggtct accagaagtt cgagaagatg ctgatcgaca agctcaacta    4920
catggtggac aagaagtcca accctgcgc caccggcggc ccctcaagg ctaccagat     4980 caccaacaag ttcgagtcct tcaagtcgat gtctacgcag aacgggttca ttttctacat    5040
cccggcgtgg ctcaccagca agatcgaccc gagcacgggc ttcgtcaacc tcctgaagac    5100
caagtacacc agcatcgcgg acagcaagaa gttcatctcc tcgttcgacc gcatcatgta    5160
cgtccccgag aagacctgt tcgagttcgc cctcgactac aagaacttct cccggacgga    5220
cgccgactac atcaaaaagt ggaagctcta cagctacggc aaccggatcc gcatcttccg    5280
caaccccaag aagaacaatg tgttcgactg ggaggaggtg tgcctgacga cgcctacaa    5340 ggagctcttc aacaagtacg gcatcaacta ccagcaaggg gacatccgcg cgctgctctg    5400
cgagcagtcc gacaaggcgt tctactcgtc gttcatggcc ctgatgagcc tcatgctcca    5460
gatgcgcaac agcatcaccg gccggacgga cgtggacttc ctgatcagcc cggtcaagaa    5520
cagcgacggc attttctacg acagccgaa ctacgaggcc caggagacg ccatcctccc    5580 caagaacgcc gacgcgaacg gcgcctacaa catcgcgcgg aaggtgctgt gggccatcgg    5640
ccagttttaa aaggcggagg acgagaagct ggacaaggtc aagatcgcca tcagcaacaa    5700
ggagtggctc gagtacgcgc agacgagcgt gaagcatgca ggatctaaga agcgtaggat    5760
caagcaagat taagaggtta attaatcgat cctccgatcc cttaattacc ataccattac    5820
accatgcatc aatatccata tatatataaa ccctttcgca cgtacttata ctatgttttg    5880
tcatacatat atatgtgtcg aacgatcgat ctatcactga tatgatatga ttgatccatc    5940
agcctgatct ctgtatcttg ttatttgtat accgtcaaat aaaagtttct tccacttgtg    6000
ttaataatta gctactctca tctcatgaac cctatatata actagtttaa tttgctgtca    6060
attgaacatg atgatcgatg                                               6080
```

<210> SEQ ID NO 41  
<211> LENGTH: 3753  
<212> TYPE: DNA  
<213> ORGANISM: Artificial Sequence  
<220> FEATURE:  
<223> OTHER INFORMATION: Synthetic polynucleotide.NLS-LbCpf1(TYC)-CO2-NLS

<400> SEQUENCE: 41

```
atgggtagca aaaagaggcg tatcaagcag gacgcgtcga agctcgagaa gttcaccaac     60
tgctactcgc tgagcaagac gctgcggttc aaggcgatcc ccgtcgggaa gacccaggag    120
aacatcgaca caagcggct cctggtcgag acgagaagc gcgccgagga ctacaagggc    180
gtcaagaagc tgctggaccg gtactacctc tccttcatca cgacgtcct gcactcgatc    240 aagctcaaga acctgaacaa ctacatctcg ctgttccgca gaagacacg gaccgagaag    300 gagaacaagg agctcgagaa cctcgagatc aacctgcgca aggagatcgc gaaggcgttc    360
aagggcaacg aggggtacaa gagcctgttc aagaaagaca tcatcgagac catcctgccg    420
gagttcctgg acgacaagga cgagatcgcg ctggtgaact cgttcaacgg gttcaccacg    480
gccttcaccg ggtttttcga caaccgggag aacatgttca gcgaggaggc caagtcgacc    540
```

```
agcatcgcct tccggtgcat caacgagaac ctcacccgct acatcagcaa catggacatc    600
ttcgagaagg tggacgccat cttcgacaag cacgaggtcc aggagatcaa ggaaaagatc    660
ctgaactcgg actacgacgt ggaagacttc tttgagggcg agttcttcaa cttcgtcctc    720
acccaggagg gcatcgacgt ctacaacgcc atcatcggcg gcttcgtgac ggagagcggc    780
gagaagatca agggcctcaa cgagtacatc aacctctaca accagaagac taagcagaag    840
ctcccgaagt tcaagccgct gtacaagcaa gtcctgagcg accgggagtc cctctcgttc    900
tacggcgagg gctacacgag cgacgaggag gtgctggagg tgttccgcaa cacgctgaac    960
aagaacagcg agatcttcag ctcgatcaag aaactcgaga gctgttcaa gaacttcgac    1020
gagtacagca gcgccggcat cttcgtcaag aacgggcccg cgatcagcac catcagcaag    1080
gacatcttcg gggagtggaa cgtgatccgc gacaagtgga acgccgagta cgacgacatc    1140
cacctcaaga aaaggcggt ggtcacggag aagtacgagg acgaccgccg gaagtccttc    1200
aagaaaatcg ggagcttcag cctcgagcag ctccaggagt acgcggacgc cgacctgagc    1260
gtggtggaga agctcaagga gatcatcatc cagaaggtcg acgagatcta caaggtctac    1320
ggctcgagcg agaagctgtt cgacgcggac ttcgtgctgg agaagtccct caagaagaac    1380
gacgccgtgg tggccatcat gaaggatctg ctcgacagcg tgaagtcgtt cgagaactac    1440
atcaaggcat tctttgggga gggcaaggag acgaaccggg acgagtcctt ctacggggac    1500
ttcgtgctcg cgtacgacat cctcctgaag gtcgaccaca tctacgacgc gatccggaac    1560
tacgtcacgc agaagcccta cagcaaggac aagttcaagc tctacttcca gaacccgcag    1620
ttcatgcgcg ggtgggacaa ggacaaggag accgactacg gggccacgat cctgcggtac    1680
gggtccaagt actacctcgc catcatggac aagaagtacg ccaagtgcct ccagaagatt    1740
gacaaggacg acgtgaacgg gaactacgag aagatcaact acaagctcct cccggggccc    1800
aacaagatgc tgccgagggt gttcttcagc aagaagtgga tggcctacta caacccctcg    1860
gaggacatcc agaagatata caagaacggc acgttcaaaa aggggacat gttcaacctg    1920
aacgactgcc acaagctgat cgactttttc aaggacagca tcagccgcta cccgaagtgg    1980
tcgaacgcct acgacttcaa cttctcggag acggagaagt acaaggacat tgcgggcttc    2040
taccgggagg tggaggagca gggctacaag gtctccttcg agagcgcctc caagaaagag    2100
gtggacaagc tcgtggagga gggcaagctg tacatgttcc agatctacaa caaggacttc    2160
tcggacaagt cgcacggcac cccgaacctc cacacgatgt acttcaagct gctgttcgac    2220
gagaacaacc acgggcagat ccgcctcagc ggcggggcgg agctgttcat cgccgcgcg    2280
tccctcaaga aggaggagct ggtcgtgcac cccgccaact ccccgatcgc gaacaagaac    2340
cccgacaacc ccaagaagac aaccaccctc tcgtacgacg tctacaagga caagcggttc    2400
tcggaggacc agtacgagct gcacatcccg atcgccatca acaagtgccc caagaacatc    2460
ttcaagatca acaccgaggt gcgggtgctg ctcaagcacg acgacaaccc ctacgtcatc    2520
gggatcgacc gcggcgagcg gaacctgctc tacatcgtgg tcgtggacgg aaggggaac    2580
atcgtggagc agtacagcct gaacgagatc atcaacaact tcaacggcat ccgcatcaag    2640
acggactacc acagcctcct ggacaagaag gagaaggagc ggttcgaggc gcggcagaac    2700
tggacctcca tcgagaacat caaggagctg aaggccggct acatcagcca ggtcgtgcac    2760
aagatctgcg agctcgtgga gaagtacgac gcggtgatcg cgctggagga cttgaacagc    2820
gggttcaaga actcccgggt caaggtcgag aagcaggtct accagaagtt cgagaagatg    2880
```

```
ctgatcgaca agctcaacta catggtggac aagaagtcca acccctgcgc caccggcggc      2940
gccctcaagg gctaccagat caccaacaag ttcgagtcct tcaagtcgat gtctacgcag      3000
aacgggttca ttttctacat cccggcgtgg ctcaccagca agatcgaccc gagcacgggc      3060
ttcgtcaacc tcctgaagac caagtacacc agcatcgcgg acagcaagaa gttcatctcc      3120
tcgttcgacc gcatcatgta cgtccccgag gaagacctgt tcgagttcgc cctcgactac      3180
aagaacttct cccggacgga cgccgactac atcaaaaagt ggaagctcta cagctacggc      3240
aaccggatcc gcatcttccg caaccccaag aagaacaatg tgttcgactg ggaggaggtg      3300
tgcctgacga cgcgccacaa ggagctcttc aacaagtacg gcatcaacta ccagcaaggg      3360
gacatccgcg cgctgctctg cgagcagtcc gacaaggcgt tctactcgtc gttcatggcc      3420
ctgatgagcc tcatgctcca gatgcgcaac agcatcaccg gccggacgga cgtggacttc      3480
ctgatcagcc cggtcaagaa cagcgacggc attttctacg acagccggaa ctacgaggcc      3540
caggagaacg ccatcctccc caagaacgcc gacgcgaacg cgcctacaa catcgcgcgg      3600 aaggtgctgt gggccatcgg ccagtttaaa aaggcggagg acgagaagct ggacaaggtc      3660
aagatcgcca tcagcaacaa ggagtggctc gagtacgcgc agacgagcgt gaagcatgca      3720
ggatctaaga agcgtaggat caagcaagat taa                                   3753

<210> SEQ ID NO 42
<211> LENGTH: 33
<212> TYPE: DNA
<213> ORGANISM: Solanum tuberosum

<400> SEQUENCE: 42
atgggtagca aaagaggcg tatcaagcag gac                                    33

<210> SEQ ID NO 43
<211> LENGTH: 1300
<212> TYPE: PRT
<213> ORGANISM: Francisella tularensis subsp. novicida U112

<400> SEQUENCE: 43

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
                20                  25                  30

Ala Arg Gly Leu Ile Leu Asp Asp Glu Lys Arg Ala Lys Asp Tyr Lys
            35                  40                  45

Lys Ala Lys Gln Ile Ile Asp Lys Tyr His Gln Phe Phe Ile Glu Glu
        50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
```

```
                    165                 170                 175
Thr Tyr Phe Lys Gly Phe His Glu Asn Arg Lys Asn Val Tyr Ser Ser
                180                 185                 190

Asn Asp Ile Pro Thr Ser Ile Ile Tyr Arg Ile Val Asp Asp Asn Leu
            195                 200                 205

Pro Lys Phe Leu Glu Asn Lys Ala Lys Tyr Glu Ser Leu Lys Asp Lys
        210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590
```

-continued

```
Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
        610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
        690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
        770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
        850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
        995                 1000                1005
```

| | | | | | | | | | |
|---|---|---|---|---|---|---|---|---|---|
| Asn | Phe | Gly | Phe | Lys | Arg | Gly | Arg | Phe | Lys | Val | Glu | Lys | Gln | Val |
| 1010 | | | | | 1015 | | | | | 1020 | | | | |

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 44
<211> LENGTH: 3897
<212> TYPE: DNA
<213> ORGANISM: Artificial Sequence
<220> FEATURE:
<223> OTHER INFORMATION: Synthetic polynucleotide.Codon optimized
    FnCpf1-Hs

<400> SEQUENCE: 44
agcatctacc aggagttcgt caacaagtat tcactgagta agacactgcg gttcgagctg    60
atcccacagg gcaagacact ggagaacatc aaggcccgag gcctgattct ggacgatgag   120
aagcgggcaa aagactataa gaaagccaag cagatcattg ataaatacca ccagttcttt   180
atcgaggaaa ttctgagctc cgtgtgcatc agtgaggatc tgctgcagaa ttactcagac   240

```
gtgtacttca agctgaagaa gagcgacgat gacaacctgc agaaggactt caagtccgcc      300
aaggacacca tcaagaaaca gattagcgag tacatcaagg actccgaaaa gtttaaaaat      360
ctgttcaacc agaatctgat cgatgctaag aaaggccagg agtccgacct gatcctgtgg      420
ctgaaacagt ctaaggacaa tgggattgaa ctgttcaagg ctaactccga tatcactgat      480
attgacgagg cactggaaat catcaagagc ttcaagggat ggaccacata ctttaaaggc      540
ttccacgaga accgcaagaa cgtgtactcc agcaacgaca ttcctacctc catcatctac      600
cgaatcgtcg atgacaatct gccaaagttc ctggagaaca aggccaaata tgaatctctg      660
aaggacaaag ctcccgaggc aattaattac gaacagatca agaagatctg gctgaggaa       720 ctgacattcg atatcgacta taagactagc gaggtgaacc agagggtctt ttccctggac      780
gaggtgtttg aaatcgccaa tttcaacaat tacctgaacc agtccggcat tactaaattc      840
aataccatca ttggcgggaa gtttgtgaac ggggagaata ccaagcgcaa gggaattaac      900
gaatacatca atctgtatag ccagcagatc aacgacaaaa ctctgaagaa atacaagatg      960
tctgtgctgt tcaaacagat cctgagtgat accgagtcca agtcttttgt cattgataaa     1020
ctggaagatg actcagacgt ggtcactacc atgcagagct tttatgagca gatcgccgct     1080
ttcaagacag tggaggaaaa atctattaag gaaactctga gtctgctgtt cgatgacctg     1140
aaagcccaga agctggacct gagtaagatc tacttcaaaa acgataagag tctgacagac     1200
ctgtcacagc aggtgtttga tgactattcc gtgattggga ccgccgtcct ggagtacatt     1260
acacagcaga tcgctccaaa gaacctggat aatccctcta agaaagagca ggaactgatc     1320
gctaagaaaa ccgagaaggc aaaatatctg agtctggaaa caattaagct ggcactggag     1380
gagttcaaca agcacaggga tattgacaaa cagtgccgct ttgaggaaat cctggccaac     1440
ttcgcagcca tccccatgat tttgatgag atcgcccaga acaaagacaa tctggctcag     1500
atcagtatta agtaccagaa ccagggcaag aaagacctgc tgcaggcttc agcagaagat     1560
gacgtgaaag ccatcaagga tctgctggac cagaccaaca tctgctgca caagctgaaa     1620 atcttccata ttagtcagtc agaggataag gctaatatcc tggataaaga cgaacacttc     1680
tacctggtgt tcgaggaatg ttacttcgag ctggcaaaca ttgtccccct gtataacaag     1740
attaggaact acatcacaca gaagccttac tctgacgaga gtttaaact gaacttcgaa      1800 aatagtaccc tggccaacgg gtgggataag aacaaggagc tgacaacac agctatcctg      1860 ttcatcaagg atgacaagta ctatctggga gtgatgaata agaaaaacaa taagatcttc      1920
gatgacaaag ccattaagga gaacaaaggg gaaggataca agaaaatcgt gtataagctg      1980
ctgcccggcg caaataagat gctgcctaag gtgttcttca gcgccaagag tatcaaattc      2040
tacaacccat ccgaggacat cctgcggatt agaaatcact caacacatac taagaacggg      2100
agcccccaga agggatatga aaatttgag ttcaacatcg aggattgcag gaagtttatt       2160
gacttctaca gcagagcat ctccaaacac cctgaatgga aggattttgg cttccggttt       2220
tccgacacac agagatataa ctctatcgac gagttctacc gcgaggtgga aaatcagggg      2280
tataagctga cttttgagaa catttctgaa agttacatcg acagcgtggt caatcaggga      2340
aagctgtacc tgttccagat ctataacaaa gattttcag catacagcaa gggcagacca      2400
aacctgcata cactgtactg gaaggccctg ttcgatgaga ggaatctgca ggacgtggtc      2460
tataaactga acggagaggc cgaactgttt taccggaagc agtctattcc taagaaaatc      2520
actcacccag ctaaggaggc catcgctaac aagaacaagg acaatcctaa gaaagagagc      2580
gtgttcgaat acgatctgat taaggacaag cggttcaccg aagataagtt cttttttccat     2640
```

```
tgtccaatca ccattaactt caagtcaagc ggcgctaaca agttcaacga cgagatcaat    2700
ctgctgctga aggaaaaagc aaacgatgtg cacatcctga gcattgaccg aggagagcgg    2760
catctggcct actataccct ggtggatggc aaagggaata tcattaagca ggatacattc    2820
aacatcattg gcaatgaccg gatgaaaacc aactaccacg ataaactggc tgcaatcgag    2880
aaggatagag actcagctag gaaggactgg aagaaaatca acaacattaa ggagatgaag    2940
gaaggctatc tgagccaggt ggtccatgag attgcaaagc tggtcatcga atacaatgcc    3000
attgtggtgt tcgaggatct gaacttcggc tttaagaggg ggcgctttaa ggtggaaaaa    3060
caggtctatc agaagctgga gaaaatgctg atcgaaaagc tgaattacct ggtgtttaaa    3120
gataacgagt tcgacaagac cggaggcgtc ctgagagcct accagctgac agctcccttt    3180
gaaactttca gaaaatggg aaaacagaca ggcatcatct actatgtgcc agccggattc    3240
acttccaaga tctgccccgt gaccggcttt gtcaaccagc tgtaccctaa atatgagtca    3300
gtgagcaagt cccaggaatt tttcagcaag ttcgataaga tctgttataa tctggacaag    3360
gggtacttcg agttttcctt cgattacaag aacttcggcg acaaggccgc taagggaaa    3420 tggaccattg cctccttcgg atctcgcctg atcaactttc gaaattccga taaaaaccac    3480
aattgggaca ctagggaggt gtacccaacc aaggagctgg aaaagctgct gaaagactac    3540
tctatcgagt atggacatgg cgaatgcatc aaggcagcca tctgtggcga gagtgataag    3600 aaattttcg ccaagctgac ctcagtgctg aatacaatcc tgcagatgcg gaactcaaag    3660
accgggacag aactggacta tctgattagc cccgtggctg atgtcaacgg aaacttcttc    3720
gacagcagac aggcacccaa aaatatgcct caggatgcag acgccaacgg ggcctaccac    3780
atcgggctga agggactgat gctgctgggc cggatcaaga acaatcagga ggggaagaag    3840
ctgaacctgg tcattaagaa cgaggaatac ttcgagtttg tccagaatag aaataac       3897
```

<210> SEQ ID NO 45
<211> LENGTH: 3900
<212> TYPE: DNA
<213> ORGANISM: Artificial Sequence
<220> FEATURE:
<223> OTHER INFORMATION: Synthetic polynucleotide.Codon optimized
      FnCpf1-CO1

<400> SEQUENCE: 45

```
atgtctatct atcaagagtt tgtcaacaag tacagcttaa gtaagacact tcgcttcgag     60
ttgatccctc aggggaagac actggaaaac atcaaggcga ggggcttat cctggacgac    120 gagaagcggg ctaaagacta caaaaaagct aaacagataa ttgacaagta tcaccaattt    180
tttattgagg atcctctc ctctgtgtgc ataagtgagg atctgctcca gaactattcg    240
gatgtttact ttaaactcaa gaagtccgat gatgacaacc ttcagaagga cttcaagtcc    300
gccaaagaca cgattaagaa acaaatcagt gagtacatca aggatagcga gaaattcaag    360
aacctgttca accagaactt aattgatgcc aaaaagggcc aagaatccga cctcatcctg    420
tggttaaagc aatctaaaga caacggtatt gagctgttca aggcaaacag cgacattaca    480
gacattgacg aggccctaga gatcatcaag tcattcaaag gctggacgac ttactttaaa    540
ggttttcacg agaaccgtaa gaatgtttac tcaagtaacg atataccaac gagcattatc    600
taccgaatag tggatgataa cctaccgaag ttccttgaga caaagcgaa gtacgagtct    660 ctcaaagaca aggcccctga ggccatcaac tacgagcaga ttaagaagga tctcgccgag    720
gagctaacct tcgacattga ctacaaaaca tcggaagtga atcagagggt gttctcgctt    780
```

```
gatgaagtat tcgagattgc taacttcaac aattacctga accagagtgg tattactaag    840
ttcaacacaa tcattggagg caaattcgtg aacggcgaaa acacaaagcg aaaagggata    900
aacgagtaca ttaacttgta cagccagcag atcaacgata agacactcaa gaagtataag    960
atgtctgtgc tgttcaaaca aatcttaagc gacacgaaa gcaagtcgtt cgtaattgac     1020
aagctggaag acgattctga cgtggttaca accatgcagt cctttacga gcagattgcc    1080 gcattcaaga ccgtggagga aaagtcgatc aaggaaacac tttcgttgct tttcgacgac    1140
cttaaagctc agaagctcga cttaagcaag atatacttta agaacgataa gagcttgaca    1200
gacttgagcc agcaagtctt tgacgactac agcgttatcg gaactgccgt tctggagtac    1260
ataacacagc agatcgcacc caagaacctt gacaacccctt ccaagaaaga caagagttg    1320 atcgccaaga agactgaaaa ggctaagtac ctctctctgg agactatcaa gctcgctctt    1380
gaggagttta acaagcacag ggacattgac aagcaatgcc gattcgagga aatactggca    1440
aacttcgcag ccatacccat gatattcgat gagatagccc agaacaagga taacttggcc    1500
caaatctcga ttaagtatca gaaccagggc aaaaaggacc ttctacaggc tagtgcagag    1560
gacgatgtga aggctattaa ggacttatta gatcagacaa caaccttct gcataagctc     1620 aagatattcc atatctccca gtcagaggac aaggccaaca ttctggataa ggacgagcac    1680
ttctatctcg tattcgagga atgttacttt gagctggcca atatcgttcc cttgtacaac    1740
aaaatccgga actacatcac acagaagccc tacagtgatg agaagttcaa attgaacttt    1800
gaaaactcaa cacttgctaa tggttgggac aagaataagg aacctgacaa cactgccatc    1860
ctctttatta aagatgataa gtactacctc ggggtgatga ataagaagaa caacaaaatc    1920
ttcgatgaca agctattaa ggagaacaaa ggtgaagggt acaagaagat tgtctacaaa     1980
ctgctgcctg gtgccaacaa aatgctacca aaggtatttt tcagcgccaa atctattaag    2040
ttctacaatc caagcgagga tattctccgg atacggaatc actctacaca taccaagaat    2100
ggaagtccac aaaagggtta cgagaaattc gagttcaaca ttgaagactg ccggaaattc    2160
attgacttct acaagcaatc catctctaaa catcctgaat ggaaagactt cggtttccgc    2220
ttcagtgata ctcaacggta caattcaatt gacgaattct accgtgaggt tgagaaccag    2280
gggtacaaac tgaccttcga gaacatatca gagagctaca tcgactcagt ggttaatcag    2340
gggaagctat atctgtttca aatctacaac aaagacttta gtgcctactc taaagggcgg    2400
ccaaacttac acacactttta ctggaaggca ctattcgacg aacgcaatct acaagatgta    2460
gtttacaaat gaacggtga ggctgagttg ttctaccgta acaatctat acccaagaag      2520 ataacacacc ctgctaaaga ggcaattgca acaaaaaca aggataatcc caaaaggag      2580 tctgtctttg agtatgacct cattaaggat aagcggttca cggaggacaa gttcttcttc    2640
cattgtccaa taaccatcaa cttcaaatca tccggcgcaa acaaattcaa tgacgagatc    2700
aacctgttac taaaggagaa ggctaacgat gttcacatct tatctattga tcgaggtgag    2760
agacacctag cctactacac tttagtggat gggaagggga acatcatcaa gcaagacacc    2820
ttcaacatca ttgggaacga caggatgaag actaactacc atgataagct cgccgctatt    2880
gaaaaggaca gggactctgc caggaaggac tggaaaaaaa ttaacaatat taaagagatg    2940
aaggagggct acctgagcca agtagtccat gagatagcaa aactggtgat tgagtacaac    3000
gcaatagtcg tattcgagga cttaaacttc ggcttcaaac gtgggcggtt taaggtggag    3060
aaacaagtct atcagaaatt ggagaagatg ctaatcgaga agctcaacta cctcgtgttt    3120
```

```
aaagacaacg agtttgacaa aactggagga gtcctgcggg cataccaact gaccgcaccc    3180
ttcgagacat tcaagaagat gggaaagcag actggcatca tctattacgt gccagcgggt    3240
tttacttcca aaatctgtcc agttacaggc ttcgtgaacc agttgtaccc gaagtacgag    3300 tctgttttcca agtcacagga attcttctca aagtttgaca agatatgtta caatctcgat    3360
aagggatact ttgagtttag tttcgactac aagaactttg gcgataaggc cgcaaaaggg    3420
aaatggacaa ttgcatcctt cgggtcacgc cttattaact ttcgtaactc agacaagaac    3480
cacaattggg acaccaggga ggtgtaccct actaaggagc tggagaagct acttaaagac    3540
tactcgattg agtacggaca tggagagtgc atcaaggcag caatatgtgg ggaatctgac    3600
aaaaagttct ttgccaagct gacctctgta ctgaacacta ttctccaaat gagaaatagt    3660
aagactggca cagagttgga ctacctgatc tctccagtgg ctgacgttaa tgggaatttt    3720
ttcgactcaa gacaagctcc caagaatatg ccacaggacg cagatgcaaa cggggcatat    3780
cacatcgggc ttaaaggact catgctacta gggcggatca agaataatca ggagggcaaa    3840
aagctgaacc tagtcatcaa gaacgaggag tacttcgaat ttgtccagaa tcgtaacaac    3900
```

<210> SEQ ID NO 46
<211> LENGTH: 3900
<212> TYPE: DNA
<213> ORGANISM: Artificial Sequence
<220> FEATURE:
<223> OTHER INFORMATION: Synthetic polynucleotide.Codon optimized
 FnCpf1-CO2

<400> SEQUENCE: 46

```
atgtccatat accaggagtt cgtcaacaag tactcgctca gcaagacgct ccgcttcgag      60
ctgatccccc agggtaagac cctggagaac atcaaggcgc gcggactcat cctcgacgac     120
gagaagcggg ctaaggacta caaaaaggcc aagcagatca tcgacaagta ccaccagttc     180
ttcatcgagg gatcctctc ctccgtctgc atctccgagg acctcctcca gaactacagc     240
gacgtctact tcaagctcaa aaagtcggac gacgacaacc tccagaagga cttcaagtcg     300
gcgaaggaca ccatcaagaa gcagatcagc gagtacatca aggactccga gaagttcaag     360
aacctgttca accagaacct gatcgacgcc aagaagggcc aggagtcgga cctgatcctg     420
tggctcaagc agagcaagga caacggcatc gagctcttca aggccaacag cgacatcacg     480
gacatcgacg aggccctgga gatcatcaag tcgttcaagg gctggacgac ctacttcaag     540
ggcttccacg agaaccgcaa gaacgtctat agctccaacg acatccccac ctcgatcatc     600
taccggatcg tggacgacaa cctccccaag ttcctggaga caaggcgcaa gtacgagtcg     660
ttgaaggaca aggcgccgga ggcgatcaac tacgagcaga tcaagaagga cctggccgag     720
gagctgacct tcgacatcga ctacaagacg tcggaggtga accagcgggt gttcagtctg     780
gacgaggtct tcgagatcgc gaacttcaac aactacctga ccagtcgggg atcaccaag     840 ttcaacacga tcataggcgg caagttcgtg acggcgaga caccaagcg caaggggata     900 aacgagtaca tcaacctgta cagccagcag atcaacgaca gacgctcaa gaagtacaag     960 atgagcgtgc tcttcaagca gatcctcagt gacaccgagt ccaagagctt cgtgatcgac    1020
aagctggagg acgacagcga cgtcgtgaca accatgcaga gcttctacga gcagatcgcc    1080
gcgttcaaga ccgtcgagga gaagtcaatc aaggagacgc tctccttgct gttcgacgac    1140
ctgaaggcac aaaagctgga cctcagcaag atctacttca agaacgacaa gtccctgacc    1200
gacctgagcc agcaggtttt cgacgactac tccgtcatcg ggactgccgt cctggagtac    1260
```

```
atcacccagc agatcgctcc gaagaacctc gacaacccgt ccaagaagga gcaggagctg    1320
attgcgaaga agacagagaa ggccaagtac ctctccctcg agaccatcaa gctcgccctg    1380
gaggagttca acaagcacag ggacattgac aagcagtgcc gtttcgagga gatcctggcc    1440
aacttcgcgg ccatccccat gatcttcgac gagatcgccc agaacaagga caacctggcg    1500
cagatctcta tcaagtacca gaaccagggg aagaaggact tgctccaggc ctcagcggag    1560
gacgacgtga aggccatcaa ggacctgctc gaccagacga caacttgct ccacaagctc    1620 aagatctttc acatcagcca gagcgaggac aaggccaaca tcctcgacaa ggacgagcac    1680
ttctacctcg tgttcgagga gtgctacttc gagctggcca acatcgtgcc actttacaac    1740
aagatccgca actacatcac gcagaagccg tactccgacg agaagttcaa gctgaacttc    1800
gagaactcca ccctcgccaa cggctgggac aagaacaagg agccggacaa caccgcgatc    1860
ctgttcataa aggacgacaa gtactacttg ggggtcatga acaagaagaa caacaagata    1920
ttcgacgaca aggccatcaa ggagaacaag ggggagggct acaagaagat cgtctacaag    1980
ctcctccccg gcgcgaacaa gatgctgcct aaggtcttct tttccgccaa gagtatcaag    2040
ttctacaacc cctccgagga catcctccgc atccggaacc acagcacgca cacaaagaac    2100
ggctcgcctc agaagggcta cgagaagttc gagttcaaca tcgaggactg ccggaagttc    2160
atcgacttct acaagcagag catctccaag cacccggagt ggaaggactt tggcttcagg    2220
ttctcagaca cccagcggta caactccatc gacgagttct accgcgaggt ggagaaccag    2280
ggctacaagc tgaccttcga gaatatatca gagtcgtaca tcgacagcgt ggtgaaccag    2340
ggcaagttgt acctgttcca gatctacaac aaggacttct ccgcctactc aaagggcgt    2400 ccaaacctgc acacgctgta ctggaaggcg ctcttcgacg agcgcaacct acaagatgtt    2460
gtatacaagc tcaacggcga ggcggaactg ttctatagga agcagtcgat ccccaagaag    2520
attacgcacc cggctaagga ggccatcgcc aacaagaaca aggacaaccc caagaaggag    2580
tccgtgttcg agtacgacct catcaaggac aagaggttca cggaggacaa gtttttcttc    2640
cactgcccaa tcactatcaa tttcaagtcg agcggagcca acaagttcaa cgacgagata    2700
aacctgctcc tcaaggagaa ggccaatgac gtgcacatcc tctccatcga ccggggcgag    2760
cggcacctgg cgtactacac gctggtggac ggcaagggca acatcatcaa gcaggacacc    2820
ttcaacatca tcgggaacga ccgcatgaag accaactacc acgacaagct cgccgccatc    2880
gagaaggaca gggactccgc gcgcaaggac tggaagaaga ttaacaacat caaggagatg    2940
aaggagggct acctcagcca ggtggtccac gagatcgcca agctcgtcat tgagtacaac    3000
gccatcgtcg tcttcgagga cctgaatttc ggcttcaagc gcggccggtt caaggtggag    3060
aagcaggtct accagaagct tgagaagatg ctgatcgaga agctgaacta cctggtgttc    3120
aaggacaacg agttcgacaa gaccggcgga gtgctgcgcg cctaccagct cacggcgcct    3180
ttcgagacgt tcaagaagat gggcaagcag acgggcatca tctactacgt gcccgccggc    3240
ttcacctcta agatctgccc agtgaccggc ttcgttaacc agctgtaccc gaagtacgag    3300
agcgtgtcca agtcccagga gttcttctcc aagttcgaca gatttgtta caacctcgac    3360 aagggctact tcgagttttc gttcgactac aagaactttg cgacaaggc ggccaagggg    3420 aagtggacca tcgcctcttt cggcagcagg ctcatcaatt tccggaactc cgacaagaac    3480
cacaactggg acacgcgcga ggtgtacccg acgaaggagc tggagaagct gctcaaggac    3540
tactccatcg agtacggcca cggcgagtgc atcaaggcgg cgatctgcgg ggagagcgac    3600
aagaagttct tgccaagct gaccagcgtg ctgaacacca tcctccagat gcggaactcc    3660
```

| | |
|---|---|
| aagaccggca ccgagctgga ctacctgatc tccccggtcg cggacgtcaa cgggaacttc | 3720 |
| ttcgactccc gacaggctcc caagaacatg ccccaggacg ccgacgcgaa cggcgcgtac | 3780 |
| cacatcggcc tcaagggcct gatgctgctg gggcgcatca agaacaacca ggagggcaag | 3840 |
| aagctgaacc tcgtgatcaa gaacgaggaa tacttcgagt tcgtgcagaa ccgcaacaac | 3900 |

<210> SEQ ID NO 47
<211> LENGTH: 3900
<212> TYPE: DNA
<213> ORGANISM: Artificial Sequence
<220> FEATURE:
<223> OTHER INFORMATION: Synthetic polynucleotide.Codon optimized FnCpf1-CO3

<400> SEQUENCE: 47

| | |
|---|---|
| atgagcatct accaggagtt cgtgaacaag tacagcctgt cgaagaccct ccggttcgag | 60 |
| ctgatccctc aggggaagac gctggagaac atcaaggcgc cggcctcat cctcgacgac | 120 |
| gagaagcggg cgaaggacta caaaaaggca agcagatca tcgacaagta ccaccaattc | 180 |
| tttattgagg agatcctcag ctccgtctgc atcagcgagg acttgctcca gaactactcc | 240 |
| gacgtctatt tcaagctcaa gaagtcagac gacgacaacc tccagaagga cttcaagtcc | 300 |
| gcgaaggaca cgatcaaaaa gcagatcagc gagtacatca aggactccga gaagttcaag | 360 |
| aacctcttca accagaacct gatcgacgcc aagaagggcc gggaatcgga cctcatcctg | 420 |
| tggctcaagc agtcgaagga caacggcatc gagctgttca aggccaactc cgacatcacc | 480 |
| gacatcgacg aggcgctgga gatcatcaag tcgttcaagg ggtggaccac ctacttcaag | 540 |
| ggcttccacg agaaccgcaa gaacgtttac tccagcaacg acatccccac ctcgatcatc | 600 |
| taccggatcg tggacgacaa cctgcccaag ttcctggaga caaggccaa gtacgagtcc | 660 |
| ctcaaggaca aggccccgga ggcgatcaac tacgagcaga ttaaaaagga ccttgctgag | 720 |
| gagctgacct tcgacatcga ctacaagacc tccgaggtga accagcgggt gttcagcctc | 780 |
| gacgaggtgt tcgagatcgc caacttcaac aactacctga accagtccgg gatcaccaag | 840 |
| ttcaacacga tcatcggcgg gaagttcgtc aacggcgaga cacgaagcg gaagggcatc | 900 |
| aacgagtaca tcaacctcta cagccagcag atcaacgaca gaccctcaa aaaatacaaa | 960 |
| atgtcggtcc tgttcaagca gatcctgtcc gacaccgagt ccaagagctt cgtcatcgac | 1020 |
| aagctggagg acgactccga cgtcgtgacc accatgcagt ccttctacga gcagatcgcc | 1080 |
| gccttcaaga ccgtggagga agtccatc aaggagaccc tcagcctcct cttcgacgac | 1140 |
| ctcaaggcgc agaagctgga cctctccaag atatacttca gaacgacaa gagcctcacc | 1200 |
| gacctgtccc agcaagtatt cgacgactac agcgtgatcg gacggcggt gctggagtac | 1260 |
| atcacccagc agatagcgcc caagaacctg gacaacccct ccaagaaaga caggagctg | 1320 |
| attgctaaaa agaccgaaaa ggctaagtac ctgtccctgg agaccatcaa gctcgcgctg | 1380 |
| gaggagttca acaagcaccg ggacatcgac aagcagtgcc ggttcgagga gatcctagca | 1440 |
| aacttcgccg cgatccccat gatcttcgac gagatcgccc agaacaagga caacctggcc | 1500 |
| cagatcagca tcaagtacca gaaccagggc aagaaggacc tcttcaagc tagtgccgag | 1560 |
| gacgacgtga aggcgattaa ggatctgctc gaccagacca acaacctgct ccacaagctc | 1620 |
| aagatattcc acatctccca gtccgaggac aaggccaaca tcctggacaa ggacgagcac | 1680 |
| ttctacctgg tgttcgagga gtgctacttc gagctggcca catcgtgcc gctgtacaac | 1740 |
| aagatccgga actacatcac ccagaagccc tactccgacg agaagttcaa gctgaacttc | 1800 |

```
gagaactcca ccctggcgaa cgggtgggac aagaacaagg agcccgacaa cacggccatc   1860
ctcttcatca aggacgacaa atattatctg ggcgtcatga acaaaaagaa caacaagata   1920
ttcgatgaca aggcgatcaa ggagaacaag ggcgagggct acaagaaaat agtatataaa   1980
ctactgcccg cgcgaacaa gatgctcccg aaggtgtttt ttagtgcaaa gtctattaag   2040
ttctacaacc ccagcgagga catcctccgc atccggaacc acagcacgca caccaagaac   2100
ggcagcccac agaagggcta cgagaagttc gagttcaaca tcgaggactg ccgcaagttc   2160
atcgacttct acaagcagtc catctccaag cacccccgagt ggaaggactt cgggttccgg   2220
ttcagcgaca cccagcgcta acagcatc gacgagttct accgggaggt cgagaaccag   2280
gggtacaagc tgacgttcga aacatctcc gagagctaca tcgacagcgt ggtgaaccag   2340 ggaagctgt acctgtttca gatatacaac aaggacttct cagcctacag caaggggcgg   2400
ccgaacctgc acaccctgta ctggaaggcc ctgttcgacg agcggaacct ccaggacgtc   2460
gtgtacaagc tcaacggcga ggcggagctg ttctaccgga agcagtccat ccccaaaaag   2520
attactcacc ccgcgaagga ggccatcgcc aacaagaaca aggacaaccc caaaaaggaa   2580
tcagtgttcg agtacgacct catcaaggac aagcgcttca ccgaggacaa attcttcttt   2640
cactgcccga tcacgatcaa cttcaagtcc tccggggcga acaagttcaa cgacgagatc   2700
aacctgctgc tcaaggagaa ggccaacgac gtgcacatcc tcagcatcga ccggggcgag   2760
cgccacctgg cctactacac cctggtggac gggaagggca acatcataaa gcaagatacc   2820
ttcaacatca tcgggaacga ccggatgaag acgaactacc acgacaagct ggcggccatc   2880
gagaaggacc gggacagcgc ccgcaaggac tggaaaaaga taaacaacat taaggagatg   2940
aaggagggct acctgtccca ggtggtccac gagatcgcca agctcgtcat cgagtacaac   3000
gccatcgtcg tgttcgagga cttgaacttc gggttcaagc ggggccggtt caaggtggag   3060
aaacaagtct atcaaaagct ggagaagatg ctcatcgaga agctcaacta cctcgtgttc   3120
aaggacaacg agttcgacaa gaccggcggc gtcctgcggg cctaccagct caccgcgccg   3180
ttcgagacgt tcaagaagat ggggaagcag acgggatca tctactacgt ccccgccggg   3240
ttcaccagca agatatgccc ggtcacgggg ttcgtcaacc agctctaccc caagtacgag   3300
tcggtgagca agagccagga gttcttcagc aagttcgaca agatctgcta caacctggac   3360
aagggctact tcgagttctc gttcgactac aagaacttcg gggacaaggc ggcgaagggc   3420
aagtggacca tcgccagctt cggctcccgc ctcatcaact tccggaactc ggacaagaac   3480
cacaactggg acacccgcga ggtgtacccc acgaaggagc tggagaagct gctcaaggac   3540
tacagcatcg agtacgggca cggcgagtgc atcaaggccg ccatctgcgg ggagtccgac   3600
aagaaattct tgccaagct gacctccgtg ctgaacacca tcctccagat gcggaacagc   3660
aagaccggga ccgagctgga ctacctgatc tccccggtcg ccgacgtcaa cggcaacttc   3720
ttcgattctc gccaggctcc caagaacatg cccaggacg ccgacgccaa cggggcctac   3780
cacatcgggc tcaagggcct catgctgctc ggcggatca agaacaacca ggagggcaag   3840
aaactcaacc tggtcatcaa gaacgaggag tactttgagt tcgtccagaa ccggaacaac   3900
```

<210> SEQ ID NO 48  
<211> LENGTH: 3900  
<212> TYPE: DNA  
<213> ORGANISM: Artificial Sequence  
<220> FEATURE:  
<223> OTHER INFORMATION: Synthetic polynucleotide.Codon optimized  
    FnCpf1-CO4

-continued

<400> SEQUENCE: 48

```
atgagcatct accaggagtt cgtgaacaag tacagcctga gcaagaccct gcgcttcgag      60
ctgattcctc aggggaagac cctggagaac atcaaggcgc gcggcctgat cctggacgac     120
gagaagcggg cgaaggacta caaaaaggcg aagcagatca tcgacaagta ccatcagttt     180
ttcatcgagg agattctcag ctccgtgtgc atcagcgaag acctgctcca gaactacagc     240
gacgtttact tcaagctcaa gaaatcggac gacgacaacc tccagaagga cttcaagagc     300
gcgaaggaca cgattaagaa acagatcagc gagtacatca aggactccga gaagttcaag     360
aacctgttca accagaacct catcgacgcc aagaaaggcc aagagtcgga cctcatcctc     420
tggctcaagc agagcaagga caacggcatc gagctgttca aggcgaacag cgacatcacc     480
gacatcgacg aggcgctgga gatcatcaag tcgttcaagg gctggacgac ctacttcaag     540
ggcttccacg agaaccgcaa gaatgtctac tcgagcaacg acatccccac gtcgatcatc     600
taccgcatcg tggacgacaa cctcccgaag ttcctggaga caaggcgaa gtacgagagc     660
ctcaaggaca aggccccgga ggccatcaac tacgagcaga tcaaaaagga tttggctgag     720
gagctgacgt tcgacatcga ctacaagacc tccgaggtga accagcgcgt cttcagcctc     780
gacgaggtgt tcgagatcgc caacttcaac aactacctca accagtcggg catcaccaag     840
ttcaacacca tcatcggcgg gaagttcgtc aacggcgaga cacgaagcg caaggggatc     900
aacgagtaca tcaacctgta cagccagcag atcaacgaca agaccctcaa gaagtataaa     960
atgtcggtgc tgttcaagca gatcctctcg gacaccgaga gcaagtcgtt cgtcatcgac    1020
aagctggagg acgacagcga cgtggtgacc accatgcaga gcttctacga gcagatcgcg    1080
gccttcaaga ccgtcgagga gaagtcgatc aaggagacgc tcagcctgct gttcgacgac    1140
ctcaaggccc agaagctcga cctgtccaag atatacttta agaacgacaa gagcctcacg    1200
gacctgtccc agcaggtatt cgacgactac agcgtgatcg ggacggccgt gctggagtac    1260
atcacccaac agatcgcgcc caagaacctg gacaacccgt ccaagaagga acaagagcta    1320
atcgccaaaa agactgagaa ggcgaagtac ctgtcgctgg agacgatcaa gctcgcgctt    1380
gaggagttta caagcaccg cgacatcgac aagcagtgcc ggttcgagga gatcctggcc    1440
aacttcgcgg cgatcccgat gatcttcgac gagatcgccc agaacaagga caacctggcg    1500
cagatcagca tcaagtacca gaaccagggc aaaaaagact tgctccaagc tagtgcggag    1560
gacgacgtga aggcgattaa ggatctgctg accagactga caatctgct gcacaagctc    1620
aagatctttc acatctctca gtcggaggac aaggcgaaca tcctggacaa ggacgagcac    1680
ttctacctag tgttcgagga gtgctacttc gagctggcga acatcgtgcc cctgtacaac    1740
aagatccgga actacatcac ccagaagccc tacagcgacg agaagttcaa gctgaacttc    1800
gagaacagca cgctggcgaa cgggtgggac aagaacaagg agcccgacaa caccgccatc    1860
ctgttcatca aggacgacaa atattacctc ggcgtcatga caaaaagaa taacaagata    1920
ttcgatgaca aggcgatcaa ggagaacaag ggcgagggct acaagaagat cgtatataaa    1980
ctcctgccgg gagcgaacaa gatgctcccg aaggttttct ttagtgccaa gtccatcaag    2040
ttctacaacc ccagcgagga catcctccgc atccggaacc actccaccca caccaagaac    2100
ggctcgccgc agaagggcta cgagaagttc gagttcaaca tcgaggactg ccgcaagttc    2160
atcgacttct acaagcagtc catctccaag caccccggagt ggaaggactt cgggttccgg    2220
ttctcccgaca cgcagcgcta caactccatc gacgagttct accgggaggt ggagaaccag    2280
```

```
ggctacaagc tgacgttcga gaacatctcg gagtcctaca tcgactccgt ggtcaaccag    2340
ggcaagctgt acctcttcca gatatacaat aaggacttct ccgcctacag caagggcgg    2400 cccaacctcc acaccctgta ctggaaggcg ctcttcgacg agcggaacct ccaggacgtc    2460
gtgtacaagc tgaacggcga ggcggagctg ttctaccgca gcagagcat ccccaagaag    2520 atcacgcacc ccgcgaagga ggccatcgcc aacaagaaca aggacaaccc caagaaggaa    2580
tcggtcttcg agtacgacct catcaaggac aagcggttca cggaggacaa attcttttc    2640 cactgcccga tcactattaa cttcaagtcc agcggcgcga acaagttcaa cgacgagatc    2700
aacctgctcc tcaaggagaa ggcgaacgac gtgcacatcc tcagcatcga ccggggcgag    2760
cgccacctcg cctactacac gctggtggac gggaagggca acatcatcaa gcaagacacc    2820
ttcaacatca tcggcaacga ccggatgaag accaactacc acgacaagct ggccgccatc    2880
gagaaggacc gcgactcggc ccgcaaggac tggaaaaaga tcaacaatat caaggagatg    2940
aaggagggct acctgagcca agttgtccac gagatcgcca agctggtgat cgagtacaac    3000
gccatcgtcg tgttcgaaga cctgaacttc ggcttcaagc gcggccggtt caaggtcgag    3060
aaacaagtct atcagaaact gagaagatg ctgatcgaga agctgaacta cctcgtcttc    3120
aaggacaacg agttcgacaa gaccggcggc gtcctccgcg cgtaccagct caccgcgccg    3180
ttcgagacgt tcaagaaaat gggcaagcag accggcatca tctactacgt gcccgccggg    3240
ttcacgagca aaatatgtcc cgtgaccggc ttcgtcaacc agctctaccc caagtacgag    3300
tccgtgtcga agtcccagga attcttcagc aagttcgaca agatatgcta caacctggac    3360
aagggctact cgagttctc cttcgactac aagaacttcg gggacaaggc ggcgaagggg    3420
aagtggacca tcgcctcgtt cgggtcgcgc ctcatcaact tccggaacag cgacaagaac    3480
cacaactggg acacccgcga ggtgtaccc acgaaggagc tggagaagct cctcaaggac    3540
tacagcatcg agtacggcca cggggagtgc atcaaggcgg ccatctgcgg cgagtcggac    3600
aaaaagttct tgccaaaact cacctcggtc ctcaacacca tcctccagat gcggaacagc    3660
aagacgggca cggagctgga ctacctcatc agcccggtgg ccgacgtgaa cggcaatttc    3720
tttgactcac gccaggcccc taagaacatg ccccaggacg ccgacgccaa cggcgcgtac    3780
cacatcggcc tcaagggcct gatgctgctc ggccggatca agaacaacca ggagggcaag    3840
aagctcaacc tggtcatcaa gaacgaggag tatttcgagt tcgtccagaa ccgcaacaac    3900
```

<210> SEQ ID NO 49
<211> LENGTH: 3900
<212> TYPE: DNA
<213> ORGANISM: Artificial Sequence
<220> FEATURE:
<223> OTHER INFORMATION: Synthetic polynucleotide.Codon optimized
      FnCpf1-CO5

<400> SEQUENCE: 49

```
atgtccatat accaggagtt tgttaataaa tatagcttgt ccaaaacccct gcggtttgaa      60 ctcataccctc aggggaagac tttggagaat atcaaagcgc ggggactgat actggacgac     120
gaaaagcgcg caaagatta caagaaagcg aacagatca tcgataaata ccatcaattt     180
ttcatagagg agattctcag ttctgtctgt atcagtgagg acctcctcca aaattattca     240
gacgtctatt taaactcaa gaagtcggac gacgacaacc ttcagaaaga ttttaagtca     300
gcaaaagaca caatcaaaaa acaaatatcg gaatacataa aggactcaga aaagttcaag     360
aatcttttta ccaaaatctc gatagacgcg aagaaaggc aggaatctga tcttatactc     420
```

```
tggcttaagc agtctaaaga caacggcata gaactcttta aggcaaacag cgatataacc    480
gacatagatg aagccctcga gataattaag tccttcaaag gctggactac atatttaaa    540 gggttccatg agaataggaa gaacgtgtat tcctcgaatg atattcccac ctcgataatc    600
taccggattg tggatgataa tctgcctaaa tttttggaaa ataaagcgaa gtacgaaagt    660
ttgaaagata aagcaccaga agcaattaat tatgaacaaa ttaagaaaga tctggctgag    720
gaacttacgt tcgatatcga ttataaaaca tcagaagtta atcagcgggt ttttagcctg    780
gatgaagttt ttgagatcgc caacttcaac aattatctta atcagagcgg gattaccaaa    840
ttcaacacta ttatcggtgg taaattcgtt aatggtgaga acacaaagag aaaaggtata    900
aacgaataca taaatttgta cagtcaacag attaacgata aaactttgaa aaagtacaag    960
atgtcagtgc ttttcaaaca aatcctttcc gacacagaat ccaaaagttt tgtgatagac   1020
aaattggaag atgatagcga cgtcgtcacg accatgcaat cattttatga gcaaattgca   1080
gccttcaaga cggttgagga aaaaagtata aagaaacgt tgtcgctctt gttcgacgac   1140
ctgaaagcac agaaattgga tttgtctaag atatacttta aaaacgacaa atccctcacg   1200
gacttgtcgc agcaagtctt tgatgattat tcggtgattg ggacagccgt gctcgaatac   1260
atcacccagc aaatcgctcc gaaaaatctg acaatccgt ctaaaaaga gcaagagctg   1320 atcgcaaaga aaaccgaaaa agcgaaatac ctgtctctgg agacaatcaa attggccttg   1380
gaagagttca ataagcacag agacattgat aaacaatgtc ggtttgagga aattcttgct   1440
aactttgccg ctatcccgat gatcttcgat gagattgcgc aaaataagga taatctggcc   1500
caaatctcga tcaagtatca aaatcagggt aagaaggacc tgcttcaagc atcggcggag   1560
gatgatgtga aagcgattaa ggacttgttg gatcagacca caatttgtt gcacaagctg   1620 aagatattcc acatctccca gagtgaggat aaggccaaca tcctggacaa ggatgaacat   1680
ttctatttgg tcttcgaaga gtgttatttt gaattggcca acatagttcc tctttataac   1740
aagatccgca attatattac acaaaagcct tattccgatg aaaaatttaa acttaacttc   1800
gaaaatagca cattggcgaa tggttgggat aaaaataagg agcctgacaa tactgctata   1860
cttttcatta aggacgataa gtactacctc ggcgttatga acaagaagaa taataagatc   1920
tttgacgaca aagcaatcaa agagaacaaa ggcgaaggtt acaaaaaaat cgtgtacaaa   1980
ctcctgcctg cgcgaataa aatgcttccg aaggttttt tcagtgcgaa gtccattaag   2040
ttttataacc cttccgagga tattttgaga attagaaatc actccaccca taccaagaat   2100
ggcagccccc agaaggggta tgaaaagttc gaatttaata tcgaagactg ccgcaagttt   2160
atagactttt ataaacagtc catatctaaa catcccgaat ggaaagattt tggtttccgg   2220
ttttctgaca ctcagaggta caacagcata gatgagttct accgcgaagt tgaaaaccaa   2280
ggctacaagc ttacatttga gaacatcagc gagtcatata ttgactcagt cgttaatcag   2340
ggcaaacttt atttgttcca aatttacaac aaagactttt cagcgtacag caagggaagg   2400
ccaaatctcc atacactgta ttggaaggcg ctgtttgacg agcggaatct tcaagatgtt   2460
gtgtataaac tcaacgggga ggccgaattg ttctacagga gcaaagcat tcctaagaaa   2520 attacccacc ccgctaagga agcgatagca aataaaaata aagacaatcc gaaaaaagag   2580
agcgtttttg agtacgacct tataaaggat aagagattca ccgaggataa gttttttcttc   2640 cactgtccaa taactattaa ctttaaatcc tccggagcca acaagtttaa cgacgaaatt   2700
aatttgctgc tgaaagagaa ggcgaacgac gttcacattc tgtcaataga cagagggag   2760 agacacttgg catactacac gctcgttgat ggaaaaggta acattattaa gcaagatact   2820
```

```
ttcaacatca ttgggaatga cagaatgaaa acaaactatc acgataaact cgcggcaatt    2880
gagaaggacc gggattcggc gaggaaagac tggaagaaaa tcaacaatat aaaggagatg    2940
aaggaaggat acctgtctca agtcgtccac gaaatagcca agcttgttat agagtataat    3000
gcgattgtgg tctttgaaga ccttaacttt ggatttaaac gcggccggtt taaagtcgag    3060
aaacaagtgt atcaaaaact ggaaaaaatg ttgatcgaga aactgaatta tctcgtcttc    3120
aaggacaacg agttcgataa aaccgggggc gtcttgcgcg cttatcaact gacggcaccg    3180
tttgaaactt tcaagaagat gggcaaacag actgggatta tctactacgt tcctgccgga    3240
ttcacctcca aaatatgccc agttactgga tttgttaacc agttgtaccc taagtacgaa    3300
tcagtcagca agtcccaaga gttttctca aaatttgata agatctgcta acctggac       3360
aaggggtact tcgagttttc cttcgactat aaaaatttcg gcgacaaggc agctaaaggt    3420
aaatggacga ttgcaagttt cggctccagg cttattaatt tcagaaacag cgacaaaaac    3480
cataactggg acacgcgcga ggtctaccct acgaaggaac tggaaaaact tctcaaggat    3540
tacagtatag aatacggaca cggggagtgt atcaaagctg cgatatgcgg agagtcggat    3600
aaaaagtttt tcgcaaagtt gacatcagtt ttgaacacta tcttgcagat gagaaattcc    3660
aagactggca cggagttgga ctaccttatt agcccagtgg cggatgtcaa cgggaacttt    3720
tttgattcga ggcaagcccc taagaatatg cctcaagacg ctgatgcaaa cggggcatat    3780
cacataggac tcaaagggtt gatgctgctg gcagaatta agaacaacca ggaaggaaag    3840
aagctcaatc ttgttatcaa aaatgaagag tactttgaat tcgttcaaaa ccggaataac    3900
```

<210> SEQ ID NO 50
<211> LENGTH: 3900
<212> TYPE: DNA
<213> ORGANISM: Artificial Sequence
<220> FEATURE:
<223> OTHER INFORMATION: Synthetic polynucleotide.Codon optimized
      FnCpf1-CO6

<400> SEQUENCE: 50

```
atgagtattt atcaagagtt cgttaataag tacagtcttt ctaagacgct caggtttgag      60
ctcattccac aaggtaagac ccttgagaat attaaagccc gcggactgat cctggacgac     120
gagaagcgcg ccaaagacta taagaaggcg aaacagatca tagataagta tcaccaattc     180
ttcatagaag agatacttag ctctgttttgt atctcagagg atctgctcca gaactactcg     240
gatgtgtact ttaaactcaa gaagtctgac gatgacaatc tccagaagga ctttaagtcc     300
gccaaagaca caatcaagaa gcagatttcg gaatacataa aggacagtga aagttcaag    360
aacttgttca accagaatct catagacgcc aagaagggtc aggagagcga tcttattctg     420
tggttgaaac aatcaaagga caacggtatt gagttgttta agcaaactc tgacatcacc       480
gacattgacg aggctctgga gatcattaag agtttaaag ggtggacaac ctactttaag      540
ggatttcatg agaatcgcaa gaacgtgtac tcgagcaatg acatacctac aagcataatc     600
tatcggatag tcgacgataa cctcccgaag ttcctcgaga taaagcgaa gtacgaatcg     660
cttaaggata aggcgccgga ggcgataaac tatgaacaga ttaagaagga tctggctgaa     720
gaattgacct ttgatattga ctataagacc agcgaagtca accaacgcgt tttcagcctg     780
gatgaagtgt ttgagatcgc caacttcaat aattacttga atcaatcggg gataacaaag     840
tttaatacga ttatcggcgg gaagtttgtc aacggggaga cacaaagag gaagggcata     900
aatgagtaca ttaatctcta tagtcaacag ataaatgaca agacgttgaa gaaatacaag    960
```

```
atgtcagtcc ttttcaagca gatcctgtct gacacagaat cgaagagctt cgtgatagat    1020
aagctggaag atgattccga cgttgtcaca accatgcaat cgttttacga gcagatcgcg    1080
gccttcaaga ccgttgagga gaagtctatt aaagagactc tttctcttct gtttgatgac    1140
ttgaaggccc agaagcttga cttgtccaag atctacttca agaacgataa atctctgaca    1200
gatctcagcc agcaagtgtt tgacgactat tctgttatcg aacggccgt gctggagtac     1260 atcacacagc agatcgcgcc taagaacctt gataatccga gcaagaaaga acaggagttg    1320
attgcaaaga agacagagaa ggccaaatac ctttctctgg acaattaa acttgcactg      1380 gaagaattca ataagcacag agatatcgac aagcagtgtc gctttgagga gatcctggca    1440
aattttgctg ccatcccaat gatttttgat gagattgccc agaacaagga caatctcgcg    1500
cagatatcaa tcaagtatca gaaccaaggc aagaaggacc tcctgcaagc ctcagccgaa    1560
gatgacgtta aggccataaa ggatctcctt gatcagacca ataacttgct gcacaagctg    1620
aagatctttc atatcagcca gtcggaagac aaagcaaata ccttgacaa ggacgagcat     1680 ttctatctgg tgttcgaaga atgctatttc gagctggcca atatcgtgcc tctgtacaat    1740
aagatccgca attatatcac gcagaagccg tatagcgacg agaagttcaa gctgaatttc    1800
gagaactcca ccttggccaa tggttgggat aagaacaaag aaccggacaa tacggccatc    1860
ttgtttatca agatgacaa gtactatctg gagtgatga ataagaagaa caataagatc      1920
ttcgatgaca aagccattaa ggagaataaa ggggaaggt acaagaagat tgtctataaa     1980
ctgctccccg gggccaacaa gatgctgccc aaagtttttt tcagtgccaa gagcatcaag    2040
ttttataatc cctcagaaga catactgaga atcagaaacc actcgaccca taccaagaac    2100
ggctctccgc agaagggta cgagaaattc gaattcaaca tcgaagactg tagaaagttc     2160
atcgattttt acaagcaatc gatatcaaag caccctgaat ggaaggattt tggttttcgc    2220
tttagtgaca ctcagcggta taatagcatt gatgagttct accgcgaagt tgagaatcag    2280
ggatacaaat tgacattcga gaatatcagc gaatcgtaca ttgatagcgt cgtcaaccag    2340
gggaaacttt acctcttcca gatttataat aaagacttct cggcgtactc caagggaaga    2400
ccaaatcttc atactctgta ttggaaggca ctcttcgatg agaaaatct tcaggatgtc     2460 gtttataaac ttaatgggga agcggagctg ttctaccgca agcagagcat ccctaagaag    2520
atcacgcacc ccgcgaagga ggcgatagcc aataagaaca aggataaccc gaagaaggag    2580
tccgtcttcg aatatgacct gatcaaggat aagagattca ctgaggacaa attcttcttc    2640
cattgcccta ttacgattaa tttaaatcg agcggcgcga taaattcaa cgacgagatc      2700 aacctgctcc tcaaagagaa ggccaatgat gtccacattc tctcaatcga cagaggggag    2760
aggcaccttg cctactatac gctcgttgat ggtaaaggta acatcattaa gcaggacacg    2820
ttcaacatca tcgggaacga ccgcatgaag acaaactatc acgataaatt ggcggcaatc    2880
gagaaggatc gggatagtgc caggaaggac tggaagaaga ttaataacat caaggagatg    2940
aaggagggat atctttctca gtcgtccac gagatcgcga agctggttat cgagtacaac     3000
gccatagtgg tcttcgaaga tctgaacttc ggattcaaga gagggagatt taaggtggag    3060
aagcaagttt atcagaaact ggagaagatg ctgatagaga agctcaacta cctcgtgttt    3120
aaagacaacg agtttgacaa gacaggtggg gtgttgaggg cctatcagct cacggccccc    3180
ttcgagacct tcaagaagat gggaaagcag acggggataa tctactacgt ccctgctggc    3240
ttcacttcga agatctgccc agttacagga ttcgttaacc agttgtatcc caaatacgag    3300
```

| | | | | |
|---|---|---|---|---|
| tccgtctcaa | agtcacaaga | attctttcct | aaattcgata | agatctgcta caacctggat | 3360 |
| aagggctact | tcgagtttag | ctttgactat | aagaatttcg | gggacaaagc ggcaaagggg | 3420 |
| aagtggacaa | tcgcaagttt | tggctcccgg | ctgattaact | ttcggaattc tgacaagaat | 3480 |
| cacaactggg | atactagaga | ggtctatcca | actaaagagt | tggagaagtt gctcaaggac | 3540 |
| tactccattg | aatatggtca | cggggaatgc | attaaagcgg | ccatctgcgg agagtccgat | 3600 |
| aagaagttct | tgccaaaact | tacatcggtc | ttgaacacca | tactgcagat gcggaacagc | 3660 |
| aagacgggaa | cggaactcga | ctaccttatc | tcacctgtgg | cggatgttaa tggaaacttt | 3720 |
| ttcgattcga | ggcaggcgcc | caagaacatg | ccgcaagatg | cagatgccaa tggagcatat | 3780 |
| cacatcggtc | ttaaagggct | catgctgctt | ggccgcatca | agaacaacca agaggggaag | 3840 |
| aagttgaacc | tggttattaa | gaacgaagaa | tacttcgaat | tgtccagaa ccgcaacaac | 3900 |

<210> SEQ ID NO 51
<211> LENGTH: 3900
<212> TYPE: DNA
<213> ORGANISM: Artificial Sequence
<220> FEATURE:
<223> OTHER INFORMATION: Synthetic polynucleotide.Codon optimized FnCpf1-CO7

<400> SEQUENCE: 51

| | | | | |
|---|---|---|---|---|
| atgtccatct | atcaggaatt | tgttaacaag | tactctctta | gcaaaactct taggttcgaa | 60 |
| ttgataccte | agggaaagac | acttgagaat | attaaggcgc | gcgggctgat acttgatgat | 120 |
| gaaaagcggg | caaggactta | agaaagct | aagcaaataa | ttgataagta ccaccagttt | 180 |
| tttattgaag | agatcctgtc | ctccgtttgt | atatccgaag | acttgcttca gaattactca | 240 |
| gatgtttatt | ttaaattgaa | gaatctgac | gatgataatc | ttcaaaagga tttcaaatcg | 300 |
| gcaaaagaca | caatcaaaaa | acagattagc | gagtacatca | aggactccga aaagtttaag | 360 |
| aatctcttta | tcagaatct | tatagacgca | agaaaggac | aggaatcgga cttgattttg | 420 |
| tggttgaagc | agtccaagga | taacgggata | gaactcttta | agccaactc cgatataacg | 480 |
| gacatcgacg | aagccctcga | aatcattaag | tcgtttaaag | gttggaccac gtacttcaaa | 540 |
| ggattccacg | agaacagaaa | gaacgtttac | tcgagcaacg | acattcctac tagcatcata | 600 |
| tatagaatag | tggatgataa | tttgcccaaa | ttccttgaga | caaggcaaa atatgaatcc | 660 |
| ctgaaagaca | aggcgcccga | agctatcaac | tacgagcaga | taagaaga tctggctgag | 720 |
| gagctgacgt | ttgacattga | ttacaaaaca | agcgaggtca | ccagagggt ttttcgctg | 780 |
| gacgaggttt | tgaaatagc | gaattttaat | aactacctga | accaatccgg catcactaaa | 840 |
| tttaacacaa | tcataggggg | gaagttcgtg | aacggagaga | acacaaagcg caagggatt | 900 |
| aatgagtaca | tcaatttgta | cagccagcag | atcaatgaca | aaacgttgaa gaaatataag | 960 |
| atgagcgtct | tgtttaagca | gattctctcg | gatacggaat | ccaaatcatt cgtcattgac | 1020 |
| aagctggagg | atgacagcga | tgtggtgaca | actatgcagt | ccttctatga caaaattgca | 1080 |
| gcttttaaaa | cggtcgaaga | gaagtcgatt | aaagaaacgc | tttcgctcct gttcgatgac | 1140 |
| ctgaaagcgc | agaagctgga | cctttcgaag | atatatttca | aaaacgataa gtcactcacg | 1200 |
| gaccttagcc | aacaggtttt | cgatgactat | tctgtcatag | gactgctgt gcttgagtat | 1260 |
| attactcagc | aaatagcccc | caaaaacctg | gacaacccgt | ctaagaagga caagagctg | 1320 |
| atagcgaaga | aaacagagaa | agctaaatat | ctttcacttg | aactataaa gcttgcactg | 1380 |
| gaggaattca | acaaacatcg | cgacatcgac | aagcagtgca | gatttgagga gatcttggcc | 1440 |

```
aacttcgcag ctattccaat gattttgac gagatagcac agaataagga caacctggca    1500
cagattagca taaaatacca gaatcagggg aagaaggatc ttcttcaggc ttcggctgag    1560
gacgatgtca aagccatcaa agatctgctc gaccagacca acaatttgtt gcataaactc    1620
aagatcttcc acatatcgca gtccgaagat aaagcgaaca tacttgacaa agacgaacat    1680
ttttatcttg ttttcgagga gtgttatttt gagttggcaa acatcgttcc cctctacaac    1740
aaaattcgca actatataac tcagaagccc tattctgacg agaaattcaa acttaatttc    1800
gaaaacagca ctctcgcaaa cggctgggat aaaaacaagg aacccgacaa caccgccata    1860
cttttattta aggatgataa atattatttg ggcgtgatga ataaaaagaa caataaaata    1920
ttcgatgata aagcaattaa ggaaaataaa ggggaagggt ataaaaaaat cgtgtataag    1980
ctgcttccag gagctaataa aatgctgcca aaagtcttct tctctgccaa gtcgatcaag    2040
ttttacaatc cttctgaaga tattttgcgg atcagaaatc actctactca cactaaaaac    2100
ggttcacccc agaaaggata cgagaagttt gagttcaaca tcgaagactg tcggaagttt    2160
atcgactttt acaagcagtc tatatcaaaa cacccgaat ggaaagattt tggttttcgg    2220
ttcagcgaca cgcagagata taattcaatt gatgagttct acaggaggt ggagaaccaa    2280 gggtataaac ttacttttga gaacattcc gaatcctata ttgattcggt ggtcaatcag    2340
gggaaactgt acctgtttca gatatataac aaagacttct ccgcgtattc taaaggacgg    2400
cccaatctcc atactctta ttggaaggcg ctgtttgacg agcggaacct tcaggatgtt    2460
gtctataagt tgaacgggga agctgagctg ttctatcgga agcagtctat tccaaaaaag    2520
ataacgcacc ccgcgaagga ggcaattgca acaagaaca aagacaatcc aaagaaggag    2580
tcggtgtttg agtacgatct gataaaagac aaaaggttta ccgaggacaa gttttttttc    2640
cactgtccga tcaccatcaa ttttaagtct tccggcgcca acaaattcaa tgacgaaata    2700
aatctgctgc tcaaggaaaa ggcaaatgat gttcatattc tgtcgataga ccgcggggaa    2760
agacacctcg cgtattatac attggtcgat gggaaaggca atattatcaa acaagacacc    2820
ttcaatatca ttggtaacga taggatgaaa acgaactatc atgataaact gcagctatt    2880 gaaaaggaca gagactcggc tcggaaagat tggaaaaaga tcaataacat caaggaaatg    2940
aaggaagggt atctctccca ggtcgttcat gaaatcgcca aactggttat tgagtacaat    3000
gctatagtgg ttttttgaaga tcttaatttt gggtttaaga gagggagatt taaagtcgag    3060
aaacaggttt atcaaaaact tgaaaaaatg ttgatagaaa aattgaacta tcttgtgttt    3120
aaggacaatg agttcgataa aaccgggggg gttttgagag cttatcaact gacggctccc    3180
ttcgagacat tcaaaaaaat ggggaagcag accggcatca tttattatgt gcccgcgggc    3240
ttcacttcta aaatttgtcc tgtgacaggg ttcgtgaacc aattgtaccc caagtacgaa    3300
agcgtctcca agtcccaaga attctttagc aagtttgaca aaatttgcta taacctggac    3360
aaagggtact tgagtttttc ctttgattat aagaatttcg gggataaagc tgcgaaaggt    3420
aagtggacga tagcctcttt cgggtcgcgc cttattaact tcaggaattc cgacaaaaac    3480
cataattggg acaccgcga ggtctaccct acaaaggaac tcgaaaagtt gcttaaggat    3540
tattcaatag agtatggtca tggcgagtgt attaaggctg ctatctgtgg tgagtcagat    3600
aagaaattct tcgcgaaatt gacatctgtt ttgaacacca tcctccaaat gaggaactct    3660
aaaacgggga cggagcttga ttatctcatc tcacccgttg ctgatgtgaa cggtaatttc    3720
tttgattcac gccaagcccc gaagaacatg ccccaagacg ccgatgctaa cggcgcttat    3780
catatagggc tgaaggggct catgcttctg gggcgcatca aaaataacca agaagggaag    3840
```

```
aaactcaatc tggttatcaa aaatgaggaa tatttcgaat tcgtgcaaaa ccgcaacaat    3900
```

<210> SEQ ID NO 52
<211> LENGTH: 705
<212> TYPE: DNA
<213> ORGANISM: Entacmaea quadricolor

<400> SEQUENCE: 52

```
gtgagcaagg gcgaggagaa taacatggcc atcatcaagg agttcatgcg cttcaaggtg      60
cgcatggagg gctccgtgaa cggccacgag ttcgagatcg agggcgaggg cgagggccgc     120
ccctacgagg gctttcagac cgctaagctg aaggtgacca aggtggcccc cctgcccttc     180
gcctgggaca tcctgtcccc tcatttcacc tacggctcca aggcctacgt gaagcacccc     240
gccgacatcc ccgactactt caagctgtcc ttccccgagg gcttcaagtg ggagcgcgtg     300
atgaactacg aggacggcgg cgtggtgacc gtgacccagg actcctccct gcaggacggc     360
gagttcatct acaaggtgaa gctgcgcggc accaacttcc cctccgacgg ccccgtgatg     420
cagaagaaga ccatgggctg ggaggcctcc tccgagcgga tgtaccccga ggacggtgcc     480
ctgaagggca agatcaagat gaggctgaag ctgaaggacg gcggccacta cacctccgag     540
gtcaagacca cctacaaggc caagaagccc gtgcagctgc ccggcgccta catcgtcgac     600
atcaagttgg acatcacctc ccacaacgag gactacacca tcgtggaaca gtacgaacgc     660
gccgagggcc gccactccac cggcggcatg gacgagctgt acaag                    705
```

<210> SEQ ID NO 53
<211> LENGTH: 4674
<212> TYPE: DNA
<213> ORGANISM: Artificial Sequence
<220> FEATURE:
<223> OTHER INFORMATION: Synthetic polynucleotide.NLS-FnCpf1-CO1-mOR-NLS

<400> SEQUENCE: 53

```
ggtagcaaaa agaggcgtat caagcaggac atgtctatct atcaagagtt tgtcaacaag      60
tacagcttaa gtaagacact tcgcttcgag ttgatccctc aggggaagac actggaaaac     120
atcaaggcga ggggccttat cctggacgac gagaagcggg ctaaagacta caaaaaagct     180
aaacagataa ttgacaagta tcaccaattt tttattgagg atcctctc ctctgtgtgc      240
ataagtgagg atctgctcca gaactattcg gatgtttact ttaaactcaa gaagtccgat     300
gatgacaacc ttcagaagga cttcaagtcc gccaaagaca cgattaagaa acaaatcagt     360
gagtacatca aggatagcga gaaattcaag aacctgttca accagaactt aattgatgcc     420
aaaaagggcc aagaatccga cctcatcctg tggttaaagc aatctaaaga caacggtatt     480
gagctgttca aggcaaacag cgacattaca gacattgacg aggccctaga gatcatcaag     540
tcattcaaag gctggacgac ttactttaaa ggttttcacg agaaccgtaa gaatgtttac     600
tcaagtaacg ataccaac gagcattatc taccgaatag tggatgataa cctaccgaag     660
ttccttgaga acaaagcgaa gtacgagtct ctcaaagaca aggcccctga ggccatcaac     720
tacgagcaga ttaagaagga tctcgccgag gagctaacct tcgacattga ctacaaaaca     780
tcggaagtga atcagagggt gttctcgctt gatgaagtat tcgagattgc taacttcaac     840
aattacctga accagagtgg tattactaag ttcaacacaa tcattggagg caaattcgtg     900
aacggcgaaa acacaaagcg aaaagggata acgagtaca ttaacttgta cagccagcag     960
atcaacgata agacactcaa gaagtataag atgtctgtgc tgttcaaaca aatcttaagc    1020
```

```
gacacggaaa gcaagtcgtt cgtaattgac aagctggaag acgattctga cgtggttaca     1080
accatgcagt ccttttacga gcagattgcc gcattcaaga ccgtggagga aaagtcgatc     1140
aaggaaacac tttcgttgct tttcgacgac cttaaagctc agaagctcga cttaagcaag     1200
atatacttta agaacgataa gagcttgaca gacttgagcc agcaagtctt tgacgactac     1260
agcgttatcg gaactgccgt tctggagtac ataacacagc agatcgcacc caagaacctt     1320
gacaacccTT ccaagaaaga caagagttg atcgccaaga agactgaaaa ggctaagtac     1380
ctctctctgg agactatcaa gctcgctctt gaggagttta caagcacag gacattgac      1440 aagcaatgcc gattcgagga atactggca aacttcgcag ccatacccat gatattcgat      1500
gagatagccc agaacaagga taacttggcc caaatctcga ttaagtatca gaaccagggc     1560
aaaaaggacc ttctacaggc tagtgcagag gacgatgtga aggctattaa ggacttatta     1620
gatcagacaa acaaccttct gcataagctc aagatattcc atatctccca gtcagaggac     1680
aaggccaaca ttctggataa ggacgagcac ttctatctcg tattcgagga atgttacttt     1740
gagctggcca atatcgttcc cttgtacaac aaaatccgga actacatcac acagaagccc     1800
tacagtgatg agaagttcaa attgaactTT gaaaactcaa cacttgctaa tggttgggac     1860
aagaataagg aacctgacaa cactgccatc ctctttatta agatgataa gtactacctc      1920 ggggtgatga ataagaagaa caacaaaatc ttcgatgaca aagctattaa ggagaacaaa     1980
ggtgaagggt acaagaagat tgtctacaaa ctgctgcctg tgccaacaa aatgctacca      2040 aaggtatttt tcagcgccaa atctattaag ttctacaatc caagcgagga tattctccgg     2100
atacggaatc actctacaca taccaagaat ggaagtccac aaaagggtta cgagaaattc     2160
gagttcaaca ttgaagactg ccggaaattc attgacttct acaagcaatc catctctaaa     2220
catcctgaat ggaaagactt cggtttccgc ttcagtgata ctcaacggta caattcaatt     2280
gacgaattct accgtgaggt tgagaaccag gggtacaaac tgaccttcga gaacatatca     2340
gagagctaca tcgactcagt ggttaatcag gggaagctat atctgtttca aatctacaac     2400
aaagacttta gtgcctactc taaagggcgg ccaaacttac acacacttta ctggaaggca     2460
ctattcgacg aacgcaatct acaagatgta gtttacaaat gaacggtga ggctgagttg      2520 ttctaccgta acaatctat acccaagaag ataacacacc ctgctaaaga ggcaattgca      2580
aacaaaaaca aggataatcc caaaaaggag tctgtctttg agtatgacct cattaaggat     2640
aagcggttca cggaggacaa gttcttcttc cattgtccaa taaccatcaa cttcaaatca     2700
tccggcgcaa acaaattcaa tgacgagatc aacctgttac taaggagaa ggctaacgat      2760 gttcacatct tatctattga tcgaggtgag agacacctag cctactacac tttagtggat     2820
gggaagggga acatcatcaa gcaagacacc ttcaacatca ttgggaacga caggatgaag     2880
actaactacc atgataagct cgccgctatt gaaaaggaca gggactctgc caggaaggac     2940
tggaaaaaaa ttaacaatat taaagagatg aaggagggct acctgagcca agtagtccat     3000
gagatagcaa aactggtgat tgagtacaac gcaatagtcg tattcgagga cttaaacttc     3060
ggcttcaaac gtgggcggtt taaggtggag aaacaagtct atcagaaatt ggagaagatg     3120
ctaatcgaga agctcaacta cctcgtgttt aaagacaacg agtttgacaa aactggagga     3180
gtcctgcggg cataccaact gaccgcaccc ttcgagacat tcaagaagat gggaaagcag     3240
actggcatca tctattacgt gccagcgggt tttacttcca aaatctgtcc agttacaggc     3300
ttcgtgaacc agttgtaccc gaagtacgag tctgtttcca gtcacagga attcttctca      3360 aagtttgaca agatatgtta caatctcgat aagggatact ttgagtttag tttcgactac     3420
```

```
aagaactttg gcgataaggc cgcaaaaggg aaatggacaa ttgcatcctt cgggtcacgc    3480
cttattaact ttcgtaactc agacaagaac cacaattggg acaccaggga ggtgtaccct    3540
actaaggagc tggagaagct acttaaagac tactcgattg agtacggaca tggagagtgc    3600
atcaaggcag caatatgtgg ggaatctgac aaaaagttct tgccaagct gacctctgta    3660 ctgaacacta ttctccaaat gagaaatagt aagactggca cagagttgga ctacctgatc    3720
tctccagtgg ctgacgttaa tgggaatttt ttcgactcaa gacaagctcc caagaatatg    3780
ccacaggacg cagatgcaaa cggggcatat cacatcgggc ttaaaggact catgctacta    3840
gggcggatca agaataatca ggagggcaaa aagctgaacc tagtcatcaa gaacgaggag    3900
tacttcgaat ttgtccagaa tcgtaacaac ggatctggag tgagcaaggg cgaggagaat    3960
aacatggcca tcatcaagga gttcatgcgc ttcaaggtgc gcatggaggg ctccgtgaac    4020
ggccacgagt tcgagatcga gggcgagggc gagggccgcc cctacgaggg ctttcagacc    4080
gctaagctga aggtgaccaa gggtggcccc ctgcccttcg cctgggacat cctgtcccct    4140
catttcacct acggctccaa ggcctacgtg aagcaccccg ccgacatccc cgactacttc    4200
aagctgtcct tccccgaggg cttcaagtgg gagcgcgtga tgaactacga ggacggcggc    4260
gtggtgaccg tgacccagga ctcctccctg caggacggcg agttcatcta caaggtgaag    4320
ctgcgcggca ccaacttccc ctccgacggc cccgtgatgc agaagaagac catgggctgg    4380
gaggcctcct ccgagcggat gtaccccgag gacggtgccc tgaagggcaa gatcaagatg    4440
aggctgaagc tgaaggacgg cggccactac acctccgagg tcaagaccac ctacaaggcc    4500
aagaagcccg tgcagctgcc cggcgcctac atcgtcgaca tcaagttgga catcacctcc    4560
cacaacgagg actacaccat cgtggaacag tacgaacgcg ccgagggccg ccactccacc    4620
ggcggcatgg acgagctgta caagggatct aagaagcgta ggatcaagca agat          4674

<210> SEQ ID NO 54
<211> LENGTH: 33
<212> TYPE: DNA
<213> ORGANISM: Artificial Sequence
<220> FEATURE:
<223> OTHER INFORMATION: Synthetic polynucleotide.MGSS7H His tag
      comprising seven Histidine residues

<400> SEQUENCE: 54
atgggcagca gccatcatca ccaccatcac cat                                   33

<210> SEQ ID NO 55
<211> LENGTH: 4710
<212> TYPE: DNA
<213> ORGANISM: Artificial Sequence
<220> FEATURE:
<223> OTHER INFORMATION: Synthetic polynucleotide.MGSS7H-NLS-FnCpf1-CO1-
      mOR-NLS

<400> SEQUENCE: 55
atgggcagca gccatcatca ccaccatcac catatgggta gcaaaaagag gcgtatcaag      60
caggacatgt ctatctatca agagtttgtc aacaagtaca gcttaagtaa gacacttcgc     120
ttcgagttga tccctcaggg gaagacactg gaaaacatca aggcgagggg ccttatcctg     180
gacgacgaga agcgggctaa agactacaaa aaagctaaac agataattga caagtatcac     240
caatttttta ttgaggagat cctctcctct gtgtgcataa gtgaggatct gctccagaac     300
tattcggatg tttactttaa actcaagaag tccgatgatg acaaccttca gaaggacttc     360
```

```
aagtccgcca aagacacgat taagaaacaa atcagtgagt acatcaagga tagcgagaaa    420
ttcaagaacc tgttcaacca gaacttaatt gatgccaaaa agggccaaga atccgacctc    480
atcctgtggt taaagcaatc taaagacaac ggtattgagc tgttcaaggc aaacagcgac    540
attacagaca ttgacgaggc cctagagatc atcaagtcat tcaaaggctg gacgacttac    600
tttaaaggtt tcacgagaaa ccgtaagaat gtttactcaa gtaacgatat accaacgagc    660
attatctacc gaatagtgga tgataaccta ccgaagttcc ttgagaacaa agcgaagtac    720
gagtctctca aagacaaggc ccctgaggcc atcaactacg agcagattaa aaggatctc     780 gccgaggagc taaccttcga cattgactac aaaacatcgg aagtgaatca gagggtgttc    840
tcgcttgatg aagtattcga gattgctaac ttcaacaatt acctgaacca gagtggtatt    900
actaagttca acacaatcat tggaggcaaa ttcgtgaacg gcgaaaacac aaagcgaaaa    960
gggataaacg agtacattaa cttgtacagc cagcagatca acgataagac actcaagaag   1020
tataagatgt ctgtgctgtt caaacaaatc ttaagcgaca cggaaagcaa gtcgttcgta   1080
attgacaagc tggaagacga ttctgacgtg gttacaacca tgcagtcctt ttacgagcag   1140
attgccgcat tcaagaccgt ggaggaaaag tcgatcaagg aaacactttc gttgcttttc   1200
gacgacctta agctcagaa gctcgactta agcaagatat actttaagaa cgataagagc    1260
ttgacagact tgagccagca agtctttgac gactacagcg ttatcggaac tgccgttctg   1320
gagtacataa cacagcagat cgcacccaag aaccttgaca cccttccaa gaaagaacaa    1380 gagttgatcg ccaagaagac tgaaaaggct aagtacctct ctctggagac tatcaagctc   1440
gctcttgagg agtttaacaa gcacaggac attgacaagc aatgccgatt cgaggaaata    1500
ctggcaaact tcgcagccat acccatgata ttcgatgaga tagcccagaa caaggataac   1560
ttggcccaaa tctcgattaa gtatcagaac cagggcaaaa aggaccttct acaggctagt   1620
gcagaggacg atgtgaaggc tattaaggac ttattagatc agacaaacaa ccttctgcat   1680
aagctcaaga tattccatat ctcccagtca gaggacaagg ccaacattct ggataaggac   1740
gagcacttct atctcgtatt cgaggaatgt tactttgagc tggccaatat cgttcccttg   1800
tacaacaaaa tccggaacta catcacacag aagccctaca gtgatgagaa gttcaaattg   1860
aactttgaaa actcaacact tgctaatggt tgggacaaga ataaggaacc tgacaacact   1920
gccatcctct ttattaaaga tgataagtac tacctcgggg tgatgaataa gaagaacaac   1980
aaaatcttcg atgacaaagc tattaaggag aacaaaggtg aagggtacaa gaagattgtc   2040
tacaaactgc tgcctggtgc caacaaaatg ctaccaaagg tattttttcag cgccaaatct   2100 attaagttct acaatccaag cgaggatatt ctccggatac ggaatcactc tacacatacc   2160
aagaatggaa gtccacaaaa gggttacgag aaattcgagt tcaacattga agactgccgg   2220
aaattcattg acttctacaa gcaatccatc tctaaacatc ctgaatggaa agacttcggt   2280
ttccgcttca gtgatactca acggtacaat tcaattgacg aattctaccg tgaggttgag   2340
aaccaggggt acaaactgac cttcgagaac atatcagaga gctacatcga ctcagtggtt   2400
aatcagggga agctatatct gtttcaaatc tacaacaaag actttagtgc ctactctaaa   2460
gggcggccaa acttacacac actttactgg aaggcactat tcgacgaacg caatctacaa   2520
gatgtagttt acaaattgaa cggtgaggct gagttgttct accgtaaaca atctataccc   2580
aagaagataa cacaccctgc taaagaggca attgcaaaca aaaacaagga taatcccaaa   2640
aaggagtctg tctttgagta tgacctcatt aaggataagc ggttcacgga ggacaagttc   2700
ttcttccatt gtccaataac catcaacttc aaatcatccg gcgcaaacaa attcaatgac   2760
```

```
gagatcaacc tgttactaaa ggagaaggct aacgatgttc acatcttatc tattgatcga    2820
ggtgagagac acctagccta ctacacttta gtggatggga aggggaacat catcaagcaa    2880
gacaccttca acatcattgg gaacgacagg atgaagacta actaccatga taagctcgcc    2940
gctattgaaa aggacaggga ctctgccagg aaggactgga aaaaaattaa caatattaaa    3000
gagatgaagg agggctacct gagccaagta gtccatgaga tagcaaaact ggtgattgag    3060
tacaacgcaa tagtcgtatt cgaggactta aacttcggct tcaaacgtgg gcggtttaag    3120
gtggagaaac aagtctatca gaaattggag aagatgctaa tcgagaagct caactacctc    3180
gtgtttaaag acaacgagtt tgacaaaact ggaggagtcc tgcgggcata ccaactgacc    3240
gcacccttcg agacattcaa gaagatggga aagcagactg gcatcatcta ttacgtgcca    3300
gcgggtttta cttccaaaat ctgtccagtt acaggcttcg tgaaccagtt gtacccgaag    3360
tacgagtctg tttccaagtc acaggaattc ttctcaaagt tgacaagat atgttacaat     3420 ctcgataagg gatactttga gtttagtttc gactacaaga actttggcga taaggccgca    3480
aaagggaaat ggacaattgc atccttcggg tcacgcctta ttaactttcg taactcagac    3540
aagaaccaca attgggacac cagggaggtg taccctacta aggagctgga gaagctactt    3600
aaagactact cgattgagta cggacatgga gagtgcatca aggcagcaat atgtggggaa    3660
tctgacaaaa agttctttgc caagctgacc tctgtactga acactattct ccaaatgaga    3720
aatagtaaga ctggcacaga gttggactac ctgatctctc cagtggctga cgttaatggg    3780
aattttttcg actcaagaca agctcccaag aatatgccac aggacgcaga tgcaaacggg    3840
gcatatcaca tcgggcttaa aggactcatg ctactagggc ggatcaagaa taatcaggag    3900
ggcaaaaagc tgaacctagt catcaagaac gaggagtact tcgaatttgt ccagaatcgt    3960
aacaacggat ctggagtgag caagggcgag gagaataaca tggccatcat caaggagttc    4020
atgcgcttca aggtgcgcat ggagggctcc gtgaacggcc acgagttcga gatcgagggc    4080
gagggcgagg gccgccccta cgagggcttt cagaccgcta agctgaaggt gaccaagggt    4140
ggccccctgc ccttcgcctg gacatcctg tcccctcatt tcacctacgg ctccaaggcc     4200
tacgtgaagc accccgccga catccccgac tacttcaagc tgtccttccc cgagggcttc    4260
aagtgggagc gcgtgatgaa ctacgaggac ggcggcgtgg tgaccgtgac ccaggactcc    4320
tccctgcagg acggcgagtt catctacaag gtgaagctgc gcggcaccaa cttcccctcc    4380
gacggccccg tgatgcagaa gaagaccatg ggctgggagg cctcctccga gcggatgtac    4440
cccgaggacg gtgccctgaa gggcaagatc aagatgaggc tgaagctgaa ggacggcggc    4500
cactacacct ccgaggtcaa gaccacctac aaggccaaga gcccgtgca gctgcccggc     4560 gcctacatcg tcgacatcaa gttggacatc acctcccaca acgaggacta caccatcgtg    4620
gaacagtacg aacgcgccga gggccgccac tccaccggcg gcatggacga gctgtacaag    4680
ggatctaaga gcgtaggat caagcaagat                                      4710
```

<210> SEQ ID NO 56
<211> LENGTH: 6465
<212> TYPE: DNA
<213> ORGANISM: Artificial Sequence
<220> FEATURE:
<223> OTHER INFORMATION: Synthetic polynucleotide.Expression cassette
      comprising 35S promoter cassette, MGSS7H-NLS-FnCpf1-CO1-mOr-NLS
      and NOS transcription termination sequence

<400> SEQUENCE: 56

```
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg gaaaagaag acgttccaac cacgtcttca      240
aagcaagtgg attgatgtga tggtccgatt gagacttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaagaa      480
gacgttccaa ccacgtcttc aaagcaagtg gattgatgtg atatctccac tgacgtaagg     540
gatgacgcac aatcccacta tccttcgcaa gacccttcct ctatataagg aagttcattt     600
catttggaga ggacacgctg acaagctgac tctagcagat ctaccgtctt cggtacgcgc     660
tcactccgcc ctctgccttt gttactgcca cgtttctctg aatgctctct tgtgtggtga     720
ttgctgagag tggtttagct ggatctagaa ttacactctg aaatcgtgtt ctgcctgtgc     780
tgattacttg ccgtcctttg tagcagcaaa atatagggac atggtagtac gaaacgaaga     840
tagaacctac acagcaatac gagaaatgtg taatttggtg cttagcggta tttatttaag     900
cacatgttgg tgttataggg cacttggatt cagaagtttg ctgttaattt aggcacaggc     960
ttcatactac atgggtcaat agtataggga ttcatattat aggcgatact ataataattt    1020
gttcgtctgc agagcttatt atttgccaaa attagatatt cctattctgt ttttgtttgt    1080
gtgctgttaa attgttaacg cctgaaggaa taaatataaa tgacgaaatt ttgatgttta    1140
tctctgctcc tttattgtga ccataagtca agatcagatg cacttgtttt aaatattgtt    1200
gtctgaagaa ataagtactg acagtatttt gatgcattga tctgcttgtt tgttgtaaca    1260
aaatttaaaa ataaagagtt ccttttttgt tgctctcctt acctcctgat ggtatctagt    1320
atctaccaac tgacactata ttgcttctct ttacatacgt atcttgctcg atgccttctc    1380
cctagtgttg accagtgtta ctcacatagt ctttgctcat tcattgtaa tgcagatacc     1440
aagcggcctc tagaggatcc aggagcaacc atgggcagca gccatcatca ccaccatcac    1500
catatgggta gcaaaagag gcgtatcaag caggacatgt ctatctatca agagtttgtc    1560
aacaagtaca gcttaagtaa gacacttcgc ttcgagttga tccctcaggg gaagacactg    1620
gaaaacatca aggcgagggg ccttatcctg acgacgaga agcgggctaa agactacaaa     1680
aaagctaaac agataattga caagtatcac caatttttta ttgaggagat cctctcctct    1740
gtgtgcataa gtgaggatct gctccagaac tattcggatg tttactttaa actcaagaag    1800
tccgatgatg acaaccttca gaaggacttc aagtccgcca agacacgat taagaaacaa     1860
atcagtgagt acatcaagga tagcgagaaa ttcaagaacc tgttcaacca gaacttaatt    1920
gatgccaaaa agggccaaga atccgacctc atcctgtggt taaagcaatc taaagacaac    1980
ggtattgagc tgttcaaggc aaacagcgac attacagaca ttgacgaggc cctagagatc    2040
atcaagtcat tcaaaggctg gacgacttac tttaaaggtt ttcacgagaa ccgtaagaat    2100
gtttactcaa gtaacgatat accaacgagc attatctacc gaatagtgga tgataaccta    2160
ccgaagttcc ttgagaacaa agcgaagtac gagtctctca agacaaggc ccctgaggcc     2220
atcaactacg agcagattaa gaaggatctc gccgaggagc taaccttcga cattgactac    2280
```

-continued

```
aaaacatcgg aagtgaatca gagggtgttc tcgcttgatg aagtattcga gattgctaac    2340
ttcaacaatt acctgaacca gagtggtatt actaagttca acacaatcat tggaggcaaa    2400
ttcgtgaacg gcgaaaacac aaagcgaaaa gggataaacg agtacattaa cttgtacagc    2460
cagcagatca acgataagac actcaagaag tataagatgt ctgtgctgtt caaacaaatc    2520
ttaagcgaca cggaaagcaa gtcgttcgta attgacaagc tggaagacga ttctgacgtg    2580
gttacaacca tgcagtcctt ttacgagcag attgccgcat tcaagaccgt ggaggaaaag    2640
tcgatcaagg aaacactttc gttgcttttc gacgacctta agctcagaa gctcgactta    2700 agcaagatat actttaagaa cgataagagc ttgacagact tgagccagca agtctttgac    2760
gactacagcg ttatcggaac tgccgttctg gagtacataa cacagcagat cgcacccaag    2820
aaccttgaca acccttccaa gaagaacaa gagttgatcg ccaagaagac tgaaaaggct    2880
aagtacctct ctctggagac tatcaagctc gctcttgagg agtttaacaa gcacagggac    2940
attgacaagc aatgccgatt cgaggaaata ctggcaaact tcgcagccat acccatgata    3000
ttcgatgaga tagcccagaa caaggataac ttggcccaaa tctcgattaa gtatcagaac    3060
cagggcaaaa aggaccttct acaggctagt gcagaggacg atgtgaaggc tattaaggac    3120
ttattagatc agacaaacaa ccttctgcat aagctcaaga tattccatat ctcccagtca    3180
gaggacaagg ccaacattct ggataaggac gagcacttct atctcgtatt cgaggaatgt    3240
tactttgagc tggccaatat cgttcccttg tacaacaaaa tccggaacta catcacacag    3300
aagccctaca gtgatgagaa gttcaaattg aactttgaaa actcaacact tgctaatggt    3360
tgggacaaga ataaggaacc tgacaacact gccatcctct ttattaaaga tgataagtac    3420
tacctcgggg tgatgaataa gaagaacaac aaaatcttcg atgacaaagc tattaaggag    3480 aacaaggtg aagggtacaa gaagattgtc tacaaactgc tgcctggtgc caacaaaatg    3540
ctaccaaagg tatttttcag cgccaaatct attaagttct acaatccaag cgaggatatt    3600
ctccggatac ggaatcactc tacacatacc aagaatggaa gtccacaaaa gggttacgag    3660
aaattcgagt tcaacattga agactgccgg aaattcattg acttctacaa gcaatccatc    3720
tctaaacatc ctgaatggaa agacttcggt ttccgcttca gtgatactca acggtacaat    3780
tcaattgacg aattctaccg tgaggttgag aaccaggggt acaaactgac cttcgagaac    3840
atatcagaga gctacatcga ctcagtggtt aatcagggga agctatatct gtttcaaatc    3900
tacaacaaag acttttagtgc ctactctaaa gggcggccaa acttacacac actttactgg    3960
aaggcactat tcgacgaacg caatctacaa gatgtagttt acaaattgaa cggtgaggct    4020
gagttgttct accgtaaaca atctataccc aagaagataa cacaccctgc taaagaggca    4080
attgcaaaca aaaacaagga taatcccaaa aaggagtctg tctttgagta tgacctcatt    4140
aaggataagc ggttcacgga ggacaagttc ttcttccatt gtccaataac catcaacttc    4200
aaatcatccg gcgcaaacaa attcaatgac gagatcaacc tgttactaaa ggagaaggct    4260
aacgatgttc acatcttatc tattgatcga ggtgagagac acctagccta ctacacttta    4320
gtggatggga aggggaacat catcaagcaa gacaccttca acatcattgg gaacgacagg    4380
atgaagacta actaccatga taagctcgcc gctattgaaa aggacaggga ctctgccagg    4440
aaggactgga aaaaattaa caatattaaa gagatgaagg agggctacct gagccaagta    4500
gtccatgaga tagcaaaact ggtgattgag tacaacgcaa tagtcgtatt cgaggactta    4560
aacttcggct tcaaacgtgg gcggtttaag gtggagaaac aagtctatca gaaattggag    4620
aagatgctaa tcgagaagct caactacctc gtgtttaaag acaacgagtt tgacaaaact    4680
```

```
ggaggagtcc tgcgggcata ccaactgacc gcacccttcg agacattcaa gaagatggga    4740
aagcagactg gcatcatcta ttacgtgcca gcgggtttta cttccaaaat ctgtccagtt    4800
acaggcttcg tgaaccagtt gtacccgaag tacgagtctg tttccaagtc acaggaattc    4860
ttctcaaagt ttgacaagat atgttacaat ctcgataagg gatactttga gtttagtttc    4920
gactacaaga actttggcga taaggccgca aagggaaat ggacaattgc atccttcggg     4980
tcacgcctta ttaactttcg taactcagac aagaaccaca attgggacac cagggaggtg    5040
taccctacta aggagctgga gaagctactt aaagactact cgattgagta cggacatgga    5100
gagtgcatca aggcagcaat atgtggggaa tctgacaaaa agttctttgc caagctgacc    5160
tctgtactga acactattct ccaaatgaga aatagtaaga ctggcacaga gttggactac    5220
ctgatctctc cagtgctga cgttaatggg aattttttcg actcaagaca agctcccaag     5280
aatatgccac aggacgcaga tgcaaacggg gcatatcaca tcgggcttaa aggactcatg    5340
ctactagggc ggatcaagaa taatcaggag ggcaaaaagc tgaacctagt catcaagaac    5400
gaggagtact tcgaatttgt ccagaatcgt aacaacggat ctggagtgag caagggcgag    5460
gagaataaca tggccatcat caaggagttc atgcgcttca aggtgcgcat ggagggctcc    5520
gtgaacggcc acgagttcga gatcgagggc gagggcgagg ccgcccccta cgagggcttt    5580
cagaccgcta agctgaaggt gaccaagggt ggcccctgc ccttcgcctg ggacatcctg     5640
tcccctcatt tcacctacgg ctccaaggcc tacgtgaagc accccgccga catccccgac    5700
tacttcaagc tgtccttccc cgagggcttc aagtgggagc gcgtgatgaa ctacgaggac    5760
ggcggcgtgg tgaccgtgac ccaggactcc tccctgcagg acggcgagtt catctacaag    5820
gtgaagctgc gcggcaccaa cttcccctcc gacggccccg tgatgcagaa gaagaccatg    5880
ggctgggagg cctcctccga gcggatgtac cccgaggacg gtgccctgaa gggcaagatc    5940
aagatgaggc tgaagctgaa ggacggcggc cactacacct ccgaggtcaa gaccacctac    6000
aaggccaaga agcccgtgca gctgcccggc gcctacatcg tcgacatcaa gttggacatc    6060
acctcccaca acgaggacta caccatcgtg aacagtacg aacgcgccga gggccgccac     6120
tccaccggcg gcatggacga gctgtacaag ggatctaaga agcgtaggat caagcaagat    6180
tagaacccag cggtactcgc tgaggaattc gcgatcgttc aaacatttgg caataaagtt    6240
tcttaagatt gaatcctgtt gccggtcttg cgatgattat catataattt ctgttgaatt    6300
acgttaagca tgtaataatt aacatgtaat gcatgacgtt atttatgaga tgggttttta    6360
tgattagagt cccgcaatta tacatttaat acgcgataga aaacaaaata tagcgcgcaa    6420
actaggataa attatcgcgc gcggtgtcat ctatgttact agatc                     6465
```

<210> SEQ ID NO 57
<211> LENGTH: 4674
<212> TYPE: DNA
<213> ORGANISM: Artificial Sequence
<220> FEATURE:
<223> OTHER INFORMATION: Synthetic polynucleotide.NLS-FnCpf1-CO2-mOR-NLS

<400> SEQUENCE: 57

```
ggtagcaaaa agaggcgtat caagcaggac atgtccatat accaggagtt cgtcaacaag      60
tactcgctca gcaagacgct ccgcttcgag ctgatccccc agggtaagac cctggagaac     120
atcaaggcgc gcggactcat cctcgacgac gagaagcggg ctaaggacta caaaaaggcc    180
aagcagatca tcgacaagta ccaccagttc ttcatcgagg agatcctctc ctccgtctgc    240
```

```
atctccgagg acctcctcca gaactacagc gacgtctact tcaagctcaa aaagtcggac      300
gacgacaacc tccagaagga cttcaagtcg gcgaaggaca ccatcaagaa gcagatcagc      360
gagtacatca aggactccga gaagttcaag aacctgttca accagaacct gatcgacgcc      420
aagaagggcc aggagtcgga cctgatcctg tggctcaagc agagcaagga caacggcatc      480
gagctcttca aggccaacag cgacatcacg gacatcgacg aggccctgga gatcatcaag      540
tcgttcaagg gctggacgac ctacttcaag ggcttccacg agaaccgcaa gaacgtctat      600
agctccaacg acatccccac ctcgatcatc taccggatcg tggacgacaa cctccccaag      660
ttcctggaga caaggcgaa gtacgagtcg ttgaaggaca aggcgccgga ggcgatcaac       720
tacgagcaga tcaagaagga cctggccgag gagctgacct tcgacatcga ctacaagacg      780
tcggaggtga accagcgggt gttcagtctg gacgaggtct tcgagatcgc gaacttcaac      840
aactacctga accagtcggg gatcaccaag ttcaacacga tcataggcgg caagttcgtg      900
aacggcgaga acaccaagcg caaggggata acgagtaca tcaacctgta cagccagcag       960
atcaacgaca agacgctcaa gaagtacaag atgagcgtgc tcttcaagca gatcctcagt     1020
gacaccgagt ccaagagctt cgtgatcgac aagctggagg acgacagcga cgtcgtgaca     1080
accatgcaga gcttctacga gcagatcgcc gcgttcaaga ccgtcgagga gaagtcaatc     1140
aaggagacgc tctccttgct gttcgacgac ctgaaggcac aaaagctgga cctcagcaag     1200
atctacttca agaacgacaa gtccctgacc gacctgagcc agcaggtttt cgacgactac     1260
tccgtcatcg ggactgccgt cctggagtac atcacccagc agatcgctcc gaagaacctc     1320
gacaacccgt ccaagaagga gcaggagctg attgcgaaga agacagagaa ggccaagtac     1380
ctctccctcg agaccatcaa gctcgccctg gaggagttca acaagcacag ggacattgac     1440
aagcagtgcc gtttcgagga gatcctggcc aacttcgcgg ccatccccat gatcttcgac     1500
gagatcgccc agaacaagga caacctggcg cagatctcta tcaagtacca gaaccagggg     1560
aagaaggact tgctccaggc ctcagcggag gacgacgtga aggccatcaa ggacctgctc     1620
gaccagacga caacttgct ccacaagctc aagatctttc acatcagcca gagcgaggac      1680
aaggccaaca tcctcgacaa ggacgagcac ttctacctcg tgttcgagga gtgctacttc     1740
gagctggcca acatcgtgcc actttacaac aagatccgca actacatcac gcagaagccg     1800
tactccgacg agaagttcaa gctgaacttc gagaactcca ccctcgccaa cggctgggac     1860
aagaacaagg agccggacaa caccgcgatc ctgttcataa aggacgacaa gtactacttg     1920
ggggtcatga caagaagaa caacaagata ttcgacgaca aggccatcaa ggagaacaag     1980
ggggagggct acaagaagat cgtctacaag ctcctccccg gcgcgaacaa gatgctgcct     2040
aaggtcttct tttccgccaa gagtatcaag ttctacaacc cctccgagga catcctccgc     2100
atccggaacc acagcacgca cacaaagaac ggctcgcctc agaagggcta cgagaagttc     2160
gagttcaaca tcgaggactg ccggaagttc atcgacttct acaagcagag catctccaag     2220
cacccggagt ggaaggactt tggcttcagg ttctcagaca cccagcggta caactccatc     2280
gacgagttct accgcgaggt ggagaaccag ggctacaagc tgaccttcga gaatatatca     2340
gagtcgtaca tcgacagcgt ggtgaaccag ggcaagttgt acctgttcca gatctacaac     2400
aaggacttct ccgcctactc aaaggggcgt ccaaacctgc acacgctgta ctggaaggcg     2460
ctcttcgacg agcgcaacct acaagatgtt gtatacaagc tcaacggcga ggcggaactg     2520
ttctatagga agcagtcgat cccccaagaag attacgcacc cggctaagga ggccatcgcc     2580
aacaagaaca aggacaaccc caagaaggag tccgtgttcg agtacgacct catcaaggac     2640
```

```
aagaggttca cggaggacaa gttttcttc cactgcccaa tcactatcaa tttcaagtcg    2700
agcggagcca acaagttcaa cgacgagata acctgctcc tcaaggagaa ggccaatgac    2760
gtgcacatcc tctccatcga ccggggcgag cggcacctgg cgtactacac gctggtggac    2820
ggcaagggca acatcatcaa gcaggacacc ttcaacatca tcgggaacga ccgcatgaag    2880
accaactacc acgacaagct cgccgccatc gagaaggaca gggactccgc gcgcaaggac    2940
tggaagaaga ttaacaacat caaggagatg aaggagggct acctcagcca ggtggtccac    3000
gagatcgcca agctcgtcat tgagtacaac gccatcgtcg tcttcgagga cctgaatttc    3060
ggcttcaagc gcggccggtt caaggtggag aagcaggtct accagaagct tgagaagatg    3120
ctgatcgaga agctgaacta cctggtgttc aaggacaacg agttcgacaa gaccggcgga    3180
gtgctgcgcg cctaccagct cacggcgcct ttcgagacgt tcaagaagat gggcaagcag    3240
acgggcatca tctactacgt gcccgccggc ttcacctcta agatctgccc agtgaccggc    3300
ttcgttaacc agctgtaccc gaagtacgag agcgtgtcca gtcccagga gttcttctcc    3360
aagttcgaca agatttgtta caacctcgac aagggctact tcgagttttc gttcgactac    3420
aagaactttg cgacaaggc ggccaagggg aagtggacca tcgcctcttt cggcagcagg    3480
ctcatcaatt tccggaactc cgacaagaac cacaactggg acacgcgcga ggtgtacccg    3540
acgaaggagc tggagaagct gctcaaggac tactccatcg agtacggcca cggcgagtgc    3600
atcaaggcgg cgatctgcgg ggagagcgac aagaagttct ttgccaagct gaccagcgtg    3660
ctgaacacca cctccagat gcggaactcc aagaccggca ccgagctgga ctacctgatc    3720
tccccggtcg cggacgtcaa cgggaacttc ttcgactccc gacaggctcc caagaacatg    3780
ccccaggacg ccgacgcgaa cggcgcgtac cacatcggcc tcaagggcct gatgctgctg    3840
gggcgcatca agaacaacca ggagggcaag aagctgaacc tcgtgatcaa gaacgaggaa    3900
tacttcgagt tcgtgcagaa ccgcaacaac ggatctggag tgagcaaggg cgaggagaat    3960
aacatggcca tcatcaagga gttcatgcgc ttcaaggtgc gcatggaggg ctccgtgaac    4020
ggccacgagt tcgagatcga gggcgagggc gaggccgcc cctacgaggg ctttcagacc    4080
gctaagctga aggtgaccaa gggtggcccc ctgcccttcg cctgggacat cctgtcccct    4140
catttcacct acggctccaa ggcctacgtg aagcaccccg ccgacatccc cgactacttc    4200
aagctgtcct tccccgaggg cttcaagtgg gagcgcgtga tgaactacga ggacggcggc    4260
gtggtgaccg tgacccagga ctcctccctg caggacggcg agttcatcta caaggtgaag    4320
ctgcgcggca ccaacttccc ctccgacggc cccgtgatgc agaagaagac catgggctgg    4380
gaggcctcct ccgagcggat gtaccccgag gacggtgccc tgaagggcaa gatcaagatg    4440
aggctgaagc tgaaggacgg cggccactac acctccgagg tcaagaccac ctacaaggcc    4500
aagaagcccg tgcagctgcc cggcgcctac atcgtcgaca tcaagttgga catcaccctc    4560
cacaacgagg actacaccat cgtggaacag tacgaacgcg ccgagggccg ccactccacc    4620
ggcggcatgg acgagctgta caagggatct aagaagcgta ggatcaagca agat          4674
```

<210> SEQ ID NO 58
<211> LENGTH: 4710
<212> TYPE: DNA
<213> ORGANISM: Artificial Sequence
<220> FEATURE:
<223> OTHER INFORMATION: Synthetic polynucleotide. MGSS7H-NLS-FnCpf1-
      CO2-mOR-NLS

<400> SEQUENCE: 58

```
atgggcagca gccatcatca ccaccatcac catatgggta gcaaaaagag gcgtatcaag      60
caggacatgt ccatatacca ggagttcgtc aacaagtact cgctcagcaa gacgctccgc     120
ttcgagctga tcccccaggg taagaccctg gagaacatca aggcgcgcgg actcatcctc     180
gacgacgaga agcgggctaa ggactacaaa aaggccaagc agatcatcga caagtaccac     240
cagttcttca tcgaggagat cctctcctcc gtctgcatct ccgaggacct cctccagaac     300
tacagcgacg tctacttcaa gctcaaaaag tcggacgacg acaacctcca gaaggacttc     360
aagtcggcga aggacaccat caagaagcag atcagcgagt acatcaagga ctccgagaag     420
ttcaagaacc tgttcaacca gaacctgatc gacgccaaga agggccagga gtcggacctg     480
atcctgtggc tcaagcagag caaggacaac ggcatcgagc tcttcaaggc caacagcgac     540
atcacggaca tcgacgaggc cctggagatc atcaagtcgt tcaagggctg gacgacctac     600
ttcaagggct tccacgagaa ccgcaagaac gtctatagct ccaacgacat ccccacctcg     660
atcatctacc ggatcgtgga cgacaacctc cccaagttcc tggagaacaa ggcgaagtac     720
gagtcgttga aggacaaggc gccggaggcg atcaactacg agcagatcaa gaaggacctg     780
gccgaggagc tgaccttcga catcgactac aagacgtcgg aggtgaacca gcgggtgttc     840
agtctggacg aggtcttcga gatcgcgaac ttcaacaact acctgaacca gtcggggatc     900
accaagttca acacgatcat aggcggcaag ttcgtgaacg gcgagaacac caagcgcaag     960
gggataaacg agtacatcaa cctgtacagc cagcagatca cgacaagac gctcaagaag    1020 tacaagatga gcgtgctctt caagcagatc ctcagtgaca ccgagtccaa gagcttcgtg    1080
atcgacaagc tggaggacga cagcgacgtc gtgacaacca tgcagagctt ctacgagcag    1140
atcgccgcgt tcaagaccgt cgaggagaag tcaatcaagg agacgctctc cttgctgttc    1200
gacgacctga aggcacaaaa gctggacctc agcaagatct acttcaagaa cgacaagtcc    1260
ctgaccgacc tgagccagca ggttttcgac gactactccg tcatcgggac tgccgtcctg    1320
gagtacatca cccagcagat cgctccgaag aacctcgaca cccgtccaa gaaggagcag    1380 gagctgattg cgaagaagac agagaaggcc aagtacctct ccctcgagac catcaagctc    1440
gccctggagg agttcaacaa gcacaggac attgacaagc agtgccgttt cgaggagatc    1500
ctggccaact cgcgggccat ccccatgatc ttcgacgaga tcgcccagaa caaggacaac    1560
ctggcgcaga tctctatcaa gtaccagaac caggggaaga aggacttgct ccaggcctca    1620
gcggaggacg acgtgaaggc catcaaggac ctgctcgacc agacgaacaa cttgctccac    1680
aagctcaaga tctttcacat cagccagagc gaggacaagg ccaacatcct cgacaaggac    1740
gagcacttct acctcgtgtt cgaggagtgc tacttcgagc tggccaacat cgtgccactt    1800
tacaacaaga tccgcaacta catcacgcag aagccgtact ccgacgagaa gttcaagctg    1860
aacttcgaga actccacccct cgccaacggc tgggacaaga caaggagcc ggacaacacc    1920 gcgatcctgt tcataaagga cgacaagtac tacttgggg tcatgaacaa gaagaacaac    1980
aagatattcg acgacaaggc catcaaggag aacaaggggg agggctacaa gaagatcgtc    2040
tacaagctcc tccccggcgc gaacaagatg ctgcctaagg tcttcttttc cgccaagagt    2100
atcaagttct acaaccctc cgaggacatc ctccgcatcc ggaaccacag cacgcacaca    2160
aagaacggct cgcctcagaa gggctacgag aagttcgagt caacatcga ggactgccgg    2220 aagttcatcg acttctacaa gcagagcatc tccaagcacc cggagtggaa ggactttggc    2280
ttcaggttct cagacaccca gcggtacaac tccatcgacg agttctaccg cgaggtggag    2340
```

```
aaccagggct acaagctgac cttcgagaat atatcagagt cgtacatcga cagcgtggtg    2400
aaccagggca agttgtacct gttccagatc tacaacaagg acttctccgc ctactcaaag    2460
gggcgtccaa acctgcacac gctgtactgg aaggcgctct tcgacgagcg caacctacaa    2520
gatgttgtat acaagctcaa cggcgaggcg aactgttct ataggaagca gtcgatcccc     2580
aagaagatta cgcacccggc taaggaggcc atcgccaaca agaacaagga caaccccaag    2640
aaggagtccg tgttcgagta cgacctcatc aaggacaaga ggttcacgga ggacaagttt    2700
ttcttccact gcccaatcac tatcaatttc aagtcgagcg gagccaacaa gttcaacgac    2760
gagataaacc tgctcctcaa ggagaaggcc aatgacgtgc acatcctctc catcgaccgg    2820
ggcgagcggc acctggcgta ctacacgctg gtggacggca agggcaacat catcaagcag    2880
gacaccttca acatcatcgg gaacgaccgc atgaagacca actaccacga caagctcgcc    2940
gccatcgaga aggacaggga ctccgcgcgc aaggactgga agaagattaa caacatcaag    3000
gagatgaagg agggctacct cagccaggtg gtccacgaga tcgccaagct cgtcattgag    3060
tacaacgcca tcgtcgtctt cgaggacctg aatttcggct tcaagcgcgg ccggttcaag    3120
gtggagaagc aggtctacca gaagcttgag aagatgctga tcgagaagct gaactacctg    3180
gtgttcaagg acaacgagtt cgacaagacc ggcggagtgc tgcgcgccta ccagctcacg    3240
gcgcctttcg agacgttcaa gaagatgggc aagcagacgg gcatcatcta ctacgtgccc    3300
gccggcttca cctctaagat ctgcccagtg accggcttcg ttaaccagct gtacccgaag    3360
tacgagagcg tgtccaagtc ccaggagttc ttctccaagt tcgacaagat tgttacaac    3420 ctcgacaagg gctacttcga gttttcgttc gactacaaga actttggcga caaggcggcc    3480
aaggggaagt ggaccatcgc ctctttcggc agcaggctca tcaatttccg gaactccgac    3540
aagaaccaca actgggacac gcgcgaggtg tacccgacga aggagctgga gaagctgctc    3600
aaggactact ccatcgagta cggccacggc gagtgcatca aggcggcgat ctgcggggag    3660
agcgacaaga agttctttgc caagctgacc agcgtgctga acaccatcct ccagatgcgg    3720
aactccaaga ccggcaccga gctggactac ctgatctccc cggtcgcgga cgtcaacggg    3780
aacttcttcg actcccgaca ggctcccaag aacatgcccc aggacgccga cgcgaacggc    3840
gcgtaccaca tcggcctcaa gggcctgatg ctgctggggc gcatcaagaa caaccaggag    3900
ggcaagaagc tgaacctcgt gatcaagaac gaggaatact tcgagttcgt gcagaaccgc    3960
aacaacggat ctggagtgag caagggcgag gagaataaca tggccatcat caaggagttc    4020
atgcgcttca aggtgcgcat ggagggctcc gtgaacggcc acgagttcga gatcgagggc    4080
gagggcgagg gccgccccta cgagggcttt cagaccgcta agctgaaggt gaccaagggt    4140
ggccccctgc ccttcgcctg gacatcctg tcccctcatt tcacctacgg ctccaaggcc    4200
tacgtgaagc accccgccga catccccgac tacttcaagc tgtccttccc cgagggcttc    4260
aagtgggagc gcgtgatgaa ctacgaggac ggcggcgtgg tgaccgtgac ccaggactcc    4320
tccctgcagg acggcgagtt catctacaag gtgaagctgc gcggcaccaa cttccctcc    4380 gacggccccg tgatgcagaa gaagaccatg ggctgggagg cctcctccga gcggatgtac    4440
cccgaggacg gtgccctgaa gggcaagatc aagatgaggc tgaagctgaa ggacggcggc    4500
cactacacct ccgaggtcaa gaccacctac aaggccaaga gcccgtgca gctgcccggc    4560 gcctacatcg tcgacatcaa gttggacatc acctcccaca acgaggacta caccatcgtg    4620
gaacagtacg aacgcgccga gggccgccac tccaccggcg gcatggacga gctgtacaag    4680
ggatctaaga agcgtaggat caagcaagat                                     4710
```

<210> SEQ ID NO 59
<211> LENGTH: 6465
<212> TYPE: DNA
<213> ORGANISM: Artificial Sequence
<220> FEATURE:
<223> OTHER INFORMATION: Synthetic polynucleotide.Expression cassette
comprising 35S promoter cassette, MGSS7H-NLS-FnCpf1-CO2-mOr-NLS
and NOS transcription termination sequence

<400> SEQUENCE: 59

```
ggtccgattg agactttca  acaaagggta atatccggaa acctcctcgg attccattgc    60
ccagctatct gtcactttat tgtgaagata gtggaaaagg aaggtggctc ctacaaatgc   120
catcattgcg ataaaggaaa ggccatcgtt gaagatgcct ctgccgacag tggtcccaaa   180
gatggacccc cacccacgag gagcatcgtg aaaaagaag acgttccaac cacgtcttca    240
aagcaagtgg attgatgtga tggtccgatt gagacttttc aacaaagggt aatatccgga   300
aacctcctcg gattccattg cccagctatc tgtcacttta ttgtgaagat agtggaaaag   360
gaaggtggct cctacaaatg ccatcattgc gataaaggaa aggccatcgt tgaagatgcc   420
tctgccgaca gtggtcccaa agatggaccc ccacccacga ggagcatcgt ggaaaaagaa   480
gacgttccaa ccacgtcttc aaagcaagtg gattgatgtg atatctccac tgacgtaagg   540
gatgacgcac aatcccacta ccttcgcaa gaccctcct ctatataagg aagttcattt    600
catttggaga ggacacgctg acaagctgac tctagcagat ctaccgtctt cggtacgcgc   660
tcactccgcc ctctgccttt gttactgcca cgtttctctg aatgctctct tgtgtggtga   720
ttgctgagag tggtttagct ggatctagaa ttacactctg aaatcgtgtt ctgcctgtgc   780
tgattacttg ccgtcctttg tagcagcaaa atatagggac atggtagtac gaaacgaaga   840
tagaacctac acagcaatac gagaaatgtg taatttggtg cttagcggta tttatttaag   900
cacatgttgg tgttataggg cacttggatt cagaagtttg ctgttaattt aggcacaggc   960
ttcatactac atgggtcaat agtataggga ttcatattat aggcgatact ataataattt  1020
gttcgtctgc agagcttatt atttgccaaa attagatatt cctattctgt ttttgtttgt  1080
gtgctgttaa attgttaacg cctgaaggaa taaatataaa tgacgaaatt ttgatgttta  1140
tctctgctcc tttattgtga ccataagtca agatcagatg cacttgtttt aaatattgtt  1200
gtctgaagaa ataagtactg acagtatttt gatgcattga tctgcttgtt tgttgtaaca  1260
aaatttaaaa ataaagagtt tccttttgt tgctctcctt acctcctgat ggtatctagt   1320
atctaccaac tgacactata ttgcttctct ttacatacgt atcttgctcg atgccttctc  1380
cctagtgttg accagtgtta ctcacatagt ctttgctcat ttcattgtaa tgcagatacc  1440
aagcggcctc tagaggatcc aggagcaacc atgggcagca gccatcatca ccaccatcac  1500
catatgggta gcaaaaagag gcgtatcaag caggacatgt ccatatacca ggagttcgtc  1560
aacaagtact cgctcagcaa gacgctccgc ttcgagctga tccccagggt aagaccctg   1620
gagaacatca aggcgcgcgg actcatcctc gacgacgaga gcgggctaa ggactacaaa   1680
aaggccaagc agatcatcga caagtaccac cagttcttca tcgaggagat cctctcctcc  1740
gtctgcatct ccgaggacct cctccagaac tacagcgacg tctacttcaa gctcaaaaag  1800
tcggacgacg acaacctcca gaaggacttc aagtcggcga aggacaccat caagaagcag  1860
atcagcgagt acatcaagga ctccgagaag ttcaagaacc tgttcaacca gaacctgatc  1920
gacgccaaga agggccagga gtcggaccctg atcctgtggc tcaagcagag caaggacaac  1980
```

```
ggcatcgagc tcttcaaggc caacagcgac atcacggaca tcgacgaggc cctggagatc    2040
atcaagtcgt tcaagggctg gacgacctac ttcaagggct tccacgagaa ccgcaagaac    2100
gtctatagct ccaacgacat ccccacctcg atcatctacc ggatcgtgga cgacaacctc    2160
cccaagttcc tggagaacaa ggcgaagtac gagtcgttga aggacaaggc gccggaggcg    2220
atcaactacg agcagatcaa gaaggacctg gccgaggagc tgaccttcga catcgactac    2280
aagacgtcgg aggtgaacca gcgggtgttc agtctggacg aggtcttcga gatcgcgaac    2340
ttcaacaact acctgaacca gtcggggatc accaagttca acacgatcat aggcggcaag    2400
ttcgtgaacg gcgagaacac caagcgcaag gggataaacg agtacatcaa cctgtacagc    2460
cagcagatca acgacaagac gctcaagaag tacaagatga gcgtgctctt caagcagatc    2520
ctcagtgaca ccgagtccaa gagcttcgtg atcgacaagc tggaggacga cagcgacgtc    2580
gtgacaacca tgcagagctt ctacgagcag atcgccgcgt tcaagaccgt cgaggagaag    2640
tcaatcaagg agacgctctc cttgctgttc gacgacctga aggcacaaaa gctggacctc    2700
agcaagatct acttcaagaa cgacaagtcc ctgaccgacc tgagccagca ggttttcgac    2760
gactactccg tcatcgggac tgccgtcctg gagtacatca cccagcagat cgctccgaag    2820
aacctcgaca acccgtccaa gaaggagcag gagctgattg cgaagaagac agagaaggcc    2880
aagtacctct ccctcgagac catcaagctc gccctggagg agttcaacaa gcacagggac    2940
attgacaagc agtgccgttt cgaggagatc ctggccaact tcgcggccat ccccatgatc    3000
ttcgacgaga tcgcccagaa caaggacaac ctggcgcaga tctctatcaa gtaccagaac    3060
caggggaaga aggacttgct ccaggcctca gcggaggacg acgtgaaggc catcaaggac    3120
ctgctcgacc agacgaacaa cttgctccac aagctcaaga tctttcacat cagccagagc    3180
gaggacaagg ccaacatcct cgacaaggac gagcacttct acctcgtgtt cgaggagtgc    3240
tacttcgagc tggccaacat cgtgccactt tacaacaaga tccgcaacta catcacgcag    3300
aagccgtact ccgacgagaa gttcaagctg aacttcgaga actccaccct cgccaacggc    3360
tgggacaaga acaaggagcc ggacaacacc gcgatcctgt tcataaagga cgacaagtac    3420
tacttggggg tcatgaacaa gaagaacaac aagatattcg acgacaaggc catcaaggag    3480
aacaaggggg agggctacaa gaagatcgtc tacaagctcc tccccggcgc gaacaagatg    3540
ctgcctaagg tcttcttttc cgccaagagt atcaagttct acaacccctc cgaggacatc    3600
ctccgcatcc ggaaccacag cacgcacaca agaacggct cgcctcagaa gggctacgag    3660
aagttcgagt tcaacatcga ggactgccgg aagttcatcg acttctacaa gcagagcatc    3720
tccaagcacc cggagtggaa ggactttggc ttcaggttct cagacaccca gcggtacaac    3780
tccatcgacg agttctaccg cgaggtggag aaccagggct acaagctgac cttcgagaat    3840
atatcagagt cgtacatcga cagcgtggtg aaccagggca agttgtacct gttccagatc    3900
tacaacaagg acttctccgc ctactcaaag gggcgtccaa acctgcacac gctgtactgg    3960
aaggcgctct tcgacgagcg caacctacaa gatgttgtat acaagctcaa cggcgaggcg    4020
gaactgttct ataggaagca gtcgatcccc aagaagatta cgcacccggc taaggaggcc    4080
atcgccaaca gaacaaggac aaccccaag aaggagtccg tgttcgagta cgacctcatc    4140
aaggacaaga ggttcacgga ggacaagttt ttcttccact gcccaatcac tatcaatttc    4200
aagtcgagcg gagccaacaa gttcaacgac gagataaacc tgctcctcaa ggagaaggcc    4260
aatgacgtgc acatcctctc catcgaccgg ggcgagcggc acctggcgta ctacacgctg    4320
gtggacggca agggcaacat catcaagcag gacaccttca acatcatcgg gaacgaccgc    4380
```

```
atgaagacca actaccacga caagctcgcc gccatcgaga aggacaggga ctccgcgcgc    4440
aaggactgga agaagattaa caacatcaag gagatgaagg agggctacct cagccaggtg    4500
gtccacgaga tcgccaagct cgtcattgag tacaacgcca tcgtcgtctt cgaggacctg    4560
aatttcggct tcaagcgcgg ccggttcaag gtggagaagc aggtctacca gaagcttgag    4620
aagatgctga tcgagaagct gaactacctg gtgttcaagg acaacgagtt cgacaagacc    4680
ggcgagtgc tgcgcgccta ccagctcacg gcgcctttcg agacgttcaa gaagatgggc    4740
aagcagacgg gcatcatcta ctacgtgccc gccggcttca cctctaagat ctgcccagtg    4800
accggcttcg ttaaccagct gtacccgaag tacgagagcg tgtccaagtc ccaggagttc    4860
ttctccaagt tcgacaagat ttgttacaac ctcgacaagg gctacttcga gttttcgttc    4920
gactacaaga actttggcga caaggcggcc aaggggaagt ggaccatcgc ctctttcggc    4980
agcaggctca tcaatttccg gaactccgac aagaaccaca actgggacac gcgcgaggtg    5040
tacccgacga aggagctgga gaagctgctc aaggactact ccatcgagta cggccacggc    5100
gagtgcatca aggcggcgat ctgcggggag agcgacaaga agttctttgc caagctgacc    5160
agcgtgctga acaccatcct ccagatgcgg aactccaaga ccggcaccga gctggactac    5220
ctgatctccc cggtcgcgga cgtcaacggg aacttcttcg actcccgaca ggctcccaag    5280
aacatgcccc aggacgccga cgcgaacggc gcgtaccaca tcggcctcaa gggcctgatg    5340
ctgctggggc gcatcaagaa caaccaggag ggcaagaagc tgaacctcgt gatcaagaac    5400
gaggaatact tcgagttcgt gcagaaccgc aacaacggat ctggagtgag caagggcgag    5460
gagaataaca tggccatcat caaggagttc atgcgcttca aggtgcgcat ggagggctcc    5520
gtgaacggcc acgagttcga gatcgagggc gagggcgagg gccgccccta cgagggcttt    5580
cagaccgcta agctgaaggt gaccaagggt ggcccctgc ccttcgcctg ggacatcctg    5640
tccctcatt tcacctacgg ctccaaggcc tacgtgaagc accccgccga catccccgac    5700
tacttcaagc tgtccttccc cgagggcttc aagtgggagc gcgtgatgaa ctacgaggac    5760
ggcggcgtgg tgaccgtgac ccaggactcc tccctgcagg acggcgagtt catctacaag    5820
gtgaagctgc gcggcaccaa cttcccctcc gacggccccg tgatgcagaa gagaccatg    5880
ggctgggagg cctcctccga gcggatgtac cccgaggacg gtgccctgaa gggcaagatc    5940
aagatgaggc tgaagctgaa ggacggcggc cactacacct ccgaggtcaa gaccacctac    6000
aaggccaaga gccccgtgca gctgcccggc gcctacatcg tcgacatcaa gttggacatc    6060
acctcccaca cgaggactac accatcgtg aacagtacg aacgcgccga gggccgccac    6120
tccaccggcg gcatggacga gctgtacaag ggatctaaga gcgtaggat caagcaagat    6180
tagaacccag cggtactcgc tgaggaattc gcgatcgttc aaacatttgg caataaagtt    6240
tcttaagatt gaatcctgtt gccggtcttg cgatgattat catataattt ctgttgaatt    6300
acgttaagca tgtaataatt aacatgtaat gcatgacgtt atttatgaga tgggttttta    6360
tgattagagt cccgcaatta tacatttaat acgcgataga aaacaaaata tagcgcgcaa    6420
actaggataa attatcgcgc gcggtgtcat ctatgttact agatc            6465
```

<210> SEQ ID NO 60
<211> LENGTH: 4671
<212> TYPE: DNA
<213> ORGANISM: Artificial Sequence
<220> FEATURE:
<223> OTHER INFORMATION: Synthetic polynucleotide.NLS-FnCpf1-Hs-mOR-NLS

```
<400> SEQUENCE: 60
ggtagcaaaa agaggcgtat caagcaggac agcatctacc aggagttcgt caacaagtat      60
tcactgagta agacactgcg gttcgagctg atcccacagg gcaagacact ggagaacatc     120
aaggcccgag gcctgattct ggacgatgag aagcgggcaa aagactataa gaaagccaag     180
cagatcattg ataaatacca ccagttcttt atcgaggaaa ttctgagctc cgtgtgcatc     240
agtgaggatc tgctgcagaa ttactcagac gtgtacttca agctgaagaa gagcgacgat     300
gacaacctgc agaaggactt caagtccgcc aaggacacca tcaagaaaca gattagcgag     360
tacatcaagg actccgaaaa gtttaaaaat ctgttcaacc agaatctgat cgatgctaag     420
aaaggccagg agtccgacct gatcctgtgg ctgaaacagt ctaaggacaa tgggattgaa     480
ctgttcaagg ctaactccga tatcactgat attgacgagg cactggaaat catcaagagc     540
ttcaagggat ggaccacata ctttaaaggc ttccacgaga accgcaagaa cgtgtactcc     600
agcaacgaca ttcctacctc catcatctac cgaatcgtcg atgacaatct gccaaagttc     660
ctggagaaca aggccaaata tgaatctctg aaggacaaag ctcccgaggc aattaattac     720
gaacagatca agaagatct ggctgaggaa ctgacattcg atatcgacta taagactagc     780
gaggtgaacc agagggtctt ttccctggac gaggtgtttg aaatcgccaa tttcaacaat     840
tacctgaacc agtccggcat tactaaattc aataccatca ttggcgggaa gtttgtgaac     900
ggggagaata ccaagcgcaa gggaattaac gaatacatca atctgtatag ccagcagatc     960
aacgacaaaa ctctgaagaa atacaagatg tctgtgctgt tcaaacagat cctgagtgat    1020
accgagtcca agtcttttgt cattgataaa ctggaagatg actcagacgt ggtcactacc    1080
atgcagagct tttatgagca gatcgccgct ttcaagacag tggaggaaaa atctattaag    1140
gaaactctga gtctgctgtt cgatgacctg aaagcccaga gctggacct gagtaagatc    1200 tacttcaaaa acgataagag tctgacagac ctgtcacagc aggtgtttga tgactattcc    1260
gtgattggga ccgccgtcct ggagtacatt acacagcaga tcgctccaaa gaacctggat    1320
aatccctcta agaaagagca ggaactgatc gctaagaaaa ccgagaaggc aaaatatctg    1380
agtctggaaa aattaagct ggcactggag gagttcaaca agcacaggga tattgacaaa    1440
cagtgccgct ttgaggaaat cctggccaac ttcgcagcca tccccatgat ttttgatgag    1500
atcgcccaga caaagacaa tctggctcag atcagtatta agtaccagaa ccagggcaag    1560
aaagacctgc tgcaggcttc agcagaagat gacgtgaaag ccatcaagga tctgctggac    1620
cagaccaaca atctgctgca caagctgaaa atcttccata ttagtcagtc agaggataag    1680
gctaatatcc tggataaaga cgaacacttc tacctggtgt tcgaggaatg ttacttcgag    1740
ctggcaaaca ttgtccccct gtataacaag attaggaact acatcacaca gaagccttac    1800
tctgacgaga gtttaaact gaacttcgaa aatagtaccc tggccaacgg gtgggataag    1860
aacaaggagc tgacaacac agctatcctg ttcatcaagg atgacaagta ctatctggga    1920
gtgatgaata gaaaaacaa taagatcttc gatgacaaag ccattaagga gaacaaaggg    1980
gaaggataca gaaaatcgt gtataagctg ctgcccggcg caaataagat gctgcctaag    2040
gtgttcttca gcgccaagag tatcaaattc tacaacccat ccgaggacat cctgcggatt    2100
agaaatcact caacacatac taagaacggg agcccccaga agggatatga gaaatttgag    2160
ttcaacatcg aggattgcag gaagtttatt gacttctaca gcagagcat ctccaaacac    2220 cctgaatgga aggattttgg cttccggttt tccgacacac agagatataa ctctatcgac    2280
gagttctacc gcgaggtgga aaatcagggg tataagctga cttttgagaa catttctgaa    2340
```

```
agttacatcg acagcgtggt caatcaggga aagctgtacc tgttccagat ctataacaaa    2400
gatttttcag catacagcaa gggcagacca aacctgcata cactgtactg gaaggccctg    2460
ttcgatgaga ggaatctgca ggacgtggtc tataaactga acggagaggc cgaactgttt    2520
taccggaagc agtctattcc taagaaaatc actcacccag ctaaggaggc catcgctaac    2580
aagaacaagg acaatcctaa gaaagagagc gtgttcgaat acgatctgat taaggacaag    2640
cggttcaccg aagataagtt cttttttccat tgtccaatca ccattaactt caagtcaagc    2700
ggcgctaaca agttcaacga cgagatcaat ctgctgctga aggaaaaagc aaacgatgtg    2760
cacatcctga gcattgaccg aggagagcgg catctggcct actataccct ggtggatggc    2820
aaagggaata tcattaagca ggatacattc aacatcattg gcaatgaccg gatgaaaacc    2880
aactaccacg ataaactggc tgcaatcgag aaggatagag actcagctag gaaggactgg    2940
aagaaaatca caacattaa ggagatgaag gaaggctatc tgagccaggt ggtccatgag    3000
attgcaaagc tggtcatcga atacaatgcc attgtggtgt cgaggatct gaacttcggc    3060 tttaagaggg ggcgctttaa ggtggaaaaa caggtctatc agaagctgga gaaaatgctg    3120
atcgaaaagc tgaattacct ggtgtttaaa gataacgagt tcgacaagac cggaggcgtc    3180
ctgagagcct accagctgac agctcccttt gaaactttca gaaaatggg aaaacagaca    3240 ggcatcatct actatgtgcc agccggattc acttccaaga tctgcccgt gaccggcttt    3300 gtcaaccagc tgtaccctaa atatgagtca gtgagcaagt cccaggaatt tttcagcaag    3360
ttcgataaga tctgttataa tctggacaag gggtacttcg agttttcctt cgattacaag    3420
aacttcggcg acaaggccgc taaggggaaa tggaccattg cctccttcgg atctcgcctg    3480
atcaactttc gaaattccga taaaaaccac aattgggaca ctaggaggt gtacccaacc    3540 aaggagctgg aaaagctgct gaaagactac tctatcgagt atggacatgg cgaatgcatc    3600
aaggcagcca tctgtggcga gagtgataag aaatttttcg ccaagctgac ctcagtgctg    3660
aatacaatcc tgcagatgcg gaactcaaag accgggacag aactggacta tctgattagc    3720
cccgtggctg atgtcaacgg aaacttcttc gacagcagac aggcacccaa aaatatgcct    3780
caggatgcag acgccaacgg ggcctaccac atcgggctga agggactgat gctgctgggc    3840
cggatcaaga acaatcagga ggggaagaag ctgaacctgg tcattaagaa cgaggaatac    3900
ttcgagtttg tccagaatag aaataacgga tctggagtga gcaagggcga ggagaataac    3960
atggccatca tcaaggagtt catgcgcttc aaggtgcgca tggagggctc cgtgaacggc    4020
cacgagttcg agatcgaggg cgagggcgag ggccgcccct acgagggctt tcagaccgct    4080
aagctgaagg tgaccaaggg tggcccctg cccttcgcct gggacatcct gtcccctcat    4140
ttcacctacg gctccaaggc ctacgtgaag caccccgccg acatcccga ctacttcaag    4200 ctgtccttcc ccgagggctt caagtgggag cgcgtgatga actacgagga cggcggcgtg    4260
gtgaccgtga cccaggactc ctccctgcag gacggcgagt tcatctacaa ggtgaagctg    4320
cgcggcacca acttcccctc cgacggcccc gtgatgcaga gaagaccat gggctgggag    4380 gcctcctccg agcggatgta ccccgaggac ggtgccctga agggcaagat caagatgagg    4440
ctgaagctga aggacggcgg ccactacacc tccgaggtca agaccaccta caaggccaag    4500
aagcccgtgc agctgcccgg cgcctacatc gtcgacatca gttggacat cacctcccac    4560 aacgaggact acaccatcgt ggaacagtac gaacgcgccg agggccgcca ctccaccggc    4620
ggcatggacg agctgtacaa gggatctaag aagcgtagga tcaagcaaga t           4671
```

<210> SEQ ID NO 61
<211> LENGTH: 4707
<212> TYPE: DNA
<213> ORGANISM: Artificial Sequence
<220> FEATURE:
<223> OTHER INFORMATION: Synthetic polynucleotide.MGSS7H-NLS-FnCpf1-Hs-mOR-NLS

<400> SEQUENCE: 61

| | |
|---|---|
| atgggcagca gccatcatca ccaccatcac catatgggta gcaaaagag gcgtatcaag | 60 |
| caggacagca tctaccagga gttcgtcaac aagtattcac tgagtaagac actgcggttc | 120 |
| gagctgatcc cacagggcaa gacactggag aacatcaagg cccgaggcct gattctggac | 180 |
| gatgagaagc gggcaaaaga ctataagaaa gccaagcaga tcattgataa ataccaccag | 240 |
| ttctttatcg aggaaattct gagctccgtg tgcatcagtg aggatctgct gcagaattac | 300 |
| tcagacgtgt acttcaagct gaagaagagc gacgatgaca acctgcagaa ggacttcaag | 360 |
| tccgccaagg acaccatcaa gaaacagatt agcgagtaca tcaaggactc cgaaaagttt | 420 |
| aaaaatctgt tcaaccagaa tctgatcgat gctaagaaag gccaggagtc cgacctgatc | 480 |
| ctgtggctga acagtctaa ggacaatggg attgaactgt tcaaggctaa ctccgatatc | 540 |
| actgatattg acgaggcact ggaaatcatc aagagcttca agggatggac acatacttt | 600 |
| aaaggcttcc acgagaaccg caagaacgtg tactccagca cgacattcc tacctccatc | 660 |
| atctaccgaa tcgtcgatga caatctgcca aagttcctgg agaacaaggc caaatatgaa | 720 |
| tctctgaagg acaaagctcc cgaggcaatt aattacgaac agatcaagaa agatctggct | 780 |
| gaggaactga cattcgatat cgactataag actagcgagg tgaaccagag ggtcttttcc | 840 |
| ctggacgagg tgtttgaaat cgccaatttc aacaattacc tgaaccagtc cggcattact | 900 |
| aaattcaata ccatcattgg cgggaagttt gtgaacgggg agaataccaa gcgcaaggga | 960 |
| attaacgaat acatcaatct gtatagccag cagatcaacg acaaaactct gaagaaatac | 1020 |
| aagatgtctg tgctgttcaa acagatcctg agtgataccg agtccaagtc ttttgtcatt | 1080 |
| gataaactgg aagatgactc agacgtggtc actaccatgc agagctttta tgagcagatc | 1140 |
| gccgctttca agacagtgga ggaaaaatct attaaggaaa ctctgagtct gctgttcgat | 1200 |
| gacctgaaag cccagaagct ggacctgagt aagatctact tcaaaaacga taagagtctg | 1260 |
| acagacctgt cacagcaggt gtttgatgac tattccgtga ttgggaccgc cgtcctggag | 1320 |
| tacattacac agcagatcgc tccaagaac ctggataatc cctctaagaa agagcaggaa | 1380 |
| ctgatcgcta gaaaaccga gaggcaaaa tatctgagtc tggaacaat taagctggca | 1440 |
| ctggaggagt tcaacaagca cagggatatt gacaaacagt gccgctttga ggaaatcctg | 1500 |
| gccaacttcg cagccatccc catgattttt gatgagatcg cccagaacaa agacaatctg | 1560 |
| gctcagatca gtattaagta ccagaaccag ggcaagaaag acctgctgca ggcttcagca | 1620 |
| gaagatgacg tgaaagccat caaggatctg ctggaccaga ccaacaatct gctgcacaag | 1680 |
| ctgaaaatct tccatattag tcagtcagag gataaggcta atatcctgga taagacgaa | 1740 |
| cacttctacc tggtgttcga ggaatgttac ttcgagctgg caaacattgt ccccctgtat | 1800 |
| aacaagatta gaactacat cacacagaag ccttactctg acgagaagtt aaactgaac | 1860 |
| ttcgaaaata gtaccctggc caacgggtgg ataagaaca aggagcctga acacacagct | 1920 |
| atcctgttca tcaaggatga caagtactat ctgggagtga tgaataagaa aaacaataag | 1980 |
| atcttcgatg acaaagccat taaggagaac aaggggaag atacaagaa aatcgtgtat | 2040 |

```
aagctgctgc ccggcgcaaa taagatgctg cctaaggtgt tcttcagcgc caagagtatc    2100
aaattctaca acccatccga ggacatcctg cggattagaa atcactcaac acatactaag    2160
aacgggagcc cccagaaggg atatgagaaa tttgagttca acatcgagga ttgcaggaag    2220
tttattgact tctacaagca gagcatctcc aaacaccctg aatggaagga ttttggcttc    2280
cggttttccg acacacagag atataactct atcgacgagt tctaccgcga ggtggaaaat    2340
caggggtata agctgacttt tgagaacatt tctgaaagtt acatcgacag cgtggtcaat    2400
cagggaaagc tgtacctgtt ccagatctat aacaaagatt tttcagcata cagcaagggc    2460
agaccaaacc tgcatacact gtactggaag gccctgttcg atgagaggaa tctgcaggac    2520
gtggtctata aactgaacgg agaggccgaa ctgttttacc ggaagcagtc tattcctaag    2580
aaaatcactc acccagctaa ggaggccatc gctaacaaga acaaggacaa tcctaagaaa    2640
gagagcgtgt tcgaatacga tctgattaag gacaagcggt tcaccgaaga taagttcttt    2700
ttccattgtc caatcaccat taacttcaag tcaagcggcg ctaacaagtt caacgacgag    2760
atcaatctgc tgctgaagga aaaagcaaac gatgtgcaca tcctgagcat tgaccgagga    2820
gagcggcatc tggcctacta taccctggtg gatggcaaag ggaatatcat taagcaggat    2880
acattcaaca tcattggcaa tgaccggatg aaaaccaact accacgataa actggctgca    2940
atcgagaagg atagagactc agctaggaag gactggaaga aaatcaacaa cattaaggag    3000
atgaaggaag gctatctgag ccaggtggtc catgagattg caaagctggt catcgaatac    3060
aatgccattg tggtgttcga ggatctgaac ttcggcttta gagggggcg ctttaaggtg    3120 gaaaaacagg tctatcagaa gctggagaaa atgctgatcg aaaagctgaa ttacctggtg    3180
tttaaagata acgagttcga caagaccgga ggcgtcctga gagcctacca gctgacagct    3240 cccctttgaaa ctttcaagaa aatgggaaaa cagacaggca tcatctacta tgtgccagcc    3300
ggattcactt ccaagatctg ccccgtgacc ggctttgtca accagctgta ccctaaatat    3360
gagtcagtga gcaagtccca ggaattttc agcaagttcg ataagatctg ttataatctg    3420 gacaagggt acttcgagtt ttccttcgat tacaagaact tcggcgacaa ggccgctaag    3480
gggaaatgga ccattgcctc cttcggatct cgcctgatca actttcgaaa ttccgataaa    3540
aaccacaatt gggacactag ggaggtgtac ccaaccaagg agctggaaaa gctgctgaaa    3600
gactactcta tcgagtatgg acatggcgaa tgcatcaagg cagccatctg tggcgagagt    3660
gataagaaat ttttcgccaa gctgacctca gtgctgaata caatcctgca gatgcggaac    3720
tcaaagaccg ggacagaact ggactatctg attagccccg tggctgatgt caacggaaac    3780
ttcttcgaca gcagacaggc acccaaaaat atgcctcagg atgcagacgc caacggggcc    3840
taccacatcg ggctgaaggg actgatgctg ctgggccgga tcaagaacaa tcaggagggg    3900
aagaagctga acctggtcat taagaacgag gaatacttcg agtttgtcca gaatagaaat    3960
aacggatctg gagtgagcaa gggcgaggag aataacatgg ccatcatcaa ggagttcatg    4020
cgcttcaagg tgcgcatgga gggctccgtg aacggccacg agttcgagat cgaggcgag    4080 ggcgagggcc gcccctacga gggctttcag accgctaagc tgaaggtgac caagggtggc    4140
cccctgccct cgcctggga catcctgtcc cctcatttca cctacggctc caaggcctac    4200
gtgaagcacc ccgccgacat ccccgactac ttcaagctgt ccttccccga gggcttcaag    4260
tgggagcgcg tgatgaacta cgaggacggc ggcgtggtga ccgtgaccca ggactcctcc    4320
ctgcaggacg gcgagttcat ctacaaggtg aagctgcgcg gcaccaactt ccctccgac    4380 ggccccgtga tgcagaagaa gaccatgggc tgggaggcct cctccgagcg gatgtacccc    4440
```

-continued

```
gaggacggtg ccctgaaggg caagatcaag atgaggctga agctgaagga cggcggccac    4500
tacacctccg aggtcaagac cacctacaag gccaagaagc ccgtgcagct gcccggcgcc    4560
tacatcgtcg acatcaagtt ggacatcacc tcccacaacg aggactacac catcgtggaa    4620
cagtacgaac gcgccgaggg ccgccactcc accggcggca tggacgagct gtacaaggga    4680
tctaagaagc gtaggatcaa gcaagat                                         4707

<210> SEQ ID NO 62
<211> LENGTH: 6462
<212> TYPE: DNA
<213> ORGANISM: Artificial Sequence
<220> FEATURE:
<223> OTHER INFORMATION: Synthetic polynucleotide.Expression cassette
      comprising 35S promoter cassette, MGSS7H-NLS-FnCpf1-Hs-mOr-NLS and
      NOS transcription termination sequence

<400> SEQUENCE: 62
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg aaaaagaag acgttccaac cacgtcttca     240
aagcaagtgg attgatgtga tggtccgatt gagacttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaaagaa     480
gacgttccaa ccacgtcttc aaagcaagtg gattgatgtg atatctccac tgacgtaagg     540
gatgacgcac aatcccacta ccttcgcaa gaccccttcct ctatataagg aagttcattt     600
catttggaga ggacacgctg acaagctgac tctagcagat ctaccgtctt cggtacgcgc     660
tcactccgcc ctctgccttt gttactgcca cgtttctctg aatgctctct tgtgtggtga     720
ttgctgagag tggtttagct ggatctagaa ttacactctg aaatcgtgtt ctgcctgtgc     780
tgattacttg ccgtcctttg tagcagcaaa atataggac atggtagtac gaaacgaaga     840
tagaacctac acagcaatac gagaaatgtg taatttggtg cttagcggta tttatttaag     900
cacatgttgg tgttataggg cacttggatt cagaagtttg ctgttaattt aggcacaggc     960
ttcatactac atgggtcaat agtataggga ttcatattat aggcgatact ataataattt    1020
gttcgtctgc agagcttatt atttgccaaa attagatatt cctattctgt ttttgtttgt    1080
gtgctgttaa attgttaacg cctgaaggaa taaatataaa tgacgaaatt ttgatgttta    1140
tctctgctcc tttattgtga ccataagtca agatcagatg cacttgtttt aaatattgtt    1200
gtctgaagaa ataagtactg acagtatttt gatgcattga tctgcttgtt tgttgtaaca    1260
aaatttaaaa ataaagagtt tcctttttgt tgctctcctt acctcctgat ggtatctagt    1320
atctaccaac tgacactata ttgcttctct ttacatacgt atcttgctcg atgccttctc    1380
cctagtgttg accagtgtta ctcacatagt ctttgctcat ttcattgtaa tgcagatacc    1440
aagcggcctc tagaggatcc aggagcaacc atgggcagca gccatcatca ccaccatcac    1500
catatgggta gcaaaagag gcgtatcaag caggacagca tctaccagga gttcgtcaac    1560
aagtattcac tgagtaagac actgcggttc gagctgatcc cacagggcaa gacactggag    1620
aacatcaagg cccgaggcct gattctggac gatgagaagc gggcaaaaga ctataagaaa    1680
```

```
gccaagcaga tcattgataa ataccaccag ttctttatcg aggaaattct gagctccgtg   1740
tgcatcagtg aggatctgct gcagaattac tcagacgtgt acttcaagct gaagaagagc   1800
gacgatgaca acctgcagaa ggacttcaag tccgccaagg acaccatcaa gaaacagatt   1860
agcgagtaca tcaaggactc cgaaaagttt aaaaatctgt tcaaccagaa tctgatcgat   1920
gctaagaaag gccaggagtc cgacctgatc ctgtggctga acagtctaa ggacaatggg   1980 attgaactgt tcaaggctaa ctccgatatc actgatattg acgaggcact ggaaatcatc   2040
aagagcttca agggatggac cacatacttt aaaggcttcc acgagaaccg caagaacgtg   2100
tactccagca acgacattcc tacctccatc atctaccgaa tcgtcgatga caatctgcca   2160
aagttcctgg agaacaaggc caaatatgaa tctctgaagg acaaagctcc cgaggcaatt   2220
aattacgaac agatcaagaa agatctggct gaggaactga cattcgatat cgactataag   2280
actagcgagg tgaaccagag ggtctttttcc ctggacgagg tgtttgaaat cgccaatttc   2340
aacaattacc tgaaccagtc cggcattact aaattcaata ccatcattgg cgggaagttt   2400
gtgaacgggg agaataccaa gcgcaaggga attaacgaat acatcaatct gtatagccag   2460
cagatcaacg acaaaactct gaagaaatac aagatgtctg tgctgttcaa acagatcctg   2520
agtgataccg agtccaagtc ttttgtcatt gataaactgg aagatgactc agacgtggtc   2580
actaccatgc agagctttta tgagcagatc gccgctttca agacagtgga ggaaaaatct   2640
attaaggaaa ctctgagtct gctgttcgat gacctgaaag cccagaagct ggacctgagt   2700
aagatctact tcaaaaacga taagagtctg acagacctgt cacagcaggt gtttgatgac   2760
tattccgtga ttgggaccgc cgtcctggag tacattacac agcagatcgc tccaaagaac   2820
ctggataatc cctctaagaa agagcaggaa ctgatcgcta gaaaaccga aaggcaaaa   2880 tatctgagtc tggaaacaat taagctggca ctggaggagt tcaacaagca cagggatatt   2940
gacaaacagt gccgctttga ggaaatcctg gccaacttcg cagccatccc catgattttt   3000
gatgagatcg cccagaacaa agacaatctg gctcagatca gtattaagta ccagaaccag   3060
ggcaagaaag acctgctgca ggcttcagca gaagatgacg tgaaagccat caaggatctg   3120
ctggaccaga ccaacaatct gctgcacaag ctgaaaatct ccatattag tcagtcagag   3180 gataaggcta atatcctgga taaagacgaa cacttctacc tggtgttcga ggaatgttac   3240
ttcgagctgg caaacattgt cccccctgtat aacaagatta ggaactacat cacacagaag   3300
ccttactctg acgagaagtt taaactgaac ttcgaaaata gtaccctggc caacgggtgg   3360
gataagaaca aggagcctga caacacagct atcctgttca tcaaggatga caagtactat   3420
ctgggagtga tgaataagaa aaacaataag atcttcgatg acaaagccat taggagaaac   3480 aaagggaag gatacaagaa aatcgtgtat aagctgctgc ccggcgcaaa taagatgctg   3540
cctaaggtgt tcttcagcgc caagagtatc aaattctaca acccatccga ggacatcctg   3600
cggattagaa atcactcaac acatactaag aacgggagcc cccagaaggg atatgagaaa   3660
tttgagttca acatcgagga ttgcaggaag tttattgact tctacaagca gagcatctcc   3720
aaacaccctg aatggaagga ttttggcttc cggttttccg acacacagag atataactct   3780
atcgacgagt tctaccgcga ggtggaaaat cagggtata agctgacttt tgagaacatt   3840
tctgaaagtt acatcgacag cgtggtcaat cagggaaagc tgtacctgtt ccagatctat   3900
aacaaagatt tttcagcata cagcaagggc agaccaaacc tgcatacact gtactggaag   3960
gccctgttcg atgagaggaa tctgcaggac gtggtctata aactgaacgg agaggccgaa   4020
ctgttttacc ggaagcagtc tattcctaag aaaatcactc acccagctaa ggaggccatc   4080
```

```
gctaacaaga acaaggacaa tcctaagaaa gagagcgtgt tcgaatacga tctgattaag    4140
gacaagcggt tcaccgaaga taagttcttt ttccattgtc caatcaccat taacttcaag    4200
tcaagcggcg ctaacaagtt caacgacgag atcaatctgc tgctgaagga aaaagcaaac    4260
gatgtgcaca tcctgagcat tgaccgagga gagcggcatc tggcctacta taccctggtg    4320
gatggcaaag ggaatatcat taagcaggat acattcaaca tcattggcaa tgaccggatg    4380
aaaaccaact accacgataa actggctgca atcgagaagg atagagactc agctaggaag    4440
gactggaaga aaatcaacaa cattaaggag atgaaggaag gctatctgag ccaggtggtc    4500
catgagattg caaagctggt catcgaatac aatgccattg tggtgttcga ggatctgaac    4560
ttcggcttta gagggggcg ctttaaggtg gaaaaacagg tctatcagaa gctggagaaa    4620
atgctgatcg aaaagctgaa ttacctggtg tttaaagata cgagttcga caagaccgga    4680 ggcgtcctga gagcctacca gctgacagct cccttttgaaa cttttcaagaa aatgggaaaa    4740 cagacaggca tcatctacta tgtgccagcc ggattcactt ccaagatctg ccccgtgacc    4800
ggctttgtca accagctgta ccctaaatat gagtcagtga gcaagtccca ggaattttttc    4860 agcaagttcg ataagatctg ttataatctg gacaaggggt acttcgagtt ttccttcgat    4920
tacaagaact tcggcgacaa ggccgctaag gggaaatgga ccattgcctc cttcggatct    4980
cgcctgatca actttcgaaa ttccgataaa aaccacaatt gggacactag ggaggtgtac    5040
ccaaccaagg agctggaaaa gctgctgaaa gactactcta tcgagtatgg acatggcgaa    5100
tgcatcaagg cagccatctg tggcgagagt gataagaaat ttttcgccaa gctgacctca    5160
gtgctgaata caatcctgca gatgcggaac tcaaagaccg ggacagaact ggactatctg    5220 attagcccg tggctgatgt caacggaaac ttcttcgaca gcagacaggc acccaaaaat    5280
atgcctcagg atgcagacgc caacgggggcc taccacatcg ggctgaaggg actgatgctg    5340
ctgggccgga tcaagaacaa tcaggagggg aagaagctga acctggtcat taagaacgag    5400
gaatacttcg agtttgtcca gaatagaaat aacggatctg gagtgagcaa gggcgaggag    5460
aataacatgg ccatcatcaa ggagttcatg cgcttcaagg tgcgcatgga gggctccgtg    5520
aacggccacg agttcgagat cgagggcgag ggcgagggcc gcccctacga gggctttcag    5580
accgctaagc tgaaggtgac caagggtggc cccctgccct tcgcctggga catcctgtcc    5640
cctcatttca cctacggctc caaggcctac gtgaagcacc ccgccgacat ccccgactac    5700
ttcaagctgt ccttccccga gggcttcaag tgggagcgcg tgatgaacta cgaggacggc    5760
ggcgtggtga ccgtgaccca ggactcctcc ctgcaggacg gcgagttcat ctacaaggtg    5820
aagctgcgcg gcaccaactt ccccctccgac ggccccgtga tgcagaagaa gaccatgggc    5880
tgggaggcct cctccgagcg gatgtacccc gaggacggtg ccctgaaggg caagatcaag    5940
atgaggctga gctgaagga cggcggccac tacacctccg aggtcaagac cacctacaag    6000
gccaagaagc ccgtgcagct gcccggcgcc tacatcgtcg acatcaagtt ggacatcacc    6060
tcccacaacg aggactacac catcgtggaa cagtacgaac gcgccgaggg ccgccactcc    6120
accggcggca tggacgagct gtacaaggga tctaagaagc gtaggatcaa gcaagattag    6180
aacccagcgg tactcgctga ggaattcgcg atcgttcaaa catttggcaa taaagtttct    6240
taagattgaa tcctgttgcc ggtcttgcga tgattatcat ataatttctg ttgaattacg    6300
ttaagcatgt aataattaac atgtaatgca tgacgttatt tatgagatgg ttttttatga    6360
ttagagtccc gcaattatac atttaatacg cgatagaaaa caaaatatag cgcgcaaact    6420
```

-continued aggataaatt atcgcgcgcg gtgtcatcta tgttactaga tc    6462

<210> SEQ ID NO 63
<211> LENGTH: 3960
<212> TYPE: DNA
<213> ORGANISM: Artificial Sequence
<220> FEATURE:
<223> OTHER INFORMATION: Synthetic polynucleotide.NLS-FnCpf1-CO3-NLS

<400> SEQUENCE: 63

| | |
|---|---|
| ggtagcaaaa agaggcgtat caagcaggac atgagcatct accaggagtt cgtgaacaag | 60 |
| tacagcctgt cgaagaccct ccggttcgag ctgatccctc aggggaagac gctggagaac | 120 |
| atcaaggcgc gcggcctcat cctcgacgac gagaagcggg cgaaggacta caaaaaggca | 180 |
| aagcagatca tcgacaagta ccaccaattc tttattgagg agatcctcag ctccgtctgc | 240 |
| atcagcgagg acttgctcca gaactactcc gacgtctatt tcaagctcaa gaagtcagac | 300 |
| gacgacaacc tccagaagga cttcaagtcc gcgaaggaca cgatcaaaaa gcagatcagc | 360 |
| gagtacatca aggactccga gaagttcaag aacctcttca accagaacct gatcgacgcc | 420 |
| aagaagggcc gggaatcgga cctcatcctg tggctcaagc agtcgaagga caacggcatc | 480 |
| gagctgttca aggccaactc cgacatcacc gacatcgacg aggcgctgga gatcatcaag | 540 |
| tcgttcaagg ggtggaccac ctacttcaag ggcttccacg agaaccgcaa gaacgtttac | 600 |
| tccagcaacg acatccccac ctcgatcatc taccggatcg tggacgacaa cctgcccaag | 660 |
| ttcctggaga caaggccaa gtacgagtcc ctcaaggaca aggccccgga ggcgatcaac | 720 |
| tacgagcaga ttaaaaagga ccttgctgag gagctgacct cgacatcga ctacaagacc | 780 |
| tccgaggtga accagcgggt gttcagcctc gacgaggtgt tcgagatcgc caacttcaac | 840 |
| aactacctga accagtccgg gatcaccaag ttcaacacga tcatcggcgg aagttcgtc | 900 |
| aacggcgaga cacgaagcg gaagggcatc aacgagtaca tcaacctcta cagccagcag | 960 |
| atcaacgaca gaccctcaa aaatacaaa atgtcggtcc tgttcaagca gatcctgtcc | 1020 |
| gacaccgagt ccaagagctt cgtcatcgac aagctggagg acgactccga cgtcgtgacc | 1080 |
| accatgcagt cctttctacga gcagatcgcc gccttcaaga ccgtggagga gaagtccatc | 1140 |
| aaggagaccc tcagcctcct cttcgacgac ctcaaggcgc agaagctgga cctctccaag | 1200 |
| atatacttca gaacgacaa gagcctcacc gacctgtccc agcaagtatt cgacgactac | 1260 |
| agcgtgatcg ggacggcggt gctggagtac atcacccagc agatagcgcc caagaacctg | 1320 |
| gacaacccct ccaagaaaga acaggagctg attgctaaaa agaccgaaaa ggctaagtac | 1380 |
| ctgtccctgg agaccatcaa gctcgcgctg gaggagttca acaagcaccg ggacatcgac | 1440 |
| aagcagtgcc ggttcgagga gatcctagca aacttcgccg cgatccccat gatcttcgac | 1500 |
| gagatcgccc agaacaagga caacctggcc cagatcagca tcaagtacca gaaccagggc | 1560 |
| aagaaggacc ttcttcaagc tagtgccgag gacgacgtga aggcgattaa ggatctgctc | 1620 |
| gaccagacca acaacctgct ccacaagctc aagatattcc acatctccca gtccgaggac | 1680 |
| aaggccaaca tcctggacaa ggacgagcac ttctacctgg tgttcgagga gtgctacttc | 1740 |
| gagctggcca acatcgtgcc gctgtacaac aagatccgga ctacatcac ccagaagccc | 1800 |
| tactccgacg agaagttcaa gctgaacttc gagaactcca ccctggcgaa cgggtgggac | 1860 |
| aagaacaagg agcccgacaa cacggccatc ctcttcatca aggacgacaa atattatctg | 1920 |
| ggcgtcatga caaaaagaa caacaagata ttcgatgaca aggcgatcaa ggagaacaag | 1980 |
| ggcgagggct acaagaaaat agtatataaa ctactgcccg cgcgaacaa gatgctcccg | 2040 |

-continued

| | |
|---|---|
| aaggtgtttt ttagtgcaaa gtctattaag ttctacaacc ccagcgagga catcctccgc | 2100 |
| atccggaacc acagcacgca caccaagaac ggcagcccac agaagggcta cgagaagttc | 2160 |
| gagttcaaca tcgaggactg ccgcaagttc atcgacttct acaagcagtc catctccaag | 2220 |
| cacccccagt ggaaggactt cgggttccgg ttcagcgaca cccagcgcta acagcatc | 2280 |
| gacgagttct accgggaggt cgagaaccag gggtacaagc tgacgttcga aacatctcc | 2340 |
| gagagctaca tcgacagcgt ggtgaaccag gggaagctgt acctgtttca gatatacaac | 2400 |
| aaggacttct cagcctacag caaggggcgg ccgaacctgc acaccctgta ctggaaggcc | 2460 |
| ctgttcgacg agcggaacct ccaggacgtc gtgtacaagc tcaacggcga ggcggagctg | 2520 |
| ttctaccgga agcagtccat ccccaaaaag attactcacc ccgcgaagga ggccatcgcc | 2580 |
| aacaagaaca aggacaaccc caaaaaggaa tcagtgttcg agtacgacct catcaaggac | 2640 |
| aagcgcttca ccgaggacaa attcttcttt cactgcccga tcacgatcaa cttcaagtcc | 2700 |
| tccggggcga acaagttcaa cgacgagatc aacctgctgc tcaaggagaa ggccaacgac | 2760 |
| gtgcacatcc tcagcatcga ccggggcgag cgccacctgg cctactacac cctggtggac | 2820 |
| gggaagggca acatcataaa gcaagatacc ttcaacatca tcgggaacga ccggatgaag | 2880 |
| acgaactacc acgacaagct ggcggccatc gagaaggacc gggacagcgc ccgcaaggac | 2940 |
| tggaaaaaga taaacaacat taaggagatg aaggagggct acctgtccca ggtggtccac | 3000 |
| gagatcgcca agctcgtcat cgagtacaac gccatcgtcg tgttcgagga cttgaacttc | 3060 |
| gggttcaagc ggggccggtt caaggtggag aaacaagtct atcaaaagct ggagaagatg | 3120 |
| ctcatcgaga agctcaacta cctcgtgttc aaggacaacg agttcgacaa gaccggcggc | 3180 |
| gtcctgcggg cctaccagct caccgcgccg ttcgagacgt tcaagaagat ggggaagcag | 3240 |
| acggggatca tctactacgt ccccgccggg ttcaccagca gatatgccc ggtcacgggg | 3300 |
| ttcgtcaacc agctctaccc caagtacgag tcggtgagca agagccagga gttcttcagc | 3360 |
| aagttcgaca agatctgcta caacctggac aagggctact cgagttctc gttcgactac | 3420 |
| aagaacttcg gggacaaggc ggcgaagggc aagtggacca tcgccagctt cggctcccgc | 3480 |
| ctcatcaact tccggaactc ggacaagaac cacaactggg acacccgcga ggtgtacccc | 3540 |
| acgaaggagc tggagaagct gctcaaggac tacagcatcg agtacgggca cggcgagtgc | 3600 |
| atcaaggccg ccatctgcgg ggagtccgac aagaaattct tgccaagct gacctccgtg | 3660 |
| ctgaacacca tcctccagat gcggaacagc aagaccggga ccgagctgga ctacctgatc | 3720 |
| tccccggtcg ccgacgtcaa cggcaacttc ttcgattctc gccaggctcc caagaacatg | 3780 |
| ccccaggacg ccgacgccaa cggggcctac cacatcgggc tcaagggcct catgctgctc | 3840 |
| gggcggatca gaacaaccag gagggcaag aaactcaacc tggtcatcaa gaacgaggag | 3900 |
| tactttgagt tcgtccagaa ccggaacaac ggatctaaga agcgtaggat caagcaagat | 3960 |

<210> SEQ ID NO 64
<211> LENGTH: 530
<212> TYPE: DNA
<213> ORGANISM: Oryza sativa

<400> SEQUENCE: 64

| | |
|---|---|
| atccaagtaa attaagttgg atcagtagag atgcatggtt ggtgttctca tgtggtctga | 60 |
| atctgtgttc tgtttcatct tttgtgtaag tgtgcaactt cgattctgta aaacttggca | 120 |
| agtagatgaa cgatgtcatt tatatgcgtg tagcttgtca aaatacaaag tagaaacctg | 180 |

```
tatctgaata agatggcatt catgaaataa tattatcgat tgaacgaacg aagcaacaga    240
atgatcttcc aaattgaagc aaaggaattg atggacaacg agttgctgta ctttggagct    300
gtaaatctgt agtacttctc aacgatgcta tggaccgtgg gccgtccata atcgctgggt    360
ggaatgagcc cactgtccat gtgcttctgc atttggcccg tgtacagccc atataatgtc    420
gaaaaaccta atacgcgcgc gccgccggcg cgcgtttcgg acccagaacg cctagcgccg    480
ctgcgccgac gtgcgcgcgt ctccactttt tttttcgttt tctttccatt              530
```

<210> SEQ ID NO 65
<211> LENGTH: 6530
<212> TYPE: DNA
<213> ORGANISM: Artificial Sequence
<220> FEATURE:
<223> OTHER INFORMATION: Synthetic polynucleotide.Expression cassette
     comprising Zea mays Ubiquitin promoter cassette, NLS-FnCpf1-CO3-
     NLS and an Oryza sativa transcription termination sequence

<400> SEQUENCE: 65

```
gtcgtgcccc tctctagaga taaagagcat tgcatgtcta aagtataaaa aattaccaca     60 tattttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240 ttatctttt agtgtgcatg tgatctctct gttttttttg caaatagctt gacctatata    300
atacttcatc cattttatta gtacatccat ttaggattta gggttgatgg tttctataga    360 ctaatttta gtacatccat tttattcttt ttagtctcta aattttttaa aactaaaact    420 ctatttagt tttttattta ataattaga tataaaatga aataaaataa attgactaca    480
aataaaacaa atacccttta agaaataaaa aaactaagca aacattttc ttgtttcgag    540 tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg cttttccctc ctcgcccgcc    840
gtaataaata gacacccct ccacaccctc tttcccccaac ctcgtgttcg ttcggagcgc    900
acacacacgc aaccagatct ccccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt taagatgatg gatggaaata tcgatctagg ataggtatac atgttgatgc   1260
gggttttact gatgcatata cagagatgct tttttctcg cttggttgtg atgatatggt    1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc ttttttcgc ttggttgtga tgatgtggtc tggttgggcg gtcgttctag   1620
atcggagtag aatactgttt caaactacct ggtggattta ttaattttgt atctttatgt   1680
```

-continued

```
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttt     1920
agccctgcct tcatacgcta tttatttgct tggtactgtt tcttttgtcc gatgctcacc    1980
ctgttgttgg gtgatacttc tgcagcggac cgacggtacc atgggtagca aaaagaggcg    2040
tatcaagcag gacatgagca tctaccagga gttcgtgaac aagtacagcc tgtcgaagac    2100
cctccggttc gagctgatcc ctcagggaa  gacgctggag aacatcaagg cgcgcggcct    2160
catcctcgac gacgagaagc gggcgaagga ctacaaaaag gcaaagcaga tcatcgacaa    2220
gtaccaccaa ttctttattg aggagatcct cagctccgtc tgcatcagcg aggacttgct    2280
ccagaactac tccgacgtct atttcaagct caagaagtca gacgacgaca acctccagaa    2340
ggacttcaag tccgcgaagg acacgatcaa aaagcagatc agcgagtaca tcaaggactc    2400
cgagaagttc aagaacctct tcaaccagaa cctgatcgac gccaagaagg gccgggaatc    2460
ggacctcatc ctgtggctca agcagtcgaa ggacaacggc atcgagctgt tcaaggccaa    2520
ctccgacatc accgacatcg acgaggcgct ggagatcatc aagtcgttca aggggtggac    2580
cacctacttc aagggcttcc acgagaaccg caagaacgtt tactccagca acgacatccc    2640
cacctcgatc atctaccgga tcgtggacga caacctgccc aagttcctgg agaacaaggc    2700
caagtacgag tccctcaagg acaaggcccc ggaggcgatc aactacgagc agattaaaaa    2760
ggaccttgct gaggagctga ccttcgacat cgactacaag acctccgagg tgaaccagcg    2820
ggtgttcagc ctcgacgagg tgttcgagat cgccaacttc aacaactacc tgaaccagtc    2880
cgggatcacc aagttcaaca cgatcatcgg cgggaagttc gtcaacggcg agaacacgaa    2940
gcggaagggc atcaacgagt acatcaacct ctacagccag cagatcaacg acaagaccct    3000
caaaaaatac aaaatgtcgg tcctgttcaa gcagatcctg tccgacaccg agtccaagag    3060
cttcgtcatc gacaagctgg aggacgactc cgacgtcgtg accaccatgc agtccttcta    3120
cgagcagatc gccgccttca gaccgtgga  ggagaagtcc atcaaggaga ccctcagcct    3180
cctcttcgac gacctcaagg cgcagaagct ggacctctcc aagatatact tcaagaacga    3240
caagagcctc accgacctgt cccagcaagt attcgacgac tacagcgtga tcgggacggc    3300
ggtgctggag tacatcaccc agcagatagc gcccaagaac ctggacaacc cctccaagaa    3360
agaacaggag ctgattgcta aaaagaccga aaaggctaag tacctgtccc tggagaccat    3420
caagctcgcg ctggaggagt tcaacaagca ccgggacatc gacaagcagt gccggttcga    3480
ggagatccta gcaaacttcg ccgcgatccc catgatcttc gacgagatcg cccagaacaa    3540
ggacaacctg cccagatca  gcatcaagta ccagaaccag ggcaagaagg accttcttca    3600
agctagtgcc gaggacgacg tgaaggcgat taaggatctg ctcgaccaga ccaacaacct    3660
gctccacaag ctcaagatat ccacatctc  ccagtccgag gacaaggcca catcctggga    3720
caaggacgag cacttctacc tggtgttcga ggagtgctac ttcgagctgg ccaacatcgt    3780
gccgctgtac aacaagatcc ggaactacat cacccagaag ccctactccg acgagaagtt    3840
caagctgaac ttcgagaact ccaccctggc gaacgggtgg gacaagaaca aggagcccga    3900
caacacggcc atcctcttca tcaaggacga caaatattat ctgggcgtca tgaacaaaaa    3960
gaacaacaag atattcgatg acaaggcgat caaggagaac aagggcgagg gctacaagaa    4020
```

| | |
|---|---|
| aatagtatat aaactactgc ccggcgcgaa caagatgctc ccgaaggtgt tttttagtgc | 4080 |
| aaagtctatt aagttctaca accccagcga ggacatcctc cgcatccgga accacagcac | 4140 |
| gcacaccaag aacggcagcc cacagaaggg ctacgagaag ttcgagttca acatcgagga | 4200 |
| ctgccgcaag ttcatcgact tctacaagca gtccatctcc aagcaccccg agtggaagga | 4260 |
| cttcggggttc cggttcagcg acacccagcg ctacaacagc atcgacgagt tctaccggga | 4320 |
| ggtcgagaac caggggtaca agctgacgtt cgagaacatc tccgagagct acatcgacag | 4380 |
| cgtggtgaac caggggaagc tgtacctgtt tcagatatac aacaaggact tctcagccta | 4440 |
| cagcaagggg cggccgaacc tgcacaccct gtactggaag gccctgttcg acgagcggaa | 4500 |
| cctccaggac gtcgtgtaca agctcaacgg cgaggcggag ctgttctacc ggaagcagtc | 4560 |
| catccccaaa aagattactc accccgcgaa ggaggccatc gccaacaaga caaggacaa | 4620 |
| ccccaaaaag gaatcagtgt cgagtacga cctcatcaag gacaagcgct tcaccgagga | 4680 |
| caaattcttc tttcactgcc cgatcacgat caacttcaag tcctccgggg cgaacaagtt | 4740 |
| caacgacgag atcaacctgc tgctcaagga gaaggccaac gacgtgcaca tcctcagcat | 4800 |
| cgaccggggc gagcgccacc tggcctacta caccctggtg gacgggaagg gcaacatcat | 4860 |
| aaagcaagat accttcaaca tcatcgggaa cgaccggatg aagacgaact accacgacaa | 4920 |
| gctggcggcc atcgagaagg accgggacag cgcccgcaag gactggaaaa agataaacaa | 4980 |
| cattaaggag atgaaggagg gctacctgtc ccaggtggtc cacgagatcg ccaagctcgt | 5040 |
| catcgagtac aacgccatcg tcgtgttcga ggacttgaac ttcgggttca agcggggccg | 5100 |
| gttcaaggtg gagaaacaag tctatcaaaa gctggagaaa atgctcatcg agaagctcaa | 5160 |
| ctacctcgtg ttcaaggaca acgagttcga caagaccggc ggcgtcctgc gggcctacca | 5220 |
| gctcaccgcg ccgttcgaga cgttcaagaa gatggggaag cagacgggga tcatctacta | 5280 |
| cgtccccgcc gggttcacca gcaagatatg cccggtcacg gggttcgtca accagctcta | 5340 |
| ccccaagtac gagtcggtga gcaagagcca ggagttcttc agcaagttcg acaagatctg | 5400 |
| ctacaacctg gacaagggct acttcgagtt ctcgttcgac tacaagaact cggggacaa | 5460 |
| ggcggcgaag ggcaagtgga ccatcgccag cttcggctcc cgcctcatca acttccggaa | 5520 |
| ctcggacaag aaccacaact gggacacccg cgaggtgtac cccacgaagg agctggagaa | 5580 |
| gctgctcaag gactacagca tcgagtacgg gcacggcgag tgcatcaagg ccgccatctg | 5640 |
| cggggagtcc gacaagaaat tctttgccaa gctgaccctcc gtgctgaaca ccatcctcca | 5700 |
| gatgcggaac agcaagaccg ggaccgagct ggactacctg atctccccgg tcgccgacgt | 5760 |
| caacggcaac ttcttcgatt ctcgccaggc tcccaagaac atgccccagg acgccgacgc | 5820 |
| caacggggcc taccacatcg ggctcaaggg cctcatgctg ctcgggcgga tcaagaacaa | 5880 |
| ccaggagggc aagaaactca acctggtcat caagaacgag gagtactttg agttcgtcca | 5940 |
| gaaccggaac aacggatcta agaagcgtag gatcaagcaa gattgattaa ttaagggccc | 6000 |
| atccaagtaa attaagttgg atcagtagag atgcatggtt ggtgttctca tgtggtctga | 6060 |
| atctgtgttc tgtttcatct tttgtgtaag tgtgcaactt cgattctgta aaacttggca | 6120 |
| agtagatgaa cgatgtcatt tatatgcgtg tagcttgtca aaatacaaag tagaaacctg | 6180 |
| tatctgaata agatggcatt catgaaataa tattatcgat tgaacgaacg aagcaacaga | 6240 |
| atgatcttcc aaattgaagc aaaggaattg atggacaacg agttgctgta ctttggagct | 6300 |
| gtaaatctgt agtacttctc aacgatgcta tggaccgtgg gccgtccata atcgctgggt | 6360 |
| ggaatgagcc cactgtccat gtgcttctgc atttggcccg tgtacagccc atataatgtc | 6420 |

```
gaaaaaccta atacgcgcgc gccgccggcg cgcgtttcgg acccagaacg cctagcgccg    6480
ctgcgccgac gtgcgcgcgt ctccactttt tttttcgttt tctttccatt              6530
```

<210> SEQ ID NO 66
<211> LENGTH: 3960
<212> TYPE: DNA
<213> ORGANISM: Artificial Sequence
<220> FEATURE:
<223> OTHER INFORMATION: Synthetic polynucleotide.NLS-FnCpf1-CO4-NLS

<400> SEQUENCE: 66

```
ggtagcaaaa agaggcgtat caagcaggac atgagcatct accaggagtt cgtgaacaag      60
tacagcctga gcaagaccct gcgcttcgag ctgattcctc aggggaagac cctggagaac     120
atcaaggcgc gcgccctgat cctggacgac gagaagcggg cgaaggacta caaaaaggcg     180
aagcagatca tcgacaagta ccatcagttt ttcatcgagg agattctcag ctccgtgtgc     240
atcagcgaag acctgctcca gaactacagc gacgtttact tcaagctcaa gaaatcggac     300
gacgacaacc tccagaagga cttcaagagc gcgaaggaca cgattaagaa acagatcagc     360
gagtacatca aggactccga gaagttcaag aacctgttca accagaacct catcgacgcc     420
aagaaaggcc aagagtcgga cctcatcctc tggctcaagc agagcaagga caacggcatc     480
gagctgttca aggcgaacag cgacatcacc gacatcgacg aggcgctgga gatcatcaag     540
tcgttcaagg gctggacgac ctacttcaag ggcttccacg agaaccgcaa gaatgtctac     600
tcgagcaacg acatccccac gtcgatcatc taccgcatcg tggacgacaa cctccccgaag    660 ttcctggaga acaaggcgaa gtacgagagc ctcaaggaca aggccccgga ggccatcaac     720
tacgagcaga tcaaaaagga tttggctgag gagctgacgt tcgacatcga ctacaagacc     780
tccgaggtga accagcgcgt cttcagcctc gacgaggtgt tcgagatcgc caacttcaac     840
aactacctca accagtcggg catcaccaag ttcaacacca tcatcggcgg aagttcgtc     900 aacggcgaga cacgaagcg caaggggatc aacgagtaca tcaacctgta cagccagcag    960
atcaacgaca agaccctcaa gaagtataaa atgtcggtgc tgttcaagca gatcctctcg    1020
gacaccgaga gcaagtcgtt cgtcatcgac aagctggagg acgacagcga cgtggtgacc    1080
accatgcaga gcttctacga gcagatcgcg gccttcaaga ccgtcgagga aagtcgatc    1140 aaggagacgc tcagcctgct gttcgacgac ctcaaggccc agaagctcga cctgtccaag    1200
atatacttta agaacgacaa gagcctcacg gacctgtccc agcaggtatt cgacgactac    1260
agcgtgatcg gacggccgt gctggagtac atcaccaac agatcgcgcc caagaacctg    1320 gacaaccgt ccaagaagga caagagcta atcgccaaaa agactgagaa ggcgaagtac    1380
ctgtcgctgg agacgatcaa gctcgcgctt gaggagttta caagcaccg cgacatcgac    1440 aagcagtgcc ggttcgagga gatcctggcc aacttcgcgg cgatcccgat gatcttcgac    1500
gagatcgccc agaacaagga caacctgcg cagatcagca tcaagtacca gaaccagggc    1560
aaaaaagact gctccaagc tagtgcggag gacgacgtga aggcgattaa ggatctgctg    1620
gaccagacta caatctgct gcacaagctc aagatcttc acatctctca gtcggaggac    1680
aaggcgaaca tcctggacaa ggacgagcac ttctacctag tgttcgagga gtgctacttc    1740
gagctggcga acatcgtgcc cctgtacaac aagatccgga actacatcac ccagaagccc    1800
tacagcgacg agaagttcaa gctgaacttc gagaacagca cgctggcgaa cgggtgggac    1860
aagaacaagg agcccgacaa caccgccatc ctgttcatca aggacgacaa atattacctc    1920
```

```
ggcgtcatga acaaaaagaa taacaagata ttcgatgaca aggcgatcaa ggagaacaag    1980
ggcgagggct acaagaagat cgtatataaa ctcctgccgg gagcgaacaa gatgctcccg    2040
aaggttttct ttagtgccaa gtccatcaag ttctacaacc ccagcgagga catcctccgc    2100
atccggaacc actccaccca caccaagaac ggctcgccgc agaagggcta cgagaagttc    2160
gagttcaaca tcgaggactg ccgcaagttc atcgacttct acaagcagtc catctccaag    2220
cacccggagt ggaaggactt cgggttccgg ttctccgaca cgcagcgcta caactccatc    2280
gacgagttct accgggaggt ggagaaccag ggctacaagc tgacgttcga gaacatctcg    2340
gagtcctaca tcgactccgt ggtcaaccag ggcaagctgt acctcttcca gatatacaat    2400
aaggacttct ccgcctacag caaggggcgg cccaacctcc acccctgta ctggaaggcg     2460 ctcttcgacg agcggaacct ccaggacgtc gtgtacaagc tgaacggcga ggcggagctg    2520
ttctaccgca agcagagcat ccccaagaag atcacgcacc ccgcgaagga ggccatcgcc    2580
aacaagaaca aggacaaccc caagaaggaa tcggtcttcg agtacgacct catcaaggac    2640
aagcggttca cggaggacaa attctttttc cactgcccga tcactattaa cttcaagtcc    2700
agcggcgcga acaagttcaa cgacgagatc aacctgctcc tcaaggagaa ggcgaacgac    2760
gtgcacatcc tcagcatcga ccggggcgag cgccacctcg cctactacac gctggtggac    2820
gggaagggca acatcatcaa gcaagacacc ttcaacatca tcggcaacga ccggatgaag    2880
accaactacc acgacaagct ggccgccatc gagaaggacc gcgactcggc ccgcaaggac    2940
tggaaaaaga tcaacaatat caaggagatg aaggagggct acctgagcca agttgtccac    3000
gagatcgcca agctggtgat cgagtacaac gccatcgtcg tgttcgaaga cctgaacttc    3060
ggcttcaagc gcggccggtt caaggtcgag aaacaagtct atcagaaact tgagaagatg    3120
ctgatcgaga agctgaacta cctcgtcttc aaggacaacg agttcgacaa gaccggcggc    3180
gtcctccgcg cgtaccagct caccgcgccg ttcgagacgt tcaagaaaat gggcaagcag    3240
accggcatca tctactacgt gcccgccggg ttcacgagca aaatatgtcc cgtgaccggc    3300
ttcgtcaacc agctctaccc caagtacgag tccgtgtcga gtcccagga attcttcagc     3360 aagttcgaca agatatgcta caacctggac aagggctact cgagttctc cttcgactac     3420 aagaacttcg ggacaaggc ggcgaagggg aagtggacca tcgcctcgtt cgggtcgcgc    3480
ctcatcaact tccggaacag cgacaagaac acaactggg acaccgcga ggtgtacccg     3540 acgaaggagc tggagaagct cctcaaggac tacagcatcg agtacggcca cggggagtgc    3600
atcaaggcgg ccatctgcgg cgagtcggac aaaaagttct tgccaaaact cacctcggtc    3660
ctcaacacca tcctccagat gcggaacagc aagacgggca cggagctgga ctacctcatc    3720
agcccggtgg ccgacgtgaa cggcaatttc tttgactcac gccaggcccc taagaacatg    3780
ccccaggacg ccgacgccaa cggcgcgtac cacatcggcc tcaagggcct gatgctgctc    3840
ggccggatca agaacaacca ggagggcaag aagctcaacc tggtcatcaa gaacgaggag    3900
tatttcgagt tcgtccagaa ccgcaacaac ggatctaaga agcgtaggat caagcaagat    3960
```

<210> SEQ ID NO 67
<211> LENGTH: 6530
<212> TYPE: DNA
<213> ORGANISM: Artificial Sequence
<220> FEATURE:
<223> OTHER INFORMATION: Synthetic polynucleotide.Expression cassette
      comprising Zea mays Ubiquitin promoter cassette, NLS-FnCpf1-CO4-
      NLS and an Oryza sativa transcription termination sequence

<400> SEQUENCE: 67

```
gtcgtgcccc tctctagaga taaagagcat tgcatgtcta aagtataaaa aattaccaca    60
tatttttttg tcacacttat ttgaagtgta gtttatctat ctctatacat atatttaaac   120
ttcactctac aaataatata gtctataata ctaaaataat attagtgttt tagaggatca   180
tataaataaa ctgctagaca tggtctaaag gataattgaa tattttgaca atctacagtt   240
ttatctttt agtgtgcatg tgatctctct gttttttg caaatagctt gacctatata    300
atacttcatc cattttatta gtacatccat ttaggattta gggttgatgg tttctataga   360
ctaatttta gtacatccat tttattcttt ttagtctcta aatttttaa aactaaaact    420
ctattttagt ttttattta ataatttaga tataaaatga aataaaataa attgactaca   480
aataaaacaa atacccttta agaaataaaa aaactaagca aacatttttc ttgtttcgag   540
tagataatga caggctgttc aacgccgtcg acgagtctaa cggacaccaa ccagcgaacc   600
agcagcgtcg cgtcgggcca agcgaagcag acggcacggc atctgtag ctgcctctgg    660
accctctcg agagttccgc tccaccgttg gacttgctcc gctgtcggca tccagaaatt   720
gcgtggcgga gcggcagacg tgaggcggca cggcaggcgg cctcttcctc ctctcacggc   780
accggcagct acggggatt cctttcccac cgctccttcg cttccttc ctcgcccgcc    840
gtaataaata gacacccct ccacaccctc tttccccaac ctcgtgttcg ttcggagcgc   900
acacacgc aaccagatct cccccaaatc cagccgtcgg cacctccgct tcaaggtacg    960
ccgctcatcc tccccccc cctctctcta ccttctctag atcggcgatc cggtccatgg   1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatgaaata tcgatctagg ataggtatac atgttgatgc   1260
gggtttact gatgcatata cagagatgct ttttttctcg cttggttgtg atgatatggt   1320
ctggttgggc ggtcgttcta gatcggagta gaatactgtt tcaaactacc tggtggatt   1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggtttac tgatgcatat   1560
acagagatgc ttttttcgc ttggttgtga tgatgtggtc tggttgggcg gtcgttctag   1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggtttact gatgcatata catgatggca tatgcggcat   1800
ctattcatat gctctaacct tgagtaccta tctattataa taaacaagta tgttttataa  1860
ttattttgat cttgatatac ttggatgatg gcatatgcag cagctatatg tggattttt   1920
agccctgcct tcatacgcta tttatttgct tggtactgtt tcttttgtcc gatgctcacc  1980
ctgttgttgg gtgatacttc tgcagcggac cgacggtacc atgggtagca aaaagaggcg  2040
tatcaagcag gacatgagca tctaccagga gttcgtgaac aagtacagcc tgagcaagac  2100
cctgcgcttc gagctgattc ctcagggaa gaccctggag aacatcaagg cgcgcggcct  2160
gatcctggac gacgagaagc gggcgaagga ctacaaaaag gcgaagcaga tcatcgacaa  2220
gtaccatcag ttttcatcg aggagattct cagctccgtg tgcatcagcg aagacctgct  2280
```

```
ccagaactac agcgacgttt acttcaagct caagaaatcg gacgacgaca acctccagaa    2340
ggacttcaag agcgcgaagg acacgattaa gaaacagatc agcgagtaca tcaaggactc    2400
cgagaagttc aagaacctgt tcaaccagaa cctcatcgac gccaagaaag gccaagagtc    2460
ggacctcatc ctctggctca agcagagcaa ggacaacggc atcgagctgt tcaaggcgaa    2520
cagcgacatc accgacatcg acgaggcgct ggagatcatc aagtcgttca agggctggac    2580
gacctacttc aagggcttcc acgagaaccg caagaatgtc tactcgagca acgacatccc    2640
cacgtcgatc atctaccgca tcgtggacga caacctcccg aagttcctgg agaacaaggc    2700
gaagtacgag agcctcaagg acaaggcccc ggaggccatc aactacgagc agatcaaaaa    2760
ggatttggct gaggagctga cgttcgacat cgactacaag acctccgagg tgaaccagcg    2820
cgtcttcagc ctcgacgagg tgttcgagat cgccaacttc aacaactacc tcaaccagtc    2880
gggcatcacc aagttcaaca ccatcatcgg cgggaagttc gtcaacggcg agaacacgaa    2940
gcgcaagggg atcaacgagt acatcaacct gtacagccag cagatcaacg acaagaccct    3000
caagaagtat aaaatgtcgg tgctgttcaa gcagatcctc tcggacaccg agagcaagtc    3060
gttcgtcatc gacaagctgg aggacgacag cgacgtggtg accaccatgc agagcttcta    3120
cgagcagatc gcggccttca agaccgtcga ggagaagtcg atcaaggaga cgctcagcct    3180
gctgttcgac gacctcaagg cccagaagct cgacctgtcc aagatatact ttaagaacga    3240
caagagcctc acgacctgt cccagcaggt attcgacgac tacagcgtga tcgggacggc    3300
cgtgctggag tacatcaccc aacagatcgc gcccaagaac ctggacaacc cgtccaagaa    3360
ggaacaagag ctaatcgcca aaaagactga gaaggcgaag tacctgtcgc tggagacgat    3420
caagctcgcg cttgaggagt ttaacaagca ccgcgacatc gacaagcagt gccggttcga    3480
ggagatcctg gccaacttcg cggcgatccc gatgatcttc gacgagatcg cccagaacaa    3540
ggacaacctg gcgcagatca gcatcaagta ccagaaccag ggcaaaaaag acttgctcca    3600
agctagtgcg gaggacgacg tgaaggcgat taaggatctg ctggaccaga ctaacaatct    3660
gctgcacaag ctcaagatct ttcacatctc tcagtcggag gacaaggcga acatcctgga    3720
caaggacgag cacttctacc tagtgttcga ggagtgctac ttcgagctgg cgaacatcgt    3780
gcccctgtac aacaagatcc ggaactacat cacccagaag ccctacagcg acgagaagtt    3840
caagctgaac ttcgagaaca gcacgctggc gaacgggtgg gacaagaaca aggagcccga    3900
caacaccgcc atcctgttca tcaaggacga caaatattac ctcggcgtca tgaacaaaaa    3960
gaataacaag atattcgatg acaaggcgat caaggagaac aagggcgagg ctacagaaga    4020
gatcgtatat aaactcctgc cgggagcgaa caagatgctc ccgaaggttt tctttagtgc    4080
caagtccatc aagttctaca accccagcga ggacatcctc cgcatccgga accactccac    4140
ccacaccaag aacggctcgc cgcagaaggg ctacgagaag ttcgagttca acatcgagga    4200
ctgccgcaag ttcatcgact tctacaagca gtccatctcc aagcacccgg agtggaagga    4260
cttcgggttc cggttctccg acacgcagcg ctacaactcc atcgacgagt ctaccgggac    4320
ggtggagaac cagggctaca agctgacgtt cgagaacatc tcggagtcct acatcgactc    4380
cgtggtcaac cagggcaagc tgtacctctt ccagatatac aataaggact ctccgcctag    4440
cagcaagggg cggcccaacc tccacaccct gtactggaag gcgctcttcg acgagcggaa    4500
cctccaggac gtcgtgtaca agctgaacgg cgaggcggag ctgttctacc gcaagcagag    4560
catccccaag aagatcacgc accccgcgaa ggaggccatc gccaacaaga acaaggacaa    4620
ccccaagaag gaatcggtct tcgagtacga cctcatcaag gacaagcggt tcacggagga    4680
```

```
caaattctttt ttccactgcc cgatcactat taacttcaag tccagcggcg cgaacaagtt    4740
caacgacgag atcaacctgc tcctcaagga gaaggcgaac gacgtgcaca tcctcagcat    4800
cgaccggggc gagcgccacc tcgcctacta cacgctggtg gacgggaagg caacatcat    4860 caagcaagac accttcaaca tcatcggcaa cgaccggatg aagaccaact accacgacaa    4920
gctggccgcc atcgagaagg accgcgactc ggcccgcaag gactggaaaa agatcaacaa    4980
tatcaaggag atgaaggagg gctacctgag ccaagttgtc cacgagatcg ccaagctggt    5040
gatcgagtac aacgccatcg tcgtgttcga agacctgaac ttcggcttca agcgcggccg    5100
gttcaaggtc gagaaacaag tctatcagaa acttgagaag atgctgatcg agaagctgaa    5160
ctacctcgtc ttcaaggaca acgagttcga caagaccggc ggcgtcctcc gcgcgtacca    5220
gctcaccgcg ccgttcgaga cgttcaagaa aatgggcaag cagaccggca tcatctacta    5280
cgtgcccgcc gggttcacga gcaaaatatg tcccgtgacc ggcttcgtca ccagctcta    5340 ccccaagtac gagtccgtgt cgaagtccca ggaattcttc agcaagttcg acaagatatg    5400
ctacaacctg gacaagggct acttcgagtt ctccttcgac tacaagaact tcggggacaa    5460
ggcggcgaag gggaagtgga ccatcgcctc gttcgggtcg cgcctcatca acttccggaa    5520
cagcgacaag aaccacaact gggacacccg cgaggtgtac ccgacgaagg agctggagaa    5580
gctcctcaag gactacagca tcgagtacgg ccacggggag tgcatcaagg cggccatctg    5640
cggcgagtcg gacaaaaagt ctctttgccaa actcacctcg gtcctcaaca ccatcctcca    5700
gatgcggaac agcaagacgg gcacggagct ggactacctc atcagcccgg tggccgacgt    5760
gaacggcaat ttcttgact cacgccaggc ccctaagaac atgccccagg acgccgacgc    5820
caacggcgcg taccacatcg gcctcaaggg cctgatgctg ctcggccgga tcaagaacaa    5880
ccaggagggc aagaagctca acctggtcat caagaacgag gagtatttcg agttcgtcca    5940
gaaccgcaac aacggatcta agaagcgtag gatcaagcaa gattagttaa ttaagggccc    6000
atccaagtaa attaagttgg atcagtagag atgcatggtt ggtgttctca tgtggtctga    6060
atctgtgttc tgtttcatct tttgtgtaag tgtgcaactt cgattctgta aaacttggca    6120
agtagatgaa cgatgtcatt tatatgcgtg tagcttgtca aaatacaaag tagaaacctg    6180
tatctgaata agatggcatt catgaaataa tattatcgat tgaacgaacg aagcaacaga    6240
atgatcttcc aaattgaagc aaaggaattg atggacaacg agttgctgta ctttggagct    6300
gtaaatctgt agtacttctc aacgatgcta tggaccgtgg gccgtccata atcgctgggt    6360
ggaatgagcc cactgtccat gtgcttctgc atttggcccg tgtacagccc atataatgtc    6420
gaaaaaccta atacgcgcgc gccgccggcg cgcgtttcgg acccagaacg cctagcgccg    6480
ctgcgccgac gtgcgcgcgt ctccactttt tttttcgttt tctttccatt            6530
```

<210> SEQ ID NO 68
<211> LENGTH: 3960
<212> TYPE: DNA
<213> ORGANISM: Artificial Sequence
<220> FEATURE:
<223> OTHER INFORMATION: Synthetic polynucleotide.NLS-FnCpf1-CO5-NLS

<400> SEQUENCE: 68

```
ggtagcaaaa agaggcgtat caagcaggac atgtccatat accaggagtt tgttaataaa     60
tatagcttgt ccaaaaccct gcggtttgaa ctcatacctc aggggaagac tttggagaat    120
atcaaagcgc ggggactgat actggacgac gaaaagcgcg caaagatta caagaaagcg    180
```

```
aaacagatca tcgataaata ccatcaattt tcatagagg agattctcag ttctgtctgt      240
atcagtgagg acctcctcca aaattattca gacgtctatt ttaaactcaa gaagtcggac      300
gacgacaacc ttcagaaaga ttttaagtca gcaaaagaca caatcaaaaa acaaatatcg      360
gaatacataa aggactcaga aaagttcaag aatcttttta accaaaatct gatagacgcg      420
aagaaagggc aggaatctga tcttatactc tggcttaagc agtctaaaga caacggcata      480
gaactcttta aggcaaacag cgatataacc gacatagatg aagccctcga gataattaag      540
tccttcaaag gctggactac atatttaaa gggttccatg agaataggaa gaacgtgtat       600
tcctcgaatg atattcccac ctcgataatc taccggattg tggatgataa tctgcctaaa      660
tttttggaaa ataaagcgaa gtacgaaagt ttgaaagata agcaccaga agcaattaat       720 tatgaacaaa ttaagaaaga tctggctgag gaacttacgt tcgatatcga ttataaaaca      780
tcagaagtta atcagcgggt ttttagcctg gatgaagttt ttgagatcgc caacttcaac      840
aattatctta atcagagcgg gattaccaaa ttcaacacta ttatcggtgg taaattcgtt      900
aatggtgaga cacaaagag aaaaggtata acgaatcaca taaatttgta cagtcaacag      960
attaacgata aaactttgaa aaagtacaag atgtcagtgc ttttcaaaca aatcctttcc     1020
gacacagaat ccaaaagttt tgtgatagac aaattggaag atgatagcga cgtcgtcacg     1080
accatgcaat cattttatga gcaaattgca gccttcaaga cggttgagga aaaaagtata     1140
aaagaaacgt tgtcgctctt gttcgacgac ctgaaagcac agaaattgga tttgtctaag     1200
atatacttta aaaacgacaa atccctcacg gacttgtcgc agcaagtctt tgatgattat     1260
tcggtgattg ggacagccgt gctcgaatac atcacccagc aaatcgctcc gaaaaatctg     1320
gacaatccgt ctaaaaaga gcaagagctg atcgcaaaga aaaccgaaaa agcgaaatac     1380
ctgtctctgg agacaatcaa attggccttg aagagttca ataagcacag agacattgat      1440
aaacaatgtc ggtttgagga aattcttgct aactttgccg ctatcccgat gatcttcgat     1500
gagattgcgc aaaataagga taatctggcc caaatctcga tcaagtatca aaatcagggt     1560
aagaaggacc tgcttcaagc atcggcggag gatgatgtga aagcgattaa ggacttgttg     1620
gatcagacca caatttgtt gcacaagctg aagatattcc acatctccca gagtgaggat      1680
aaggccaaca tcctggacaa ggatgaacat ttctatttgg tcttcgaaga gtgttatttt     1740
gaattggcca acatagttcc tctttataac aagatccgca attatattac acaaaagcct     1800
tattccgatg aaaaatttaa acttaacttc gaaaatagca cattggcgaa tggttgggat     1860
aaaaataagg agcctgacaa tactgctata cttttcatta aggacgataa gtactacctc     1920
ggcgttatga acaagaagaa taataagatc tttgacgaca aagcaatcaa agagaacaaa     1980
ggcgaaggtt acaaaaaat cgtgtacaaa ctcctgcctg gcgcgaataa aatgcttccg     2040
aaggtttttt tcagtgcgaa gtccattaag ttttataacc cttccgagga tattttgaga     2100
attagaaatc actccaccca taccaagaat ggcagccccc agaaggggta tgaaaagttc     2160
gaatttaata tcgaagactg ccgcaagttt atagactttt ataaacagtc catatctaaa     2220
catcccgaat ggaaagattt tggttttccgg ttttctgaca ctcagaggta caacagcata     2280
gatgagttct accgcgaagt tgaaaaccaa ggctacaagc ttacatttga gaacatcagc     2340
gagtcatata ttgactcagt cgttaatcag ggcaaacttt atttgttcca aatttacaac     2400
aaagactttt cagcgtacag caagggaagg ccaaatctcc atacactgta ttggaaggcg     2460
ctgtttgacg agcggaatct tcaagatgtt gtgtataaac tcaacgggga ggccgaattg     2520
ttctacagga agcaaagcat tcctaagaaa attacccacc ccgctaagga agcgatagca     2580
```

```
aataaaaata aagacaatcc gaaaaaagag agcgtttttg agtacgacct tataaaggat      2640
aagagattca ccgaggataa gttttctt cactgtccaa taactattaa ctttaaatcc      2700
tccggagcca acaagtttaa cgacgaaatt aatttgctgc tgaaagagaa ggcgaacgac      2760
gttcacattc tgtcaataga cagaggggag agacacttgg catactacac gctcgttgat      2820
ggaaaaggta acattattaa gcaagatact ttcaacatca ttgggaatga cagaatgaaa      2880
acaaactatc acgataaact cgcggcaatt gagaaggacc gggattcggc gaggaaagac      2940
tggaagaaaa tcaacaatat aaaggagatg aaggaaggat acctgtctca agtcgtccac      3000
gaaatagcca agcttgttat agagtataat gcgattgtgg tctttgaaga ccttaacttt      3060
ggatttaaac gcggccggtt taaagtcgag aaacaagtgt atcaaaaact ggaaaaaatg      3120
ttgatcgaga aactgaatta tctcgtcttc aaggacaacg agttcgataa accgggggc      3180 gtcttgcgcg cttatcaact gacggcaccg tttgaaactt tcaagaagat gggcaaacag      3240
actgggatta tctactacgt tcctgccgga ttcacctcca aaatatgccc agttactgga      3300
tttgttaacc agttgtaccc taagtacgaa tcagtcagca agtcccaaga gttttctca      3360 aaatttgata agatctgcta taacctggac aaggggtact tcgagttttc cttcgactat      3420
aaaaatttcg gcgacaaggc agctaaaggt aaatggacga ttgcaagttt cggctccagg      3480
cttattaatt tcagaaacag cgacaaaaac cataactggg acacgcgcga ggtctaccct      3540
acgaaggaac tggaaaaact tctcaaggat tacagtatag aatacggaca cggggagtgt      3600
atcaaagctg cgatatgcgg agagtcggat aaaaagtttt tcgcaaagtt gacatcagtt      3660
ttgaacacta tcttgcagat gagaaattcc aagactggca cggagttgga ctaccttatt      3720
agcccagtgg cggatgtcaa cgggaacttt tttgattcga ggcaagcccc taagaatatg      3780
cctcaagacg ctgatgcaaa cggggcatat cacataggac tcaaagggtt gatgctgctg      3840
ggcagaatta gaacaaccaa ggaaggaaag aagctcaatc ttgttatcaa aaatgaagag      3900
tactttgaat tcgttcaaaa ccggaataac ggatctaaga agcgtaggat caagcaagat      3960
```

<210> SEQ ID NO 69
<211> LENGTH: 6530
<212> TYPE: DNA
<213> ORGANISM: Artificial Sequence
<220> FEATURE:
<223> OTHER INFORMATION: Synthetic polynucleotide.Expression cassette
      comprising Zea mays Ubiquitin promoter cassette, NLS-FnCpf1-CO5-
      NLS and an Oryza sativa transcription termination sequence

<400> SEQUENCE: 69

```
gtcgtgcccc tctctagaga taaagagcat tgcatgtcta aagtataaaa aattaccaca        60
tatttttttg tcacacttat ttgaagtgta gtttatctat ctctatacat atatttaaac       120
ttcactctac aaataatata gtctataata ctaaaataat attagtgttt tagaggatca       180
tataaataaa ctgctagaca tggtctaaag gataattgaa tattttgaca atctacagtt       240
ttatcttttt agtgtgcatg tgatctctct gtttttttg caaatagctt gacctatata       300
atacttcatc cattttatta gtacatccat ttaggattta gggttgatgg tttctataga       360 ctaatttta gtacatccat tttattcttt ttagtctcta aatttttta aactaaaact       420 ctatttagt tttttattta ataattaga tataaaatga aataaaataa attgactaca       480
aataaaacaa atacccttta agaaataaaa aaactaagca acatttttc ttgtttcgag       540 tagataatga caggctgttc aacgccgtcg acgagtctaa cggacaccaa ccagcgaacc       600
```

-continued

| | |
|---|---|
| agcagcgtcg cgtcgggcca agcgaagcag acggcacggc atctctgtag ctgcctctgg | 660 |
| acccctctcg agagttccgc tccaccgttg gacttgctcc gctgtcggca tccagaaatt | 720 |
| gcgtggcgga gcggcagacg tgaggcggca cggcaggcgg cctcttcctc ctctcacggc | 780 |
| accggcagct acgggggatt cctttcccac cgctccttcg cttccccttc ctcgcccgcc | 840 |
| gtaataaata gacaccccct ccacaccctc tttccccaac ctcgtgttcg ttcggagcgc | 900 |
| acacacacgc aaccagatct cccccaaatc cagccgtcgg cacctccgct tcaaggtacg | 960 |
| ccgctcatcc tcccccccc cctctctcta ccttctctag atcggcgatc cggtccatgg | 1020 |
| ttagggcccg gtagttctac ttctgttcat gtttgtgtta gagcaaacat gttcatgttc | 1080 |
| atgtttgtga tgatgtggtc tggttgggcg gtcgttctag atcggagtag gatactgttt | 1140 |
| caagctacct ggtggattta ttaattttgt atctgtatgt gtgtgccata catcttcata | 1200 |
| gttacgagtt aagatgatg gatggaaata tcgatctagg ataggtatac atgttgatgc | 1260 |
| gggttttact gatgcatata cagagatgct ttttttctcg cttggttgtg atgatatggt | 1320 |
| ctggttgggc ggtcgttcta gatcggagta gaatactgtt tcaaactacc tggtggattt | 1380 |
| attaaaggat aaagggtcgt tctagatcgg agtagaatac tgtttcaaac tacctggtgg | 1440 |
| atttattaaa ggatctgtat gtatgtgcct acatcttcat agttacgagt taagatgat | 1500 |
| ggatggaaat atcgatctag gataggtata catgttgatg cgggttttac tgatgcatat | 1560 |
| acagagatgc ttttttcgc ttggttgtga tgatgtggtc tggttgggcg gtcgttctag | 1620 |
| atcggagtag aatactgttt caaactacct ggtggattta ttaattttgt atctttatgt | 1680 |
| gtgtgccata catcttcata gttacgagtt aagatgatg gatggaaata ttgatctagg | 1740 |
| ataggtatac atgttgatgt gggttttact gatgcatata catgatggca tatgcggcat | 1800 |
| ctattcatat gctctaacct tgagtaccta tctattataa taaacaagta tgttttataa | 1860 |
| ttattttgat cttgatatac ttggatgatg gcatatgcag cagctatatg tggattttt | 1920 |
| agccctgcct tcatacgcta tttatttgct tggtactgtt tcttttgtcc gatgctcacc | 1980 |
| ctgttgttgg gtgatacttc tgcagcggac cgacggtacc atgggtagca aaaagaggcg | 2040 |
| tatcaagcag gacatgtcca tataccagga gtttgttaat aaatatagct tgtccaaaac | 2100 |
| cctgcggttt gaactcatac ctcaggggaa gactttggag aatatcaaag cgcggggact | 2160 |
| gatactggac gacgaaaagc gcgcaaaaga ttacaagaaa gcgaaacaga tcatcgataa | 2220 |
| ataccatcaa ttttttcatag aggagattct cagttctgtc tgtatcagtg aggacctcct | 2280 |
| ccaaaattat tcagacgtct attttaaact caagaagtcg gacgacgaca accttcagaa | 2340 |
| agatttaag tcagcaaaag acacaatcaa aaaacaaata tcggaataca taaaggactc | 2400 |
| agaaaagttc aagaatcttt ttaaccaaaa tctgatagac gcgaagaaag ggcaggaatc | 2460 |
| tgatcttata ctctggctta agcagtctaa agacaacggc atagaactct ttaaggcaaa | 2520 |
| cagcgatata accgacatag atgaagccct cgagataatt aagtccttca aaggctggac | 2580 |
| tacatatttt aaagggttcc atgagaatag gaagaacgtg tattcctcga atgatattcc | 2640 |
| cacctcgata atctaccgga ttgtggatga taatctgcct aaattttgg aaaataaagc | 2700 |
| gaagtacgaa agtttgaaag ataaagcacc agaagcaatt aattatgaac aaattaagaa | 2760 |
| agatctggct gaggaactta cgttcgatat cgattataaa acatcagaag ttaatcagcg | 2820 |
| ggttttagc ctggatgaag ttttgagat cgccaacttc aacaattatc ttaatcagag | 2880 |
| cgggattacc aaaattcaaca ctattatcgg tggtaaattc gttaatggtg agaacacaaa | 2940 |
| gagaaaaggt ataaacgaat acataaattt gtacagtcaa cagattaacg ataaaacttt | 3000 |

```
gaaaaagtac aagatgtcag tgcttttcaa acaaatcctt tccgacacag aatccaaaag    3060
ttttgtgata gacaaattgg aagatgatag cgacgtcgtc acgaccatgc aatcatttta    3120
tgagcaaatt gcagccttca agacggttga ggaaaaaagt ataaagaaa cgttgtcgct     3180 cttgttcgac gacctgaaag cacagaaatt ggatttgtct aagatatact ttaaaaacga    3240
caaatccctc acggacttgt cgcagcaagt cttttgatgat tattcggtga ttgggacagc   3300
cgtgctcgaa tacatcaccc agcaaatcgc tccgaaaaat ctggacaatc cgtctaaaaa    3360
agagcaagag ctgatcgcaa agaaaaccga aaaagcgaaa tacctgtctc tggagacaat    3420
caaattggcc ttggaagagt tcaataagca cagagacatt gataaacaat gtcggtttga    3480
ggaaattctt gctaactttg ccgctatccc gatgatcttc gatgagattg cgcaaaataa    3540
ggataatctg gcccaaatct cgatcaagta tcaaaatcag ggtaagaagg acctgcttca    3600
agcatcggcg gaggatgatg tgaaagcgat taaggacttg ttggatcaga ccaacaattt    3660
gttgcacaag ctgaagatat tccacatctc ccagagtgag gataaggcca acatcctgga    3720
caaggatgaa catttctatt tggtcttcga agagtgttat tttgaattgg ccaacatagt    3780
tcctctttat aacaagatcc gcaattatat tacacaaaag ccttattccg atgaaaaatt    3840
taaacttaac ttcgaaaata gcacattggc gaatggttgg gataaaaata aggagcctga    3900
caatactgct atacttttca ttaaggacga taagtactac ctcggcgtta tgaacaagaa    3960
gaataataag atctttgacg acaaagcaat caaagagaac aaaggcgaag gttacaaaaa    4020
aatcgtgtac aaactcctgc ctggcgcgaa taaaatgctt ccgaaggttt ttttcagtgc    4080
gaagtccatt aagttttata acccttccga ggatattttg agaattagaa atcactccac    4140
ccataccaag aatggcagcc cccagaaggg gtatgaaaag ttcgaattta atatcgaaga    4200
ctgccgcaag tttatagact tttataaaca gtccatatct aaacatcccg aatggaaaga    4260
ttttggtttc cggttttctg acactcgagg tacaacagc atagatgagt ctaccgcga    4320 agttgaaaac caaggctaca agcttacatt tgagaacatc agcgagtcat atattgactc    4380
agtcgttaat cagggcaaac tttatttgtt ccaaatttac aacaaagact tttcagcgta    4440
cagcaaggga aggccaaatc tccatacact gtattggaag gcgctgtttg acgagcggaa    4500
tcttcaagat gttgtgtata aactcaacgg ggaggccgaa ttgttctaca ggaagcaaag    4560
cattcctaag aaaattaccc accccgctaa ggaagcgata gcaaataaaa ataaagacaa    4620
tccgaaaaaa gagagcgttt ttgagtacga ccttataaag gataagagat tcaccgagga    4680
taagtttttc ttccactgtc aataactat aactttaaa tcctccggag ccaacaagtt     4740
taacgacgaa attaatttgc tgctgaaaga gaaggcgaac gacgttcaca ttctgtcaat    4800
agacagaggg gagagacact tggcatacta cacgctcgtt gatggaaaag gtaacattat    4860
taagcaagat actttcaaca tcattgggaa tgacagaatg aaaacaaact atcacgataa    4920
actcgcggca attgagaagg accgggattc ggcgaggaaa gactggaaga aaatcaacaa    4980
tataaaggag atgaaggaag gataaatgtc tcaagtcgtc cacgaaatag ccaagcttgt    5040
tatagagtat aatgcgattg tggtctttga agaccttaac tttggattta aacgcggccg    5100
gtttaaagtc gagaaacaag tgtatcaaaa actggaaaaa atgttgatcg agaaactgaa    5160
ttatctcgtc ttcaaggaca acgagttcga taaaaccggg ggcgtcttgc gcgcttatca    5220
actgacggca ccgttgaaa cttttcagaa gatgggcaaa cagactggga ttatctacta    5280
cgttcctgcc ggattcacct ccaaaatatg cccagttact ggatttgtta accagttgta    5340
```

```
ccctaagtac gaatcagtca gcaagtccca agagttttc tcaaaatttg ataagatctg      5400
ctataacctg gacaaggggt acttcgagtt ttccttcgac tataaaaatt tcggcgacaa      5460
ggcagctaaa ggtaaatgga cgattgcaag tttcggctcc aggcttatta atttcagaaa      5520
cagcgacaaa aaccataact gggacacgcg cgaggtctac cctacgaagg aactggaaaa      5580
acttctcaag gattacagta tagaatacgg acacggggag tgtatcaaag ctgcgatatg      5640
cggagagtcg gataaaaagt ttttcgcaaa gttgacatca gttttgaaca ctatcttgca      5700
gatgagaaat tccaagactg gcacggagtt ggactacctt attagcccag tggcggatgt      5760
caacgggaac ttttttgatt cgaggcaagc ccctaagaat atgcctcaag acgctgatgc      5820
aaacggggca tatcacatag gactcaaagg gttgatgctg ctgggcagaa ttaagaacaa      5880
ccaggaagga aagaagctca atcttgttat caaaaatgaa gagtactttg aattcgttca      5940
aaaccggaat aacggatcta agaagcgtag gatcaagcaa gattgattaa ttaagggccc      6000
atccaagtaa attaagttgg atcagtagag atgcatggtt ggtgttctca tgtggtctga      6060
atctgtgttc tgtttcatct tttgtgtaag tgtgcaactt cgattctgta aaacttggca      6120
agtagatgaa cgatgtcatt tatatgcgtg tagcttgtca aaatacaaag tagaaacctg      6180
tatctgaata agatggcatt catgaaataa tattatcgat tgaacgaacg aagcaacaga      6240
atgatcttcc aaattgaagc aaaggaattg atggacaacg agttgctgta ctttggagct      6300
gtaaatctgt agtacttctc aacgatgcta tggaccgtgg gccgtccata atcgctgggt      6360
ggaatgagcc cactgtccat gtgcttctgc atttggcccg tgtacagccc atataatgtc      6420
gaaaaaccta atacgcgcgc gccgccggcg cgcgtttcgg acccagaacg cctagcgccg      6480
ctgcgccgac gtgcgcgcgt ctccactttt tttttcgttt tctttccatt             6530
```

<210> SEQ ID NO 70
<211> LENGTH: 3960
<212> TYPE: DNA
<213> ORGANISM: Artificial Sequence
<220> FEATURE:
<223> OTHER INFORMATION: Synthetic polynucleotide.NLS-FnCpf1-CO6-NLS

<400> SEQUENCE: 70

```
ggtagcaaaa agaggcgtat caagcaggac atgagtattt atcaagagtt cgttaataag       60
tacagtcttt ctaagacgct caggtttgag ctcattccac aaggtaagac ccttgagaat      120
attaaagccc gcggactgat cctggacgac gagaagcgcg ccaaagacta taagaaggcg      180
aaacagatca tagataagta tcaccaattc ttcatagaag agatacttag ctctgtttgt      240
atctcagagg atctgctcca gaactactcg gatgtgtact ttaaactcaa gaagtctgac      300
gatgacaatc tccagaagga ctttaagtcc gccaaagaca caatcaagaa gcagatttcg      360
gaatacataa aggacagtga aagttcaag aacttgttca accagaatct catagacgcc      420
aagaagggtc aggagagcga tcttattctg tggttgaaac aatcaaagga caacggtatt      480
gagttgttta agcaaactc tgacatcacc gacattgacg aggctctgga gatcattaag      540
agttttaaag ggtggacaac ctactttaag ggatttcatg agaatcgcaa gaacgtgtac      600
tcgagcaatg acatacctac aagcataatc tatcggatag tcgacgataa cctcccgaag      660
ttcctcgaga ataaagcgaa gtacgaatcg cttaaggata aggcgccgga ggcgataaac      720
tatgaacaga ttaagaagga tctggctgaa gaattgacct tgatattga ctataagacc      780
agcgaagtca ccaacgcgt tttcagcctg gatgaagtgt tgagatcgc caacttcaat      840
aattacttga atcaatcggg gataacaaag tttaatacga ttatcggcgg gaagtttgtc      900
```

```
aacggggaga acacaaagag aaggggcata aatgagtaca ttaatctcta tagtcaacag    960
ataaatgaca agacgttgaa gaaatacaag atgtcagtcc ttttcaagca gatcctgtct   1020
gacacagaat cgaagagctt cgtgatagat aagctggaag atgattccga cgttgtcaca   1080
accatgcaat cgttttacga gcagatcgcg gccttcaaga ccgttgagga gaagtctatt   1140
aaagagactc tttctcttct gtttgatgac ttgaaggccc agaagcttga cttgtccaag   1200
atctacttca agaacgataa atctctgaca gatctcagcc agcaagtgtt tgacgactat   1260
tctgttatcg gaacggccgt gctggagtac atcacacagc agatcgcgcc taagaacctt   1320
gataatccga gcaagaaaga acaggagttg attgcaaaga agacagagaa ggccaaatac   1380
ctttctctgg agacaattaa acttgcactg gaagaattca ataagcacag agatatcgac   1440
aagcagtgtc gctttgagga gatcctggca aattttgctg ccatcccaat gattttgat   1500
gagattgccc agaacaagga caatctcgcg cagatatcaa tcaagtatca gaaccaaggc   1560
aagaaggacc tcctgcaagc ctcagccgaa gatgacgtta aggccataaa ggatctcctt   1620
gatcagacca ataacttgct gcacaagctg aagatctttc atatcagcca gtcggaagac   1680
aaagcaaata tccttgacaa ggacgagcat ttctatctgg tgttcgaaga atgctatttc   1740
gagctggcca atatcgtgcc tctgtacaat aagatccgca attatatcac gcagaagccg   1800
tatagcgacg agaagttcaa gctgaatttc gagaactcca ccttggccaa tggttgggat   1860
aagaacaaag aaccggacaa tacggccatc ttgtttatca aagatgacaa gtactatctg   1920
ggagtgatga ataagaagaa caataagatc ttcgatgaca aagccattaa ggagaataaa   1980
ggggaaggtt acaagaagat tgtctataaa ctgctccccg gggccaacaa gatgctgccc   2040
aaagtttttt tcagtgccaa gagcatcaag ttttataatc cctcagaaga catactgaga   2100
atcagaaacc actcgaccca taccaagaac ggctctccgc agaagggta cgagaaattc   2160
gaattcaaca tcgaagactg tagaaagttc atcgatttt acaagcaatc gatatcaaag   2220
caccctgaat ggaaggattt tggttttcgc tttagtgaca ctcagcggta taatagcatt   2280
gatgagttct accgcgaagt tgagaatcag ggatacaaat tgacattcga gaatatcagc   2340
gaatcgtaca ttgatagcgt cgtcaaccag gggaaacttt acctcttcca gatttataat   2400
aaagacttct cggcgtactc caagggaaga ccaaatcttc atactctgta ttggaaggca   2460
ctcttcgatg agaaaatct tcaggatgtc gtttataaac ttaatgggga agcggagctg   2520
ttctaccgca agcagagcat ccctaagaag atcacgcacc ccgcgaagga ggcgatagcc   2580
aataagaaca aggataaccc gaagaaggag tccgtcttcg aatatgacct gatcaaggat   2640
aagagattca ctgaggacaa attcttcttc cattgcccta ttacgattaa ttttaaatcg   2700
agcggcgcga ataaattcaa cgacgagatc aacctgctcc tcaaagagaa ggccaatgat   2760
gtccacattc tctcaatcga cagaggggag aggcaccttg cctactatac gctcgttgat   2820
ggtaaaggta acatcattaa gcaggacacg ttcaacatca tcgggaacga ccgcatgaag   2880
acaaactatc acgataaatt ggcggcaatc gagaaggatc gggatagtgc caggaaggac   2940
tggaagaaga ttaataacat caaggagatg aaggagggat atctttctca agtcgtccac   3000
gagatcgcga agctggttat cgagtacaac gccatagtgg tcttcgaaga tctgaacttc   3060
ggattcaaga gagggagatt taaggtggag aagcaagttt atcagaaact ggagaagatg   3120
ctgatagaga agctcaacta cctcgtgttt aaagacaacg agtttgacaa gacaggtgggg   3180
gtgttgaggg cctatcagct cacggccccc ttcgagacct tcaagaagat gggaaagcag   3240
```

| | |
|---|---|
| acggggataa tctactacgt ccctgctggc ttcacttcga agatctgccc agttacagga | 3300 |
| ttcgttaacc agttgtatcc caaatacgag tccgtctcaa agtcacaaga attcttttct | 3360 |
| aaattcgata agatctgcta caacctggat aagggctact tcgagtttag ctttgactat | 3420 |
| aagaatttcg gggacaaagc ggcaaggggg aagtggacaa tcgcaagttt tggctcccgg | 3480 |
| ctgattaact ttcggaattc tgacaagaat cacaactggg atactagaga ggtctatcca | 3540 |
| actaaagagt tggagaagtt gctcaaggac tactccattg aatatggtca cggggaatgc | 3600 |
| attaaagcgg ccatctgcgg agagtccgat aagaagttct tgccaaaact tacatcggtc | 3660 |
| ttgaacacca tactgcagat gcggaacagc aagacgggaa cggaactcga ctaccttatc | 3720 |
| tcacctgtgg cggatgttaa tggaaacttt ttcgattcga ggcaggcgcc caagaacatg | 3780 |
| ccgcaagatg cagatgccaa tggagcatat cacatcggtc ttaaagggct catgctgctt | 3840 |
| ggccgcatca agaacaacca agaggggaag aagttgaacc tggttattaa gaacgaagaa | 3900 |
| tacttcgaat tgtccagaa ccgcaacaac ggatctaaga agcgtaggat caagcaagat | 3960 |

<210> SEQ ID NO 71
<211> LENGTH: 6530
<212> TYPE: DNA
<213> ORGANISM: Artificial Sequence
<220> FEATURE:
<223> OTHER INFORMATION: Synthetic polynucleotide.Expression cassette
      comprising Zea mays Ubiquitin promoter cassette, NLS-FnCpf1-CO6-
      NLS and an Oryza sativa transcription termination sequence

<400> SEQUENCE: 71

| | |
|---|---|
| gtcgtgcccc tctctagaga taaagagcat tgcatgtcta aagtataaaa aattaccaca | 60 |
| tattttttg tcacacttat ttgaagtgta gtttatctat ctctatacat atatttaaac | 120 |
| ttcactctac aaataatata gtctataata ctaaaataat attagtgttt tagaggatca | 180 |
| tataaataaa ctgctagaca tggtctaaag gataattgaa tattttgaca atctacagtt | 240 |
| ttatcttttt agtgtgcatg tgatctctct gttttttttg caaatagctt gacctatata | 300 |
| atacttcatc cattttatta gtacatccat ttaggattta gggttgatgg tttctataga | 360 |
| ctaattttta gtacatccat tttattcttt ttagtctcta aattttttaa aactaaaact | 420 |
| ctattttagt tttttatttta ataatttaga tataaaatga aataaaataa attgactaca | 480 |
| aataaaacaa ataccctta agaaataaaa aaactaagca aacatttttc ttgtttcgag | 540 |
| tagataatga caggctgttc aacgccgtcg acgagtctaa cggacaccaa ccagcgaacc | 600 |
| agcagcgtcg cgtcgggcca agcgaagcag acggcacggc atctctgtag ctgcctctgg | 660 |
| accccctctcg agagttccgc tccaccgttg gacttgctcc gctgtcggca tccagaaatt | 720 |
| gcgtggcgga gcggcagacg tgaggcggca cggcaggcgg cctcttcctc ctctcacggc | 780 |
| accggcagct acggggggatt cctttcccac cgctccttcg ctttcccttc ctcgcccgcc | 840 |
| gtaataaata gacacccct ccacaccctc tttccccaac ctcgtgttcg ttcggagcgc | 900 |
| acacacacgc aaccagatct cccccaaatc cagccgtcgg cacctccgct tcaaggtacg | 960 |
| ccgctcatcc tccccccccc cctctctcta ccttctctag atcggcgatc cggtccatgg | 1020 |
| ttagggcccg gtagttctac ttctgttcat gtttgtgtta gagcaaacat gttcatgttc | 1080 |
| atgtttgtga tgatgtggtc tggttgggcg gtcgttctag atcggagtag gatactgttt | 1140 |
| caagctacct ggtggattta ttaattttgt atctgtatgt gtgtgccata catcttcata | 1200 |
| gttacgagtt aagatgatg gatggaaata tcgatctagg ataggtatac atgttgatgc | 1260 |
| gggttttact gatgcatata cagagatgct ttttttctcg cttggttgtg atgatatggt | 1320 |

```
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc ttttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt aagatgatg gatggaaata ttgatctagg    1740
ataggtatac atgttgatgt gggttttact gatgcatata catgatggca tatgcggcat    1800
ctattcatat gctctaacct gagtaccta tctattataa taaacaagta tgttttataa    1860
ttattttgat cttgatatac ttggatgatg gcatatgcag cagctatatg tggattttt    1920 agccctgcct tcatacgcta tttatttgct tggtactgtt tcttttgtcc gatgctcacc    1980
ctgttgttgg gtgatacttc tgcagcggac cgacggtacc atgggtagca aaaagaggcg    2040
tatcaagcag gacatgagta tttatcaaga gttcgttaat aagtacagtc tttctaagac    2100
gctcaggttt gagctcattc cacaaggtaa gacccttgag aatattaaag cccgcggact    2160
gatcctggac gacgagaagc gcgccaaaga ctataagaag gcgaaacaga tcatagataa    2220
gtatcaccaa ttcttcatag aagagatact tagctctgtt tgtatctcag aggatctgct    2280
ccagaactac tcggatgtgt actttaaact caagaagtct gacgatgaca atctccagaa    2340
ggactttaag tccgccaaag acacaatcaa gaagcagatt tcggaataca taaaggacag    2400
tgagaagttc aagaacttgt tcaaccagaa tctcatagac gccaagaagg gtcaggagag    2460
cgatcttatt ctgtggttga acaatcaaa ggacaacggt attgagttgt ttaaagcaaa    2520
ctctgacatc accgacattg acgaggctct ggagatcatt aagagtttta aagggtggac    2580
aacctacttt aagggatttc atgagaatcg caagaacgtg tactcgagca atgacatacc    2640
tacaagcata atctatcgga tagtcgacga taacctcccg aagttcctcg agaataaagc    2700
gaagtacgaa tcgcttaagg ataaggcgcc ggaggcgata aactatgaac agattaagaa    2760
ggatctggct gaagaattga cctttgatat tgactataag accagcgaag tcaaccaacg    2820
cgttttcagc ctggatgaag tgtttgagat cgccaacttc aataattact gaatcaatc    2880 ggggataaca aagtttaata cgattatcgg cgggaagttt gtcaacgggg agaacacaaa    2940
gaggaagggc ataaatgagt acattaatct ctatagtcaa cagataaatg acaagacgtt    3000
gaagaaatac aagatgtcag tccttttcaa gcagatcctg tctgacacag aatcgaagag    3060
cttcgtgata gataagctgg aagatgattc cgacgttgtc acaaccatgc aatcgtttta    3120
cgagcagatc gcggccttca agaccgttga ggagaagtct attaaagaga ctctttctct    3180
tctgtttgat gacttgaagg cccagaagct tgacttgtcc aagatctact tcaagaacga    3240
taaatctctg acagatctca gccagcaagt gtttgacgac tattctgtta tcggaacggc    3300
cgtgctggag tacatcacac agcagatcgc gcctaagaac cttgataatc gagcaagaa    3360 agaacaggag ttgattgcaa agaagacaga gaaggccaaa taccttctc tggagacaat    3420 taaacttgca ctggaagaat tcaataagca cagagatatc gacaagcagt gtcgctttga    3480
ggagatcctg gcaaattttg ctgccatccc aatgattttt gatgagattg cccagaacaa    3540
ggacaatctc gcgcagatat caatcaagta tcagaaccaa ggcaagaagg acctcctgca    3600
agcctcagcc gaagatgacg ttaaggccat aaaggatctc cttgatcaga ccaataactt    3660
```

```
gctgcacaag ctgaagatct ttcatatcag ccagtcggaa gacaaagcaa atatccttga    3720
caaggacgag catttctatc tggtgttcga agaatgctat ttcgagctgg ccaatatcgt    3780
gcctctgtac aataagatcc gcaattatat cacgcagaag ccgtatagcg acgagaagtt    3840
caagctgaat ttcgagaact ccaccttggc caatggttgg gataagaaca agaaccgga    3900 caatacggcc atcttgttta tcaaagatga caagtactat ctgggagtga tgaataagaa    3960
gaacaataag atcttcgatg acaaagccat taaggagaat aaaggggaag gttacaagaa    4020
gattgtctat aaactgctcc ccggggccaa caagatgctg cccaaagttt tttcagtgc     4080 caagagcatc aagttttata atccctcaga agacatactg agaatcagaa accactcgac    4140
ccataccaag aacggctctc cgcagaaggg gtacgagaaa ttcgaattca acatcgaaga    4200
ctgtagaaag ttcatcgatt tttacaagca atcgatatca aagcaccctg aatggaagga    4260 ttttggttt cgctttagtg acactcagcg gtataatagc attgatgagt tctaccgcga     4320
agttgagaat cagggataca aattgacatt cgagaatatc agcgaatcgt acattgatag    4380
cgtcgtcaac caggggaaac tttacctctt ccagatttat aataaagact ctcggcgta    4440 ctccaaggga agaccaaatc ttcatactct gtattggaag gcactcttcg atgagagaaa    4500
tcttcaggat gtcgtttata aacttaatgg ggaagcggag ctgttctacc gcaagcagag    4560
catccctaag aagatcacgc accccgcgaa ggaggcgata gccaataaga acaaggataa    4620
cccgaagaag gagtccgtct tcgaatatga cctgatcaag gataagagat tcactgagga    4680
caaattcttc ttccattgcc ctattacgat taatttttaaa tcgagcggcg cgaataaatt    4740
caacgacgag atcaacctgc tcctcaaaga gaaggccaat gatgtccaca ttctctcaat    4800
cgacagaggg gagaggcacc ttgcctacta tacgctcgtt gatggtaaag gtaacatcat    4860
taagcaggac acgttcaaca tcatcgggaa cgaccgcatg aagacaaaact atcacgataa    4920 attggcggca atcgagaagg atcgggatag tgccaggaag gactggaaga agattaataa    4980
catcaaggag atgaaggagg gatatctttc tcaagtcgtc cacgagatcg cgaagctggt    5040
tatcgagtac aacgccatag tggtcttcga agatctgaac ttcggattca agagagggag    5100
atttaaggtg gagaagcaag tttatcagaa actggagaag atgctgatag agaagctcaa    5160
ctacctcgtg tttaaagaca acgagtttga caagacaggt ggggtgttga gggcctatca    5220
gctcacggcc cccttcgaga ccttcaagaa gatgggaaag cagacgggga taatctacta    5280
cgtccctgct ggcttcactt cgaagatctg cccagttaca ggattcgtta accagttgta    5340
tcccaaatac gagtccgtct caaagtcaca agaattcttt tctaaattcg ataagatctg    5400
ctacaacctg gataagggct acttcgagtt tagctttgac tataagaatt tcggggacaa    5460
agcggcaaag gggaagtgga caatcgcaag ttttggctcc cggctgatta actttcggaa    5520
ttctgacaag aatcacaact gggatactag agaggtctat ccaactaaag agttggagaa    5580
gttgctcaag gactactcca ttgaatatgg tcacggggaa tgcattaaag cggccatctg    5640
cggagagtcc gataagaagt tctttgccaa acttacatcg gtcttgaaca ccatactgca    5700
gatgcggaac agcaagacgg gaacggaact cgactacctt atctcacctg tggcggatgt    5760
taatggaaac ttttcgatt cgaggcaggc gcccaagaac atgccgcaag atgcagatgc    5820
caatggagca tatcacatcg gtcttaaagg gctcatgctg cttggccgca tcaagaacaa    5880
ccaagagggg aagaagttga acctggttat taagaacgaa gaatacttcg aatttgtcca    5940
gaaccgcaac aacggatcta agaagcgtag gatcaagcaa gattgattaa ttaagggccc    6000
atccaagtaa attaagttgg atcagtagag atgcatggtt ggtgttctca tgtggtctga    6060
```

```
atctgtgttc tgtttcatct tttgtgtaag tgtgcaactt cgattctgta aaacttggca    6120
agtagatgaa cgatgtcatt tatatgcgtg tagcttgtca aaatacaaag tagaaacctg    6180
tatctgaata agatggcatt catgaaataa tattatcgat tgaacgaacg aagcaacaga    6240
atgatcttcc aaattgaagc aaaggaattg atggacaacg agttgctgta ctttggagct    6300
gtaaatctgt agtacttctc aacgatgcta tggaccgtgg gccgtccata atcgctgggt    6360
ggaatgagcc cactgtccat gtgcttctgc atttggcccg tgtacagccc atataatgtc    6420
gaaaaaccta atacgcgcgc gccgccggcg cgcgtttcgg acccagaacg cctagcgccg    6480
ctgcgccgac gtgcgcgcgt ctccactttt tttttcgttt tctttccatt              6530

<210> SEQ ID NO 72
<211> LENGTH: 3960
<212> TYPE: DNA
<213> ORGANISM: Artificial Sequence
<220> FEATURE:
<223> OTHER INFORMATION: Synthetic polynucleotide.NLS-FnCpf1-CO7-NLS

<400> SEQUENCE: 72
ggtagcaaaa agaggcgtat caagcaggac atgtccatct atcaggaatt tgttaacaag      60
tactctctta gcaaaactct taggttcgaa ttgataccte agggaaagac acttgagaat     120
attaaggcgc gcgggctgat acttgatgat gaaaagcggg caaggactta agaaaagct      180
aagcaaataa ttgataagta ccaccagttt tttattgaag agatcctgtc ctccgtttgt     240
atatccgaag acttgcttca gaattactca gatgtttatt ttaaattgaa gaaatctgac     300
gatgataatc ttcaaaagga tttcaaatcg gcaaaagaca caatcaaaaa acagattagc     360
gagtacatca aggactccga aaagtttaag aatctcttta tcagaatctc tatagacgca     420
aagaaaggac aggaatcgga cttgattttg tggttgaagc agtccaagga taacgggata     480
gaactctttta aagccaactc cgatataacg gacatcgacg aagccctcga atcattaag     540
tcgtttaaag gttggaccac gtacttcaaa ggattccacg agaacagaaa gaacgtttac     600
tcgagcaacg acattcctac tagcatcata tatagaatag tggatgataa tttgcccaaa     660
ttccttgaga acaaggcaaa atatgaatcc ctgaaagaca aggcgcccga agctatcaac     720
tacgagcaga taagaaagaa tctggctgag gagctgacgt tgacattga ttacaaaaca     780
agcgaggtca accagagggt ttttttcgctg gacgaggttt ttgaaatagc gaattttaat     840
aactacctga accaatccgg catcactaaa tttaacacaa tcatagggg gaagttcgtg     900
aacgagagga cacaaagcg caagggatt aatgagtaca tcaatttgta cagccagcag     960
atcaatgaca aaacgttgaa gaaatataag atgagcgtct tgtttaagca gattctctcg    1020
gatacggaat ccaaatcatt cgtcattgac aagctggagg atgacagcga tgtggtgaca    1080
actatgcagt ccttctatga acaaattgca gcttttaaaa cggtcgaaga gaagtcgatt    1140
aaagaaacgc tttcgctcct gttcgatgac ctgaaagcgc agaagctgga cctttcgaag    1200
atatatttca aaaacgataa gtcactcacg gaccttagcc aacaggtttt cgatgactat    1260
tctgtcatag ggactgctgt gcttgagtat attactcagc aaatagcccc caaaaacctg    1320
gacaacccgt ctaagaagga acaagagctg atagcgaaga aacagagaa agctaaatat    1380
cttttcactt gaaactataa agcttgcactg gaggaattca caaacatcg cgacatcgac    1440
aagcagtgca gatttgagga gatcttggcc aacttcgcag ctattccaat gatttttgac    1500
gagatagcac agaataagga caacctggca cagattagca taaaatacca gatcaggggg    1560
```

```
aagaaggatc ttcttcaggc ttcggctgag gacgatgtca aagccatcaa agatctgctc    1620
gaccagacca acaatttgtt gcataaactc aagatcttcc acatatcgca gtccgaagat    1680
aaagcgaaca tacttgacaa agacgaacat ttttatcttg ttttcgagga gtgttatttt    1740
gagttggcaa acatcgttcc cctctacaac aaaattcgca actatataac tcagaagccc    1800
tattctgacg agaaattcaa acttaatttc gaaaacagca ctctcgcaaa cggctgggat    1860
aaaaacaagg aacccgacaa caccgccata cttttttatta aggatgataa atattatttg   1920
ggcgtgatga ataaaagaa caataaaata ttcgatgata aagcaattaa ggaaaataaa     1980
ggggaagggt ataaaaaaat cgtgtataag ctgcttccag gagctaataa aatgctgcca    2040
aaagtcttct tctctgccaa gtcgatcaag ttttacaatc cttctgaaga tattttgcgg    2100
atcagaaatc actctactca cactaaaaac ggttcacccc agaaaggata cgagaagttt    2160
gagttcaaca tcgaagactg tcggaagttt atcgactttt acaagcagtc tatatcaaaa    2220
caccccgaat ggaaagattt tggttttcgg ttcagcgaca cgcagagata taattcaatt    2280
gatgagttct acagggaggt ggagaaccaa gggtataaac ttacttttga gaacatttcc    2340
gaatcctata ttgattcggt ggtcaatcag gggaaactgt acctgtttca gatatataac    2400
aaagacttct ccgcgtattc taaaggacgg cccaatctcc atactcttta ttggaaggcg    2460
ctgtttgacg agcggaacct tcaggatgtt gtctataagt tgaacgggga agctgagctg    2520
ttctatcgga agcagtctat tccaaaaaag ataacgcacc ccgcgaagga ggcaattgca    2580
aacaagaaca aagacaatcc aaagaaggag tcggtgtttg agtacgatct gataaaagac    2640
aaaaggttta ccgaggacaa gttttttttc cactgtccga tcaccatcaa ttttaagtct    2700
tccggcgcca acaaattcaa tgacgaaata aatctgctgc tcaaggaaaa ggcaaatgat    2760
gttcatattc tgtcgataga ccgcgggaa agacacctcg cgtattatac attggtcgat     2820
gggaaaggca atattatcaa acaagacacc ttcaatatca ttggtaacga taggatgaaa    2880
acgaactatc atgataaact tgcagctatt gaaaaggaca gagactcggc tcggaaagat    2940
tggaaaaaga tcaataacat caaggaaatg aaggaagggt atctctccca ggtcgttcat    3000
gaaatcgcca aactggttat tgagtacaat gctatagtgg tttttgaaga tcttaatttt    3060
gggtttaaga gagggagatt taaagtcgag aaacaggttt atcaaaaact tgaaaaaatg    3120
ttgatagaaa aattgaacta tcttgtgttt aaggacaatg agttcgataa aaccgggggg    3180
gttttgagag cttatcaact gacggctccc ttcgagacat tcaaaaaaat ggggaagcag    3240
accggcatca tttattatgt gcccgcgggc ttcacttcta aaatttgtcc tgtgacaggg    3300
ttcgtgaacc aattgtaccc caagtacgaa agcgtctcca gtcccaaga attctttagc     3360 aagtttgaca aaatttgcta taacctggac aaagggtact ttgagttttc ctttgattat    3420
aagaatttcg gggataaagc tgcgaaaggt aagtggacga tagcctcttt cgggtcgcgc    3480
cttattaact tcaggaattc cgacaaaaac cataattggg acaccgcgca ggtctaccct    3540
acaaaggaac tcgaaaagtt gcttaaggat tattcaatag agtatggtca tggcgagtgt    3600
attaaggctg ctatctgtgg tgagtcagat aagaaattct tcgcgaaatt gacatctgtt    3660
ttgaacacca tcctccaaat gaggaactct aaaacgggga cggagcttga ttatctcatc    3720
tcacccgttg ctgatgtgaa cggtaatttc ttttgattcac gccaagcccc gaagaacatg    3780
ccccaagacg ccgatgctaa cggcgcttat catataggc tgaagggct catgcttctg       3840 gggcgcatca aaaataacca agaagggaag aaactcaatc tggttatcaa aaatgaggaa    3900
tatttcgaat tcgtgcaaaa ccgcaacaat ggatctaaga agcgtaggat caagcaagat    3960
```

<210> SEQ ID NO 73
<211> LENGTH: 6530
<212> TYPE: DNA
<213> ORGANISM: Artificial Sequence
<220> FEATURE:
<223> OTHER INFORMATION: Synthetic polynucleotide.Expression cassette
comprising Zea mays Ubiquitin promoter cassette, NLS-FnCpf1-CO7-
NLS and an Oryza sativa transcription termination sequence

<400> SEQUENCE: 73

```
gtcgtgcccc tctctagaga taaagagcat tgcatgtcta aagtataaaa aattaccaca      60
tattttttg tcacacttat ttgaagtgta gtttatctat ctctatacat atatttaaac     120
ttcactctac aaataatata gtctataata ctaaaataat attagtgttt tagaggatca     180
tataaataaa ctgctagaca tggtctaaag gataattgaa tatttttgaca atctacagtt    240
ttatctttt agtgtgcatg tgatctctct gttttttttg caaatagctt gacctatata     300
atacttcatc cattttatta gtacatccat ttaggattta gggttgatgg tttctataga    360
ctaatttta gtacatccat tttattcttt ttagtctcta aatttttaa aactaaaact    420
ctattttagt ttttttattta ataatttaga tataaaatga aataaaataa attgactaca    480
aataaaacaa ataccctta agaaataaaa aaactaagca aacatttttc ttgtttcgag     540
tagataatga caggctgttc aacgccgtcg acgagtctaa cggacaccaa ccagcgaacc     600
agcagcgtcg cgtcgggcca agcgaagcag acggcacggc atctctgtag ctgcctctgg    660
accctctcg agagttccgc tccaccgttg gacttgctcc gctgtcggca tccagaaatt    720
gcgtggcgga gcggcagacg tgaggcggca cggcaggcgg cctcttcctc ctctcacggc     780
accggcagct acgggggatt ccttcccac cgctccttcg ctttcccttc ctcgcccgcc    840
gtaataaata gacacccct ccacaccctc tttcccaac ctcgtgttcg ttcggagcgc    900
acacacgc aaccagatct cccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt    1140
caagctacct ggtggattta ttaattttgt atctgtatgt gtgtgccata catcttcata    1200
gttacgagtt taagatgatg gatggaaata tcgatctagg ataggtatac atgttgatgc    1260
gggttttact gatgcatata cagagatgct ttttttctcg cttggttgtg atgatatggt    1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc ttttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttt    1920
agccctgcct tcatacgcta tttatttgct tggtactgtt tcttttgtcc gatgctcacc    1980
```

```
ctgttgttgg gtgatacttc tgcagcggac cgacggtacc atgggtagca aaagaggcg    2040 tatcaagcag gacatgtcca tctatcagga atttgttaac aagtactctc ttagcaaaac    2100
tcttaggttc gaattgatac ctcagggaaa gacacttgag aatattaagg cgcgcgggct    2160
gatacttgat gatgaaaagc gggcaaagga ctataagaaa gctaagcaaa taattgataa    2220
gtaccaccag ttttttattg aagagatcct gtcctccgtt tgtatatccg aagacttgct    2280
tcagaattac tcagatgttt atttttaaatt gaagaaatct gacgatgata atcttcaaaa    2340
ggatttcaaa tcggcaaaag acacaatcaa aaaacagatt agcgagtaca tcaaggactc    2400
cgaaaagttt aagaatctct ttaatcagaa tcttatagac gcaaagaaag gacaggaatc    2460
ggacttgatt ttgtggttga agcagtccaa ggataacggg atagaactct ttaaagccaa    2520
ctccgatata acggacatcg acgaagccct cgaaatcatt aagtcgttta aaggttggac    2580
cacgtacttc aaaggattcc acgagaacag aaagaacgtt tactcgagca cgacattcc    2640 tactagcatc atatatagaa tagtggatga taatttgccc aaattccttg agaacaaggc    2700
aaaatatgaa tccctgaaag acaaggcgcc cgaagctatc aactacgagc agataaagaa    2760
agatctggct gaggagctga cgtttgacat tgattacaaa acaagcgagg tcaaccagag    2820
ggttttttcg ctgacgagg ttttgaaat agcgaatttt aataactacc tgaaccaatc    2880
cggcatcact aaatttaaca caatcatagg ggggaagttc gtgaacggag agaacacaaa    2940
gcgcaaaggg attaatgagt acatcaattt gtacagccag cagatcaatg acaaaacgtt    3000
gaagaaatat aagatgagcg tcttgtttaa gcagattctc tcggatacgg aatccaaatc    3060
attcgtcatt gacaagctgg aggatgacag cgatgtggtg acaactatgc agtccttcta    3120
tgaacaaatt gcagcttttta aaacggtcga agagaagtcg attaaagaaa cgctttcgct    3180
cctgttcgat gacctgaaag cgcagaagct ggaccttcg aagatatatt tcaaaaacga    3240
taagtcactc acggaccta gccaacaggt tttcgatgac tattctgtca tagggactgc    3300
tgtgcttgag tatattactc agcaaatagc ccccaaaaac ctggacaacc cgtctaagaa    3360
ggaacaagag ctgatagcga agaaaacaga gaaagctaaa tatcttttcac ttgaaactat    3420 aaagcttgca ctggaggaat tcaacaaaca tcgcgacatc gacaagcagt gcagatttga    3480
ggagatcttg gccaacttcg cagctattcc aatgattttt gacgagatag cacagaataa    3540
ggacaacctg gcacagatta gcataaaata ccagaatcag gggaagaagg atcttcttca    3600
ggcttcggct gaggacgatg tcaaagccat caaagatctg ctcgaccaga ccaacaattt    3660
gttgcataaa ctcaagatct ccacatatc gcagtccgaa gataaagcga acatacttga    3720
caaagacgaa cattttttatc ttgttttcga ggagtgttat tttgagttgg caaacatcgt    3780
tcccctctac aacaaaattc gcaactatat aactcagaag ccctattctg acgagaaatt    3840
caaacttaat ttcgaaaaca gcactctcgc aaacggctgg gataaaaaca aggaacccga    3900
caacaccgcc atactttta ttaaggatga taaatattat ttgggcgtga tgaataaaaa    3960
gaacaataaa atattcgatg ataaagcaat taaggaaaat aaaggggaag gtataaaaaa    4020
aatcgtgtat aagctgcttc caggagctaa taaaatgctg ccaaaagtct tcttctctgc    4080
caagtcgatc aagttttaca atccttctga agatattttg cggatcagaa atcactctac    4140
tcacactaaa aacggttcac cccagaaagg atacgagaag tttgagttca acatcgaaga    4200
ctgtcggaag tttatcgact tttacaagca gtctatatca aaacaccccg aatggaaaga    4260 ttttggttttt cggttcagcg acacgcagag atataattca attgatgagt ctctcagggga    4320 ggtggagaac caagggtata aacttacttt tgagaacatt tccgaatcct atattgattc    4380
```

```
ggtggtcaat caggggaaac tgtacctgtt tcagatatat aacaaagact tctccgcgta    4440
ttctaaagga cggcccaatc tccatactct ttattggaag gcgctgtttg acgagcggaa    4500
ccttcaggat gttgtctata agttgaacgg ggaagctgag ctgttctatc ggaagcagtc    4560
tattccaaaa aagataacgc accccgcgaa ggaggcaatt gcaaacaaga acaaagacaa    4620
tccaaagaag gagtcggtgt ttgagtacga tctgataaaa gacaaaaggt ttaccgagga    4680
caagtttttt ttccactgtc cgatcaccat caattttaag tcttccggcg ccaacaaatt    4740
caatgacgaa ataaatctgc tgctcaagga aaaggcaaat gatgttcata ttctgtcgat    4800
agaccgcggg gaaagacacc tcgcgtatta tacattggtc gatgggaaag gcaatattat    4860
caaacaagac accttcaata tcattggtaa cgataggatg aaaacgaact atcatgataa    4920
acttgcagct attgaaaagg acagagactc ggctcggaaa gattggaaaa agatcaataa    4980
catcaaggaa atgaaggaag ggtatctctc ccaggtcgtt catgaaatcg ccaaactggt    5040
tattgagtac aatgctatag tggttttga agatcttaat tttgggttta agagagggag    5100
atttaaagtc gagaaacagg tttatcaaaa acttgaaaaa atgttgatag aaaaattgaa    5160
ctatcttgtg tttaaggaca atgagttcga taaaaccggg ggggttttga gagcttatca    5220
actgacggct cccttcgaga cattcaaaaa aatggggaag cagaccggca tcatttatta    5280
tgtgcccgcg ggcttcactt ctaaaatttg tcctgtgaca gggttcgtga accaattgta    5340
ccccaagtac gaaagcgtct ccaagtccca agaattcttt agcaagtttg acaaaatttg    5400
ctataacctg gacaaagggt actttgagtt ttcctttgat tataagaatt cggggataaa    5460
agctgcgaaa ggtaagtgga cgatagcctc tttcgggtcg cgccttatta acttcaggaa    5520
ttccgacaaa aaccataatt gggacacccg cgaggtctac cctacaaagg aactcgaaaa    5580
gttgcttaag gattattcaa tagagtatgg tcatggcgag tgtattaagg ctgctatctg    5640
tggtgagtca gataagaaat tcttcgcgaa attgacatct gttttgaaca ccatcctcca    5700
aatgaggaac tctaaaacgg ggacggagct tgattatctc atctcacccg ttgctgatgt    5760
gaacggtaat ttctttgatt cacgccaagc cccgaagaac atgccccaag acgccgatgc    5820
taacggcgct tatcatatag ggctgaaggg gctcatgctt ctggggcgca tcaaaaataa    5880
ccaagaaggg aagaaactca atctggttat caaaaatgag gaatatttcg aattcgtgca    5940
aaaccgcaac aatggatcta agaagcgtag gatcaagcaa gattgattaa ttaagggccc    6000
atccaagtaa attaagttgg atcagtagag atgcatggtt ggtgttctca tgtggtctga    6060
atctgtgttc tgtttcatct tttgtgtaag tgtgcaactt cgattctgta aaacttggca    6120
agtagatgaa cgatgtcatt tatatgcgtg tagcttgtca aaatacaaag tagaaacctg    6180
tatctgaata agatggcatt catgaaataa tattatcgat tgaacgaacg aagcaacaga    6240
atgatcttcc aaattgaagc aaaggaattg atggacaacg agttgctgta ctttggagct    6300
gtaaatctgt agtacttctc aacgatgcta tggaccgtgg gccgtccata atcgctgggt    6360
ggaatgagcc cactgtccat gtgcttctgc atttggcccg tgtacagccc atataatgtc    6420
gaaaaaccta atacgcgcgc gccgccggcg cgcgtttcgg acccagaacg cctagcgccg    6480
ctgcgccgac gtgcgcgcgt ctccactttt tttttcgttt tctttccatt              6530
```

<210> SEQ ID NO 74
<211> LENGTH: 6062
<212> TYPE: DNA
<213> ORGANISM: Artificial Sequence
<220> FEATURE:

<223> OTHER INFORMATION: Synthetic polynucleotide.Expression cassette comprising Zea mays Ubiquitin promoter cassette, NLS-LbCpf1-CO2-NLS and an Oryza sativa transcription termination sequence

<400> SEQUENCE: 74

```
gtcgtgcccc tctctagaga taaagagcat tgcatgtcta aagtataaaa aattaccaca      60
tatttttttg tcacacttat ttgaagtgta gtttatctat ctctatacat atatttaaac     120
ttcactctac aaataatata gtctataata ctaaaataat attagtgttt tagaggatca     180
tataaataaa ctgctagaca tggtctaaag gataattgaa tattttgaca atctacagtt     240
ttatcttttt agtgtgcatg tgatctctct gttttttttg caaatagctt gacctatata     300
atacttcatc cattttatta gtacatccat ttaggattta gggttgatgg tttctataga     360
ctaattttta gtacatccat tttattcttt ttagtctcta aattttttaa aactaaaact     420
ctattttagt ttttttattta ataatttaga tataaaatga aataaaataa attgactaca     480
aataaaacaa ataccctttta agaaataaaa aaactaagca aacattttc ttgtttcgag     540
tagataatga caggctgttc aacgccgtcg acgagtctaa cggacaccaa ccagcgaacc     600
agcagcgtcg cgtcgggcca agcgaagcag acggcacggc atctctgtag ctgcctctgg     660
accccctctcg agagttccgc tccaccgttg gacttgctcc gctgtcggca tccagaaatt     720
gcgtggcgga gcggcagacg tgaggcggca cggcaggcgg cctcttcctc ctctcacggc     780
accggcagct acggggatt cctttcccac cgctccttcg cttccccttc ctcgcccgcc     840
gtaataaata gacacccct ccacacccctc tttccccaac ctcgtgttcg ttcggagcgc     900
acacacacgc aaccagatct cccccaaatc cagccgtcgg cacctccgct tcaaggtacg     960
ccgctcatcc tcccccccccc cctctctcta ccttctctag atcggcgatc cggtccatgg    1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt    1140
caagctacct ggtggattta ttaattttgt atctgtatgt gtgtgccata catcttcata    1200
gttacgagtt taagatgatg gatggaaata tcgatctagg ataggtatac atgttgatgc    1260
gggttttact gatgcatata cagagatgct tttttttctcg cttggttgtg atgatatggt    1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc tttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttt     1920
agccctgcct tcatacgcta tttatttgct tggtactgtt tcttttgtcc gatgctcacc    1980
ctgttgtttg gtgatacttc tgcaggtcgc cgccatggcg ggatctaaga agagaagaat    2040
taaacaagat tcgaagctcg agaagttcac caactgctac tcgctgagca agacgctgcg    2100
gttcaaggcg atccccgtcg ggaagaccca ggagaacatc gacaacaagc ggctcctggt    2160
cgaggacgag aagcgcgccg aggactacaa gggcgtcaag aagctgctgg accggtacta    2220
```

```
cctctccttc atcaacgacg tcctgcactc gatcaagctc aagaacctga acaactacat    2280
ctcgctgttc cgcaagaaga cacggaccga gaaggagaac aaggagctcg agaacctcga    2340
gatcaacctg cgcaaggaga tcgcgaaggc gttcaagggc aacgaggggt acaagagcct    2400
gttcaagaaa gacatcatcg agaccatcct gccggagttc ctggacgaca aggacgagat    2460
cgcgctggtg aactcgttca acgggttcac cacggccttc accgggtttt cgacaaccg     2520
ggagaacatg ttcagcgagg aggccaagtc gaccagcatc gccttccggt gcatcaacga    2580
gaacctcacc cgctacatca gcaacatgga catcttcgag aaggtggacg ccatcttcga    2640
caagcacgag gtccaggaga tcaaggaaaa gatcctgaac tcggactacg acgtggaaga    2700
cttctttgag ggcgagttct tcaacttcgt cctcacccag gagggcatcg acgtctacaa    2760
cgccatcatc ggcggcttcg tgacggagag cggcgagaag atcaagggcc tcaacgagta    2820
catcaacctc tacaaccaga agactaagca gaagctcccg aagttcaagc cgctgtacaa    2880
gcaagtcctg agcgaccggg agtccctctc gttctacggc gagggctaca cgagcgacga    2940
ggaggtgctg gaggtgttcc gcaacacgct gaacaagaac agcgagatct tcagctcgat    3000
caagaaactc gagaagctgt tcaagaactt cgacagagtac agcagcgccg gcatcttcgt    3060
caagaacggg cccgcgatca gcaccatcag caaggacatc ttcggggagt ggaacgtgat    3120
ccgcgacaag tggaacgccg agtacgacga catccacctc aagaaaaagg cggtggtcac    3180
ggagaagtac gaggacgacc gccggaagtc cttcaagaaa atcgggagct tcagcctcga    3240
gcagctccag gagtacgcgg acgccgacct gagcgtggtg gagaagctca aggagatcat    3300
catccagaag gtcgacgaga tctacaaggt ctacggctcg agcgagaagc tgttcgacgc    3360
ggacttcgtg ctggagaagt ccctcaagaa gaacgacgcc gtggtggcca tcatgaagga    3420
tctgctcgac agcgtgaagt cgttcgagaa ctacatcaag gcattctttg gggagggcaa    3480
ggagacgaac cggacgagt ccttctacgg ggacttcgtg ctcgcgtacg acatcctcct     3540
gaaggtcgac cacatctacg acgcgatccg gaactacgtc acgcagaagc cctacagcaa    3600
ggacaagttc aagctctact ccagaacccg gcagttcatg ggcggtgg gacaaggacaa     3660
ggagaccgac taccgggcca cgatcctgcg gtacgggtcc aagtactacc tcgccatcat    3720
ggacaagaag tacgccaagt gcctccagaa gattgacaag gacgacgtga cggaaacta    3780
cgagaagatc aactacaagc tcctcccggg gcccaacaag atgctgccga aggtgttctt    3840
cagcaagaag tggatggcct actacaaccc ctcggaggac atccagaaga tatacaagaa    3900
cggcacgttc aaaaagggg acatgttcaa cctgaacgca tgccacaagc tgatcgactt    3960
tttcaaggac agcatcagcc gctacccgaa gtggtcgaac gcctacgact tcaacttctc    4020
ggagacggag aagtacaagg acattgcggg cttctaccgg gaggtggagg cagggcta     4080
caaggtctcc ttcgagagcg cctccaagaa agaggtggac aagctcgtgg aggagggcaa    4140
gctgtacatg ttccagatct acaacaagga cttctcggac aagtcgcacg caccccgaa     4200
cctccacacg atgtacttca agctgctgtt cgacgagaac aaccacgggc agatccgcct    4260
cagcggcggg gcggagctgt tcatgcgccg cgcgtccctc aagaaggagg agctggtcgt    4320
gcaccccgcc aactccccga tcgcgaacaa gaaccccgac aaccccaaga agacaaccac    4380
cctctcgtac gacgtctaca aggacaagcg gttctcggag gaccagtacg agctgcacat    4440
cccgatcgcc atcaacaagt gccccaagaa catcttcaag atcaacaccg aggtgcgggt    4500
gctgctcaag cacgacgaca accectacgt catcgggatc gaccgcggcg agcggaacct    4560
```

```
gctctacatc gtggtcgtgg acgggaaggg gaacatcgtg gagcagtaca gcctgaacga    4620
gatcatcaac aacttcaacg gcatccgcat caagacggac taccacagcc tcctggacaa    4680
gaaggagaag gagcggttcg aggcgcggca gaactggacc tccatcgaga acatcaagga    4740
gctgaaggcc ggctacatca gccaggtcgt gcacaagatc tgcgagctcg tggagaagta    4800
cgacgcggtg atcgcgctgg aggacttgaa cagcgggttc aagaactccc gggtcaaggt    4860
cgagaagcag gtctaccaga agttcgagaa gatgctgatc gacaagctca actacatggt    4920
ggacaagaag tccaaccect cgccaccgg cggcgccctc aagggctacc agatcaccaa    4980
caagttcgag tccttcaagt cgatgtctac gcagaacggg ttcatttct acatcccggc    5040 gtggctcacc agcaagatcg acccgagcac gggcttcgtc aacctcctga agaccaagta    5100
caccagcatc gcggacagca agaagttcat ctcctcgttc gaccgcatca tgtacgtccc    5160
cgaggaagac ctgttcgagt cgccctcga ctacaagaac ttctcccgga cggacgccga    5220
ctacatcaaa agtgtgaagc tctacagcta cggcaaccgg atccgcatct ccgcaaccc    5280 caagaagaac aatgtgttcg actgggagga ggtgtgcctg acgagcgcct acaaggagct    5340
cttcaacaag tacggcatca actaccagca aggggacatc cgcgcgctgc tctgcgagca    5400
gtccgacaag gcgttctact cgtcgttcat ggccctgatg agcctcatgc tccagatgcg    5460
caacagcatc accggccgga cggacgtgga cttcctgatc agcccggtca gaacagcga    5520 cggcatttc tacgacagcc ggaactacga ggcccaggag aacgccatcc tccccaagaa    5580
cgccgacgcg aacggcgcct acaacatcgc gcggaaggtg ctgtgggcca tcggccagtt    5640
taaaaaggcg gaggacgaga agctggacaa ggtcaagatc gccatcagca caaggagtg    5700 gctcgagtac gcgcagacga gcgtgaagca cggatctaag aagagaagaa ttaaacaaga    5760
ttgataatcg atcctccgat cccttaatta ccataccatt acaccatgca tcaatatcca    5820
tatatatata aaccctttcg cacgtactta tactatgttt tgtcatacat atatatgtgt    5880
cgaacgatcg atctatcact gatatgatat gattgatcca tcagcctgat ctctgtatct    5940
tgttatttgt ataccgtcaa ataaagtttt cttccacttg tgttaataat tagctactct    6000
catctcatga accctatata taactagttt aatttgctgt caattgaaca tgatgatcga    6060
tg                                                                   6062
```

<210> SEQ ID NO 75
<211> LENGTH: 3684
<212> TYPE: DNA
<213> ORGANISM: Artificial Sequence
<220> FEATURE:
<223> OTHER INFORMATION: Synthetic polynucleotide.Codon optimized
      LbCpf1(TAT)- CO2

<400> SEQUENCE: 75

```
atgtcgaagc tcgagaagtt caccaactgc tactcgctga gcaagacgct gcggttcaag      60
gcgatccccg tcgggaagac ccaggagaac atcgacaaca gcggctcct ggtcgaggac     120 gagaagcgcg ccgaggacta caagggcgtc aagaagctgc tggaccggta ctacctctcc     180
ttcatcaacg acgtcctgca ctcgatcaag ctcaagaacc tgaacaacta catctcgctg     240
ttccgcaaga gacacggac cgagaaggag aacaaggagc tcgagaacct cgagatcaac     300
ctgcgcaagg agatcgcgaa ggcgttcaag ggcaacgagg ggtacaagag cctgttcaag     360
aaagacatca tcgagaccat cctgccggag ttcctggacg acaaggacga gatcgcgctg     420
gtgaactcgt tcaacgggtt caccacggcc ttcaccgggt tttcgacaa ccgggagaac     480
```

```
atgttcagcg aggaggccaa gtcgaccagc atcgccttcc ggtgcatcaa cgagaacctc    540
acccgctaca tcagcaacat ggacatcttc gagaaggtgg acgccatctt cgacaagcac    600
gaggtccagg agatcaagga aaagatcctg aactcggact acgacgtgga agacttcttt    660
gagggcgagt tcttcaactt cgtcctcacc caggagggca tcgacgtcta caacgccatc    720
atcggcggct tcgtgacgga gagcggcgag aagatcaagg cctcaacga gtacatcaac    780 ctctacaacc agaagactaa gcagaagctc ccgaagttca gccgctgta caagcaagtc    840 ctgagcgacc gggagtccct ctcgttctac ggcgagggct acacgagcga cgaggaggtg    900
ctggaggtgt tccgcaacac gctgaacaag aacagcgaga tcttcagctc gatcaagaaa    960
ctcgagaagc tgttcaagaa cttcgacgag tacagcagcg ccggcatctt cgtcaagaac   1020
gggcccgcga tcagcaccat cagcaaggac atcttcgggg agtggaacgt gatccgcgac   1080
aagtggaacg ccgagtacga cgacatccac ctcaagaaaa aggcggtggt cacggagaag   1140
tacgaggacg accgccggaa gtccttcaag aaaatcggga gcttcagcct cgagcagctc   1200
caggagtacg cggacgccga cctgagcgtg gtggagaagc tcaaggagat catcatccag   1260
aaggtcgacg agatctacaa ggtctacggc tcgagcgaga gctgttcga cgcggacttc   1320 gtgctggaga agtccctcaa gaagaacgac gccgtggtgg ccatcatgaa ggatctgctc   1380
gacagcgtga agtcgttcga gaactacatc aaggcattct tggggagggg caaggagacg   1440
aaccgggacg agtcctcta cggggacttc gtgctcgcgt acgacatcct cctgaaggtc   1500
gaccacatct acgacgcgat ccggaactac gtcacgcaga gccctacag caaggacaag   1560 ttcaagctct acttccagaa cccgcagttc atgcgcgggt gggacaagga cgtggagacc   1620
gaccgccggg ccacgatcct gcggtacggg tccaagtact acctcgccat catggacaag   1680
aagtacgcca agtgcctcca gaagattgac aaggacgacg tgaacgggaa ctacgagaag   1740
atcaactaca agctcctccc ggggcccaac aagatgctgc cgaaggtgtt cttcagcaag   1800
aagtggatgg cctactacaa cccctcggag gacatccaga agatatacaa gaacggcacg   1860
ttcaaaaagg gggacatgtt caacctgaac gactgccaca agctgatcga cttttttcaag   1920 gacagcatca gccgctaccc gaagtggtcg aacgcctacg acttcaactt ctcggagacg   1980
gagaagtaca aggacattgc gggcttctac cgggaggtgg aggagcaggg ctacaaggtc   2040
tccttcgaga gcgcctccaa gaaagaggtg gacaagctcg tggaggaggg caagctgtac   2100
atgttccaga tctacaacaa ggacttctcg gacaagtcgc acggcacccc gaacctccac   2160
acgatgtact tcaagctgct gttcgacgag aacaaccacg gcagatccg cctcagcggc   2220 ggggcggagc tgttcatgcg ccgcgcgtcc ctcaagaagg aggagctggt cgtgcacccc   2280
gccaactccc cgatcgcgaa caagaacccc gacaacccca gaagacaac cacctctcg   2340 tacgacgtct acaaggacaa gcggttctcg gaggaccagt acgagctgca catcccgatc   2400
gccatcaaca agtgccccaa gaacatcttc aagatcaaca ccgaggtgcg ggtgctgctc   2460
aagcacgacg acaaccccta cgtcatcggg atcgaccgcg cgagcggaa cctgctctac   2520 atcgtggtcg tggacgggaa ggggaacatc gtggagcagt acagcctgaa cgagatcatc   2580
aacaacttca cggcatccg catcaagacg gactaccaca gctcctgga caagaaggag   2640 aaggagcggt cgaggcgcg gcagaactgg acctccatcg agaacatcaa ggagctgaag   2700
gccggctaca tcagccaggt cgtgcacaag atctgcgagc tcgtggagaa gtacgacgcg   2760
gtgatcgcgc tggaggactt gaacagcggg ttcaagaact cccgggtcaa ggtcgagaag   2820
caggtctacc agaagttcga gaagatgctg atcgacaagc tcaactacat ggtggacaag   2880
```

```
aagtccaacc cctgcgccac cggcggcgcc ctcaagggct accagatcac caacaagttc   2940
gagtccttca gtcgatgtc tacgcagaac gggttcattt tctacatccc ggcgtggctc     3000
accagcaaga tcgacccgag cacgggcttc gtcaacctcc tgaagaccaa gtacaccagc   3060
atcgcggaca gcaagaagtt catctcctcg ttcgaccgca tcatgtacgt ccccgaggaa   3120
gacctgttcg agttcgccct cgactacaag aacttctccc ggacggacgc cgactacatc   3180
aaaaagtgga agctctacag ctacggcaac cggatccgac tcttccgcaa ccccaagaag   3240
aacaatgtgt tcgactggga ggaggtgtgc ctgacgagcg cctacaagga gctcttcaac   3300
aagtacggca tcaactacca gcaagggac atccgcgcgc tgctctgcga gcagtccgac   3360
aaggcgttct actcgtcgtt catggccctg atgagcctca tgctccagat gcgcaacagc   3420
atcaccggcc ggacggacgt ggacttcctg atcagcccgg tcaagaacag cgacggcatt   3480
ttctacgaca gccggaacta cgaggcccag gagaacgcca tcctccccaa gaacgccgac   3540
gcgaacggcg cctacaacat cgcgcggaag gtgctgtggg ccatcggcca gtttaaaaag   3600
gcggaggacg agaagctgga caaggtcaag atcgccatca gcaacaagga gtggctcgag   3660
tacgcgcaga cgagcgtgaa gcac                                          3684
```

<210> SEQ ID NO 76  
<211> LENGTH: 1228  
<212> TYPE: PRT  
<213> ORGANISM: Artificial Sequence  
<220> FEATURE:  
<223> OTHER INFORMATION: Synthetic polypeptide.LbCpf1(TAT)-CO2  
     comprising G532R/K538V/Y542R substitutions

<400> SEQUENCE: 76

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205
```

-continued

```
Ile Leu Asn Ser Asp Tyr Asp Val Glu Asp Phe Phe Glu Gly Glu Phe
210                 215                 220
Phe Asn Phe Val Leu Thr Gln Glu Gly Ile Asp Val Tyr Asn Ala Ile
225                 230                 235                 240
Ile Gly Gly Phe Val Thr Glu Ser Gly Glu Lys Ile Lys Gly Leu Asn
                    245                 250                 255
Glu Tyr Ile Asn Leu Tyr Asn Gln Lys Thr Lys Gln Lys Leu Pro Lys
                260                 265                 270
Phe Lys Pro Leu Tyr Lys Gln Val Leu Ser Asp Arg Glu Ser Leu Ser
            275                 280                 285
Phe Tyr Gly Glu Gly Tyr Thr Ser Asp Glu Glu Val Leu Glu Val Phe
290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
                325                 330                 335
Phe Val Lys Asn Gly Pro Ala Ile Ser Thr Ile Ser Lys Asp Ile Phe
            340                 345                 350
Gly Glu Trp Asn Val Ile Arg Asp Lys Trp Asn Ala Glu Tyr Asp Asp
355                 360                 365
Ile His Leu Lys Lys Lys Ala Val Val Thr Glu Lys Tyr Glu Asp Asp
370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
                420                 425                 430
Glu Lys Leu Phe Asp Ala Asp Phe Val Leu Glu Lys Ser Leu Lys Lys
            435                 440                 445
Asn Asp Ala Val Val Ala Ile Met Lys Asp Leu Leu Asp Ser Val Lys
450                 455                 460
Ser Phe Glu Asn Tyr Ile Lys Ala Phe Phe Gly Glu Gly Lys Glu Thr
465                 470                 475                 480
Asn Arg Asp Glu Ser Phe Tyr Gly Asp Phe Val Leu Ala Tyr Asp Ile
                485                 490                 495
Leu Leu Lys Val Asp His Ile Tyr Asp Ala Ile Arg Asn Tyr Val Thr
                500                 505                 510
Gln Lys Pro Tyr Ser Lys Asp Lys Phe Lys Leu Tyr Phe Gln Asn Pro
            515                 520                 525
Gln Phe Met Arg Gly Trp Asp Lys Asp Val Glu Thr Asp Arg Arg Ala
530                 535                 540
Thr Ile Leu Arg Tyr Gly Ser Lys Tyr Tyr Leu Ala Ile Met Asp Lys
545                 550                 555                 560
Lys Tyr Ala Lys Cys Leu Gln Lys Ile Asp Lys Asp Asp Val Asn Gly
                565                 570                 575
Asn Tyr Glu Lys Ile Asn Tyr Lys Leu Leu Pro Gly Pro Asn Lys Met
            580                 585                 590
Leu Pro Lys Val Phe Phe Ser Lys Lys Trp Met Ala Tyr Tyr Asn Pro
            595                 600                 605
Ser Glu Asp Ile Gln Lys Ile Tyr Lys Asn Gly Thr Phe Lys Lys Gly
610                 615                 620
Asp Met Phe Asn Leu Asn Asp Cys His Lys Leu Ile Asp Phe Phe Lys
```

```
                625           630             635             640
        Asp Ser Ile Ser Arg Tyr Pro Lys Trp Ser Asn Ala Tyr Asp Phe Asn
                        645             650             655

Phe Ser Glu Thr Glu Lys Tyr Lys Asp Ile Ala Gly Phe Tyr Arg Glu
                        660             665             670

Val Glu Glu Gln Gly Tyr Lys Val Ser Phe Glu Ser Ala Ser Lys Lys
                        675             680             685

Glu Val Asp Lys Leu Val Glu Glu Gly Lys Leu Tyr Met Phe Gln Ile
                690             695             700

Tyr Asn Lys Asp Phe Ser Asp Lys Ser His Gly Thr Pro Asn Leu His
        705             710             715             720

Thr Met Tyr Phe Lys Leu Leu Phe Asp Glu Asn Asn His Gly Gln Ile
                        725             730             735

Arg Leu Ser Gly Gly Ala Glu Leu Phe Met Arg Arg Ala Ser Leu Lys
                        740             745             750

Lys Glu Glu Leu Val Val His Pro Ala Asn Ser Pro Ile Ala Asn Lys
                        755             760             765

Asn Pro Asp Asn Pro Lys Lys Thr Thr Thr Leu Ser Tyr Asp Val Tyr
                770             775             780

Lys Asp Lys Arg Phe Ser Glu Asp Gln Tyr Glu Leu His Ile Pro Ile
        785             790             795             800

Ala Ile Asn Lys Cys Pro Lys Asn Ile Phe Lys Ile Asn Thr Glu Val
                        805             810             815

Arg Val Leu Leu Lys His Asp Asp Asn Pro Tyr Val Ile Gly Ile Asp
                        820             825             830

Arg Gly Glu Arg Asn Leu Leu Tyr Ile Val Val Val Asp Gly Lys Gly
                        835             840             845

Asn Ile Val Glu Gln Tyr Ser Leu Asn Glu Ile Ile Asn Asn Phe Asn
                850             855             860

Gly Ile Arg Ile Lys Thr Asp Tyr His Ser Leu Leu Asp Lys Lys Glu
        865             870             875             880

Lys Glu Arg Phe Glu Ala Arg Gln Asn Trp Thr Ser Ile Glu Asn Ile
                        885             890             895

Lys Glu Leu Lys Ala Gly Tyr Ile Ser Gln Val Val His Lys Ile Cys
                        900             905             910

Glu Leu Val Glu Lys Tyr Asp Ala Val Ile Ala Leu Glu Asp Leu Asn
                        915             920             925

Ser Gly Phe Lys Asn Ser Arg Val Lys Val Glu Lys Gln Val Tyr Gln
                930             935             940

Lys Phe Glu Lys Met Leu Ile Asp Lys Leu Asn Tyr Met Val Asp Lys
        945             950             955             960

Lys Ser Asn Pro Cys Ala Thr Gly Gly Ala Leu Lys Gly Tyr Gln Ile
                        965             970             975

Thr Asn Lys Phe Glu Ser Phe Lys Ser Met Ser Thr Gln Asn Gly Phe
                        980             985             990

Ile Phe Tyr Ile Pro Ala Trp Leu Thr Ser Lys Ile Asp Pro Ser Thr
                        995             1000            1005

Gly Phe Val Asn Leu Leu Lys Thr Lys Tyr Thr Ser Ile Ala Asp
                1010            1015            1020

Ser Lys Lys Phe Ile Ser Ser Phe Asp Arg Ile Met Tyr Val Pro
                1025            1030            1035

Glu Glu Asp Leu Phe Glu Phe Ala Leu Asp Tyr Lys Asn Phe Ser
                1040            1045            1050
```

```
Arg Thr Asp Ala Asp Tyr Ile Lys Lys Trp Lys Leu Tyr Ser Tyr
    1055            1060            1065

Gly Asn Arg Ile Arg Ile Phe Arg Asn Pro Lys Lys Asn Asn Val
    1070            1075            1080

Phe Asp Trp Glu Glu Val Cys Leu Thr Ser Ala Tyr Lys Glu Leu
    1085            1090            1095

Phe Asn Lys Tyr Gly Ile Asn Tyr Gln Gln Gly Asp Ile Arg Ala
    1100            1105            1110

Leu Leu Cys Glu Gln Ser Asp Lys Ala Phe Tyr Ser Ser Phe Met
    1115            1120            1125

Ala Leu Met Ser Leu Met Leu Gln Met Arg Asn Ser Ile Thr Gly
    1130            1135            1140

Arg Thr Asp Val Asp Phe Leu Ile Ser Pro Val Lys Asn Ser Asp
    1145            1150            1155

Gly Ile Phe Tyr Asp Ser Arg Asn Tyr Glu Ala Gln Glu Asn Ala
    1160            1165            1170

Ile Leu Pro Lys Asn Ala Asp Ala Asn Gly Ala Tyr Asn Ile Ala
    1175            1180            1185

Arg Lys Val Leu Trp Ala Ile Gly Gln Phe Lys Lys Ala Glu Asp
    1190            1195            1200

Glu Lys Leu Asp Lys Val Lys Ile Ala Ile Ser Asn Lys Glu Trp
    1205            1210            1215

Leu Glu Tyr Ala Gln Thr Ser Val Lys His
    1220            1225
```